US012740982B2

(12) United States Patent
Zhang et al.

(10) Patent No.: US 12,740,982 B2
(45) Date of Patent: Sep. 22, 2026

(54) INHIBITORS OF TYROSINE KINASE

(71) Applicant: BridGene Biosciences, Inc., San Jose, CA (US)

(72) Inventors: Chao Zhang, San Jose, CA (US); Ping Cao, San Jose, CA (US); Michael J. Bishop, San Jose, CA (US)

(73) Assignee: BridGene Biosciences, Inc., San Jose, CA (US)

( * ) Notice: Subject to any disclaimer, the term of this patent is extended or adjusted under 35 U.S.C. 154(b) by 964 days.

(21) Appl. No.: 17/626,486

(22) PCT Filed: Jul. 17, 2020

(86) PCT No.: PCT/US2020/042591

§ 371 (c)(1),
(2) Date: Jan. 11, 2022

(87) PCT Pub. No.: WO2021/016102

PCT Pub. Date: Jan. 28, 2021

(65) Prior Publication Data

US 2022/0288069 A1 Sep. 15, 2022

Related U.S. Application Data

(60) Provisional application No. 62/876,520, filed on Jul. 19, 2019.

(51) Int. Cl.

| | |
|---|---|
| ***A61K 31/506*** | (2006.01) |
| ***A61K 31/404*** | (2006.01) |
| ***A61K 31/4439*** | (2006.01) |
| ***A61K 31/5377*** | (2006.01) |
| ***A61K 45/06*** | (2006.01) |
| ***C07D 209/34*** | (2006.01) |
| ***C07D 403/06*** | (2006.01) |
| ***C07D 403/12*** | (2006.01) |
| ***C07D 403/14*** | (2006.01) |
| ***C07D 413/14*** | (2006.01) |
| ***C07D 417/12*** | (2006.01) |
| ***C07D 417/14*** | (2006.01) |

(52) U.S. Cl.

CPC .......... *A61K 31/506* (2013.01); *A61K 31/404* (2013.01); *A61K 31/4439* (2013.01); *A61K 31/5377* (2013.01); *A61K 45/06* (2013.01); *C07D 209/34* (2013.01); *C07D 403/06* (2013.01); *C07D 403/12* (2013.01); *C07D 403/14* (2013.01); *C07D 413/14* (2013.01); *C07D 417/12* (2013.01); *C07D 417/14* (2013.01)

(58) Field of Classification Search

CPC .................................................... A61K 31/506
USPC .......................................................... 514/236
See application file for complete search history.

(56) References Cited

U.S. PATENT DOCUMENTS

| | | | |
|---|---|---|---|
| 4,861,916 | A | 8/1989 | Koehler et al. |
| 10,787,428 | B2 | 9/2020 | Dango et al. |
| 2014/0142099 | A1 | 5/2014 | Owens et al. |
| 2015/0045339 | A1 | 2/2015 | Takasaki et al. |
| 2019/0010136 | A1 | 1/2019 | Dango et al. |

FOREIGN PATENT DOCUMENTS

| | | | | |
|---|---|---|---|---|
| CN | 102250069 A | 11/2011 | |
| EP | 3845530 A1 | 7/2021 | |
| KR | 20180002093 A | 1/2018 | |
| TW | 200827351 A | 7/2008 | |
| WO | WO-2010/123870 A1 | 10/2010 | |
| WO | WO 2011/034907 A2 | 3/2011 | |
| WO | WO-2013157540 A1 * | 10/2013 | ........... C07D 47/104 |
| WO | WO-2020/045941 A1 | 3/2020 | |
| WO | WO-2020108516 A1 * | 6/2020 | ........... A61K 31/506 |

OTHER PUBLICATIONS

Nishizawa et al., Studies on hydrolysis of chiral, achiral and racemic alcohol esters with Pseudomonas cepacia lipase: mechanism of stereospecificity of the enzyme, J. Chem. Soc., Perkin Trans. 2, 1997, pp. 1293-1298 (Year: 1997).*
WO 2020108516, Google Patents, English translation, pp. 1-40. (Year: 2020).*
WO 2020108516, Google Patents, English translation, pp. 41-81. (Year: 2020).*
Hanks et al. The eukaryotic protein kinase superfamily: kinase (catalytic) domain structure and classification, Protein Kinases 6, the FASEB Journal, 1995, vol. 9(8), pp. 576-596. (Year: 1995).*
WO 2013157540 A1, English translation, Google Patents (Year: 2013).*
CN Office Action in Chinese Application No. 202080059769.4, dated Apr. 29, 2023, 19 pages (with English translation).
EP Extended Search Report in European Application No. 20844017.2, dated Jun. 1, 2023, 8 pages.
Hurst et al., "Sodium Methyl Carbonate as an Effective C1 Synthon. Synthesis of Carboxylic Acids, Benzophenones, and Unsymmetrical Ketones," *Org. Lett.* (2019), 21:3882-3885, American Chemical Institute.
Prashanth et al., "Synthesis of (4-Benzoyl-Phenoxy)-Acetic Acid Derivatives and their Efficacy as Antioxidant Agents," *Free Radicals and Antioxidants* (2013), 3:S50-S54, Reed Elsevier India Pvt. Ltd.
Pubchem 59966731 deposited on Aug. 20, 2012, pp. 1-7.
Registry (STN) [online], CAS 2201400-21-5; 2200104-71-6; 2199252-99-6; 2198907-01-4; 2197891-24-8 (2018) (2 pages).
Wang, H., et al., "Dynamic transcriptomes of human myeloid leukemia cells." Genomics, 102(4), Jun. 2013, 250-256 (7 Pages).
Skopek, R., et al., "Choosing the Right Cell Line for Acute Myeloid Leukemia (AML) Research." International journal of molecular sciences, 24(6), 5377, Mar. 2023, (34 Pages).

(Continued)

*Primary Examiner* — Jeffrey H Murray
*Assistant Examiner* — Rilla Marie Samsell
(74) *Attorney, Agent, or Firm* — Clark & Elbing LLP

(57) ABSTRACT

The present disclosure provides compounds and compositions thereof which are useful as inhibitors of tyrosine kinase and which exhibit desirable characteristics for the same. Further disclosed herein are methods of treating cancer using these tyrosine kinase inhibitor compounds.

12 Claims, No Drawings

(56) References Cited

OTHER PUBLICATIONS

Larizza, L., et al., "The Kasumi-1 cell line: a t(8;21)-kit mutant model for acute myeloid leukemia". Leukemia & lymphoma, 46(2), Feb. 2005, 247-255 (9 Pages).

Lappin, K. M., et al., "A compound combination screening approach with potential to identify new treatment options for paediatric acute myeloid leukaemia." Scientific reports, 10(1), 18514, Oct. 2020, (13 Pages).

* cited by examiner

INHIBITORS OF TYROSINE KINASE

CROSS-REFERENCE TO RELATED APPLICATIONS

This application is a 35 USC § 371 National Stage application of International Application No. PCT/US2020/042591 filed Jul. 17, 2020, now pending; which claims the benefit under 35 USC § 119(e) to U.S. Application Ser. No. 62/876,520 filed Jul. 19, 2019, now expired. The disclosure of each of the prior applications is considered part of and is incorporated by reference in the disclosure of this application.

FIELD

The present disclosure relates generally to the field of compounds, pharmaceutical compositions, and methods of using the compounds and compositions containing them. The present disclosure specifically relates to tyrosine kinase inhibitor compounds and compositions containing them, and the use of the compounds and compositions for the treatment of cancer.

BACKGROUND

In recent years, inhibition of specific cancer-associated tyrosine kinases has emerged as an important approach for cancer therapy. Tyrosine kinases as mediators of cell signaling, play a role in many diverse physiological pathways including cell growth and differentiation. Deregulation of tyrosine kinases activity can result in cellular transformation leading to the development of cancer.

SUMMARY

Disclosed herein are compounds used as tyrosine kinase inhibitors, pharmaceutical compositions containing the compounds, and method of using the compounds and compositions for the treatment of cancer. Because many of the disclosed compounds can afford covalent inhibition of particular tyrosine kinases, they exhibit high potency and outstanding selectivity toward these kinases. In some embodiments, the present disclosure provides a compound of Formula (I)

Formula (I)

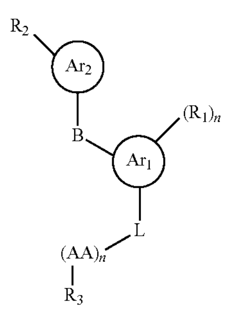

or an optically pure stereoisomer, pharmaceutically acceptable salt, or solvate thereof. In some aspects, n can be an integer selected from 0 to 2, m can be an integer selected from 0 to 4.

In some aspects, An can be selected from the group consisting of phenyl, naphthyl, anthracene,

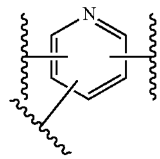 , 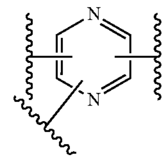 , 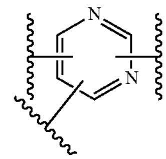 ,

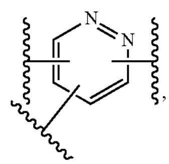 , 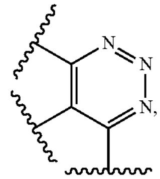 , 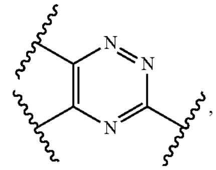 ,

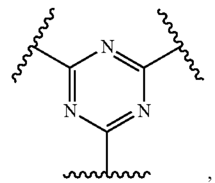 , 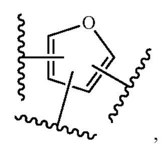 , 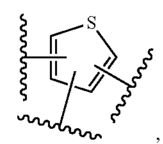 ,

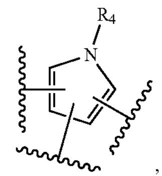 , 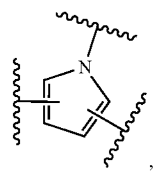 , 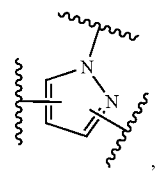 ,

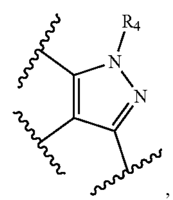 , 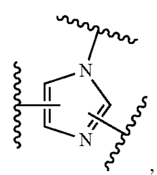 , 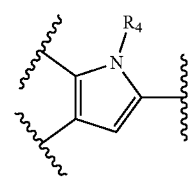 ,

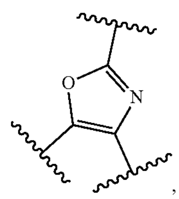 , 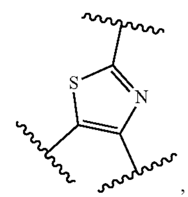 , 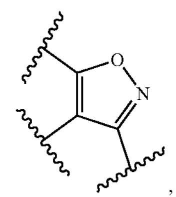 ,

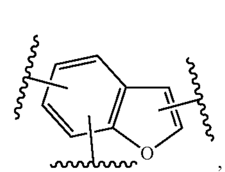 , 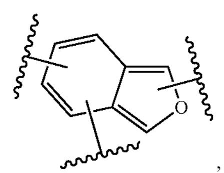 ,

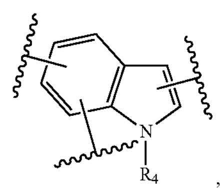 , 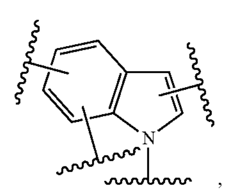 ,

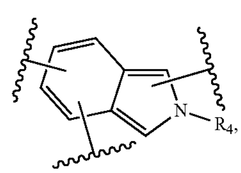 , 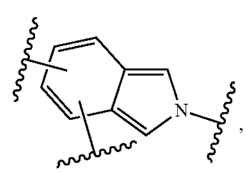 ,

-continued
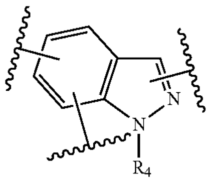,
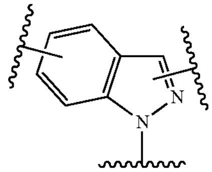,
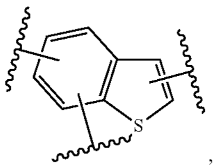,
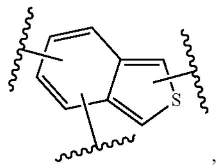,
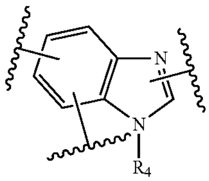,
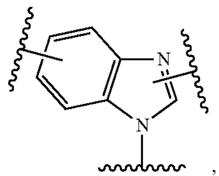,
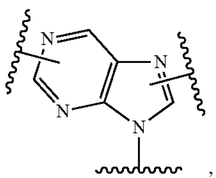,
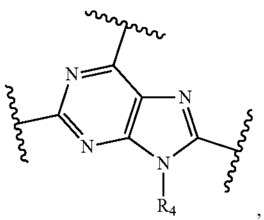,
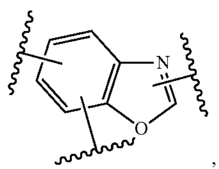,
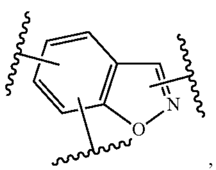,
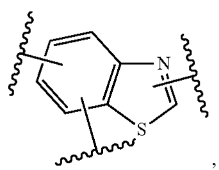,
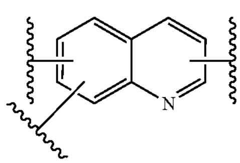,
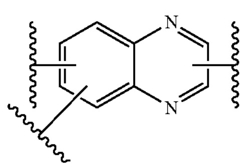,
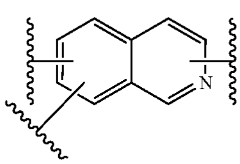,
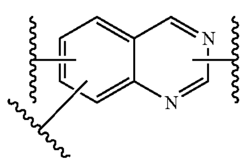,
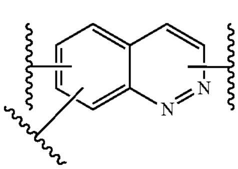,
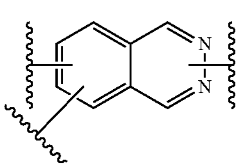, and
-continued
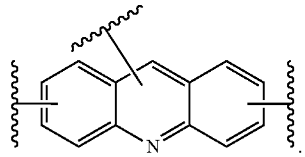.
$Ar_2$ can be selected from the group consisting of phenyl,
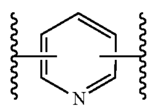,
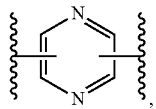,
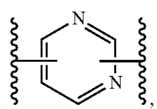,
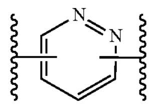,
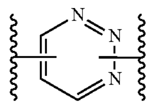,
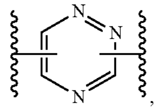,
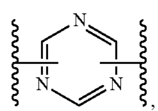,
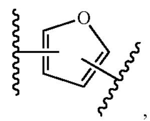,
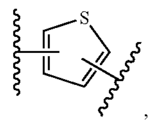,
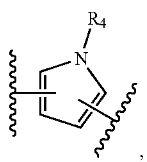,
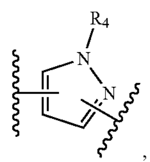,
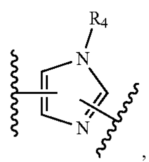,
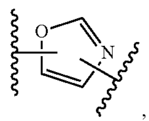,
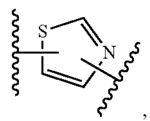, and
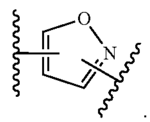.
B can be —CO—, —COO—, —$CONR_4$—, —$(CH_2)_{1-5}$—, —O—, —OPO—, —$OPO_2$—, —S—, —SO—, or —$SO_2$—.
L can be —$O(CH_2)_{1-5}O$—, —$O(CH_2)_{1-5}NR_4$—, —$NR_4(CH_2)_{1-5}NR_4$—, —$CONR_4(CH_2)_{1-5}NR_4$—, —$NR_4CO(CH_2)_{1-5}NR_4$—, —$(CH_2)_{1-5}NR_4$—, —$(CH_2)_{1-5}O$—, —$(CH_2)_{1-5}OOC$—, —$(CH_2)_{1-5}CONR_4$—,
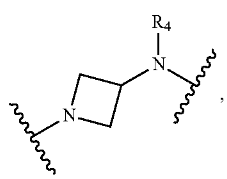,
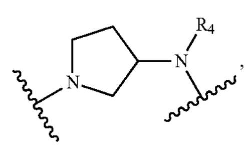, or
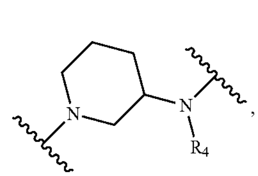,
each of which can be optionally substituted by $R_6$.
AA can be a natural or unnatural amino acid selected from the group consisting of

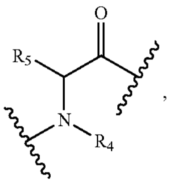, 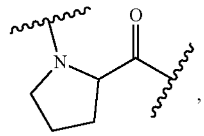,

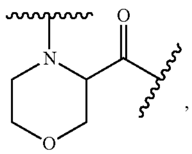, and 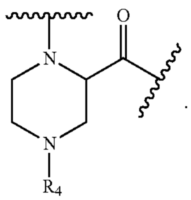.

$R_1$ can be selected from the group consisting of H, F, Br, Cl, $CF_3$, CN, $N_3$. $NH_2$, $NO_2$, OH, $OCH_3$, methyl, ethyl, propyl, isopropyl, cyclopropyl, or -D-$Ar_3$, wherein D can be —CO—, —COO—, —$CONR_4$—, —$NR_4$—, —$(CH_2)_{1-5}$—, —O—, —OPO—, —$OPO_2$—, —S—, —SO—, or —$SO_2$—, $Ar_3$ can be phenyl,

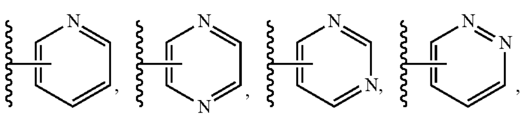

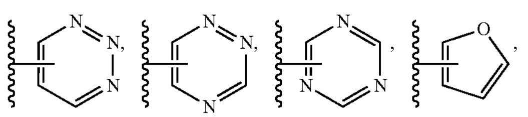

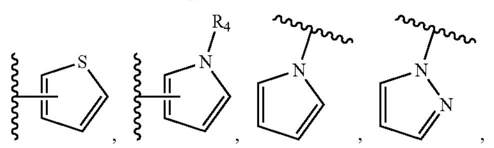

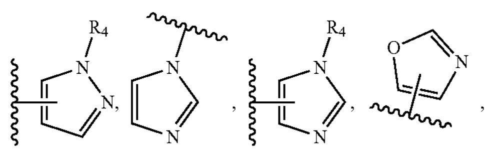

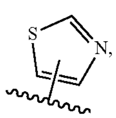 or 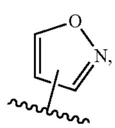

each of which can be optionally substituted by F. Br, Cl, $CF_3$, CN, $N_3$, $NH_2$, $NO_2$, OH, $OCH_3$, methyl, $CH_2CN$, ethyl, propyl, isopropyl, or cyclopropyl.

In one aspect, $R_1$ can be

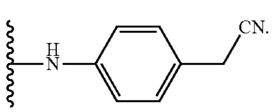 [SMILES: *Nc1ccc(CC#N)cc1]

$R_2$ can be selected from the group consisting of H, F, Br, Cl, $CF_3$, CN, $N_3$, $NH_2$, $NO_2$, OH, $OCH_3$, methyl, ethyl, propyl, isopropyl,

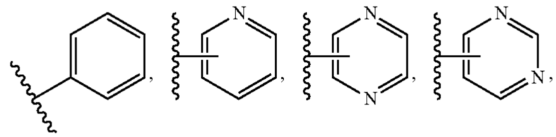

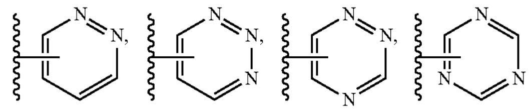

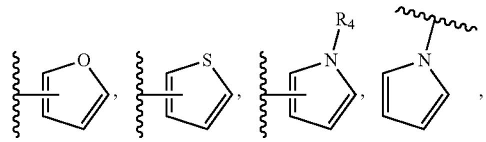

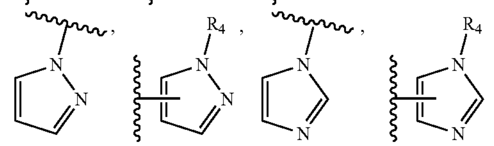

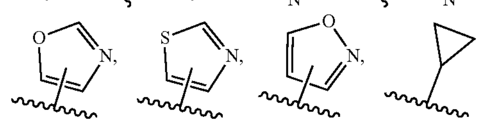

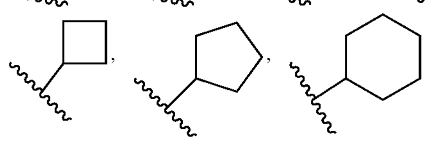

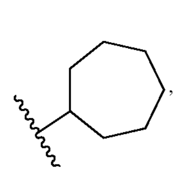, and 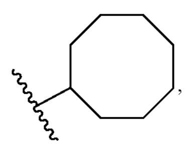, each of which can be substituted by one, two, three, or four $R_6$.

In some aspects, $R_3$ can be selected from the group consisting of $CO(CH_2)_{0-5}CH_3$, $CONR_4(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_4(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_{0-5}CH{=}CHCH_3$, $CONR_4(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_4(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_4(CH_2)_{0-5}C{\equiv}CCH_3$, and $SO_2(CH_2)_{0-5}C{\equiv}CCH_3$, each of which can be optionally substituted by one, two, three, or four $R_6$.

In some aspects, $R_3$ can be selected from the group consisting of

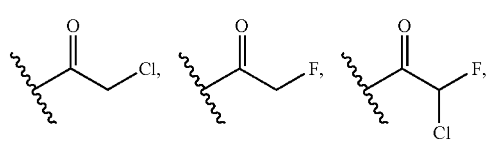

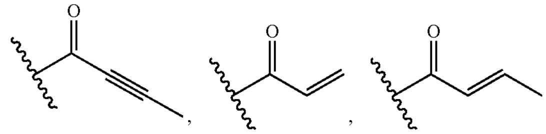

-continued

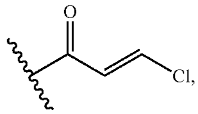

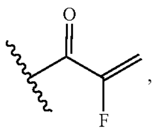

,

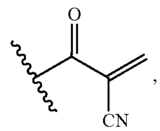

, and

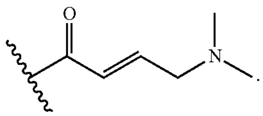

$R_4$ can be H, methyl, ethyl, propyl, isopropyl, cyclopropyl, or cyclobutyl.

$R_5$ can be H, methyl, ethyl, propyl, isopropyl, butyl, isobutyl, tert-butyl, $-CH_2CH_2SCH_3$, $-CH_2Ph$, $-CH_2PhOH$, $-CH_2OH$, $-CHOHCH_3$, $-CH_2CONH_2$, $-CH_2CH_2CONH_2$, $-CH_2SH$, $-CH_2SeH$, $-CH_2COOH$, $-CH_2CH_2COOH$, $-CH_2CH_2CH_2CH_2NH_2$,

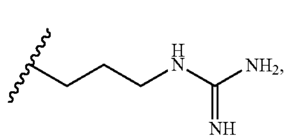

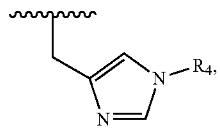

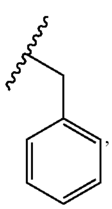

,

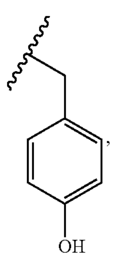

, and

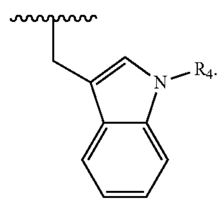

Each $R_6$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Also disclosed herein is a compound of Formula (II)

Formula (II)

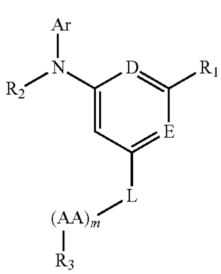

or an optically pure stereoisomer, pharmaceutically acceptable salt, or solvate thereof.

In one aspect, each D and E can be independently N or CH. m can be an integer selected from 0 to 4.

Ar can be selected from the group consisting of

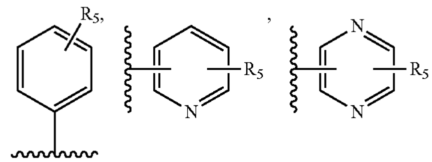

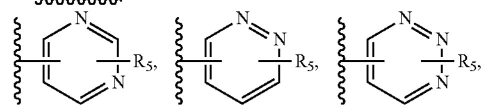

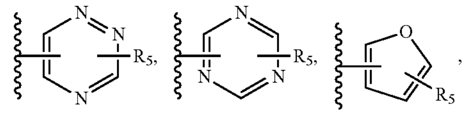

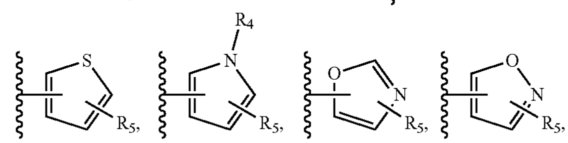

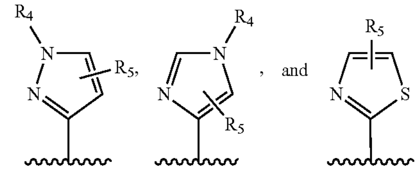

and

L can be $-O(CH_2)_{1-5}O-$, $-O(CH_2)_{1-5}NR_4-$, $-NR_4(CH_2)_{1-5}NR_4-$, $-CONR_4CH_2)_{1-5}NR_4-$, $-NR_4CO(CH_2)_{1-5}NR_4-$, $-(CH_2)_{1-5}NR_4-$, $-(CH_2)_{1-5}O-$, $-(CH_2)_{1-5}OCO-$, $-(CH_2)_{1-5}CONR_4-$,

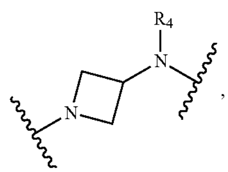

,

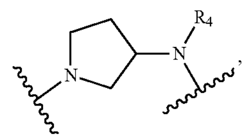

, or

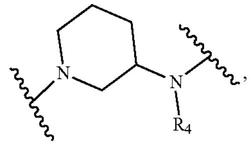

each of which can be optionally substituted by $R_6$.

In another aspect, $R_1$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl, or $-B-Ar_1$, wherein B can be $-CO-$, $-COO-$, $-CONR_4-$, $-NR_4-$, $-(CH_2)_{1-5}-$, $-O-$, $-OPO-$, $-OPO_2-$, $-S-$, $-SO-$, or $-SO_2-$, $Ar_1$ can be phenyl,

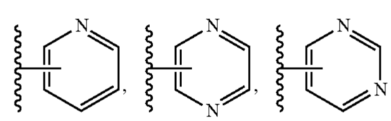

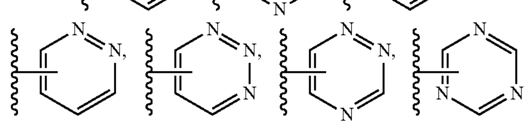

-continued

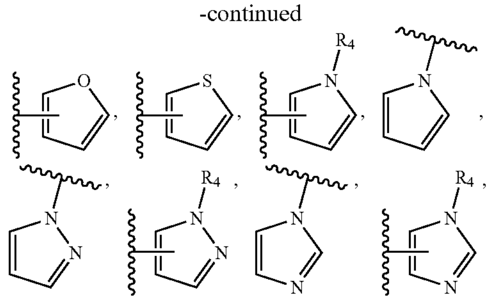

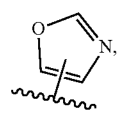

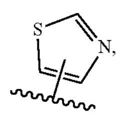

or

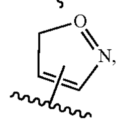

each of which can be optionally substituted by F, Br, Cl, $CF_3$, CN, $N_3$, $NH_2$, $NO_2$, OH, $OCH_3$, methyl, $CH_2CN$, ethyl, propyl, isopropyl, or cyclopropyl. In certain aspects, $R_1$ can be

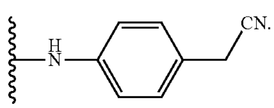

$R_2$ can be H, methyl, ethyl, propyl, isopropyl, cyclopropyl, or cyclobutyl, each of which can be substituted by one, two, three, or four $R_6$.

In some aspects, $R_3$ can be selected from the group consisting of $CO(CH_2)_{0-5}CH_3$, $CONR_4(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_4(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_4(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_4(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_4(CH_2)_{0-5}C{\equiv}CCH_3$, and $SO_2(CH_2)_{0-5}C{\equiv}CCH_3$, each of which can be optionally substituted by one, two, three, or four $R_6$.

In some aspects, $R_3$ can be selected from the group consisting of

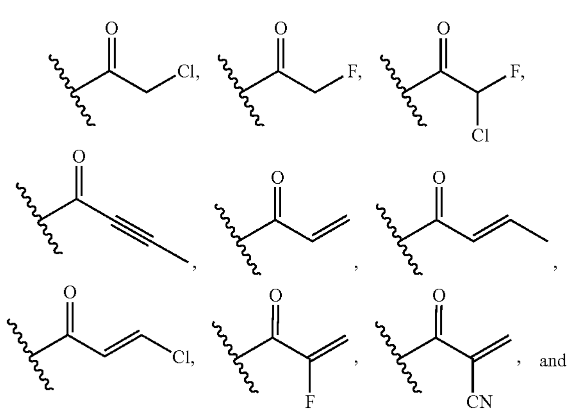

and

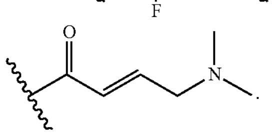

AA can be a natural or unnatural amino acid selected from the group consisting of

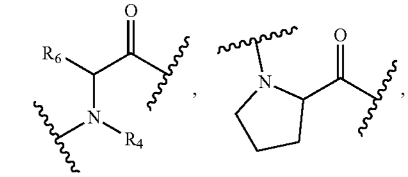

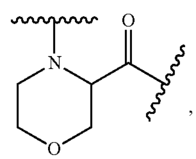

and

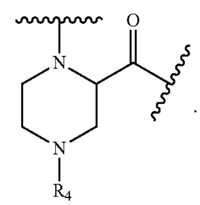

Each $R_4$ can be independently H, methyl, ethyl, propyl, isopropyl, cyclopropyl, or cyclobutyl.

$R_5$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl,

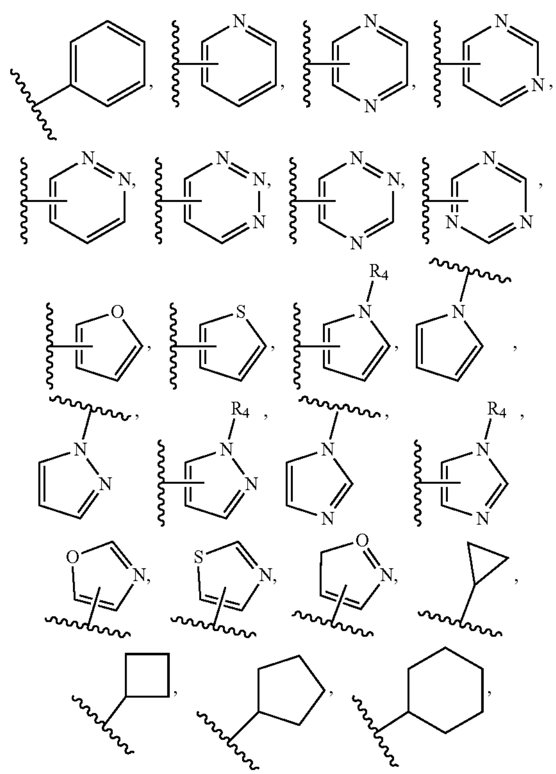

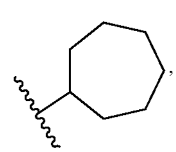

and

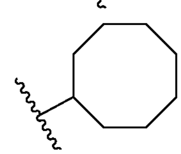

each of which can be optionally substituted by one, two, three, or four $R_6$.

$R_6$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Further disclosed herein is a compound of Formula (III)

Formula (III)

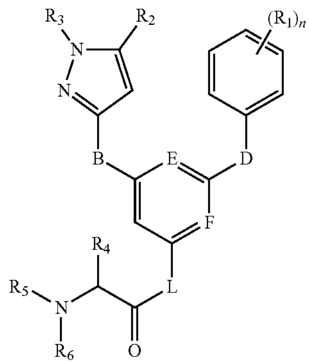

or an optically pure stereoisomer, pharmaceutically acceptable salt, or solvate thereof. In one aspect, n can be an integer selected from 0 to 5. Each B and D can be independently —CO—, —COO—, —$CONR_7$—, —$(CH_2)_{1-5}$—, —O—, —OPO—, —$OPO_2$—, —S—, —SO—, or —$SO_2$—. Each E and F can be independently N or CH.

L can be —$O(CH_2)_{1-5}O$—, —$O(CH_2)_{1-5}NR_7$—, —$NR_7(CH_2)_{1-5}NR_7$—, —$CONR_7(CH_2)_{1-5}NR_7$—, —$NR_7CO(CH_2)_{1-5}NR_7$—, —$(CH_2)_{1-5}NR_7$—, —$(CH_2)_{1-5}O$—, —$(CH_2)_{1-5}OCO$—, —$(CH_2)_{1-5}CONR_7$—,

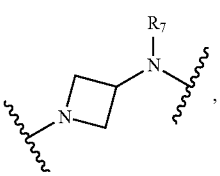, 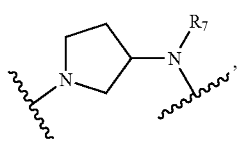, or

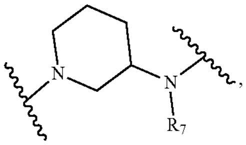, each of which can be optionally substituted by $R_8$.

In some aspects, $R_1$ can be selected from the group consisting of H, F, Br, Cl, $CF_3$, CN, $N_3$, $NH_2$, $NO_2$, OH, $OCH_3$, methyl, $CH_2CN$, ethyl, propyl, isopropyl, and cyclopropyl, each of which can be optionally substituted by one, two, three, or four $R_8$.

In another aspect, $R_2$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl,

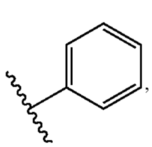, 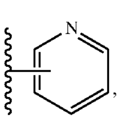, 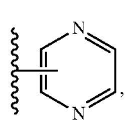, 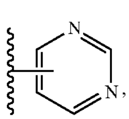,

-continued

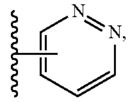, 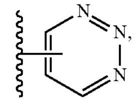, 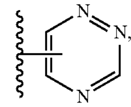, 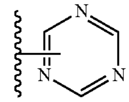,

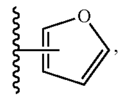, 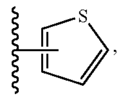, 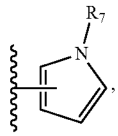, 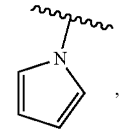,

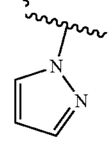, 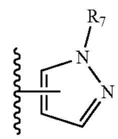, 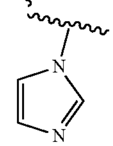, 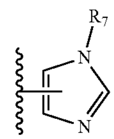,

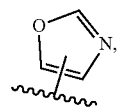, 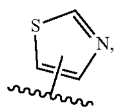, 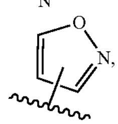, 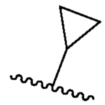,

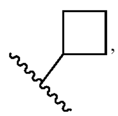, 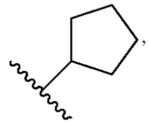, 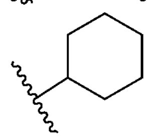,

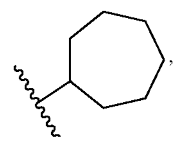, and 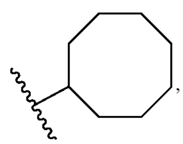, each of which can be optionally substituted by one, two, three, or four $R_8$.

In yet another aspect, $R_3$ can be selected from the group consisting of H, $CF_3$, methyl, ethyl, propyl, and isopropyl, each of which can be optionally substituted by one, two, three, or four $R_8$.

In certain aspects, $R_4$ can be H, methyl, ethyl, propyl, isopropyl, butyl, isobutyl, or tert-butyl.

In some aspects, $R_5$ can be selected from the group consisting of H, methyl, ethyl, propyl, and isopropyl. Or $R_4$ and $R_5$ together can form

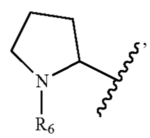, 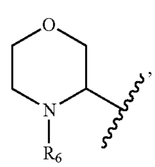, or 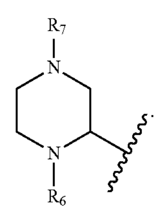.

In some aspects, $R_6$ can be selected from the group consisting of $CO(CH_2)_{0-5}CH_3$, $CONR_7(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_7(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_7(CH_2)_{0-5}CH{=}CHCH_3$, $SO_2(CH_2)_{0-5}CH{=}CHCH_3$, $CO(CH_2)_{0-5}CCH$, $COO(CH_2)_{0-5}CCH$, $CONR_7(CH_2)_{0-5}CCH$, $SO_2(CH_2)_{0-5}CCH$, $CO(CH_2)_{0-5}CCCH_3$, $COO(CH_2)_{0-5}CCCH_3$, $CONR_7(CH_2)_{0-5}CCCH_3$, and $SO_2(CH_2)_{0-5}CCCH_3$, each of which can be optionally substituted by one, two, three, or four $R_8$.

In some aspects, $R_6$ can be selected from the group consisting of

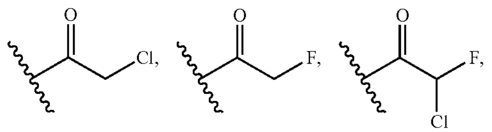

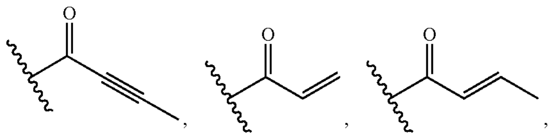

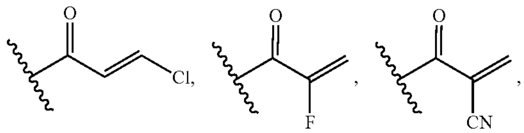

and

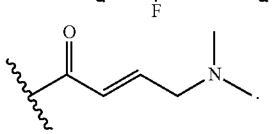

$R_7$ can be H, methyl, ethyl, propyl, or isopropyl.

$R_8$ can be H, F, Br, Cl, $CF_3$, CN, $N_3$, $NH_2$, $NO_2$, OH, $OCH_3$, methyl, ethyl, propyl, isopropyl, butyl, isobutyl, or tert-butyl.

Further disclosed herein is a compound of Formula (IV)

Formula (IV)

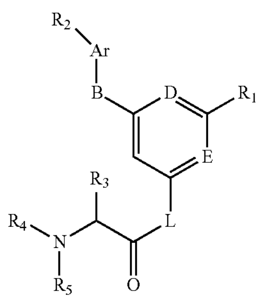

or an optically pure stereoisomer, pharmaceutically acceptable salt, or solvate thereof.

In one aspect, each D and E can be independently N or CH. B can be —$NR_6$—, —O—, —$CONR_6$—, —COO—, —$SO_2$— or —$SO_2NR_6$—.

L can be —$O(CH_2)_{1-5}O$—, —$O(CH_2)_{1-5}NR_6$—, —$NR_6(CH_2)_{1-5}NR_6$—, —$CONR_6(CH_2)_{1-5}NR_6$—, —$NR_6CO(CH_2)_{1-5}NR_6$—, —$(CH_2)_{1-5}NR_6$—, —$(CH_2)_{1-5}O$—, —$(CH_2)_{1-5}OCO$—, —$(CH_2)_{1-5}CONR_6$—,

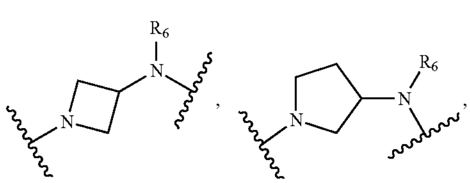

or

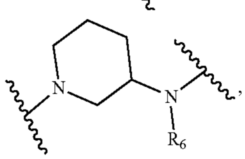

each of which can be optionally substituted by one, two, three, or four $R_7$.

Ar can be selected from the group consisting of phenyl,

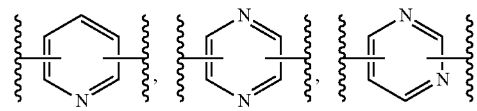

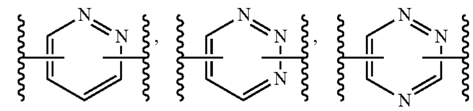

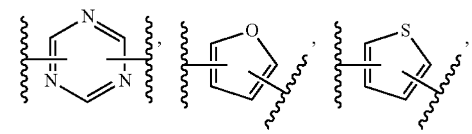

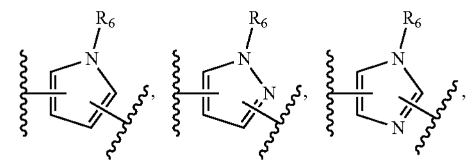

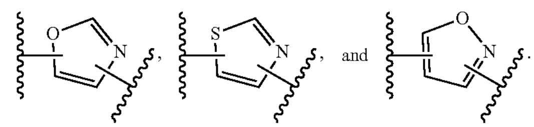

In another aspect, $R_1$ can be selected from the group consisting of H, F, Cl, Br, OH, $N_3$, $NO_2$, $CF_3$, CN, methyl, ethyl, propyl, and isopropyl. In some aspects, $R_1$ can be —G—$Ar_1$, wherein G can be —CO—, —COO—, —$CONR_6$—, —$NR_6$—, —$(CH_2)_{1-5}$—, —O—, —OPO—, —$OPO_2$—, —S—, —SO—, or —$SO_2$—, $Ar_1$ can be phenyl,

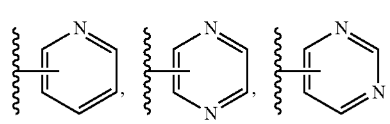

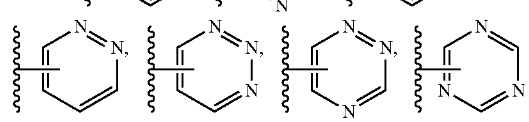

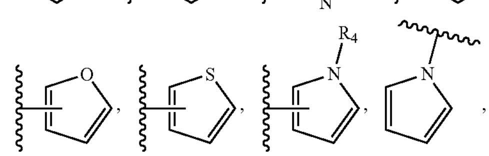

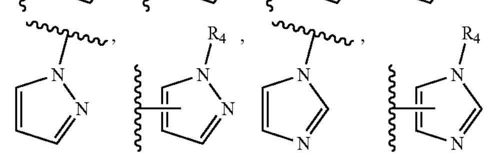

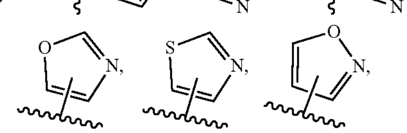

each of which can be optionally substituted by F, Br, Cl, $CF_3$, CN, $N_3$, $NH_2$, $NO_2$, OH, $OCH_3$, methyl, $CH_2CN$, ethyl, propyl, isopropyl, or cyclopropyl. In certain aspects, $R_1$ can be

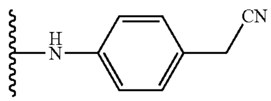

In yet another aspect, $R_2$ can be selected from the group consisting of H, F, Br, Cl, $CF_3$, CN, $N_3$, $NH_2$, $NO_2$, OH, $OCH_3$, methyl, ethyl, propyl, isopropyl,

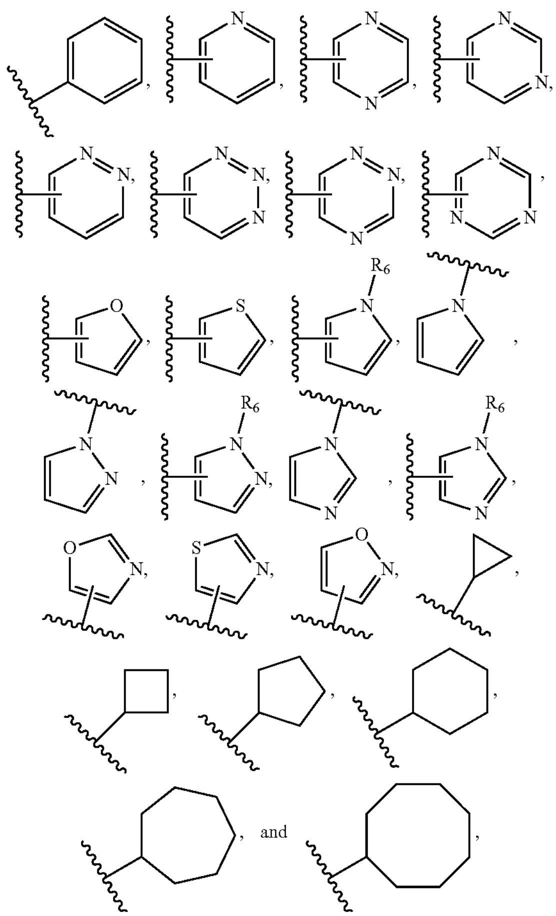

each of which can be substituted by one, two, three, or four $R_7$.

In certain aspects, $R_3$ can be H, methyl, ethyl, propyl, isopropyl, butyl, isobutyl, or tert-butyl, each of which can be substituted by one, two, three, or four $R_7$.

In some aspects, $R_4$ can be selected from the group consisting of H, methyl, ethyl, propyl, and isopropyl. Or $R_4$ and $R_3$ together can form

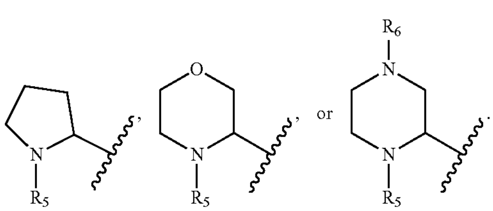

In some aspects, $R_5$ can be selected from the group consisting of $CO(CH_2)_{0-5}CH_3$, $CONR_6(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_6(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_6(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_6(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_6(CH_2)_{0-5}C{\equiv}CCH_3$, and $SO_2(CH_2)_{0-5}CCCH_3$, each of which can be optionally substituted by one, two, three, or four $R_7$.

In some aspects, $R_5$ can be selected from the group consisting of

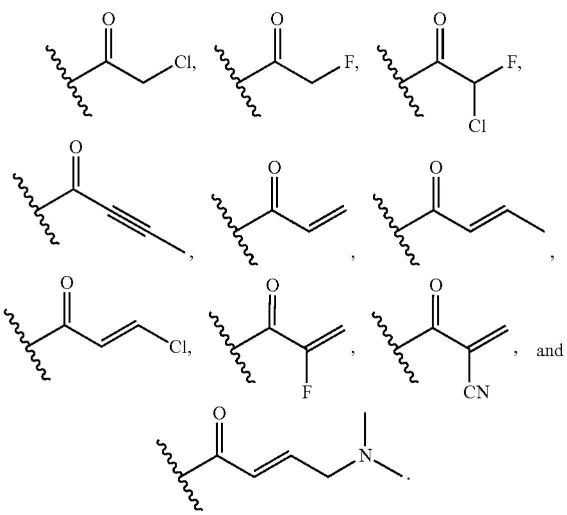

Each $R_6$ can be independently H, methyl, ethyl, propyl, isopropyl, cyclopropyl, or cyclobutyl.

Each $R_7$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Further disclosed herein is a compound of Formula (V)

Formula (V)

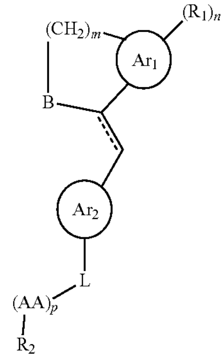

or an optically pure stereoisomer, pharmaceutically acceptable salt, or solvate thereof. In one aspect, n can be an integer selected from 0 to 2. In another aspect, m can be an integer selected from 0 to 3. In some aspects, p can be an integer selected from 0 to 4. ═══ can be a single bond or a double bond. B can be —CO—, —COO—, —$CONR_4$—, —$SO_2$—, —$SO_2NR_4$—, —SO—, —$SONR_4$—, —OPO—, —$OPONR_4$—, —$OPO_2$—, or —$OPO_2NR_4$—.

In certain aspects, $Ar_1$ can be selected from the group consisting of
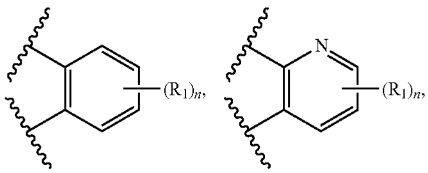
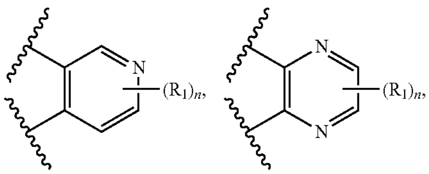
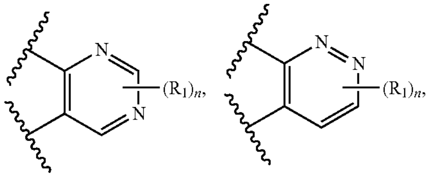
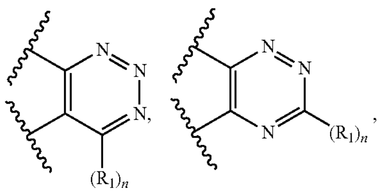
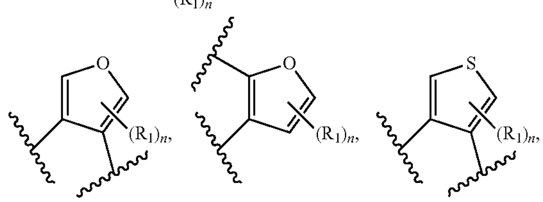
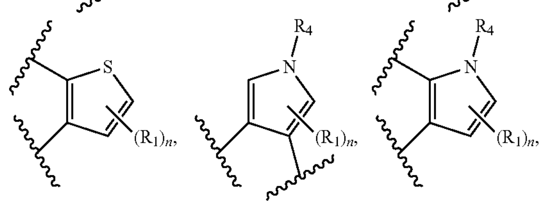
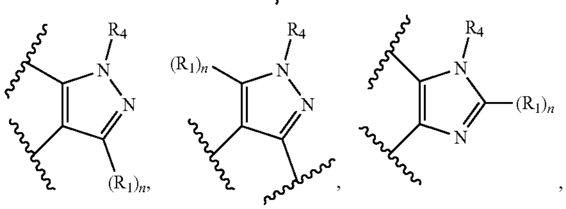
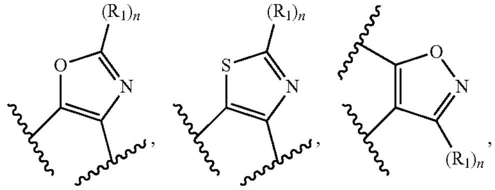
and
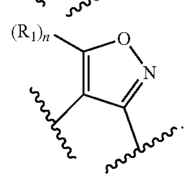
In another aspect, Are can be selected from the group consisting of
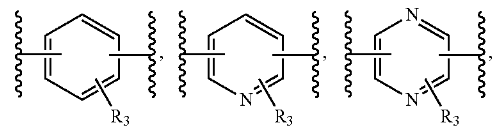
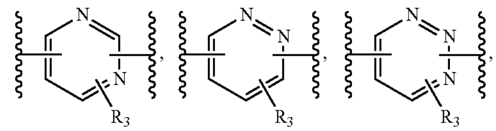
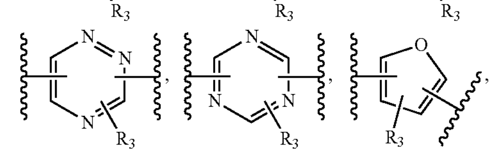
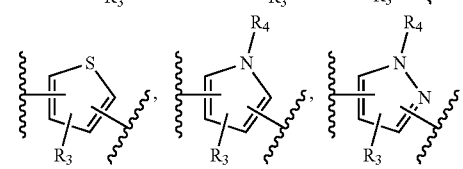
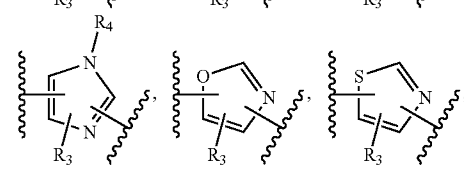
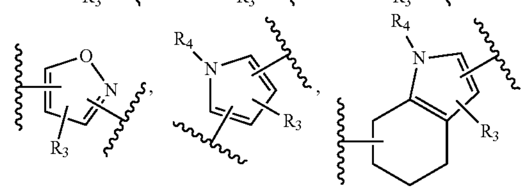
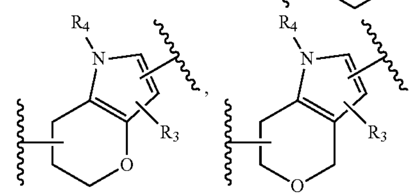
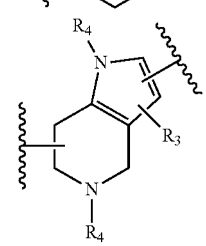
and
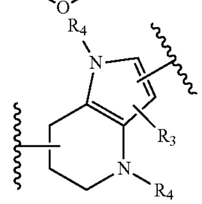
L can be —$O(CH_2)_{1-5}O$—, —$O(CH_2)_{1-5}NR_4$—, —$NR_4(CH_2)_{1-5}NR_4$—, —$CONR_4(CH_2)_{1-5}NR_4$—, —$NR_4CO(CH_2)_{1-5}NR_4$—, —$(CH_2)_{1-5}NR_4$—, —$(CH_2)_{1-5}O$—, —$(CH_2)_{1-5}OCO$—, —$(CH_2)_{1-5}CONR_4$—,
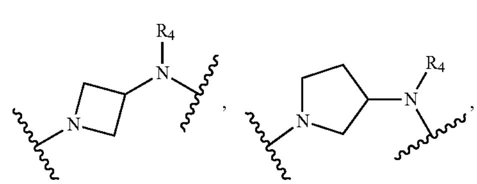
or -continued

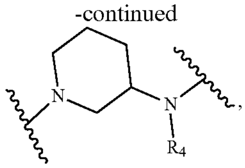

each of which can be optionally substituted by $R_6$.

$R_1$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_6$.

In some aspects, $R_2$ can be selected from the group consisting of $CO(CH_2)_{0-5}CH_3$, $CONR_4(CH_2)_{0-5}CH_3$, $COO(CH_2)_{0-5}CH_3$, $SO_2(CH_2)_{0-5}CH_3$, $CO(CH_2)_{0-5}CH—CH_2$, $CONR_4(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_4(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_4(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_4(CH_2)_{0-5}C{\equiv}CCH_3$, and $SO_2(CH_2)_{0-5}C{\equiv}CCH_3$, each of which can be optionally substituted by one, two, three, or four $R_6$.

In some aspects, $R_2$ can be selected from the group consisting of

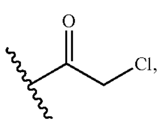 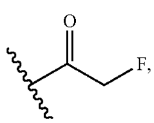 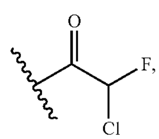

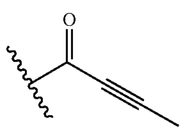, 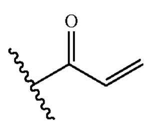, 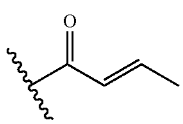,

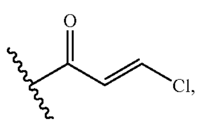 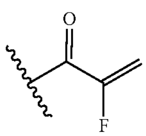, 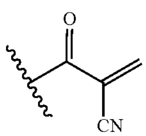, and

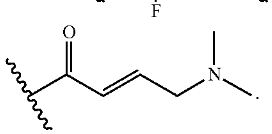

$R_3$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_6$.

$R_4$ can be H, methyl, ethyl, propyl, or isopropyl.

AA can be a natural or unnatural amino acid selected from the group consisting of

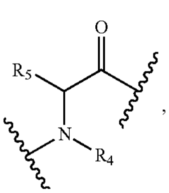, 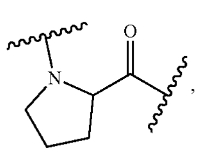,

-continued

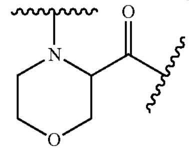, and 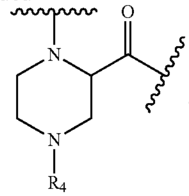.

$R_5$ can be H, methyl, ethyl, propyl, isopropyl, butyl, isobutyl, tert-butyl, $—CH_2CH_2SCH_3$, $—CH_2Ph$, $—CH_2PhOH$, $—CH_2OH$, $—CHOHCH_3$, $—CH_2CONH_2$, $—CH_2CH_2CONH_2$, $—CH_2SH$, $—CH_2SeH$, $—CH_2COOH$, $—CH_2CH_2COOH$, $—CH_2CH_2CH_2CH_2NH_2$,

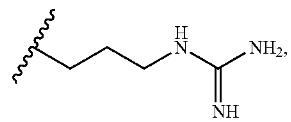 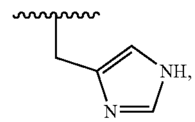

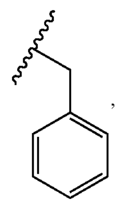, 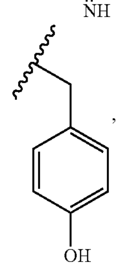, or 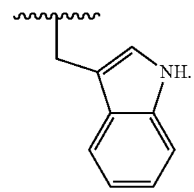

$R_6$ can be H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Further disclosed herein is a compound of Formula (VI)

Formula (VI)

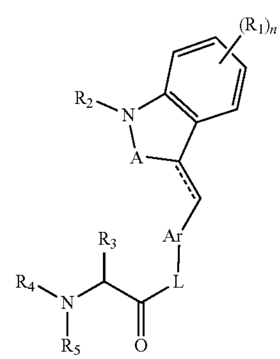

or an optically pure stereoisomer, pharmaceutically acceptable salt, or solvate thereof. In some aspects, n can be an integer selected from 0 to 4.

In one aspect, A can be —CO—, —SO—, $—SO_2—$, —OPO—, or $—OPO_2—$. ═══ can be a single bond or a double bond.

$R_1$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_8$.

$R_2$ can be selected from the group consisting of H, methyl, ethyl, propyl, and isopropyl, each of which can be optionally substituted by one, two, three, or four $R_8$.

In another aspect, Ar can be selected from the group consisting of

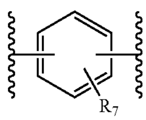, 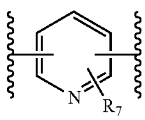, 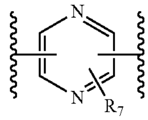, 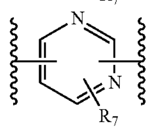, 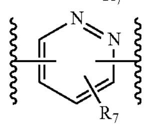, 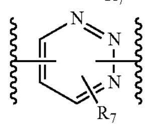, 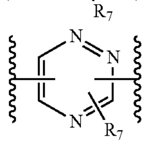, 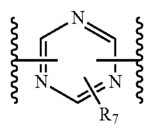, 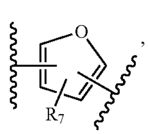, 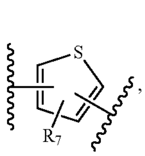, 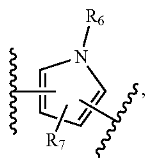, 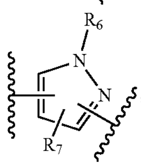, 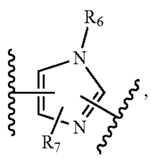, 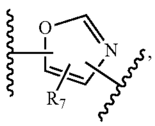, 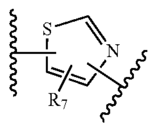, 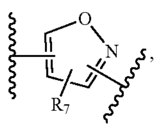, 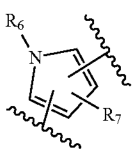, 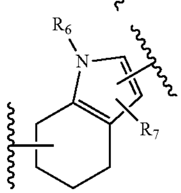, 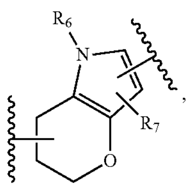, 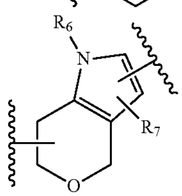, 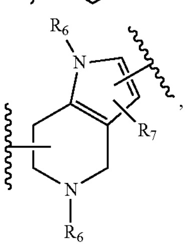, and 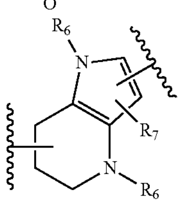.

L can be $-O(CH_2)_{1-5}O-$, $-O(CH_2)_{1-5}NR_6-$, $-NR_6(CH_2)_{1-5}NR_6-$, $-CONR_6(CH_2)_{1-5}NR_6-$, $-NR_6CO(CH_2)_{1-5}NR_6-$, $-(CH_2)_{1-5}NR_6-$, $-(CH_2)_{1-5}O-$, $-(CH_2)_{1-5}OCO-$, $-(CH_2)_{1-5}CONR_6-$,

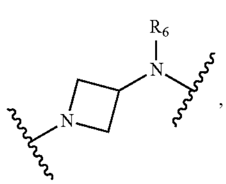, 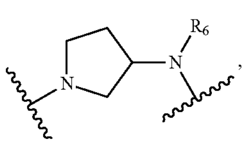, or

-continued

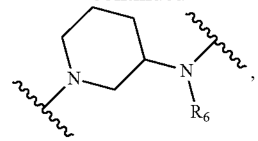, each of which can be optionally substituted by one, two, three, or four $R_8$.

In certain aspects, $R_3$ can be H, methyl, ethyl, propyl, isopropyl, butyl, isobutyl, or tert-butyl, each of which can be optionally substituted by one, two, three, or four $R_8$.

In some aspects, $R_4$ can be selected from the group consisting of H, methyl, ethyl, propyl, and isopropyl. Or $R_4$ and $R_3$ together can form

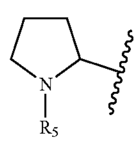, 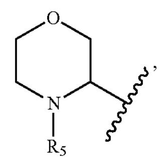, or 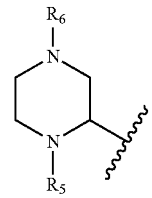.

In some aspects, $R_5$ can be selected from the group consisting of $CO(CH_2)_{0-5}CH_3$, $CONR_6(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_6(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_6(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_6(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_6(CH_2)_{0-5}C{\equiv}CCH_3$, and $SO_2(CH_2)_{0-5}C{\equiv}CCH_3$, each of which can be optionally substituted by one, two, three, or four $R_8$.

In some aspects, $R_5$ can be selected from the group consisting of

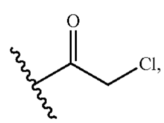, 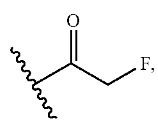, 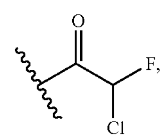, 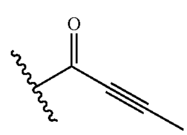, 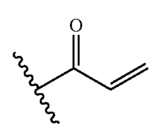, 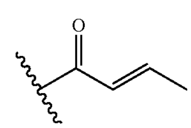, 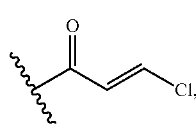, 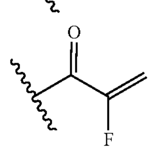, 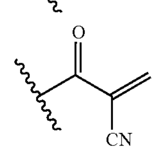, and 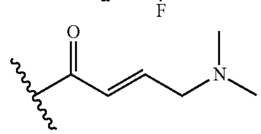.

Each $R_6$ can be independently H, methyl, ethyl, propyl, isopropyl.

$R_7$ can be H, F, Br, Cl, $CF_3$, CN, $N_3$, $NH_2$, $NO_2$, OH, $OCH_3$, methyl, ethyl, propyl, or isopropyl, each of which can be optionally substituted by one, two, three, or four $R_8$.

Each $R_8$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure also provides a compound of Formula (VII)

Formula (VII)

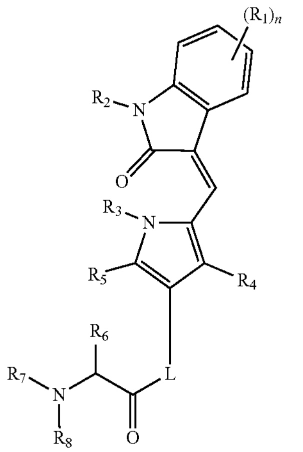

or an optically pure stereoisomer, pharmaceutically acceptable salt, or solvate thereof. In one aspect, n can be an integer selected from 0 to 4.

In still another aspect, each $R_1$ can be independently selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

In some aspects, each $R_2$ and $R_3$ can be independently selected from the group consisting of H, methyl, ethyl, propyl, and isopropyl, each of which can be optionally substituted by one, two, three, or four $R_9$.

In certain aspects, $R_4$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

$R_5$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

L can be $-O(CH_2)_{1-5}O-$, $-O(CH_2)_{1-5}NR_{10}-$, $-NR_6(CH_2)_{1-5}NR_{10}-$, $-CONR_{10}(CH_2)_{1-5}NR_{10}-$, $-NR_{10}CO(CH_2)_{1-5}NR_{10}-$, $-(CH_2)_{1-5}NR_{10}-$, $-(CH_2)_{1-5}O-$, $-(CH_2)_{1-5}OCO-$, $-(CH_2)_{1-5}CONR_{10}-$,

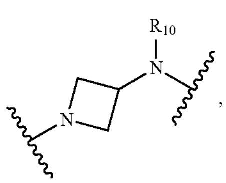
,
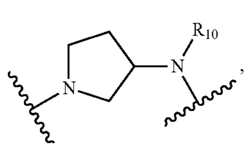
, or
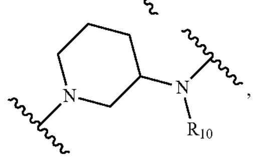
, each of which can be optionally substituted by one, two, three, or four $R_9$, Or $R_5$ and L together can form

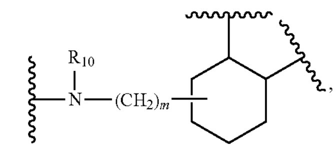
,
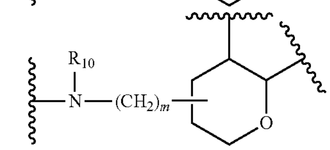
,
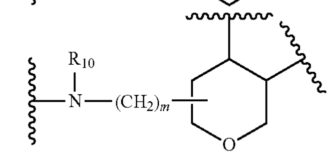
,
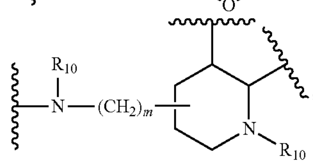
, or
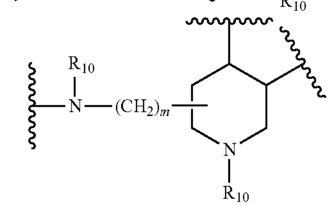
.

m can be an integer selected from 0 to 4.

$R_6$ can be H, methyl, ethyl, propyl, isopropyl, butyl, isobutyl, or tert-butyl, each of which can be optionally substituted by one, two, three, or four $R_9$.

In some aspects, $R_7$ can be selected from the group consisting of H, methyl, ethyl, propyl, and isopropyl. Or $R_6$ and $R_7$ together can form

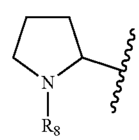
,
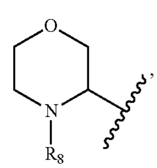
, or
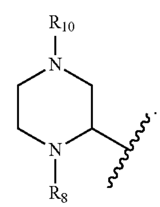
.

In some aspects, $R_8$ can be selected from the group consisting of $CO(CH_2)_{0-5}CH_3$, $CONR_{10}(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_{10}(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_{10}(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_{10}(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_{10}(CH_2)_{0-5}C{\equiv}CCH_3$, and $SO_2(CH_2)_{0-5}C{\equiv}CCH_3$, each of which can be optionally substituted by one, two, three, or four $R_9$.

In some aspects, $R_8$ can be selected from the group consisting of

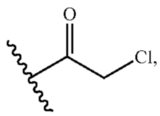, 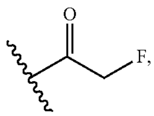, 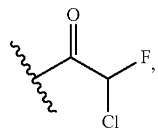,

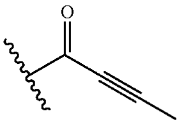, 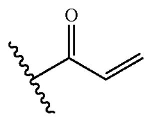, 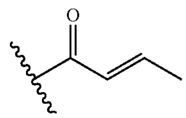,

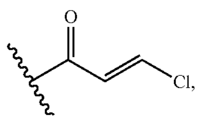, 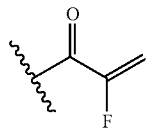,

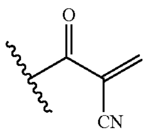, and 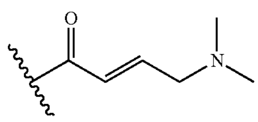.

Each $R_9$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Each $R_{10}$ can be independently H, methyl, ethyl, propyl, or isopropyl.

Also disclosed herein is a pharmaceutical composition including a compound according Formula (I), Formula (II), Formula (III), Formula (IV), Formula (V), Formula (VI), or Formula (VII).

Further disclosed herein is a method for treating cancer in a subject including administering a compound of Formula (I), Formula (II), Formula (III), Formula (IV), Formula (V), Formula (VI), or Formula (VII). In some embodiments, the cancer can be selected from the group consisting of breast, lung, bladder, prostate, ovarian, endometrial, rhabdomyosarcoma, liver and gastric. In some embodiments, the method also includes administering a chemotherapeutic agent, the compound can be administered prior to, simultaneously with or following the administration of the chemotherapeutic agent.

Also disclosed herein is a method of inhibiting a tyrosine kinase activity including contacting a cell with a compound of Formula (I), Formula (II), Formula (III), Formula (IV), Formula (V), Formula (VI), or Formula (VII). In some embodiments, the disclosed compounds exhibit covalent inhibition of FMS, KIT, FLT-3, FGR, or RON.

Other features and advantages can become apparent from the following detailed description.

Description

Below are some acronyms used in the present disclosure. n-BuOK refers to potassium tert-butoxide; DMF refers to dimethylformamide; Boc refers to tert-Butyloxycarbonyl protecting group; DMSO refers to dimethyl sulfoxide; HATU refers to 1-[bis(dimethylamino)methylene]-1H-1,2,3-triazolo[4,5-b]pyridinium 3-oxide hexafluorophosphate; DIEA refers to N,N-Diisopropylethylamine; DIPEA refers to N,N-Diisopropylethylamine; TFA refers to trifluoroacetic acid.

The term "about" will be understood by persons of ordinary skill in the art. Whether the term "about" is used explicitly or not, every quantity given herein refers to the actual given value, and it is also meant to refer to the approximation to such given value that would be reasonably inferred based on the ordinary skill in the art.

Alkyl groups refer to univalent groups derived from alkanes by removal of a hydrogen atom from any carbon atom, which include straight chain and branched chain with from 1 to 12 carbon atoms, and typically from 1 to about 10 carbons or in some embodiments, from 1 to about 6 carbon atoms, or in other embodiments having 1, 2, 3 or 4 carbon atoms. Examples of straight chain alkyl groups include, but are not limited to, methyl, ethyl, n-propyl, n-butyl, n-pentyl, and n-hexyl groups. Examples of branched chain alkyl groups include, but are not limited to isopropyl, isobutyl, sec-butyl and tert-butyl groups. Alkyl groups may be substituted or unsubstituted. Representative substituted alkyl groups may be mono-substituted or substituted more than once, such as, but not limited to, mono-, di-, or tri-substituted. As used herein, the term alkyl, unless otherwise stated, refers to both cyclic and noncyclic groups.

The terms "cyclic alkyl" or "cycloalkyl" refer to univalent groups derived from cycloalkanes by removal of a hydrogen atom from a ring carbon atom. Cycloalkyl groups are saturated or partially saturated non-aromatic structures with a single ring or multiple rings including isolated, fused, bridged, and Spiro ring systems, having 3 to 14 carbon atoms, or in some embodiments, from 3 to 12, or 3 to 10, or 3 to 8, or 3, 4, 5, 6 or 7 carbon atoms. Cycloalkyl groups may be substituted or unsubstituted. Representative substituted cycloalkyl groups may be mono-substituted or substituted more than once, such as, but not limited to, mono-, di-, or tri-substituted. Examples of monocyclic cycloalkyl groups include, but are not limited to cyclopropyl, cyclobutyl, cyclopentyl, and cyclohexyl groups. Examples of multicyclic ring systems include, but are not limited to, bicycle [4.4.0]decane, bicycle[2.2.1]heptane, spiro[2.2]pentane, and the like.

Alkenyl groups refer to straight and branched chain and cycloalkyl groups as defined above, with one or more double bonds between two carbon atoms. Alkenyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkenyl groups may be substituted or unsubstituted. Representative substituted alkenyl groups may be mono-substituted or substituted more than once, such as, but not limited to, mono-, di-, or tri-substituted. Examples of alkenyl groups include, but are not limited to, vinyl, allyl, $-CH{=}CH(CH_3)$, $-CH{=}C(CH_3)_2$, $-C(CH_3){=}CH_2$, cyclopentenyl, cyclohexenyl, butadienyl, pentadienyl, and hexadienyl, among others.

Alkynyl groups refer to straight and branched chain and cycloalkyl groups as defined above, with one or more triple bonds between two carbon atoms. Alkynyl groups may have 2 to about 12 carbon atoms, or in some embodiment from 1 to about 10 carbons or in other embodiments, from 1 to about 6 carbon atoms, or 1, 2, 3 or 4 carbon atoms in other embodiments. Alkynyl groups may be substituted or unsubstituted. Representative substituted alkynyl groups may be mono-substituted or substituted more than once, such as, but not limited to, mono-, di-, or tri-substituted. Exemplary alkynyl groups include, but are not limited to, ethynyl, propargyl, and $-C{\equiv}C(CH_3)$, among others.

Aryl groups are cyclic aromatic hydrocarbons that include single and multiple ring compounds, including multiple ring compounds that contain separate and/or fused aryl groups. Aryl groups may contain from 6 to about 18 ring carbons, or in some embodiments from 6 to 14 ring carbons or even 6 to 10 ring carbons in other embodiments. Aryl group also includes heteroaryl groups, which are aromatic ring compounds containing 5 or more ring members, one or more ring carbon atoms of which are replaced with heteroatom such as, but not limited to, N, O, and S. Aryl groups may be substituted or unsubstituted. Representative substituted aryl groups may be mono-substituted or substituted more than once, such as, but not limited to, mono-, di-, or tri-substituted. Aryl groups include, but are not limited to, phenyl, biphenylenyl, triphenylenyl, naphthyl, anthryl, and pyrenyl groups.

Suitable heterocyclyl groups include cyclic groups with atoms of at least two different elements as members of its rings, of which one or more is a heteroatom such as, but not limited to, N, O, or S. Heterocyclyl groups may include 3 to about 20 ring members, or 3 to 18 in some embodiments, or about 3 to 15, 3 to 12, 3 to 10, or 3 to 6 ring members. The ring systems in heterocyclyl groups may be unsaturated, partially saturated, and/or saturated. Heterocyclyl groups may be substituted or unsubstituted. Representative substituted heterocyclyl groups may be mono-substituted or substituted more than once, such as, but not limited to, mono-, di-, or tri-substituted. Exemplary heterocyclyl groups include, but are not limited to, pyrrolidinyl, tetrahydrofuryl, dihydrofuryl, tetrahydrothienyl, tetrahydrothiopyranyl, piperidyl, morpholinyl, thiomorpholinyl, thioxanyl, piperazinyl, azetidinyl, aziridinyl, imidazolidinyl, pyrazolidinyl, thiazolidinyl, tetrahydrothiophenyl, tetrahydrofuranyl, dioxolyl, furanyl, thiophenyl, pyrrolyl, imidazolyl, pyrazolyl, pyrazolinyl, triazolyl, tetrazolyl, oxazolyl, isoxazolyl, thiazolyl, thiazolinyl, oxetanyl, thietanyl, homopiperidyl, oxepanyl, thiepanyl, oxazepinyl, diazepinyl, thiazepinyl, 1,2,3,6-tetrahydropyridyl, indolinyl, 2H-pyranyl, 4H-pyranyl, dioxolanyl, dioxanyl, purinyl, quinolizinyl, cinnolinyl, phthalazinyl, pteridinyl, and benzothiazolyl groups.

Polycyclic or polycyclyl groups refer to two or more rings in which two or more carbons are common to the two adjoining rings, wherein the rings are "fused rings"; if the rings are joined by one common carbon atom, these are "spiro" ring systems. Rings that are joined through non-adjacent atoms are "bridged" rings. Polycyclic groups may be substituted or unsubstituted. Representative polycyclic groups may be substituted one or more times.

Halogen groups include F, Cl, Br, and I; nitro group refers to —$NO_2$; cyano group refers to —CN; isocyano group refers to —N≡C; epoxy groups encompass structures in which an oxygen atom is directly attached to two adjacent or non-adjacent carbon atoms of a carbon chain or ring system, which is essentially a cyclic ether structure. An epoxide is a cyclic ether with a three-atom ring.

An alkoxy group is a substituted or unsubstituted alkyl group, as defined above, singular bonded to oxygen. Alkoxy groups may be substituted or unsubstituted. Representative substituted alkoxy groups may be substituted one or more times. Exemplary alkoxy groups include, but are not limited to, methoxy, ethoxy, propoxy, butoxy, pentoxy, hexoxy, isopropoxy, sec-butoxy, tert-butoxy, cyclopropyloxy, cyclobutyloxy, cyclopentyloxy, and cyclohexyloxy groups.

The terms "amine" and "amino" refer to derivatives of ammonia, wherein one of more hydrogen atoms have been replaced by a substituent which include, but are not limited to alkyl, alkenyl, aryl, and heterocyclyl groups. Carbamate groups refers to —O(C═O)$NR_1R_2$, where $R_1$ and $R_2$ are independently hydrogen, aliphatic groups, aryl groups, or heterocyclyl groups.

Pharmaceutically acceptable salts of compounds described herein include conventional nontoxic salts or quaternary ammonium salts of a compound, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. In other cases, described compounds may contain one or more acidic functional groups and, thus, are capable of forming pharmaceutically acceptable salts with pharmaceutically acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

The present disclosure provides a compound of Formula (I)

Formula (I)

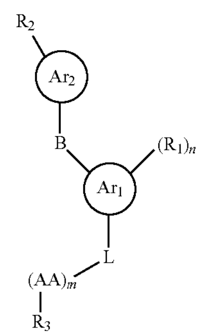

or an optically pure stereoisomer, pharmaceutically acceptable salt, or solvate thereof.

In some aspects, n can be an integer selected from 0 to 2, m can be an integer selected from 0 to 4.

In some aspects, $Ar_1$ can be selected from the group consisting of phenyl, naphthyl, anthracene,

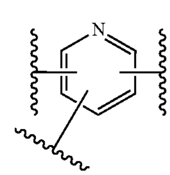, 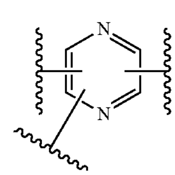, 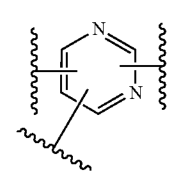,

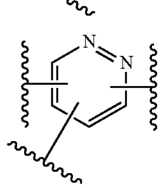, 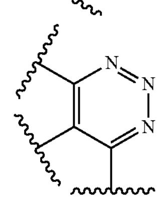, 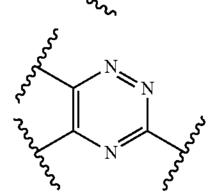,

-continued
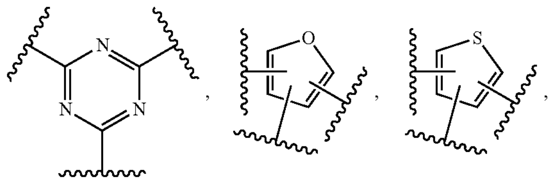
, , ,
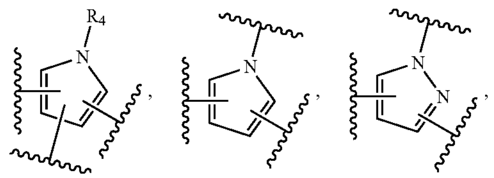
, , ,
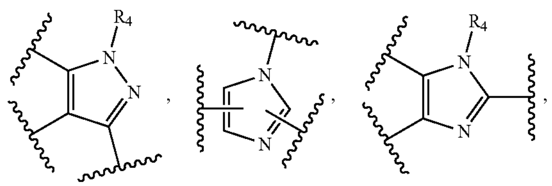
, , ,
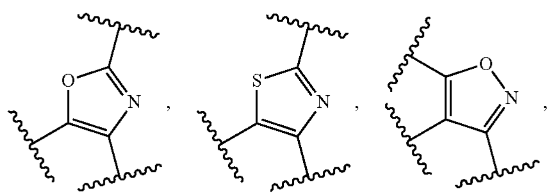
, , ,
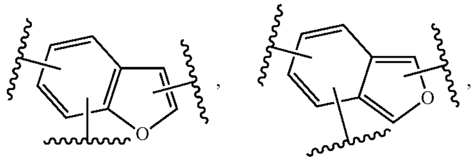
, ,
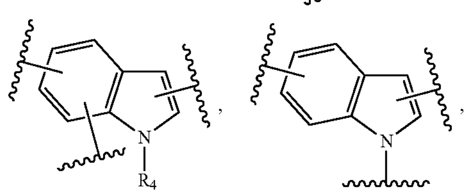
, ,
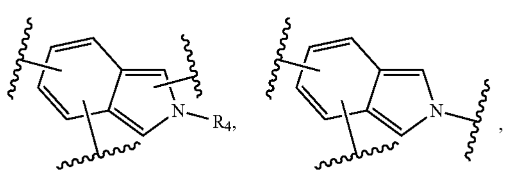
$R_4$, ,
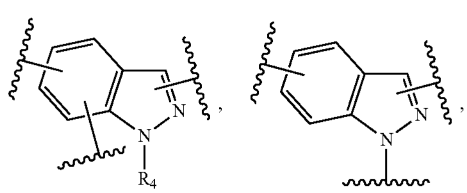
, ,
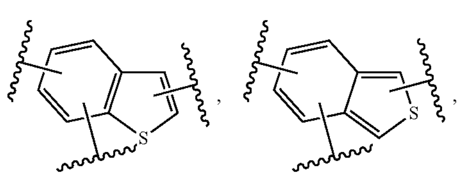
, ,
-continued
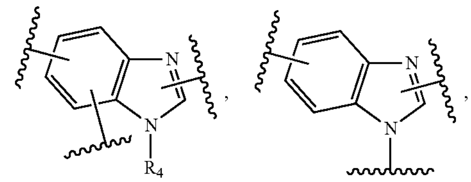
, ,
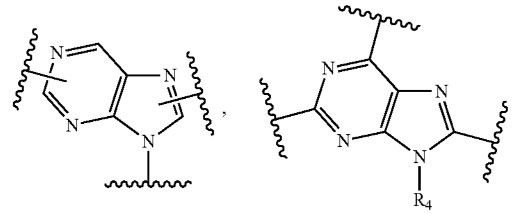
, ,
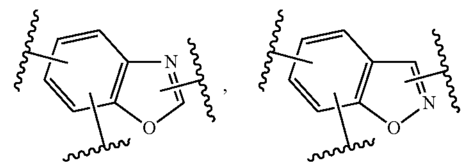
, ,
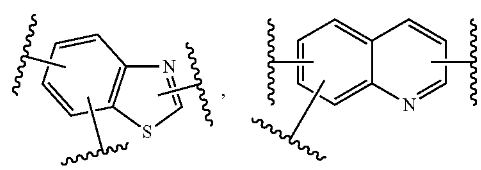
, ,
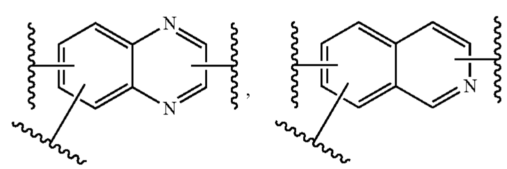
, ,
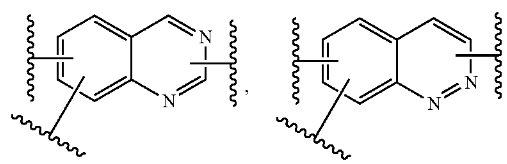
, ,
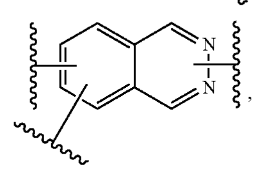
, and
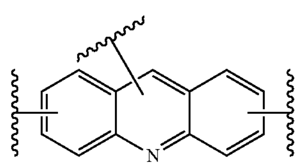
.
Are can be selected from the group consisting of phenyl,
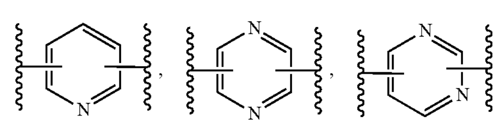
, , ,
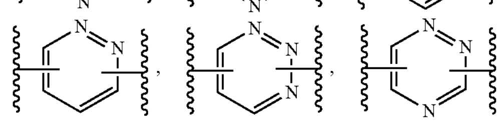
, , , -continued

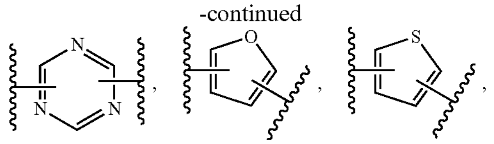,

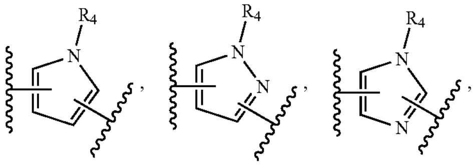,

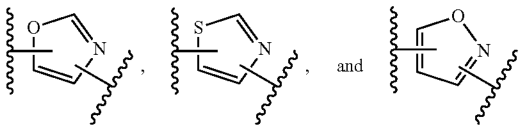.

B can be —CO—, —COO—, —$CONR_4$—, —$(CH_2)_{1-5}$—, —O—, —OPO—, —$OPO_2$—, —S—, —SO—, or —$SO_2$—.

L can be —$O(CH_2)_{1-5}O$—, —$O(CH_2)_{1-5}NR_4$—, —$NR_4(CH_2)_{1-5}NR_4$—, —$CONR_4(CH_2)_{1-5}NR_4$—, —$NR_4CO(CH_2)_{1-5}NR_4$—, —$(CH_2)_{1-5}NR_4$—, —$(CH_2)_{1-5}O$—, —$(CH_2)_{1-5}OCO$—, —$(CH_2)_{1-5}CONR_4$—,

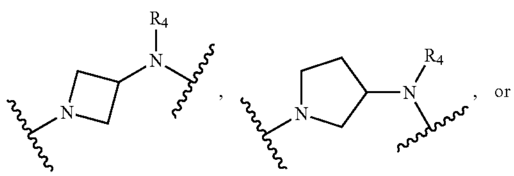

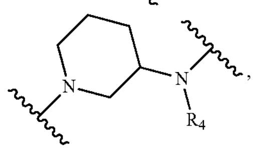, each of which can be optionally substituted by $R_6$.

AA can be a natural or unnatural amino acid selected from the group consisting of

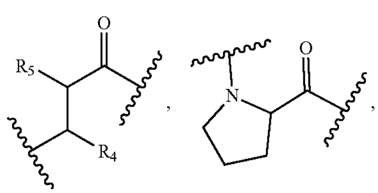,

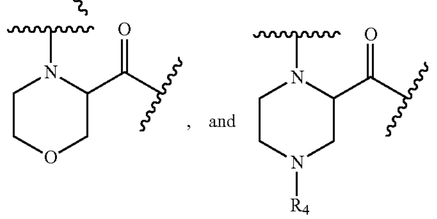.

$R_1$ can be selected from the group consisting of H, F, Br, Cl, $CF_3$, CN, $N_3$. $NH_2$, $NO_2$, OH, $OCH_3$, methyl, ethyl, propyl, isopropyl, cyclopropyl, or -D-$Ar_3$, wherein D can be —CO—, —COO—, —$CONR_4$—, —$NR_4$—, —$(CH_2)_{1-5}$—, —O—, —OPO—, —$OPO_2$—, —S—, —SO—, or —$SO_2$—, $Ar_3$ can be phenyl,

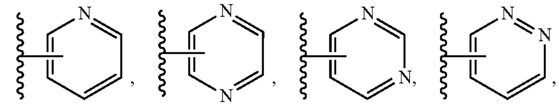,

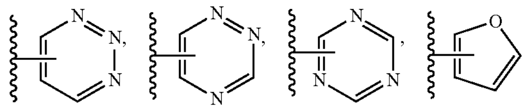,

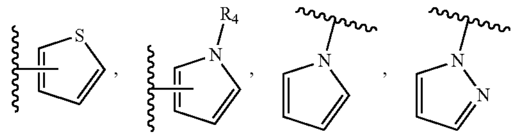,

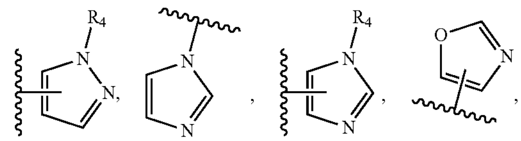,

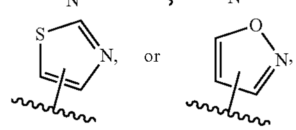

each of which can be optionally substituted by F. Br, Cl, $CF_3$, CN, $N_3$, $NH_2$, $NO_2$, OH, $OCH_3$, methyl, $CH_2CN$, ethyl, propyl, isopropyl, or cyclopropyl.

In one aspect, $R_1$ can be

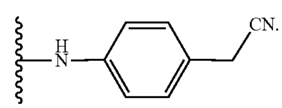 [SMILES: *Nc1ccc(CC#N)cc1]

$R_2$ can be selected from the group consisting of H, F, Br, Cl, $CF_3$, CN, $N_3$, $NH_2$, $NO_2$, OH, $OCH_3$, methyl, ethyl, propyl, isopropyl,

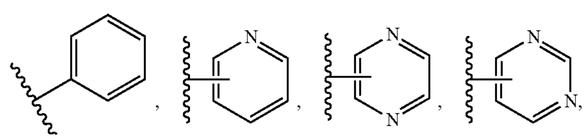,

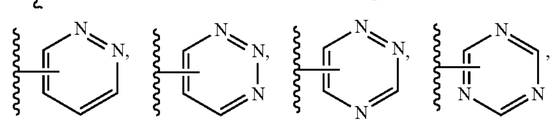,

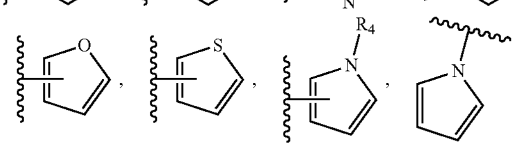,

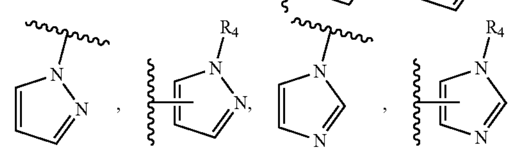,

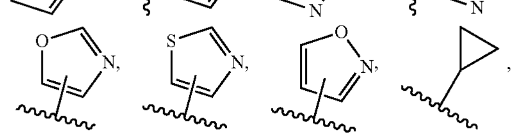,

-continued

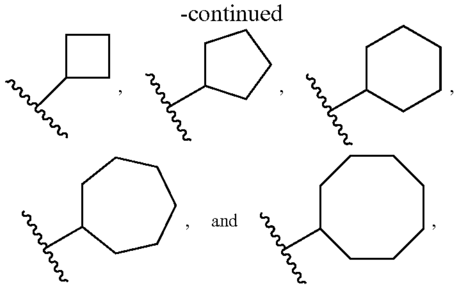

each of which can be substituted by one, two, three, or four $R_6$.

In some aspects, $R_3$ can be selected from the group consisting of $CO(CH_2)_{0-5}CH_3$, $CONR_4(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_4(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_4(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_4(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_4(CH_2)_{0-5}C{\equiv}CCH_3$, and $SO_2(CH_2)_{0-5}C{\equiv}CCH_3$, each of which can be optionally substituted by one, two, three, or four $R_6$.

In some aspects, $R_3$ can be selected from the group consisting of

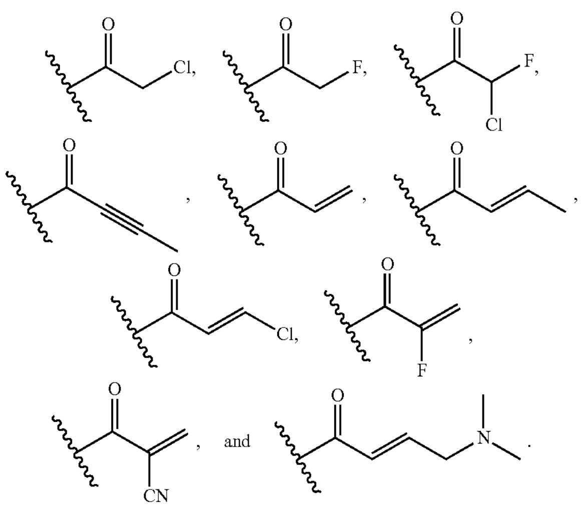

$R_4$ can be H, methyl, ethyl, propyl, isopropyl, cyclopropyl, or cyclobutyl.

$R_5$ can be H, methyl, ethyl, propyl, isopropyl, butyl, isobutyl, tert-butyl, $—CH_2CH_2SCH_3$, $—CH_2Ph$, $—CH_2PhOH$, $—CH_2OH$, $—CHOHCH_3$, $—CH_2CONH_2$, $—CH_2CH_2CONH_2$, $—CH_2SH$, $—CH_2SeH$, $—CH_2COOH$, $—CH_2CH_2COOH$, $—CH_2CH_2CH_2CH_2NH_2$,

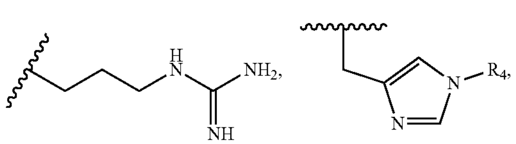

-continued

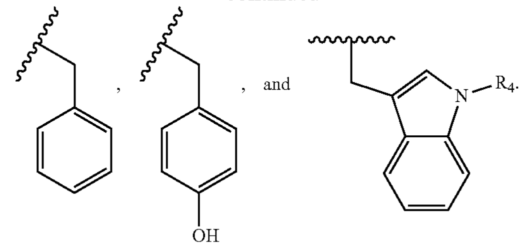

Each $R_6$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure provides a compound of Formula (II)

Formula (II)

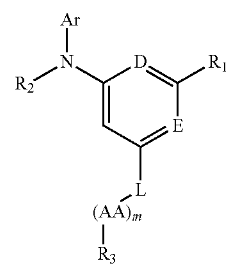

or an optically pure stereoisomer, pharmaceutically acceptable salt, or solvate thereof.

In one aspect, each D and E can be independently N or CH. m can be an integer selected from 0 to 4.

Ar can be selected from the group consisting of

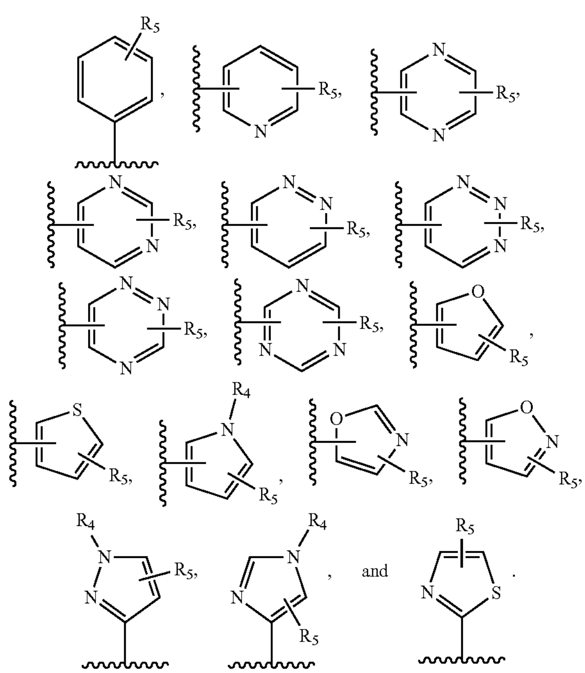

L can be $—O(CH_2)_{1-5}O—$, $—O(CH_2)_{1-5}NR_4—$, $—NR_4(CH_2)_{1-5}NR_4—$, $—CONR_4(CH_2)_{1-5}NR_4—$, $—NR_4CO$ $(CH_2)_{1-5}NR_4$—, —$(CH_2)_{1-5}NR_4$—, —$(CH_2)_{1-5}O$—, —$(CH_2)_{1-5}OCO$—, —$(CH_2)_{1-5}CONR_4$—,

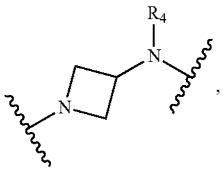, 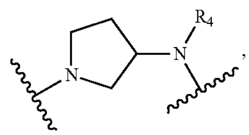, or 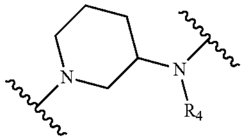, each of which can be optionally substituted by $R_6$.

In another aspect, $R_1$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl, or —B—$Ar_1$, wherein B can be —CO—, —COO—, —$CONR_4$—, —$NR_4$—, —$(CH_2)_{1-5}$—, —O—, —OPO—, —$OPO_2$—, —S—, —SO—, or —$SO_2$—, $Ar_1$ can be phenyl,

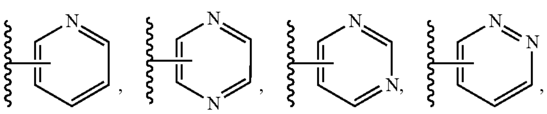

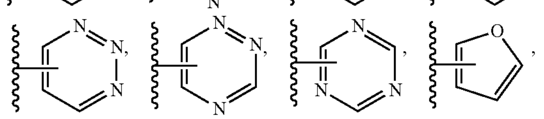

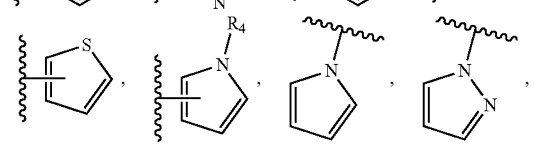

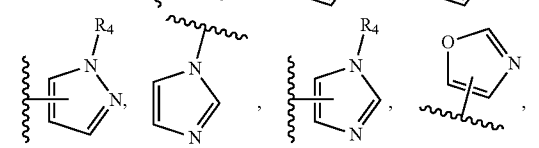

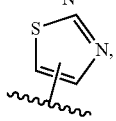 or 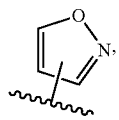

each of which can be optionally substituted by F, Br, Cl, $CF_3$, CN, $N_3$, $NH_2$, $NO_2$, OH, $OCH_3$, methyl, $CH_2CN$, ethyl, propyl, isopropyl, or cyclopropyl. In certain aspects, $R_1$ can be

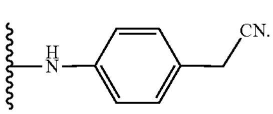

$R_2$ can be H, methyl, ethyl, propyl, isopropyl, cyclopropyl, or cyclobutyl, each of which can be substituted by one, two, three, or four $R_6$.

In some aspects, $R_3$ can be selected from the group consisting of $CO(CH_2)_{0-5}CH_3$, $CONR_4(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_4(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_4(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_4(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_4(CH_2)_{0-5}C{\equiv}CCH_3$, and $SO_2(CH_2)_{0-5}C{\equiv}CCH_3$, each of which can be optionally substituted by one, two, three, or four $R_6$.

In some aspects, $R_3$ can be selected from the group consisting of

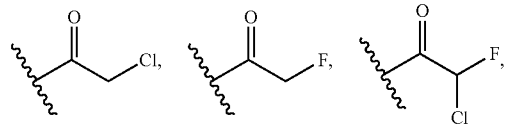

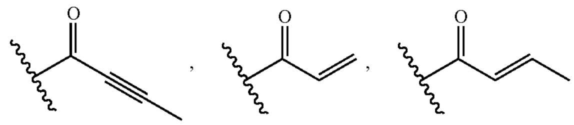

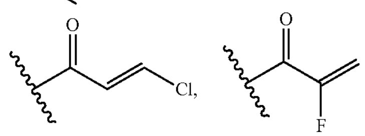

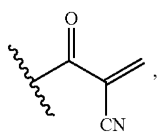, and 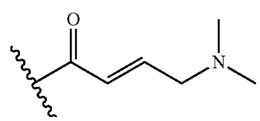.

AA can be a natural or unnatural amino acid selected from the group consisting of

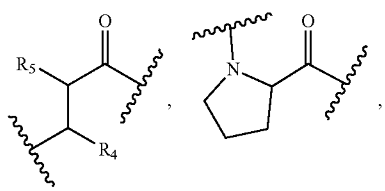

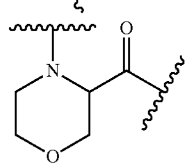, and 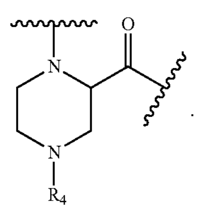.

Each $R_4$ can be independently H, methyl, ethyl, propyl, isopropyl, cyclopropyl, or cyclobutyl.

$R_5$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl,

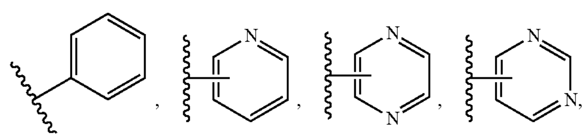

-continued

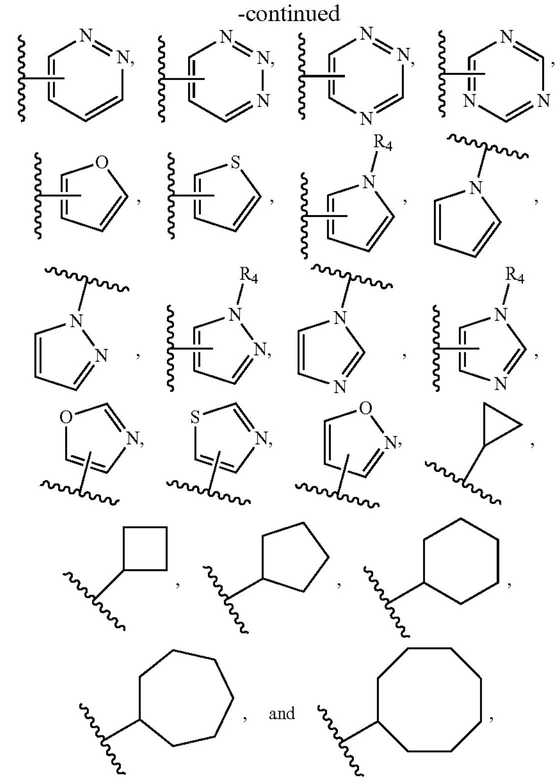

, and , each of which can be optionally substituted by one, two, three, or four $R_6$.

Each $R_6$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure also provides a compound of Formula (III)

Formula (III)

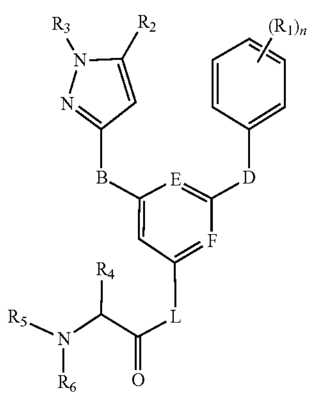

or an optically pure stereoisomer, pharmaceutically acceptable salt, or solvate thereof. n can be an integer selected from 0 to 5. Each B and D can be independently —CO—, —COO—, —$CONR_7$—, —$NR_7$, —$(CH_2)_{1-5}$—, —O—, —OPO—, —$OPO_2$—, —S—, —SO—, or —$SO_2$—. Each E and F can be independently N or CH.

L can be —$O(CH_2)_{1-5}O$—, —$O(CH_2)_{1-5}NR_7$—, —$NR_7(CH_2)_{1-5}NR_7$—, —$CONR_7(CH_2)_{1-5}NR_7$—, —$NR_7CO(CH_2)_{1-5}NR_7$—, —$(CH_2)_{1-5}NR_7$—, —$(CH_2)_{1-5}O$—, —$(CH_2)_{1-5}OCO$—, —$(CH_2)_{1-5}CONR_7$—,

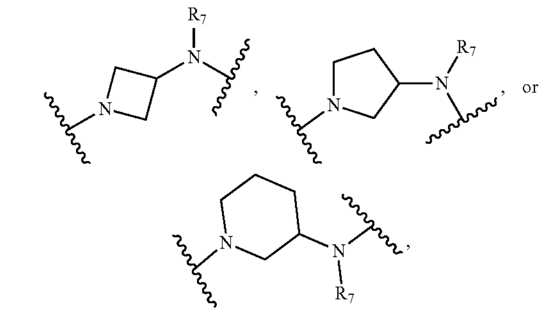

, , or , each of which can be optionally substituted by $R_8$.

In some aspects, $R_1$ can be selected from the group consisting of H, F, Br, Cl, $CF_3$, CN, $N_3$, $NH_2$, $NO_2$, OH, $OCH_3$, methyl, $CH_2CN$, ethyl, propyl, isopropyl, and cyclopropyl, each of which can be optionally substituted by one, two, three, or four $R_8$.

In another aspect, $R_2$ can be selected from the group consisting of H, F, Br, Cl, $CF_3$, CN, $N_3$, $NH_2$, $NO_2$, OH, $OCH_3$, methyl, ethyl, propyl, isopropyl, cyclopropyl,

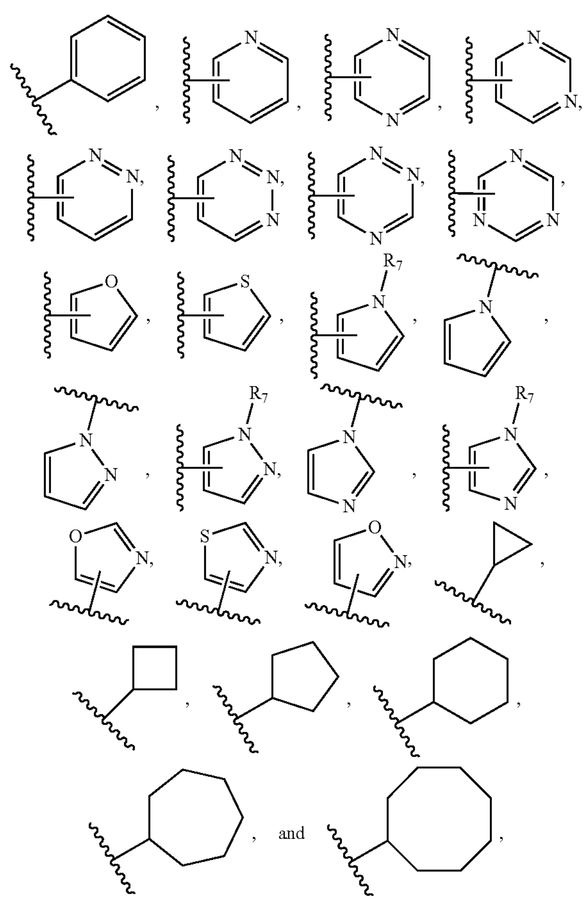

, and , each of which can be optionally substituted by one, two, three, or four $R_8$.

In yet another aspect, $R_3$ can be selected from the group consisting of H, $CF_3$, methyl, ethyl, propyl, and isopropyl, each of which can be optionally substituted by one, two, three, or four $R_8$.

In certain aspects, $R_4$ can be H, methyl, ethyl, propyl, isopropyl, butyl, isobutyl, or tert-butyl.

In some aspects, $R_5$ can be selected from the group consisting of H, methyl, ethyl, propyl, and isopropyl. Or $R_4$ and $R_5$ together can form

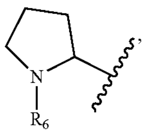, 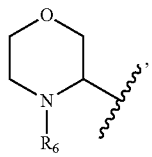, or 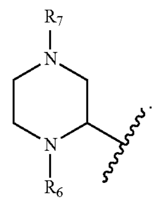.

In some aspects, $R_6$ can be selected from the group consisting of $CO(CH_2)_{0-5}CH_3$, $CONR_7(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_7(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_7(CH_2)_{0-5}CH{=}CHCH_3$, $SO_2(CH_2)_{0-5}CH{=}CHCH_3$, $CO(CH_2)_{0-5}CCH$, $COO(CH_2)_{0-5}CCH$, $CONR_7(CH_2)_{0-5}CCH$, $SO_2(CH_2)_{0-5}CCH$, $CO(CH_2)_{0-5}CCCH_3$, $COO(CH_2)_{0-5}CCCH_3$, $CONR_7(CH_2)_{0-5}CCCH_3$, and $SO_2(CH_2)_{0-5}CCCH_3$, each of which can be optionally substituted by one, two, three, or four $R_8$.

In some aspects, $R_6$ can be selected from the group consisting of

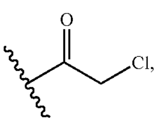, 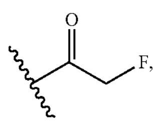, 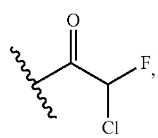,

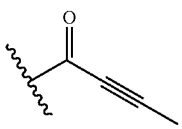, 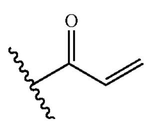, 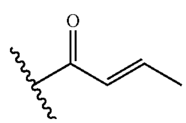,

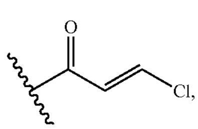, 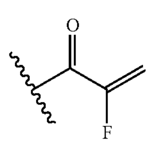,

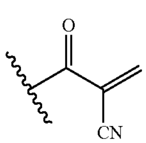, and 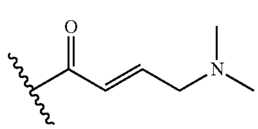.

$R_7$ can be H, methyl, ethyl, propyl, or isopropyl.

$R_8$ can be H, F, Br, Cl, $CF_3$, CN, $N_3$, $NH_2$, $NO_2$, OH, $OCH_3$, methyl, ethyl, propyl, isopropyl, butyl, isobutyl, or tert-butyl.

The present disclosure also provides a compound of Formula (IV)

Formula (IV)

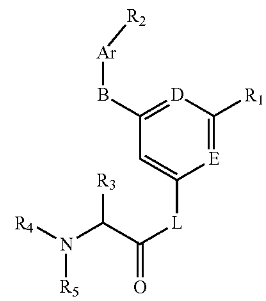

or an optically pure stereoisomer, pharmaceutically acceptable salt, or solvate thereof.

In one aspect, each D and E can be independently N or CH. B can be $—NR_6—$, —O—, $—CONR_6—$, —COO—, $—SO_2—$ or $—SO_2NR_6—$.

L can be $—O(CH_2)_{1-5}O—$, $—O(CH_2)_{1-5}NR_6—$, $—NR_6(CH_2)_{1-5}NR_6—$, $—CONR_6(CH_2)_{1-5}NR_6—$, $—NR_6CO(CH_2)_{1-5}NR_6—$, $—(CH_2)_{1-5}NR_6—$, $—(CH_2)_{1-5}O—$, $—(CH_2)_{1-5}OCO—$, $—(CH_2)_{1-5}CONR_6—$,

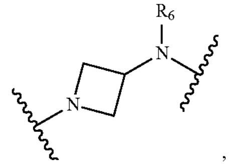, 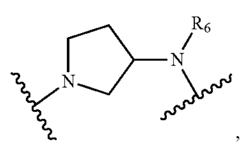, or

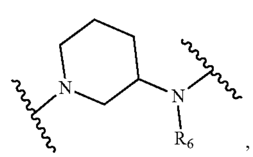, each of which can be optionally substituted by one, two, three, or four $R_7$.

Ar can be selected from the group consisting of phenyl,

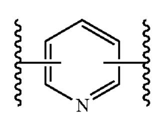, 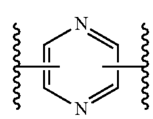, 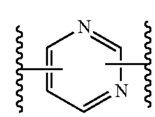,

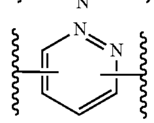, 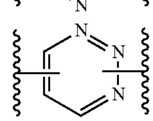, 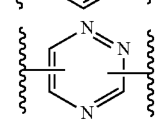,

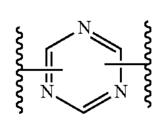, 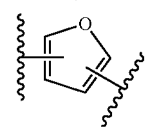, 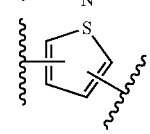,

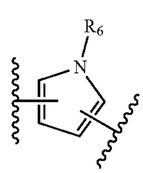, 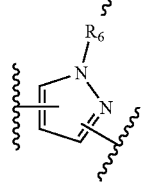, 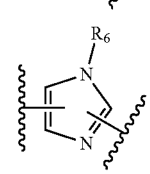,

-continued

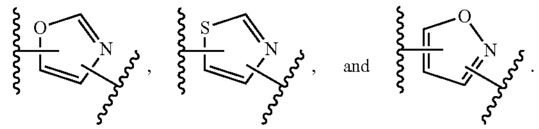

In another aspect, $R_1$ can be selected from the group consisting of H, F, Cl, Br, OH, $N_3$, $NO_2$, $CF_3$, CN, methyl, ethyl, propyl, and isopropyl. In some aspects, $R_1$ can be —G—$Ar_1$, wherein G can be —CO—, —COO—, —$CONR_6$—, —$NR_6$—, —$(CH_2)_{1-5}$—, —O—, —OPO—, —$OPO_2$—, —S—, —SO—, or —$SO_2$—, $Ar_1$ can be phenyl,

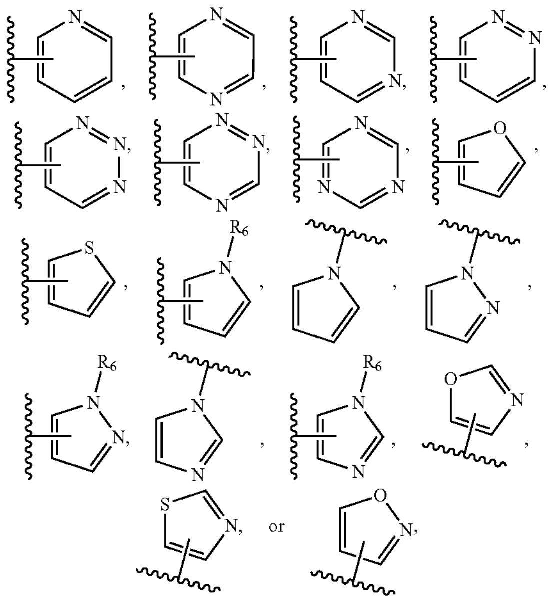

each of which can be optionally substituted by F, Br, Cl, $CF_3$, CN, $N_3$, $NH_2$, $NO_2$, OH, $OCH_3$, methyl, $CH_2CN$, ethyl, propyl, isopropyl, or cyclopropyl. In certain aspects, $R_1$ can be

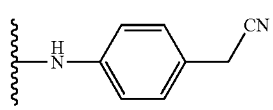 [SMILES: *Nc1ccc(CC#N)cc1]

In yet another aspect, $R_2$ can be selected from the group consisting of H, F, Br, Cl, $CF_3$, CN, $N_3$, $NH_2$, $NO_2$, OH, $OCH_3$, methyl, ethyl, propyl, isopropyl.

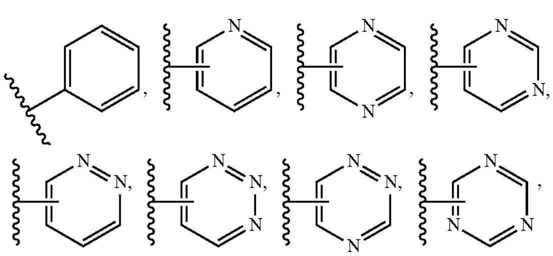

-continued

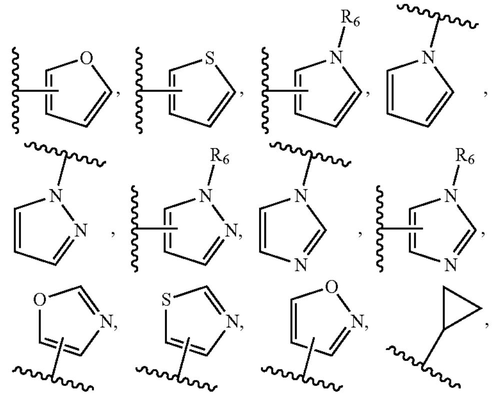

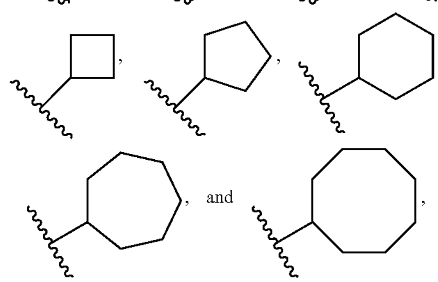

each of which can be substituted by one, two, three, or four $R_7$.

In certain aspects, $R_3$ can be H, methyl, ethyl, propyl, isopropyl, butyl, isobutyl, or tert-butyl, each of which can be substituted by one, two, three, or four $R_7$.

In some aspects, $R_4$ can be selected from the group consisting of H, methyl, ethyl, propyl, and isopropyl. Or $R_4$ and $R_3$ together can form

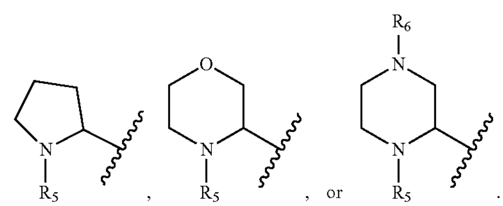

In some aspects, $R_5$ can be selected from the group consisting of $CO(CH_2)_{0-5}CH_3$, $CONR_6(CH_2)_{0-5}CH_3$, $COO(CH_2)O_4H_3$, $SO_2(CH_2)_{0-5}CH_3$, $CO(CH_2)_{0-5}CH{=}CH_2$, $CONR_6(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_6(CH_2)O_4H{=}CHCH_3$, $SO_2(CH_2)_{0-5}CH{=}CHCH_3$, $CO(CH_2)O_4{\equiv}CH$, $COO(CH_2)O_4{\equiv}CH$, $CONR_6(CH_2)O_4{\equiv}CH$, $SO_2(CH_2)_{0-5}C{\equiv}CH$, $CO(CH_2)_{05}C{\equiv}CCH_3$, $COO(CH_2)_{0-5}C{\equiv}CCH_3$, $CONR_6(CH_2)O_4{\equiv}CCH_3$, and $SO_2(CH_2)_{0-5}C{\equiv}CCH_3$, each of which can be optionally substituted by one, two, three, or four $R_7$.

In some aspects, $R_5$ can be selected from the group consisting of

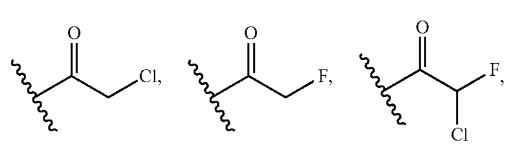

-continued

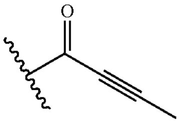, 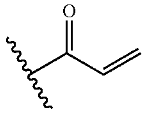, 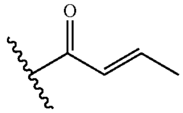,

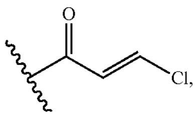 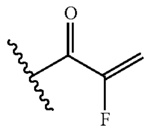,

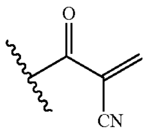, and 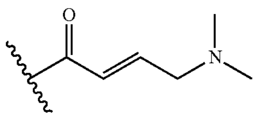.

Each $R_6$ can be independently H, methyl, ethyl, propyl, isopropyl, cyclopropyl, or cyclobutyl.

Each $R_7$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure provides a compound of Formula (V)

Formula (V)

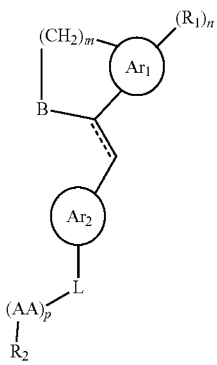

or an optically pure stereoisomer, pharmaceutically acceptable salt, or solvate thereof. In one aspect, n can be an integer selected from 0 to 2. In another aspect, m can be an integer selected from 0 to 3. In some aspects, p can be an integer selected from 0 to 4. ═ ═ can be a single bond or a double bond. B can be —CO—, —COO—, —CONR$_4$—, —SO$_2$—, —SO$_2$NR$_4$—, —SO—, —SONR$_4$—, —OPO—, —OPONR$_4$—, —OPO$_2$—, or —OPO$_2$NR$_4$—.

In certain aspects, An can be selected from the group consisting of

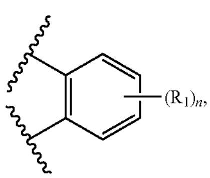 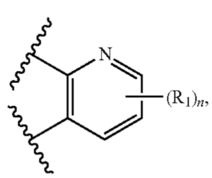

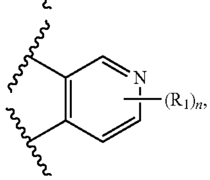 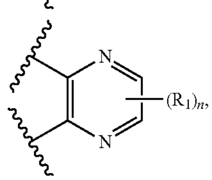

-continued

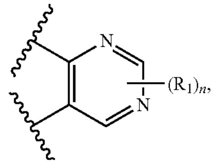 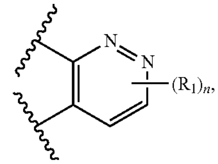

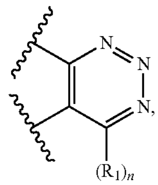 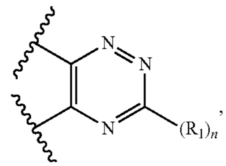,

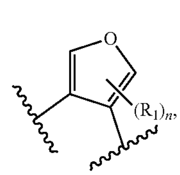 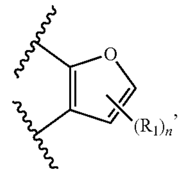 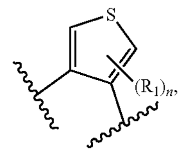

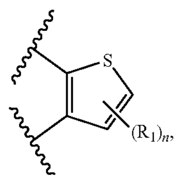 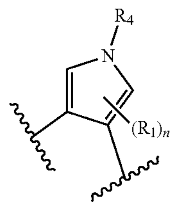, 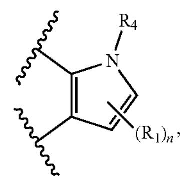,

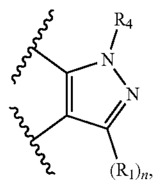 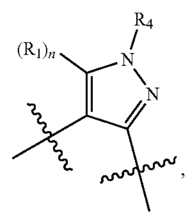,

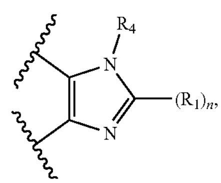 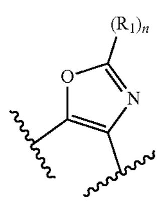, 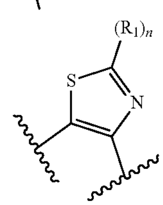,

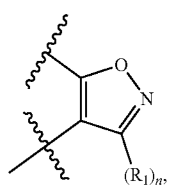 and 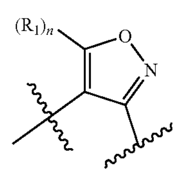.

In another aspect, $Ar_2$ can be selected from the group consisting of

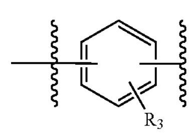, 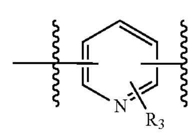,

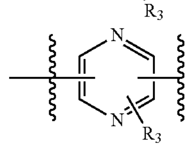, 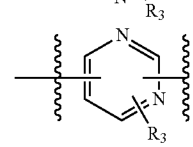,

-continued

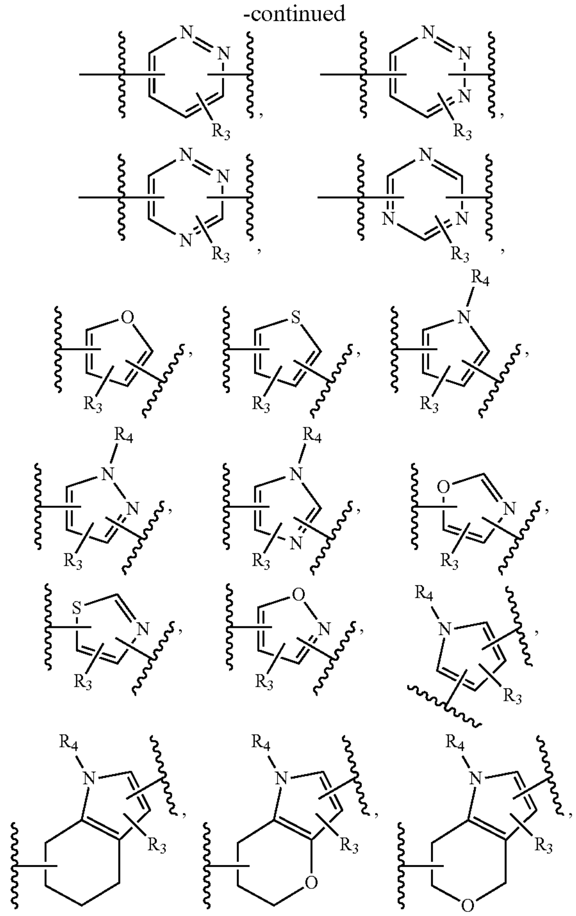

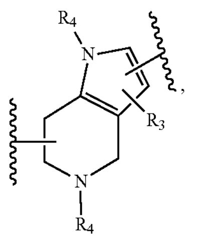

and

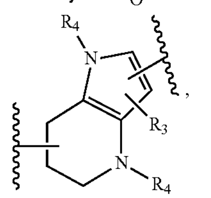

L can be —O(CH$_2$)$_{1-5}$O—, —O(CH$_2$)$_{1-5}$NR$_4$—, —NR$_4$(CH$_2$)$_{1-5}$NR$_4$—, —CONR$_4$(CH$_2$)$_{1-5}$NR$_4$—, —NR$_4$CO(CH$_2$)$_{1-5}$NR$_4$—, —(CH$_2$)$_{1-5}$NR$_4$—, —(CH$_2$)$_{1-5}$O—, —(CH$_2$)$_{1-5}$OCO—, —(CH$_2$)$_{1-5}$CONR$_4$—,

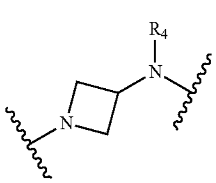

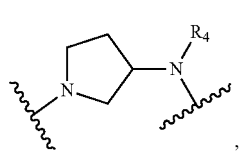

or

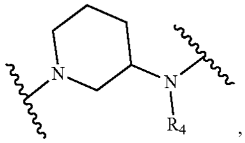

each of which can be optionally substituted by R$_6$.

R$_1$ can be selected from the group consisting of H, F, Br, Cl, CF$_3$, CN, N$_3$, NH$_2$, NO$_2$, OH, OCH$_3$, methyl, ethyl, propyl, and isopropyl, each of which can be optionally substituted by one, two, three, or four R$_6$.

In some aspects, R$_2$ can be selected from the group consisting of CO(CH$_2$)$_{0-5}$CH$_3$, CONR$_4$(CH$_2$)$_{0-5}$CH$_3$, COO(CH$_2$)$_{0-5}$CH$_3$, SO$_2$(CH$_2$)$_{0-5}$CH$_3$, CO(CH$_2$)$_{0-5}$CH═CH$_2$, CONR$_4$(CH$_2$)$_{0-5}$CH═CH$_2$, COO(CH$_2$)$_{0-5}$CH═CH$_2$, SO$_2$(CH$_2$)$_{0-5}$CH═CH$_2$, CO(CH$_2$)$_{0-5}$CH═CHCH$_3$, COO(CH$_2$)$_{0-5}$CH═CHCH$_3$, CONR$_4$(CH$_2$)$_{0-5}$CH═CHCH$_3$, SO$_2$(CH$_2$)$_{0-5}$CH═CHCH$_3$, CO(CH$_2$)$_{0-5}$C≡CH, COO(CH$_2$)$_{0-5}$C≡CH, CONR$_4$(CH$_2$)$_{0-5}$C≡CH, SO$_2$(CH$_2$)$_{0-5}$C≡CH, CO(CH$_2$)$_{0-5}$C≡CCH$_3$, COO(CH$_2$)$_{0-5}$C≡CCH$_3$, CONR$_4$(CH$_2$)$_{0-5}$≡CCH$_3$, and SO$_2$(CH$_2$)$_{0-5}$C≡CCH$_3$, each of which can be optionally substituted by one, two, three, or four R$_6$.

In some aspects, R$_2$ can be selected from the group consisting of

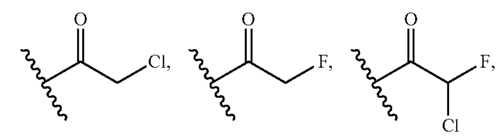

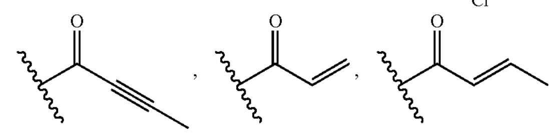

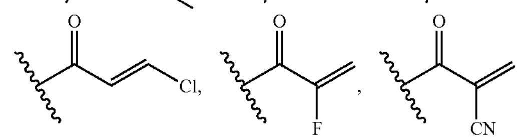

and

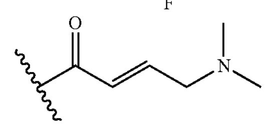

R$_3$ can be selected from the group consisting of H, F, Br, Cl, CF$_3$, CN, N$_3$, NH$_2$, NO$_2$, OH, OCH$_3$, methyl, ethyl, propyl, and isopropyl, each of which can be optionally substituted by one, two, three, or four R$_6$.

R$_4$ can be H, methyl, ethyl, propyl, or isopropyl.

AA can be a natural or unnatural amino acid selected from the group consisting of

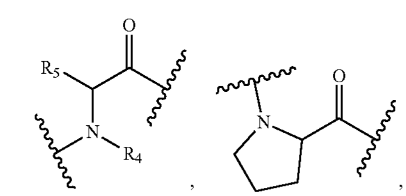

and

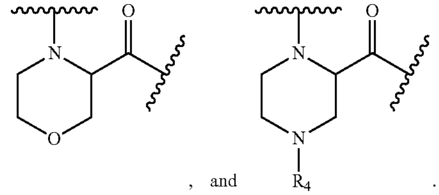

R$_5$ can be H, methyl, ethyl, propyl, isopropyl, butyl, isobutyl, tert-butyl, —CH$_2$CH$_2$SCH$_3$, —CH$_2$Ph, —CH$_2$PhOH, —CH$_2$OH, —CHOHCH$_3$, —CH$_2$CONH$_2$, —CH$_2$CH$_2$CONH$_2$, —CH$_2$SH, —CH$_2$SeH, —CH$_2$COOH, —CH$_2$CH$_2$COOH, —CH$_2$CH$_2$CH$_2$CH$_2$NH$_2$,

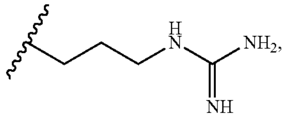,
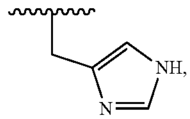,
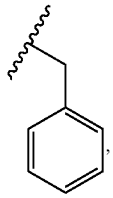,
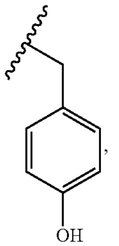, or
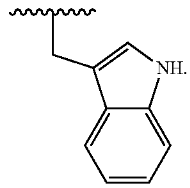.

$R_6$ can be H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure also provides a compound of Formula (VI)

Formula (VI)

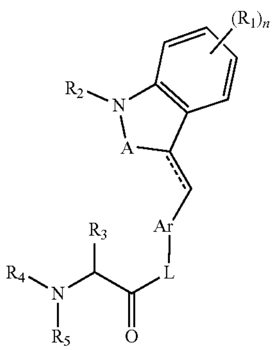

or an optically pure stereoisomer, pharmaceutically acceptable salt, or solvate thereof. n can be an integer selected from 0 to 4.

In one aspect, A can be —CO—, —SO—, —$SO_2$—, —OPO—, or —$OPO_2$—. ⎓ can be a single bond or a double bond.

$R_1$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_8$.

$R_2$ can be selected from the group consisting of H, methyl, ethyl, propyl, and isopropyl, each of which can be optionally substituted by one, two, three, or four $R_8$.

In another aspect, Ar can be selected from the group consisting of

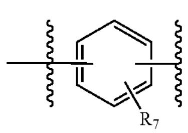,
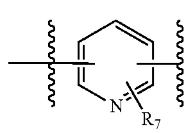,
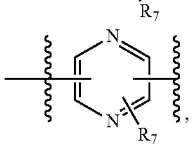,
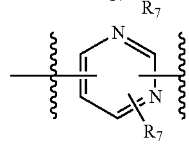,

-continued

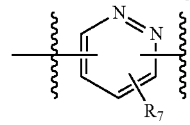,
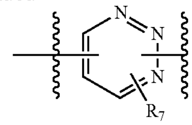,
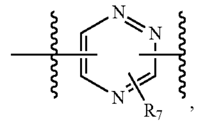,
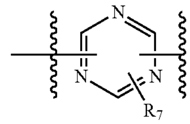,
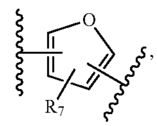,
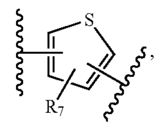,
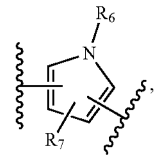,
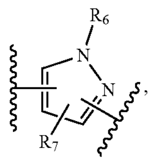,
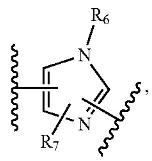,
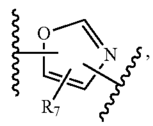,
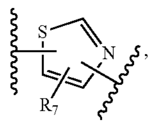,
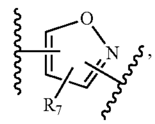,
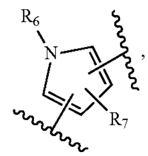,
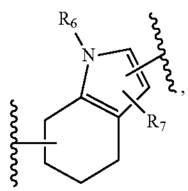,
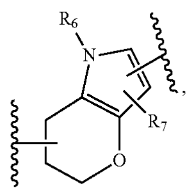,
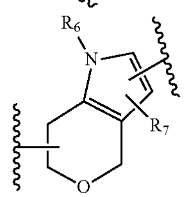,
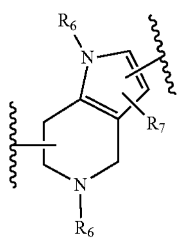, and
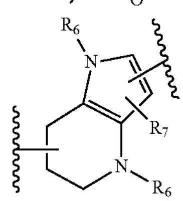.

L can be —$O(CH_2)_{1-5}O$—, —$O(CH_2)_{1-5}NR_6$—, —$NR_6(CH_2)_{1-5}NR_6$—, —$CONR_6(CH_2)_{1-5}NR_6$—, —$NR_6CO(CH_2)_{1-5}NR_6$—, —$(CH_2)_{1-5}NR_6$—, —$(CH_2)_{1-5}O$—, —$(CH_2)_{1-5}OCO$—, —$(CH_2)_{1-5}CONR_6$—,

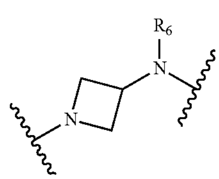,
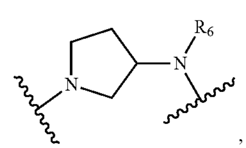, or
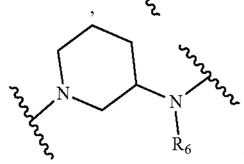, each of which can be optionally substituted by one, two, three, or four $R_8$.

In certain aspects, $R_3$ can be H, methyl, ethyl, propyl, isopropyl, butyl, isobutyl, or tert-butyl, each of which can be optionally substituted by one, two, three, or four $R_8$.

In some aspects, $R_4$ can be selected from the group consisting of H, methyl, ethyl, propyl, and isopropyl. Or $R_4$ and $R_3$ together can form

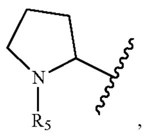, 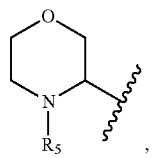, or 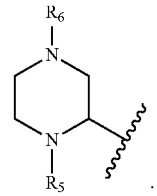.

In some aspects, $R_5$ can be selected from the group consisting of $CO(CH_2)_{0-5}CH_3$, $CONR_6(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_6(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_6(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_6(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_6(CH_2)_{0-5}C{\equiv}CCH_3$, and $SO_2(CH_2)_{0-5}C{\equiv}CCH_3$, each of which can be optionally substituted by one, two, three, or four $R_8$.

In some aspects, $R_5$ can be selected from the group consisting of

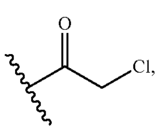 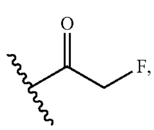 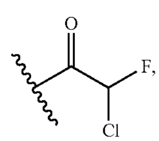

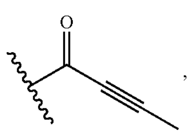, 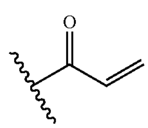, 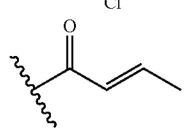,

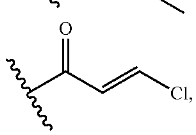 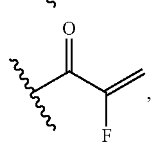, 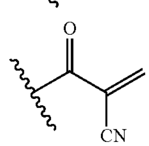, and

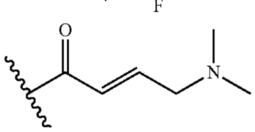.

Each $R_6$ can be independently H, methyl, ethyl, propyl, isopropyl.

$R_7$ can be H, F, Br, Cl, $CF_3$, CN, $N_3$, $NH_2$, $NO_2$, OH, $OCH_3$, methyl, ethyl, propyl, or isopropyl, each of which can be optionally substituted by one, two, three, or four $R_8$.

Each $R_8$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

The present disclosure also provides a compound of Formula (VII)

Formula (VII)

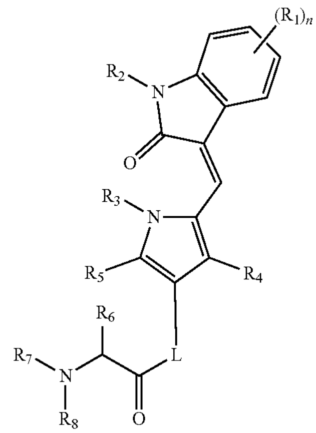

or an optically pure stereoisomer, pharmaceutically acceptable salt, or solvate thereof. In one aspect, n can be an integer selected from 0 to 4.

In still another aspect, each $R_1$ can be independently selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

In some aspects, each $R_2$ and $R_3$ can be independently selected from the group consisting of H, methyl, ethyl, propyl, and isopropyl, each of which can be optionally substituted by one, two, three, or four $R_9$.

In certain aspects, $R_4$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

$R_5$ can be selected from the group consisting of H, F, Br, Cl, $CF_3$, CN, $N_3$, $NH_2$, $NO_2$, OH, $OCH_3$, methyl, ethyl, propyl, and isopropyl, each of which can be optionally substituted by one, two, three, or four $R_9$.

L can be $—O(CH_2)_{1-5}O—$, $—O(CH_2)_{1-5}NR_{10}—$, $—NR_6(CH_2)_{1-5}NR_{10}—$, $—CONR_{10}(CH_2)_{1-5}NR_{10}—$, $—NR_{10}CO(CH_2)_{1-5}NR_{10}—$, $—(CH_2)_{1-5}NR_{10}—$, $—(CH_2)_{1-5}O—$, $—(CH_2)_{1-5}OCO—$, $—(CH_2)_{1-5}CONR_{10}—$,

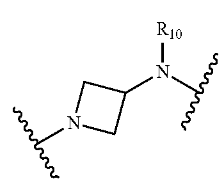, 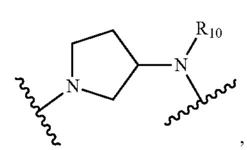, or

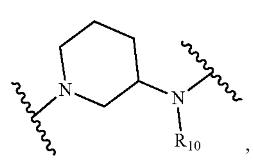, each of which can be optionally substituted by one, two, three, or four $R_9$.

Or $R_5$ and L together can form

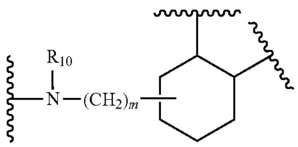,

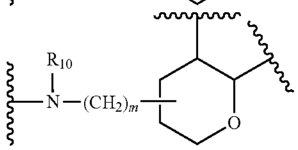,

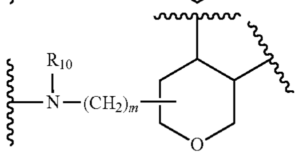,

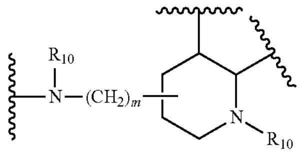, or

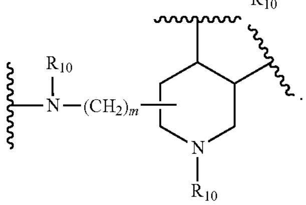.

m can be an integer selected from 0 to 4.

$R_6$ can be H, methyl, ethyl, propyl, isopropyl, butyl, isobutyl, or tert-butyl, each of which can be optionally substituted by one, two, three, or four $R_9$.

In some aspects, $R_7$ can be selected from the group consisting of H, methyl, ethyl, propyl, and isopropyl. Or $R_6$ and $R_7$ together can form

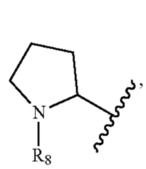, 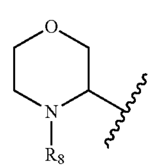, or 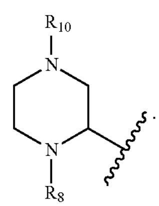.

In some aspects, $R_8$ can be selected from the group consisting of $CO(CH_2)_{0-5}CH_3$, $CONR_{10}(CH_2)_{0-5}CH_3$, $COO(CH_2)_{0-5}CH_3$, $SO_2(CH_2)_{0-5}CH_3$, $CO(CH_2)_{0-5}CH{=}CH_2$, $CONR_{10}(CH_2)_{0-5}CH{=}CH_2$, $COO(CH_2)_{0-5}CH{=}CH_2$, $SO_2(CH_2)_{0-5}CH{=}CH_2$, $CO(CH_2)_{0-5}CH{=}CHCH_3$, $COO(CH_2)_{0-5}CH{=}CHCH_3$, $CONR_{10}(CH_2)_{0-5}CH{=}CHCH_3$, $SO_2(CH_2)_{0-5}CH{=}CHCH_3$, $CO(CH_2)_{0-5}C{\equiv}CH$, $COO(CH_2)_{0-5}C{\equiv}CH$, $CONR_{10}(CH_2)_{0-5}C{\equiv}CH$, $SO_2(CH_2)_{0-5}C{\equiv}CH$, $CO(CH_2)_{0-5}C{\equiv}CCH_3$, $COO(CH_2)_{0-5}C{\equiv}CCH_3$, $CONR_{10}(CH_2)_{0-5}C{\equiv}CCH_3$, and $SO_2(CH_2)_{0-5}C{\equiv}CCH_3$, each of which can be optionally substituted by one, two, three, or four $R_9$.

In some aspects, $R_8$ can be selected from the group consisting of

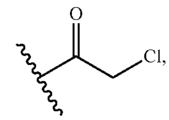, 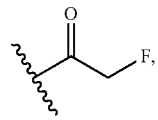, 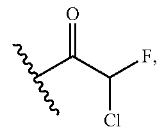,

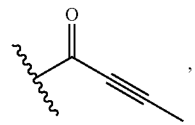, 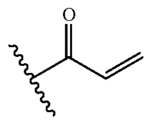, 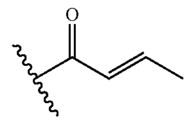,

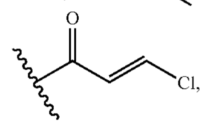, 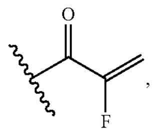, 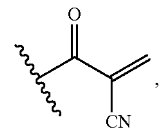, and

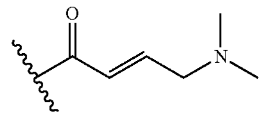.

Each $R_9$ can be independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

Each $R_{10}$ can be independently H, methyl, ethyl, propyl, or isopropyl.

The present disclosure also provides a pharmaceutical formulation including the compound according to Formula (I), Formula (II), Formula (III), Formula (IV), Formula (V), Formula (VI), Formula (VII) or an optically pure stereoisomer or pharmaceutically acceptable salt thereof. The present disclosure further provides a method for treating cancer in a subject including administering a compound with the structure of Formula (I), Formula (II), Formula (III), Formula (IV), Formula (V), Formula (VI), Formula (VII), or an optically pure stereoisomer or pharmaceutically acceptable salt thereof to the subject. The present disclosure also provides a method of inhibiting a kinase activity including contacting a cell with a compound with the structure of Formula (I), Formula (II), Formula (III), Formula (IV), Formula (V), Formula (VI), Formula (VII), or an optically pure stereoisomer or pharmaceutically acceptable salt thereof. In some embodiments, the kinase can be feline Gardner-Rasheed sarcoma viral oncogene homolog (FGR), fms like tyrosine kinase 3 (FLT3), macrophage colony-stimulating factor 1 receptor (FMS), mast/stem cell growth factor receptor Kit (KIT), macrophage-stimulating protein receptor (RON), cytoplasmic tyrosine-protein kinase BMX (BMX), or tyrosine-protein kinase Tec (TEC). The cell can be a cancer cell. The cancer cell can be a breast, myeloid, lung, bladder, prostate, ovarian, endometrial, rhabdomyosarcoma, liver, gastric or intestinal cancer cell.

Compounds of the present disclosure are synthesized by an appropriate combination of generally established synthetic methods. Techniques useful in synthesizing the compounds of the disclosure are both readily apparent and accessible to those of skill in the relevant art. The discussion below is offered to illustrate certain of the diverse methods available for use in assembling the compounds of the disclosure. However, the discussion is not intended to define the scope of reactions or reaction sequences that are useful in preparing the compounds of the present disclosure.

The synthesis of the disclosed compounds in the present application are shown in Schemes 1-3 using Formula (III), Formula (IV) and Formula (VI) as examples.

Scheme 1. Synthesis of the tyrosine kinase inhibitor compounds in the present disclosure using Formula (III) as an example.
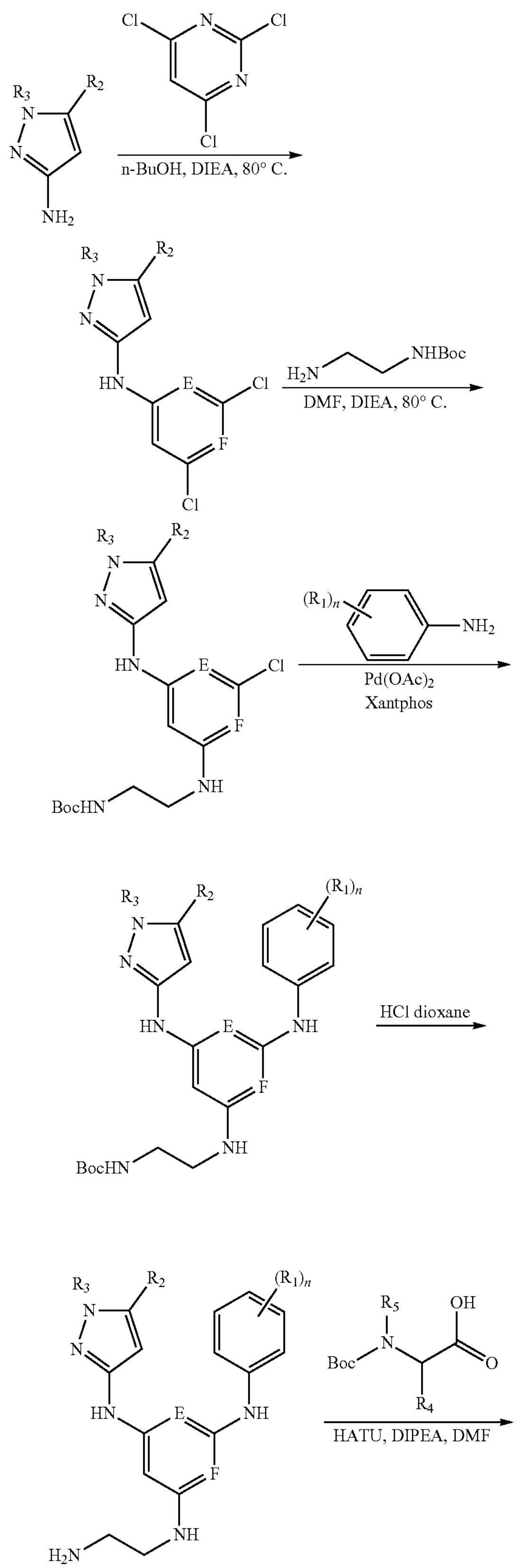
-continued
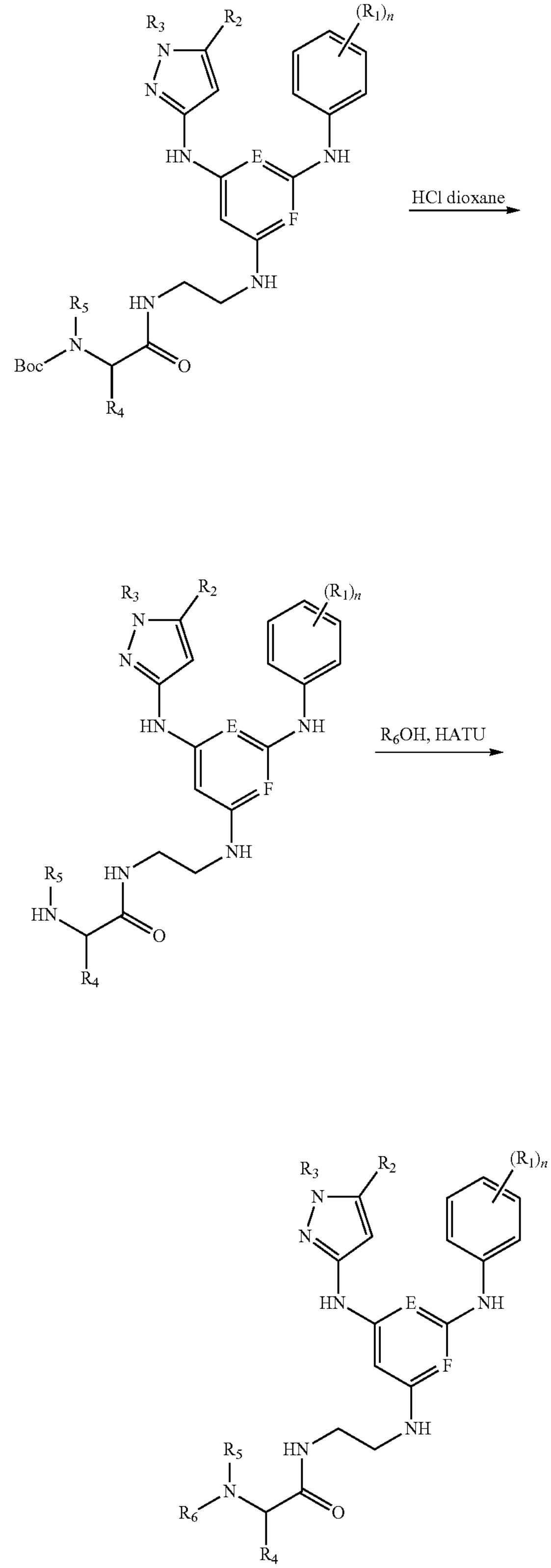
Formula (III)
Note: assuming B=D= —NH—; L= $-NHCH_2CH_2NH-$.

Scheme 2. Synthesis of the tyrosine kinase inhibitor compounds in the present disclosure using Formula (IV) as an example.
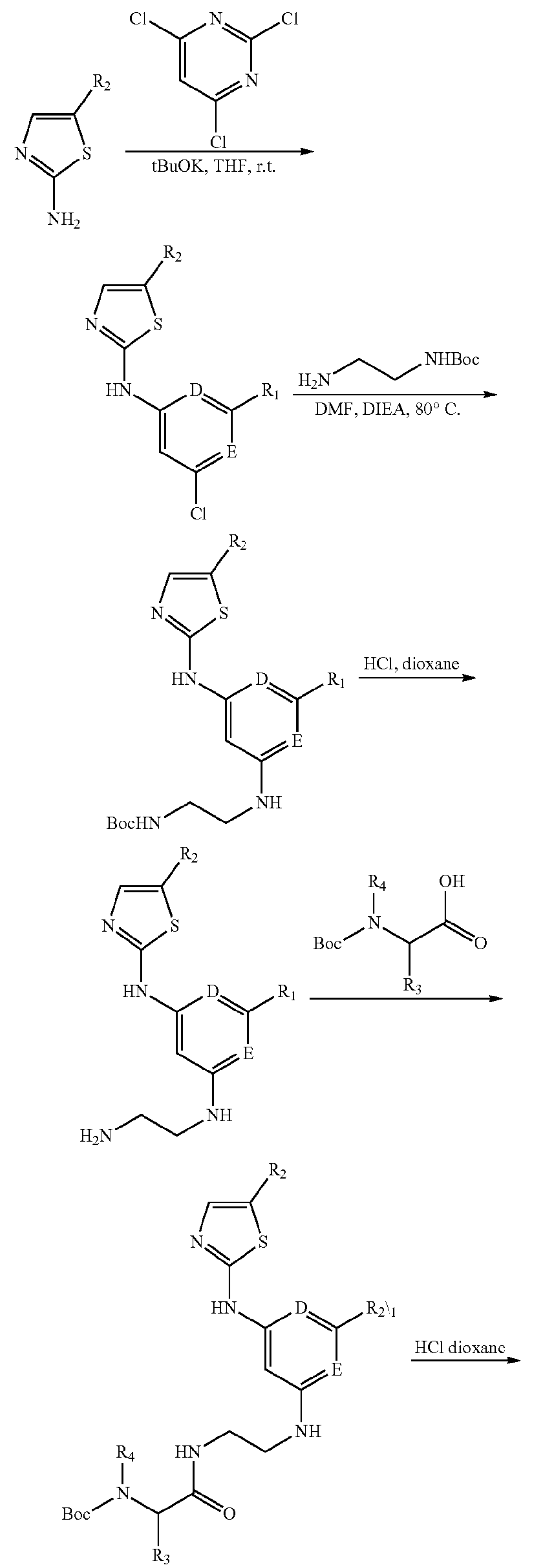
-continued
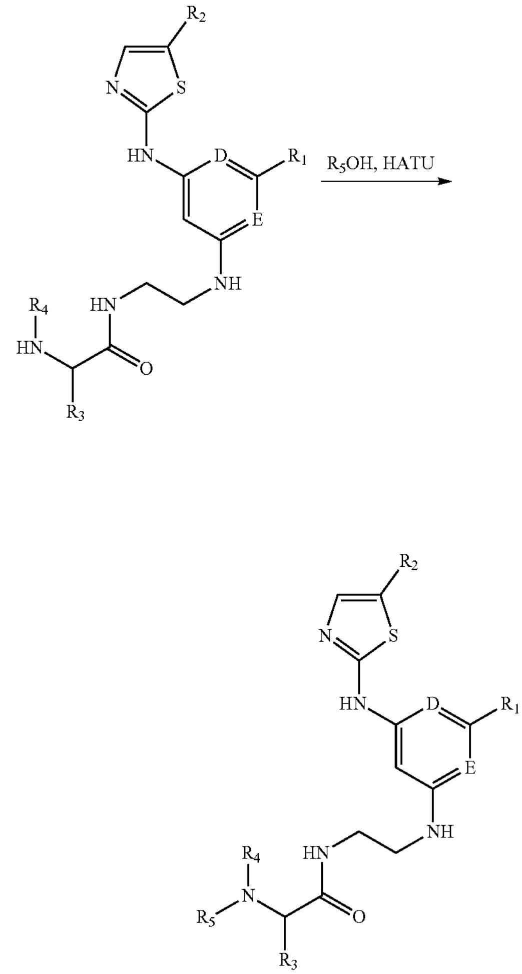
Formula (IV)
Note: assuming —NH— ; L== —NHCH$_2$CH$_2$NH— ;
Ar is 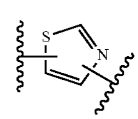 .
Scheme 3. Synthesis of the tyrosine kinase inhibitor compounds in the present disclosure using Formula (VII) as an example.
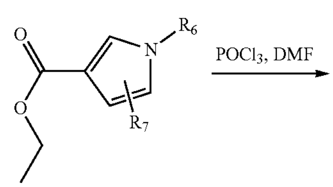

-continued
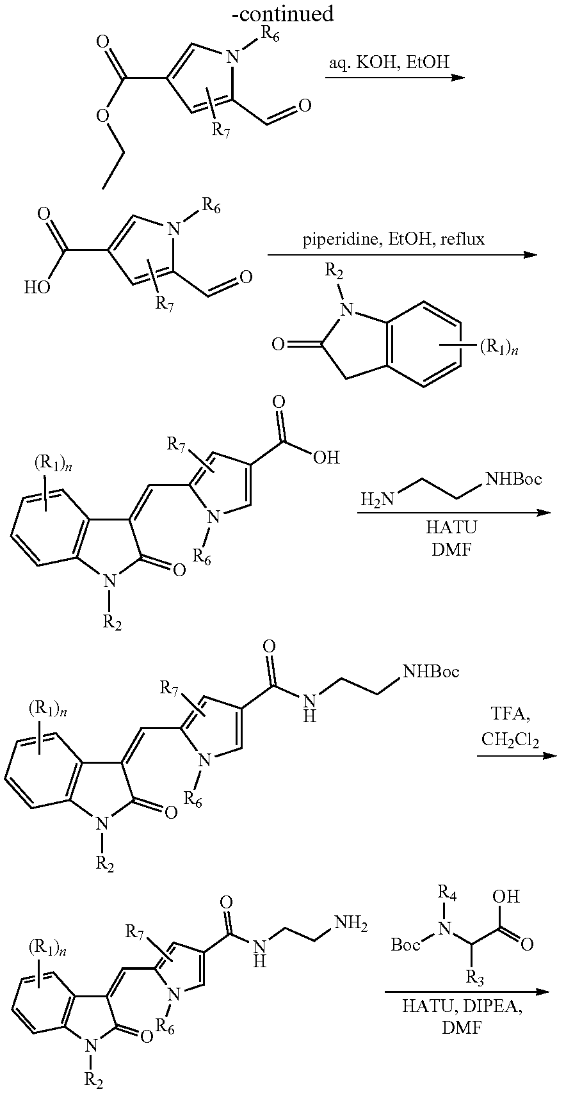
-continued
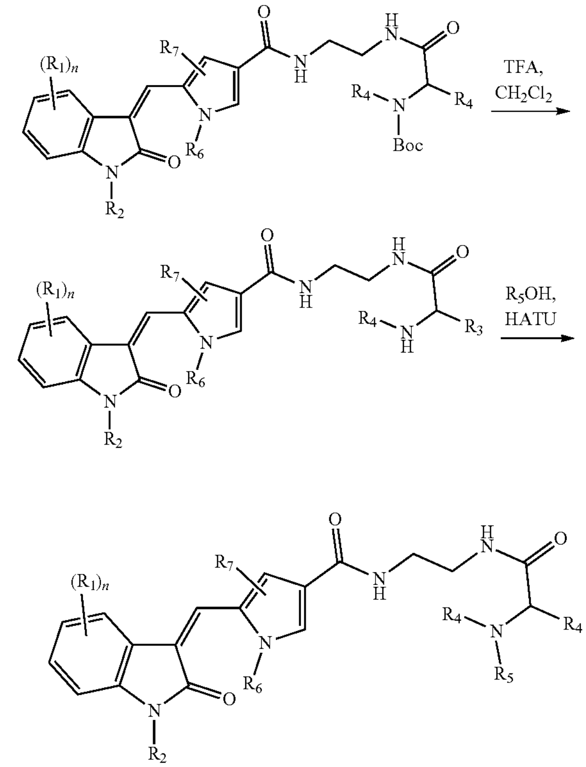
Formula (VII)
Note: assuming is a double bond, Ar is,
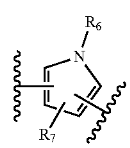
, and L is —$CONHCH_2CH_2NH$—.
Table 1 below shows all the tyrosine kinase inhibitor compounds disclosed in the present application.
TABLE 1
| The tyrosine kinase inhibitor compounds in the present disclosure. | |
|---|---|
| Compound No. | Molecular Structure |
| Compound 1 | 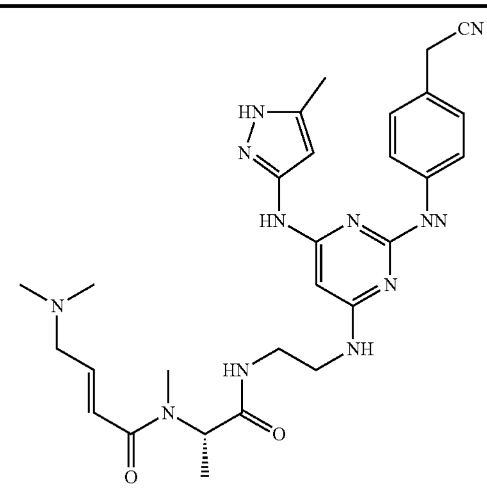 |

TABLE 1-continued
| The tyrosine kinase inhibitor compounds in the present disclosure. | |
|---|---|
| Compound No. | Molecular Structure |
| Compound 2 | 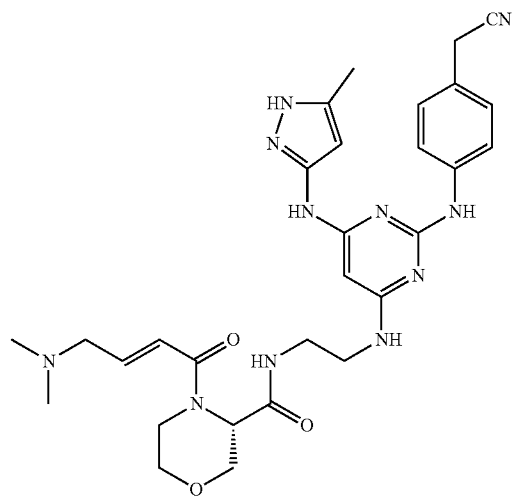 [SMILES: Cc1cc(Nc2cc(NCCNC(=O)[C@@H]3COCCN3C(=O)/C=C/CN(C)C)nc(Nc3ccc(CC#N)cc3)n2)n[nH]1] |
| Compound 3 | 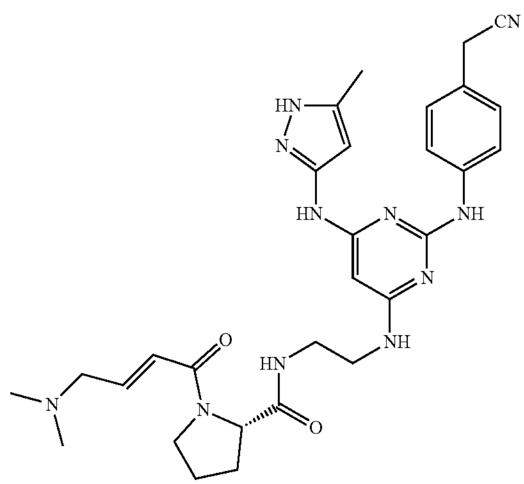 [SMILES: Cc1cc(Nc2cc(NCCNC(=O)[C@@H]3CCCN3C(=O)/C=C/CN(C)C)nc(Nc3ccc(CC#N)cc3)n2)n[nH]1] |
| Compound 4 | 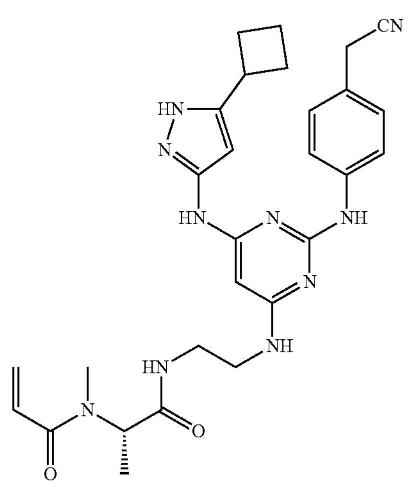 [SMILES: C=CC(=O)N(C)[C@@H](C)C(=O)NCCNc1cc(Nc2cc(C3CCC3)[nH]n2)nc(Nc2ccc(CC#N)cc2)n1] |

TABLE 1-continued
| The tyrosine kinase inhibitor compounds in the present disclosure. | |
|---|---|
| Compound No. | Molecular Structure |
| Compound 5 | 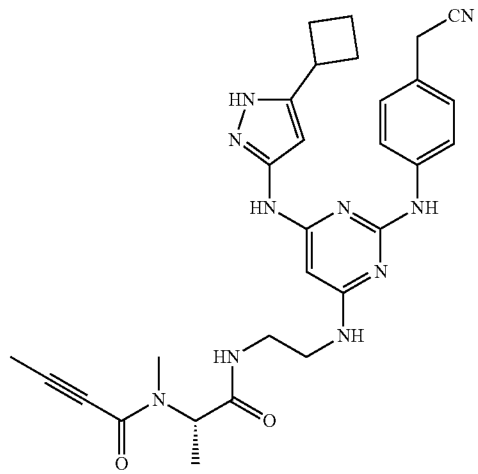 [SMILES: CC#CC(=O)N(C)[C@@H](C)C(=O)NCCNc1cc(Nc2cc(C3CCC3)[nH]n2)nc(Nc2ccc(CC#N)cc2)n1] |
| Compound 6 | 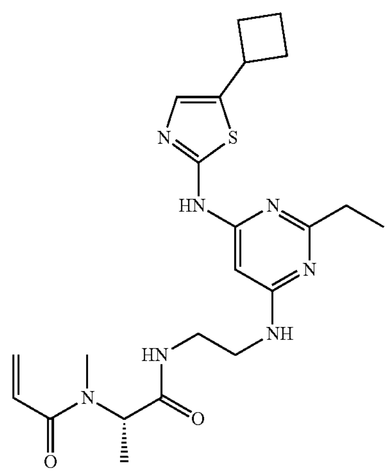 [SMILES: C=CC(=O)N(C)[C@@H](C)C(=O)NCCNc1cc(Nc2ncc(C3CCC3)s2)nc(CC)n1] |
| Compound 7 | 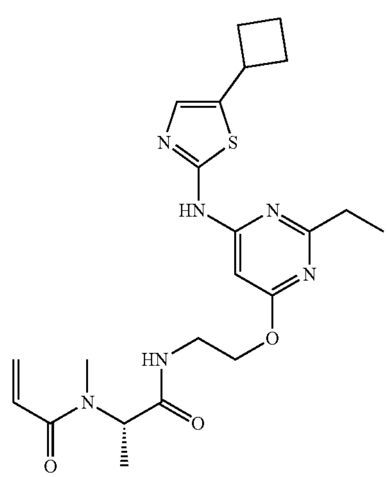 [SMILES: C=CC(=O)N(C)[C@@H](C)C(=O)NCCOc1cc(Nc2ncc(C3CCC3)s2)nc(CC)n1] |

TABLE 1-continued
| The tyrosine kinase inhibitor compounds in the present disclosure. | |
|---|---|
| Compound No. | Molecular Structure |
| Compound 8 | 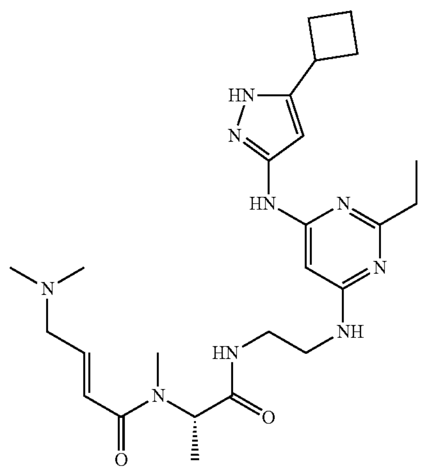 [SMILES: CCc1nc(NCCNC(=O)[C@H](C)N(C)C(=O)/C=C/CN(C)C)cc(Nc2cc(C3CCC3)[nH]n2)n1] |
| Compound 9 | 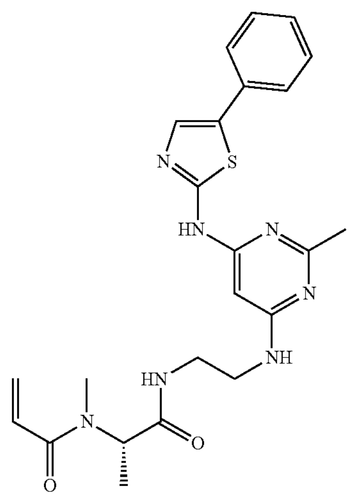 [SMILES: C=CC(=O)N(C)[C@@H](C)C(=O)NCCNc1cc(Nc2ncc(-c3ccccc3)s2)nc(C)n1] |
| Compound 10 | 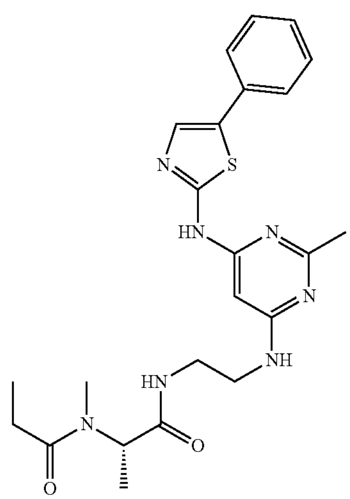 [SMILES: CCC(=O)N(C)[C@@H](C)C(=O)NCCNc1cc(Nc2ncc(-c3ccccc3)s2)nc(C)n1] |

TABLE 1-continued
| The tyrosine kinase inhibitor compounds in the present disclosure. | |
|---|---|
| Compound No. | Molecular Structure |
| Compound 11 | 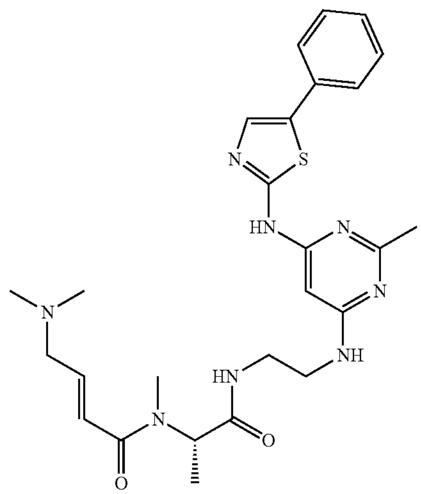 |
| Compound 12 | 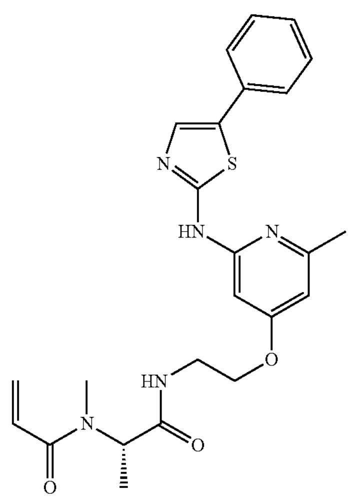 [SMILES: C=CC(=O)N(C)[C@@H](C)C(=O)NCCOc1cc(C)nc(Nc2ncc(-c3ccccc3)s2)c1] |
| Compound 13 | 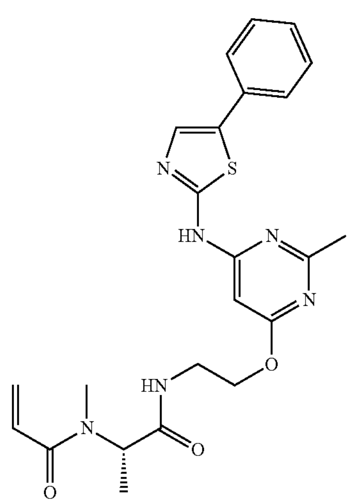 [SMILES: C=CC(=O)N(C)[C@@H](C)C(=O)NCCOc1cc(Nc2ncc(-c3ccccc3)s2)nc(C)n1] |

TABLE 1-continued
| The tyrosine kinase inhibitor compounds in the present disclosure. | |
|---|---|
| Compound No. | Molecular Structure |
| Compound 14 | 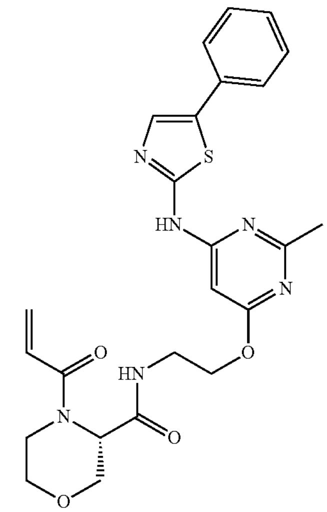 [SMILES: C=CC(=O)N1CCOC[C@H]1C(=O)NCCOc1cc(Nc2ncc(-c3ccccc3)s2)nc(C)n1] |
| Compound 15 | 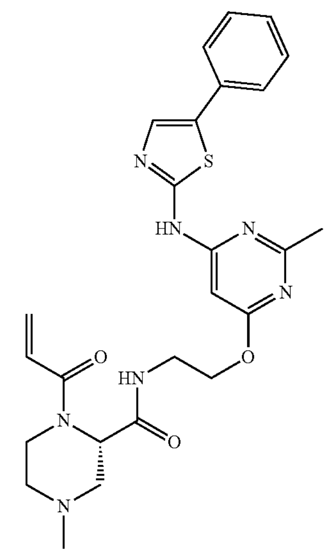 [SMILES: C=CC(=O)N1CCN(C)C[C@H]1C(=O)NCCOc1cc(Nc2ncc(-c3ccccc3)s2)nc(C)n1] |
| Compound 16 | 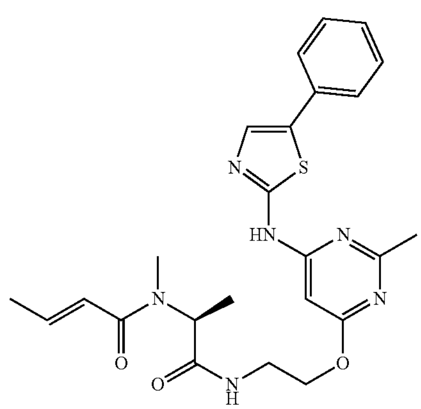 [SMILES: C/C=C/C(=O)N(C)[C@@H](C)C(=O)NCCOc1cc(Nc2ncc(-c3ccccc3)s2)nc(C)n1] |

TABLE 1-continued
| The tyrosine kinase inhibitor compounds in the present disclosure. | |
|---|---|
| Compound No. | Molecular Structure |
| Compound 17 | 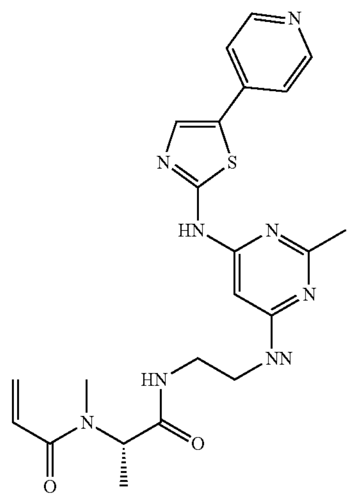 |
| Compound 18 | 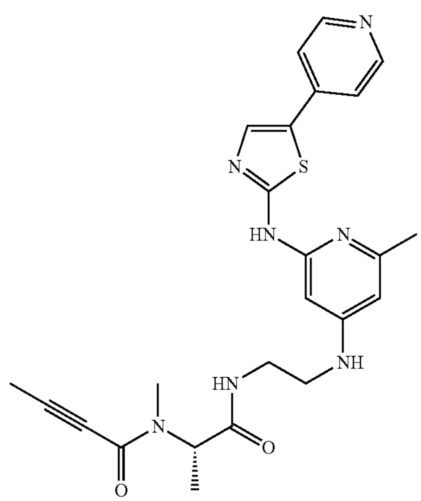 |
| Compound 19 | 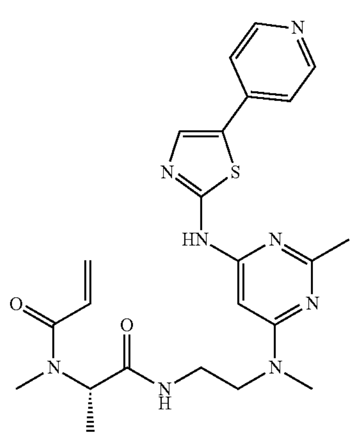 [SMILES: C=CC(=O)N(C)[C@@H](C)C(=O)NCCN(C)c1cc(Nc2ncc(-c3ccncc3)s2)nc(C)n1] |

TABLE 1-continued
| The tyrosine kinase inhibitor compounds in the present disclosure. | |
|---|---|
| Compound No. | Molecular Structure |
| Compound 20 | 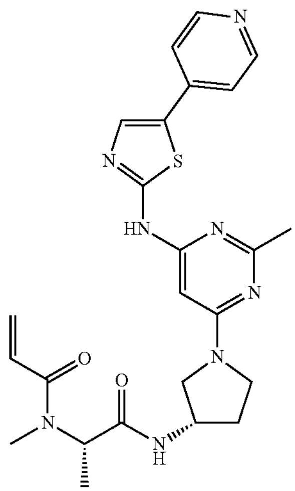 [SMILES: C=CC(=O)N(C)[C@@H](C)C(=O)N[C@H]1CCN(c2cc(Nc3ncc(-c4ccncc4)s3)nc(C)n2)C1] |
| Compound 21 | 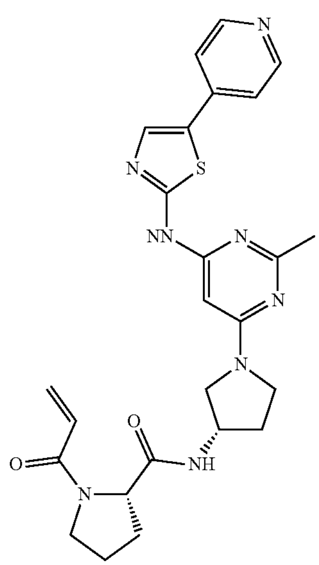 |

TABLE 1-continued
| The tyrosine kinase inhibitor compounds in the present disclosure. | |
|---|---|
| Compound No. | Molecular Structure |
| Compound 22 | 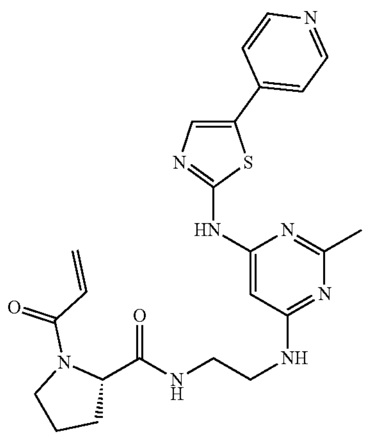 [SMILES: C=CC(=O)N1CCC[C@H]1C(=O)NCCNc1cc(Nc2ncc(-c3ccncc3)s2)nc(C)n1] |
| Compound 23 | 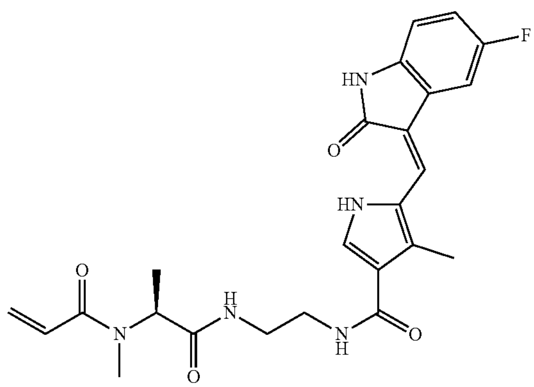 [SMILES: C=CC(=O)N(C)[C@@H](C)C(=O)NCCNC(=O)c1c[nH]c(/C=C2\C(=O)Nc3ccc(F)cc32)c1C] |
| Compound 24 | 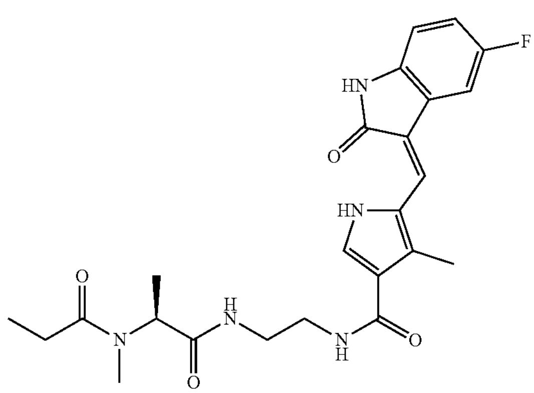 [SMILES: CCC(=O)N(C)[C@@H](C)C(=O)NCCNC(=O)c1c[nH]c(/C=C2\C(=O)Nc3ccc(F)cc32)c1C] |

TABLE 1-continued
| The tyrosine kinase inhibitor compounds in the present disclosure. | |
|---|---|
| Compound No. | Molecular Structure |
| Compound 25 | 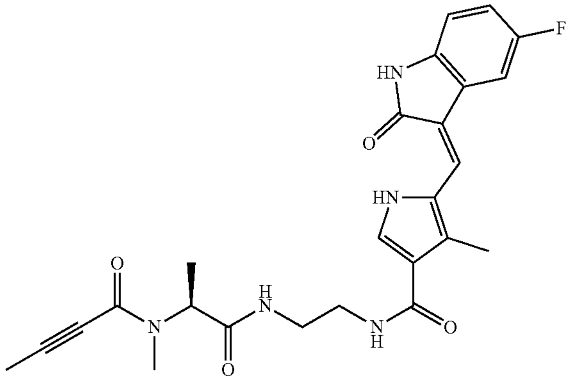 [SMILES: CC#CC(=O)N(C)[C@@H](C)C(=O)NCCNC(=O)c1c[nH]c(/C=C2\C(=O)Nc3ccc(F)cc32)c1C] |
| Compound 26 | 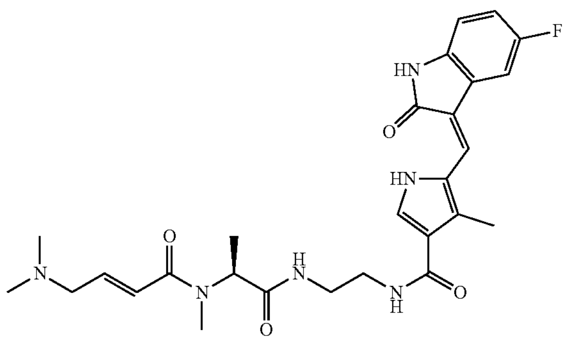 [SMILES: Cc1c(C(=O)NCCNC(=O)[C@H](C)N(C)C(=O)/C=C/CN(C)C)c[nH]c1/C=C1\C(=O)Nc2ccc(F)cc21] |
| Compound 27 | 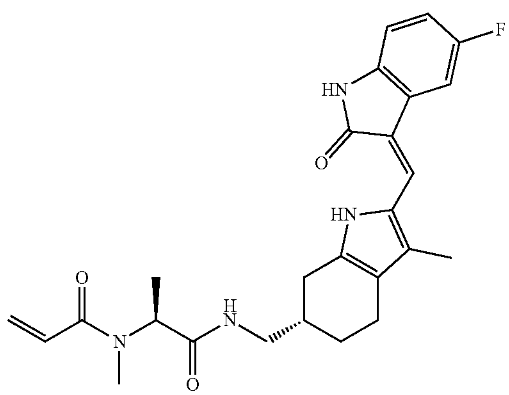 [SMILES: C=CC(=O)N(C)[C@@H](C)C(=O)NC[C@H]1CCc2c([nH]c(/C=C3\C(=O)Nc4ccc(F)cc43)c2C)C1] |
| Compound 28 | 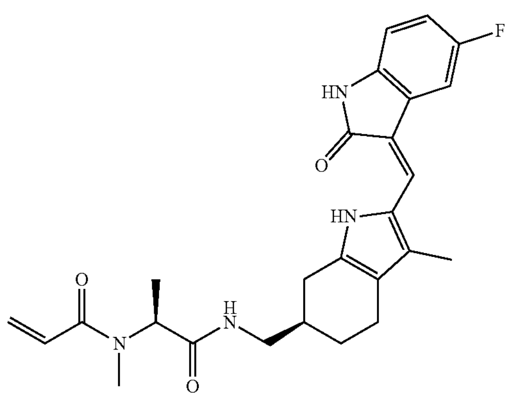 [SMILES: C=CC(=O)N(C)[C@@H](C)C(=O)NC[C@@H]1CCc2c([nH]c(/C=C3\C(=O)Nc4ccc(F)cc43)c2C)C1] |

TABLE 1-continued

| The tyrosine kinase inhibitor compounds in the present disclosure. | |
|---|---|
| Compound No. | Molecular Structure |
| Compound 29 | 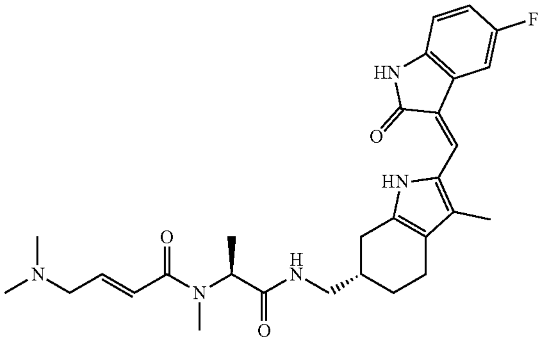 [SMILES: Cc1c(/C=C2\C(=O)Nc3ccc(F)cc32)[nH]c2c1CC[C@H](CNC(=O)[C@H](C)N(C)C(=O)/C=C/CN(C)C)C2] |
| Compound 30 | 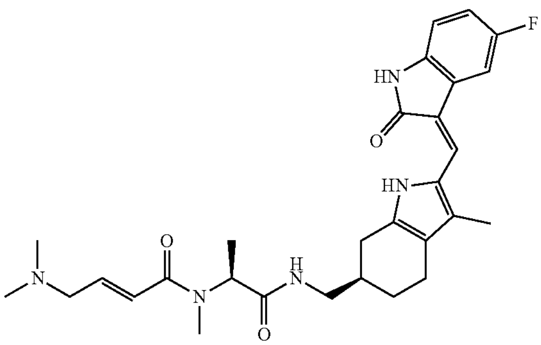 [SMILES: Cc1c(/C=C2\C(=O)Nc3ccc(F)cc32)[nH]c2c1CC[C@@H](CNC(=O)[C@H](C)N(C)C(=O)/C=C/CN(C)C)C2] |

The term "treatment" is used interchangeably herein with the term "therapeutic method" and refers to both 1) therapeutic treatments or measures that cure, slow down, lessen symptoms of, and/or halt progression of a diagnosed pathologic conditions, disease or disorder, and 2) and prophylactic/preventative measures. Those in need of treatment may include individuals already having a particular medical disease or disorder as well as those who may ultimately acquire the disorder (i.e., those needing preventive measures).

The term "subject" as used herein refers to any individual or patient to which the subject methods are performed. Generally, the subject is human, although as will be appreciated by those in the art, the subject may be an animal.

The terms "therapeutically effective amount", "effective dose", "therapeutically effective dose", "effective amount," or the like refer to the amount of a subject compound that will elicit the biological or medical response in a tissue, system, animal or human that is being sought by administering said compound. Generally, the response is either amelioration of symptoms in a patient or a desired biological outcome. Such amount should be sufficient to inhibit tyrosine kinase enzymatic activity.

Also disclosed herein are pharmaceutical compositions including compounds with the structures of Formula (I), Formula (II), Formula (III), Formula (IV), Formula (V), Formula (VI), or Formula (VII). The term "pharmaceutically acceptable carrier" refers to a non-toxic carrier that may be administered to a patient, together with a compound of this disclosure, and which does not destroy the pharmacological activity thereof. Pharmaceutically acceptable carriers that may be used in these compositions include, but are not limited to, ion exchangers, alumina, aluminum stearate, lecithin, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable carriers that may be used in the pharmaceutical compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, wool fat and self-emulsifying drug delivery systems (SEDDS) such as α-tocopherol, polyethyleneglycol 1000 succinate, or other similar polymeric delivery matrices.

In pharmaceutical composition comprising only the compounds described herein as the active component, methods for administering these compositions may additionally comprise the step of administering to the subject an additional agent or therapy. Such therapies include, but are not limited to, an anemia therapy, a diabetes therapy, a hypertension therapy, a cholesterol therapy, neuropharmacologic drugs, drugs modulating cardiovascular function, drugs modulating inflammation, immune function, production of blood cells; hormones and antagonists, drugs affecting gastrointestinal function, chemotherapeutics of microbial diseases, and/or chemotherapeutics of neoplastic disease. Other pharmacological therapies can include any other drug or biologic found in any drug class. For example, other drug classes can comprise allergy/cold/ENT therapies, analgesics, anesthetics, anti-inflammatories, antimicrobials, antivirals, asthma/pulmonary therapies, cardiovascular therapies, dermatology therapies, endocrine/metabolic therapies, gastrointestinal therapies, cancer therapies, immunology therapies, neurologic therapies, ophthalmic therapies, psychiatric therapies or rheumatologic therapies. Other examples of agents or therapies that can be administered with the compounds described herein include a matrix metalloprotease inhibitor, a lipoxygenase inhibitor, a cytokine antagonist, an immunosuppressant, a cytokine, a growth factor, an immunomodulator, a prostaglandin or an anti-vascular hyperproliferation compound.

The term "therapeutically effective amount" as used herein refers to the amount of active compound or pharmaceutical agent that elicits the biological or medicinal response in a tissue, system, animal, individual or human that is being sought by a researcher, veterinarian, medical doctor or other clinician, which includes one or more of the following: (1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

The compounds of this disclosure may be employed in a conventional manner for controlling the disease described herein, including, but not limited to, cancer. Such methods of treatment, their dosage levels and requirements may be selected by those of ordinary skill in the art from available methods and techniques. For example, the compounds of this disclosure may be combined with a pharmaceutically acceptable adjuvant for administration to a patient suffering from cancer in a pharmaceutically acceptable manner and in an amount effective to treat cancer.

Alternatively, the compounds of this disclosure may be used in compositions and methods for treating or protecting individuals against the diseases described herein, including but not limited to a cancer, over extended periods of time. The compounds may be employed in such compositions either alone or together with other compounds of this disclosure in a manner consistent with the conventional utilization of such compounds in pharmaceutical compositions. For example, a compound of this disclosure may be combined with pharmaceutically acceptable adjuvants conventionally employed in vaccines and administered in prophylactically effective amounts to protect individuals over an extended period of time against the diseases described herein, including, but not limited to, cancer.

As used herein, the terms "combination," "combined," and related terms refer to the simultaneous or sequential administration of therapeutic agents in accordance with this disclosure. For example, a described compound may be administered with another therapeutic agent simultaneously or sequentially in separate unit dosage forms or together in a single unit dosage form. Accordingly, the present disclosure provides a single unit dosage form comprising a described compound, an additional therapeutic agent, and a pharmaceutically acceptable carrier, adjuvant, or vehicle. Two or more agents are typically considered to be administered "in combination" when a patient or individual is simultaneously exposed to both agents. In many embodiments, two or more agents are considered to be administered "in combination" when a patient or individual simultaneously shows therapeutically relevant levels of the agents in a particular target tissue or sample (e.g., in brain, in serum, etc.).

When the compounds of this disclosure are administered in combination therapies with other agents, they may be administered sequentially or concurrently to the patient. Alternatively, pharmaceutical or prophylactic compositions according to this disclosure comprise a combination of ivermectin, or any other compound described herein, and another therapeutic or prophylactic agent. Additional therapeutic agents that are normally administered to treat a particular disease or condition may be referred to as "agents appropriate for the disease, or condition, being treated."

The compounds utilized in the compositions and methods of this disclosure may also be modified by appending appropriate functionalities to enhance selective biological properties. Such modifications are known in the art and include those, which increase biological penetration into a given biological system (e.g., blood, lymphatic system, or central nervous system), increase oral availability, increase solubility to allow administration by injection, alter metabolism and/or alter rate of excretion.

According to a preferred embodiment, the compositions of this disclosure are formulated for pharmaceutical administration to a subject or patient, e.g., a mammal, preferably a human being. Such pharmaceutical compositions are used to ameliorate, treat or prevent any of the diseases described herein including but not limited to cancer in a subject.

Agents of the disclosure are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In some embodiments, the present disclosure provides pharmaceutically acceptable compositions comprising a therapeutically effective amount of one or more of a described compound, formulated together with one or more pharmaceutically acceptable carriers (additives) and/or diluents for use in treating the diseases described herein, including, but not limited to cancer. While it is possible for a described compound to be administered alone, it is preferable to administer a described compound as a pharmaceutical formulation (composition) as described herein. Described compounds may be formulated for administration in any convenient way for use in human or veterinary medicine, by analogy with other pharmaceuticals.

As described in detail, pharmaceutical compositions of the present disclosure may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations for use in accordance with the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient, which can be combined with a carrier material, to produce a single dosage form will vary depending upon the host being treated, and the particular mode of administration. The amount of active ingredient that can be combined with a carrier material to produce a single dosage form will generally be that amount of the compound, which produces a therapeutic effect. Generally, this amount will range from about 1% to about 99% of active ingredient. In some embodiments, this amount will range from about 5% to about 70%, from about 10% to about 50%, or from about 20% to about 40%.

In certain embodiments, a formulation as described herein comprises an excipient selected from the group consisting of cyclodextrins, liposomes, micelle forming agents, e.g., bile acids, and polymeric carriers, e.g., polyesters and polyanhydrides; and a compound of the present disclosure. In certain embodiments, an aforementioned formulation renders orally bioavailable a described compound of the present disclosure.

Methods of preparing formulations or compositions comprising described compounds include a step of bringing into association a compound of the present disclosure with the carrier and, optionally, one or more accessory ingredients. In general, formulations may be prepared by uniformly and intimately bringing into association a compound of the present disclosure with liquid carriers, or finely divided solid carriers, or both, and then, if necessary, shaping the product.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as those described in Pharmacopeia Helvetica, or a similar alcohol. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In some cases, in order to prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the described compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

The pharmaceutical compositions of this disclosure may be orally administered in any orally acceptable dosage form including, but not limited to, capsules, tablets, and aqueous suspensions and solutions. In the case of tablets for oral use, carriers, which are commonly used include lactose and corn starch. Lubricating agents, such as magnesium stearate, are also typically added. For oral administration in a capsule form, useful diluents include lactose and dried cornstarch. When aqueous suspensions and solutions and propylene glycol are administered orally, the active ingredient is combined with emulsifying and suspending agents. If desired, certain sweetening and/or flavoring and/or coloring agents may be added.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compounds described herein may also be administered as a bolus, electuary or paste.

In solid dosage forms for oral administration (capsules, tablets, pills, dragees, powders, granules and the like), an active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and nonionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

Tablets may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent. If a solid carrier is used, the preparation can be in tablet form, placed in a hard gelatin capsule in powder or pellet form, or in the form of a troche or lozenge. The amount of solid carrier will vary, e.g., from about 25 to 800 mg, preferably about 25 mg to 400 mg. When a liquid carrier is used, the preparation can be, e.g., in the form of a syrup, emulsion, soft gelatin capsule, sterile injectable liquid such as an ampule or nonaqueous liquid suspension. Where the composition is in the form of a capsule, any routine encapsulation is suitable, for example, using the aforementioned carriers in a hard gelatin capsule shell.

Tablets and other solid dosage forms, such as dragees, capsules, pills and granules, may optionally be scored or prepared with coatings and shells, such as enteric coatings and other coatings well known in the pharmaceutical-formulating art. They may alternatively or additionally be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, oral compositions can also include adjuvants such as wetting agents, emulsifying and suspending agents, sweetening, flavoring, coloring, perfuming and preservative agents.

Suspensions, in addition to active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The pharmaceutical compositions of this disclosure may also be administered in the form of suppositories for rectal administration. These compositions can be prepared by mixing a compound of this disclosure with a suitable non-irritating excipient, which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this disclosure is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this disclosure include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this disclosure may also be topically applied to the lower intestinal tract by rectal suppository formulation or in a suitable enema formulation. Topically-administered transdermal patches are also included in this disclosure.

The pharmaceutical compositions of this disclosure may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

Transdermal patches have the added advantage of providing controlled delivery of a compound of the present disclosure to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Examples of suitable aqueous and nonaqueous carriers, which may be employed in the pharmaceutical compositions of the disclosure, include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Such compositions may also contain adjuvants such as preservatives, wetting agents, emulsifying agents and dispersing agents. Inclusion of one or more antibacterial and/or antifungal agents, for example, paraben, chlorobutanol, phenol sorbic acid, and the like, may be desirable in certain embodiments. It may alternatively or additionally be desirable to include isotonic agents, such as sugars, sodium chloride, and the like into the compositions. In addition, prolonged absorption of the injectable pharmaceutical form may be brought about by the inclusion of agents, which delay absorption such as aluminum monostearate and gelatin.

In certain embodiments, a described compound or pharmaceutical preparation is administered orally. In other embodiments, a described compound or pharmaceutical preparation is administered intravenously. Alternative routes of administration include sublingual, intramuscular, and transdermal administrations.

When compounds described herein are administered as pharmaceuticals, to humans and animals, they can be given per se or as a pharmaceutical composition containing, for example, 0.1% to 99.5% of active ingredient in combination with a pharmaceutically acceptable carrier. In some embodiments, 0.5% to 90% of active ingredient can be used.

Preparations described herein may be given orally, parenterally, topically, or rectally. They are of course given in forms suitable for the relevant administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

Such compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, compounds described herein which may be used in a suitable hydrated form, and/or the pharmaceutical compositions of the present disclosure, are formulated into pharmaceutically-acceptable dosage forms by conventional methods known to those of skill in the art.

Actual dosage levels of the active ingredients in the pharmaceutical compositions of the disclosure may be varied so as to obtain an amount of the active ingredient that is effective to achieve the desired therapeutic response for a particular patient, composition, and mode of administration, without being toxic to the patient.

The terms "administration of" and or "administering" should be understood to mean providing a pharmaceutical composition in a therapeutically effective amount to the subject in need of treatment. Administration routes can be enteral, topical or parenteral. As such, administration routes include but are not limited to intracutaneous, subcutaneous, intravenous, intraperitoneal, intraarterial, intrathecal, intracapsular, intraorbital, intracardiac, intradermal, transdermal, transtracheal, subcuticular, intraarticular, subcapsular, subarachnoid, intraspinal and intrasternal, oral, sublingual buccal, rectal, vaginal, nasal ocular administrations, as well infusion, inhalation, and nebulization.

The term "cancer" refers to a group diseases characterized by abnormal and uncontrolled cell proliferation starting at one site (primary site) with the potential to invade and to spread to others sites (secondary sites, metastases) which differentiate cancer (malignant tumor) from benign tumor. Virtually all the organs can be affected, leading to more than 100 types of cancer that can affect humans. Cancers can result from many causes including genetic predisposition, viral infection, exposure to ionizing radiation, exposure environmental pollutant, tobacco and or alcohol use, obesity, poor diet, lack of physical activity or any combination thereof.

Exemplary cancers include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Gejin Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood;

Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia; Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood', Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland'Cancer, Childhood; Sarcoma, Ewing's Family of Tumors; Sarcoma, Kaposi's; Sarcoma (OsteosarcomaVMalignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor.

In certain aspects, cancer include Lung cancer, Breast cancer, Colorectal cancer, Prostate cancer, Stomach cancer, Liver cancer, cervical cancer, Esophageal cancer, Bladder cancer, Non-Hodgkin lymphoma, Leukemia, Pancreatic cancer, Kidney cancer, endometrial cancer, Head and neck cancer, Lip cancer, oral cancer, Thyroid cancer, Brain cancer, Ovary cancer, Melanoma, Gallbladder cancer, Laryngeal cancer, Multiple myeloma, Nasopharyngeal cancer, Hodgkin lymphoma, Testis cancer and Kaposi sarcoma.

In certain aspects, the method further includes administering a chemotherapeutic agent. The compounds of the disclosure can be administered in combination with one or more additional therapeutic agents. The phrases "combination therapy", "combined with" and the like refer to the use of more than one medication or treatment simultaneously to increase the response. The tyrosine kinase inhibitor of the present disclosure might for example be used in combination with other drugs or treatment in use to treat cancer. In various aspect, the compound is administered prior to, simultaneously with or following the administration of the chemotherapeutic agent.

The term "anti-cancer therapy" refers to any therapy or treatment that can be used for the treatment of a cancer. Anti-cancer therapies include, but are not limited to, surgery, radiotherapy, chemotherapy, immune therapy and targeted therapies.

Examples of chemotherapeutic agents or anti-cancer agents include, but are not limited to, Actinomycin, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fiuorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, Vinorelbine, panitumamab, Erbitux (cetuximab), matuzumab, IMC-IIF 8, TheraCIM hR3, denosumab, Avastin (bevacizumab), Humira (adalimumab), Herceptin (trastuzumab), Remicade (infliximab), rituximab, Synagis (palivizumab), Mylotarg (gemtuzumab oxogamicin), Raptiva (efalizumab), Tysabri (natalizumab), Zenapax (dacliximab), NeutroSpec (Technetium (99mTc) fanolesomab), tocilizumab, ProstaScint (Indium-Ill labeled Capromab Pendetide), Bexxar (tositumomab), Zevalin (ibritumomab tiuxetan (IDEC-Y2B8) conjugated to yttrium 90), Xolair (omalizumab), MabThera (Rituximab), ReoPro (abciximab), MabCampath (alemtuzumab), Simulect (basiliximab), LeukoScan (sulesomab). CEA-Scan (arcitumomab), Verluma (nofetumomab), Panorex (Edrecolomab), alemtuzumab, CDP 870, natalizumab Gilotrif (afatinib), Lynparza (olaparib), Perjeta (pertuzumab), Otdivo (nivolumab), Bosulif (bosutinib), Cabometyx (cabozantinib), Ogivri (trastuzumab-dkst), Sutent (sunitinib malate), Adcetris (brentuximab vedotin), Alecensa (alectinib), Calquence (acalabrutinib), Yescarta (ciloleucel), Verzenio (abemaciclib), Keytruda (pembrolizumab), Aliqopa (copanlisib), Nerlynx (neratinib), Imfinzi (durvalumab), Darzalex (daratumumab), Tecentriq (atezolizumab), and Tarceva (erlotinib). Examples of immunotherapeutic agent include, but are not limited to, interleukins (Il-2, Il-7, Il-12), cytokines (Interferons, G-CSF, imiquimod), chemokines (CCL3, CCl26, CXCL7), immunomodulatory imide drugs (thalidomide and its analogues).

In treatment, the dose of agent optionally ranges from about 0.0001 mg/kg to about 100 mg/kg, about 0.01 mg/kg to about 5 mg/kg, about 0.15 mg/kg to about 3 mg/kg, 0.5 mg/kg to about 2 mg/kg and about 1 mg/kg to about 2 mg/kg of the subject's body weight. In other embodiments the dose ranges from about 100 mg/kg to about 5 g/kg, about 500 mg/kg to about 2 mg/kg and about 750 mg/kg to about 1.5 g/kg of the subjects body weight. For example, depending on the type and severity of the disease, about 1 μg/kg to 15 mg/kg (e.g., 0.1-20 mg/kg) of agent is a candidate dosage for administration to the patient, whether, for example, by one or more separate administrations, or by continuous infusion. A typical daily dosage is in the range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. Unit doses can be in the range, for instance of about 5 mg to 500 mg, such as 50 mg, 100 mg, 150 mg, 200 mg, 250 mg and 300 mg. The progress of therapy is monitored by conventional techniques and assays.

In some embodiments, an agent is administered to a human patient at an effective amount (or dose) of less than about 1 μg/kg, for instance, about 0.35 to about 0.75 μg/kg or about 0.40 to about 0.60 μg/kg. In some embodiments, the dose of an agent is about 0.35 μg/kg, or about 0.40 μg/kg, or about 0.45 μg/kg, or about 0.50 μg/kg, or about 0.55 μg/kg, or about 0.60 μg/kg, or about 0.65 μg/kg, or about 0.70 μg/kg, or about 0.75 μg/kg, or about 0.80 μg/kg, or about 0.85 μg/kg, or about 0.90 μg/kg, or about 0.95 μg/kg or about 1 μg/kg. In various embodiments, the absolute dose of an agent is about 2 μg/subject to about 45 μg/subject, or about 5 to about 40, or about 10 to about 30, or about 15 to about 25 μg/subject. In some embodiments, the absolute dose of an agent is about 20 μg, or about 30 μg, or about 40 μg.

In various embodiments, the dose of an agent may be determined by the human patient's body weight. For example, an absolute dose of an agent of about 2 μg for a pediatric human patient of about 0 to about 5 kg (e.g. about 0, or about 1, or about 2, or about 3, or about 4, or about 5 kg); or about 3 μg for a pediatric human patient of about 6 to about 8 kg (e.g. about 6, or about 7, or about 8 kg), or about 5 μg for a pediatric human patient of about 9 to about 13 kg (e.g. 9, or about 10, or about 11, or about 12, or about 13 kg); or about 8 μg for a pediatric human patient of about 14 to about 20 kg (e.g. about 14, or about 16, or about 18, or about 20 kg), or about 12 μg for a pediatric human patient of about 21 to about 30 kg (e.g. about 21, or about 23, or about 25, or about 27, or about 30 kg), or about 13 μg for a pediatric human patient of about 31 to about 33 kg (e.g. about 31, or about 32, or about 33 kg), or about 20 μg for an adult human patient of about 34 to about 50 kg (e.g. about 34, or about 36, or about 38, or about 40, or about 42, or about 44, or about 46, or about 48, or about 50 kg), or about 30 μg for an adult human patient of about 51 to about 75 kg (e.g. about 51, or about 55, or about 60, or about 65, or about 70, or about 75 kg), or about 45 μg for an adult human patient of greater than about 114 kg (e.g. about 114, or about 120, or about 130, or about 140, or about 150 kg).

In certain embodiments, an agent in accordance with the methods provided herein is administered subcutaneously (s.c.), intraveneously (i.v.), intramuscularly (i.m.), intranasally or topically. Administration of an agent described herein can, independently, be one to four times daily or one to four times per month or one to six times per year or once every two, three, four or five years. Administration can be for the duration of one day or one month, two months, three months, six months, one year, two years, three years, and may even be for the life of the human patient. The dosage may be administered as a single dose or divided into multiple doses. In some embodiments, an agent is administered about 1 to about 3 times (e.g. 1, or 2 or 3 times).

Presented below are examples discussing the design and evaluation of efficacy of new tyrosine kinase inhibitors, contemplated for the discussed applications. The following examples are provided to further illustrate the embodiments of the present disclosure, but are not intended to limit the scope of the disclosure. While they are typical of those that might be used, other procedures, methodologies, or techniques known to those skilled in the art may alternatively be used.

EXAMPLES

Example 1

(S,E)-N-(1-((2-((2-((4-(cyanomethyl)phenyl)amino)-6-(5-methyl-1H-pyrazol-3-yl)amino)pyrimidin-4-yl)amino)ethyl)amino)-1-oxopropan-2-yl)-4-(dimethylamino)-N-methylbut-2-enamide (Compound 1)

Scheme 4. Synthesis of compound 1.

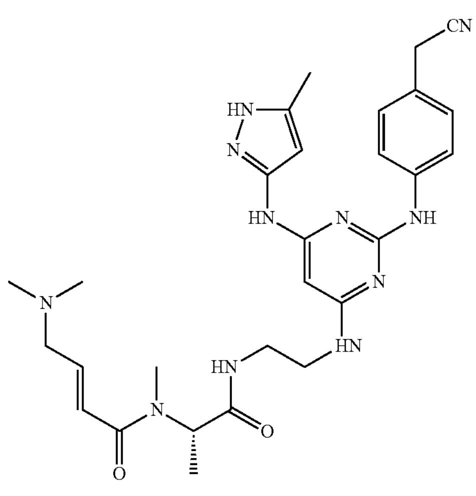

-continued
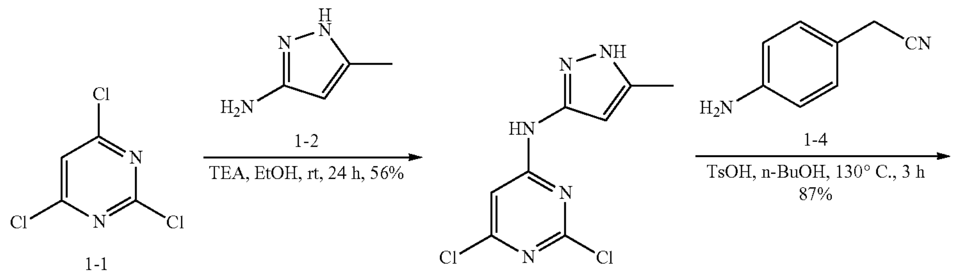
1-1
1-3
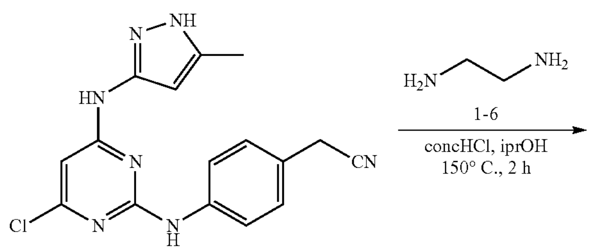
1-5
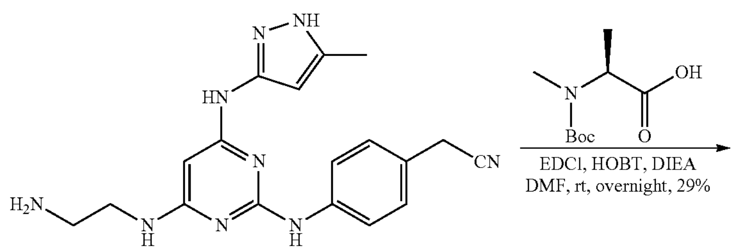
1-7
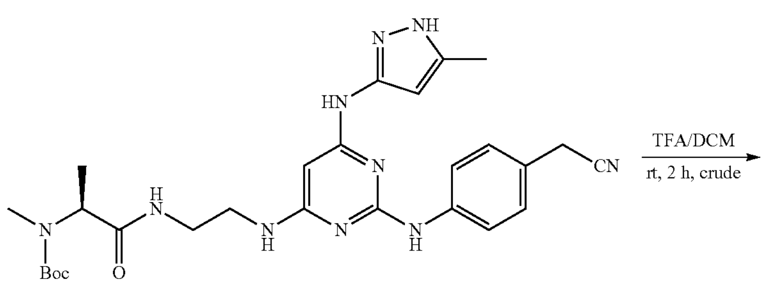
1-9
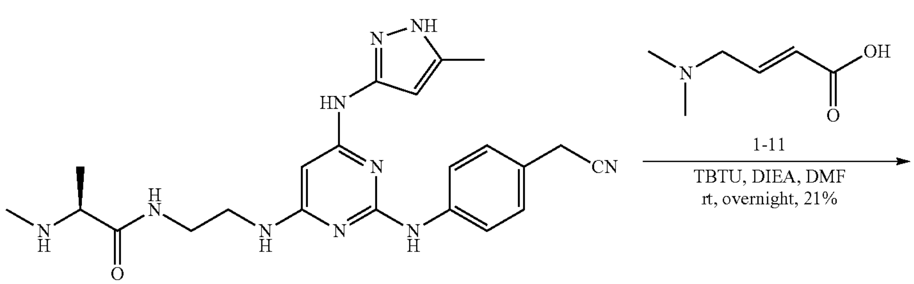
1-10

-continued

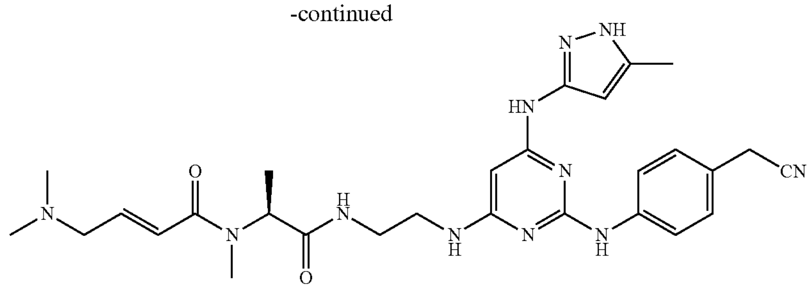

compound 1

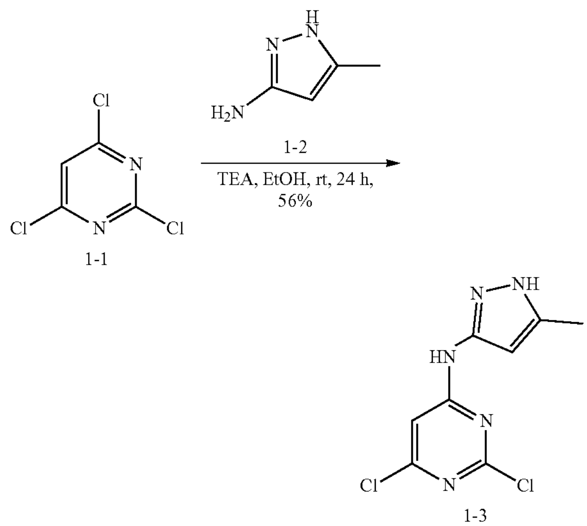

To a solution of compound 1-1 (10 g, 55.0 mmol, 1.0 eq) and compound 1-2 (6.4 g, 66.0 mmol, 1.2 eq) in ethanol (100 mL) was added triethylamine (11.1 g, 110 mmol. 2.0 eq) at room temperature. Then the resulting suspension was stirred for 24 h at room temperature. The reaction was monitored by TLC. The ethanol was removed by vacuo. Then the residue was diluted with ethyl acetate (200 mL) and water (100 mL). The organic phase and aqueous phase were separated. The aqueous phase was extracted with ethyl acetate (200 mL×2). The organic phase was dried with anhydrous sodium sulfate and concentrated in vacuo. The residue was purified by column chromatography on a silica gel (dichloromethane: methanol; 10:1) to get compound 1-3 (7.5 g, 56%) as yellow solid. TLC: dichloromethane:methanol=10:1, UV 254 nm. $R_f$ (compound 3)=0.3

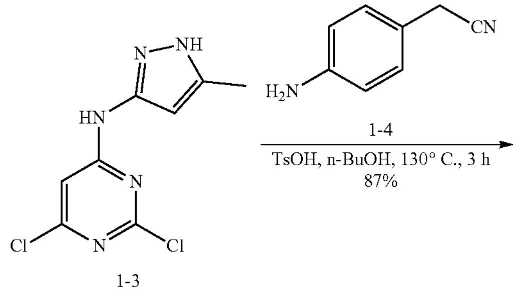

-continued

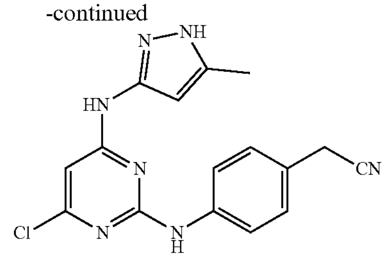

1-5

To a solution of compound 1-3 (5 g, 20.5 mmol, 1.0 eq) and compound 1-4 (3.3 g, 24.6 mmol, 1.2 eq) in n-butanol (100 mL) was added p-Toluenesulfonic acid (0.72 g, 4.1 mmol, 0.2 eq) at room temperature. Then the resulting suspension was heated to 130° C. for 3 h. The reaction was monitored by TLC. The n-butanol was removed by vacuo. Then the residue was diluted with ethyl acetate (200 mL) and water (100 mL). The organic phase and aqueous phase were separated. The aqueous phase was extracted with ethyl acetate (200 mL×2). The organic phase was dried with anhydrous sodium sulfate and concentrated in vacuo. The residue was purified by column chromatography on a silica gel (dichloromethane:methanol; 10:1) to get compound 1-5 (6.2 g, 87%) as yellow solid. TLC: dichloromethane:methanol=10:1, UV 254 nm. $R_f$ (compound 5)=0.2

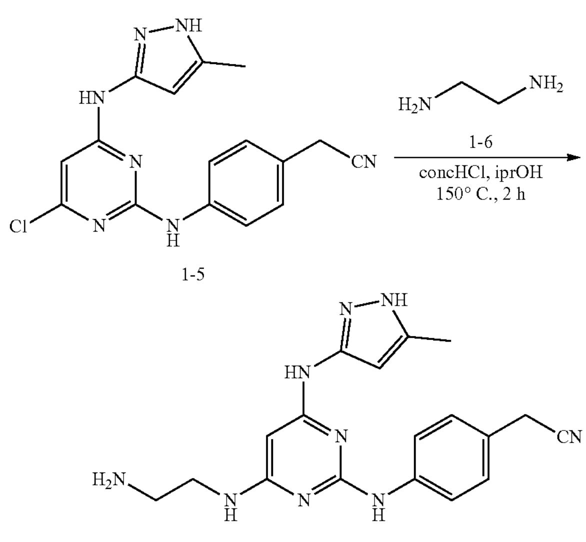

Compound 1-5 (1.3 g, 3.8 mmol, 1.0 eq) and ethylenediamine (1.15 g, 19 mmol, 5.0 eq) were dissolved in isopropanol (10 mL), two drops conc. HCl was added, then the mixture was treated with microwave at 150° C. for 2 h. The solvent and excess ethylenediamine was removed in vacuo, the residue was purified via reverse phase column to afford compound 1-7 (480 mg, 35%) as white solid. $^1$H NMR (400 MHz, $CD_3OH$): δ 8.55-8.45 (br. s, 1H), 7.69-7.67 (d, J=8.4 Hz, 2H), 7.29-7.27 (d, J=8.0 Hz, 2H), 6.73-6.59 (m, 2H), 5.81 (s, 1H), 5.30-5.25 (m, 1H), 3.83 (s, 2H), 3.68-3.41 (m, 7H), 2.96 (s, 3H), 2.80-2.65 (m, 6H), 2.23 (s, 3H) and 1.31-1.29 (m, 3H). LCMS: [M+1]=560, [M−1]=558.

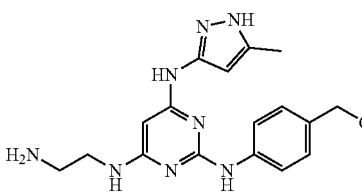

1-7

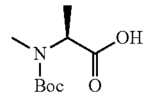

1-8

EDCl, HOBT,
DIEA
DMF, rt,
overnight, 29%

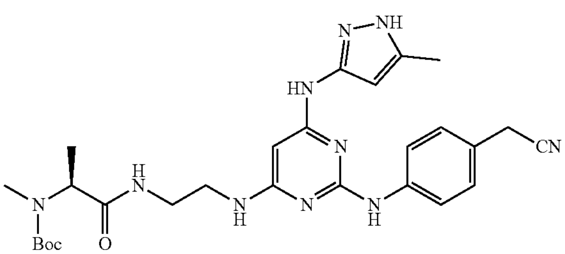

1-9

To the mixture of compound 1-7 (480 mg, 1.32 mmol, 1.0 eq), 1-ethyl-3-(3-dimethylaminopropyl)carbodiimide hydrochloride (380 mg, 1.98 mmol, 1.5 eq), 1-Hydroxybenzotriazole (357 mg, 2.64 mmol, 2.0 eq) and N,N-diisopropylethylamine (510 mg, 3.96 mmol, 3.0 eq) in dimethylformamide (10 mL) was added compound 1-8 (268 mg, 1.32 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified by column chromatography on a silica gel (dichloromethane:methanol, 10:1) to give compound 1-9 (213 mg, 29%) as white solid. TLC: dichloromethane:methanol=10:1 UV 254 nm; $R_f$ (compound 9)=0.1

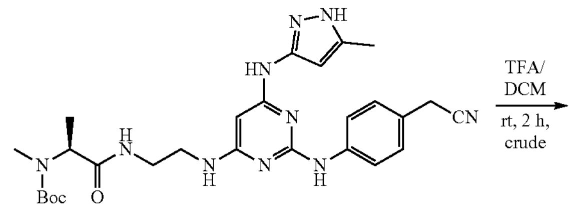

1-7

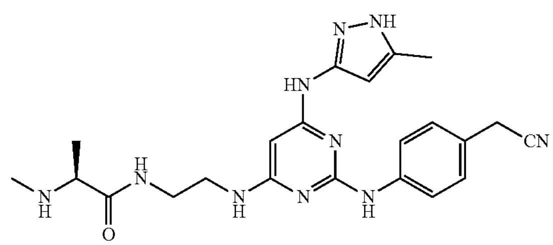

1-10

The mixture of compound 1-9 (213 mg, 0.39 mmol, 1.0 eq) in Trifluoroacetic acid/dichloromethane (2 mL/2 mL) was stirred at room temperature for 2 h under nitrogen atmosphere. LCMS analysis of the reaction mixture showed full conversion to the desired product. The residue was concentrated under reduced pressure to give compound 1-10 (310 mg, crude) as yellow solid.

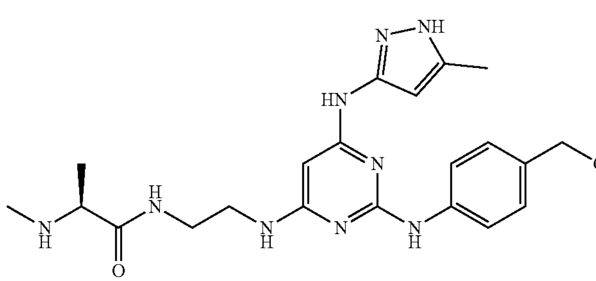

1-10

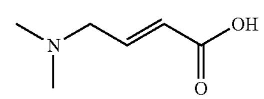

1-11

TBTU, DIEA, DMF
rt, overnight, 21%

-continued

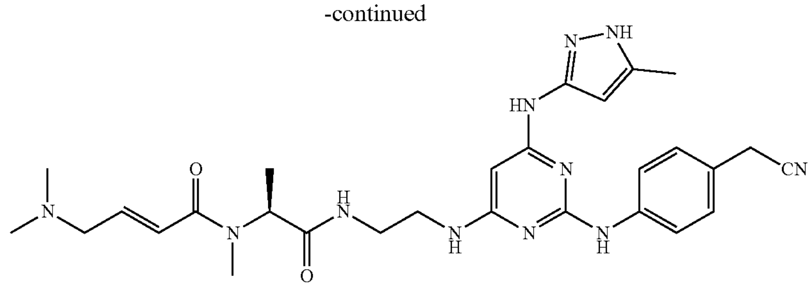

compound 1

To the mixture of compound 1-10 (310 mg, 0.69 mmol, 1.0 eq), 2-(7-Aza-1H-Benzotriazole-1-yl)-1,1,3,3-Tetramethyluronium Hexafluorophosphate (393 mg, 1.04 mmol, 1.5 eq) and N,N-diisopropylethylamine (222 mg, 1.72 mmol, 2.5 eq) in dimethylformamide (10 mL) was added compound 1-11 (89 mg, 0.69 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified via reverse phase column to afford compound 1 (8.0 mg, 21%) as yellow solid. $^{1}H$ NMR (400 MHz, $CD_3OH$): δ 8.55-8.45 (br. s, 1H), 7.69-7.67 (d, J=8.4 Hz, 2H), 7.29-7.27 (d, J=8.0 Hz, 2H), 6.73-6.59 (m, 2H), 5.81 (s, 1H), 5.30-5.25 (m, 1H), 3.83 (s, 2H), 3.68-3.41 (m, 7H), 2.96 (s, 3H), 2.80-2.65 (m, 6H), 2.23 (s, 3H) and 1.31-1.29 (m, 3H). LCMS: [M+1]=560, [M−1]=558.

Example 2

Compound 2

Scheme 5. Synthesis of compound 2.

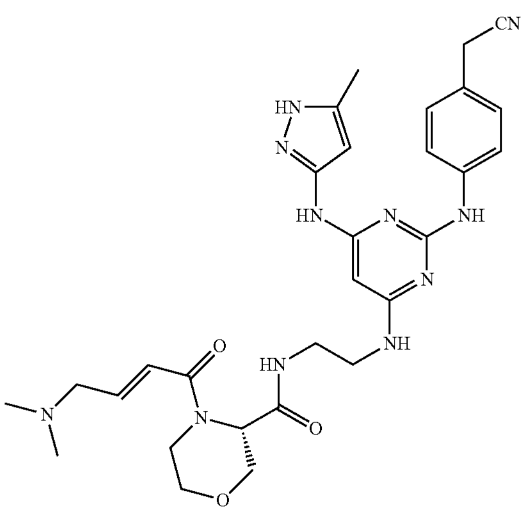

-continued

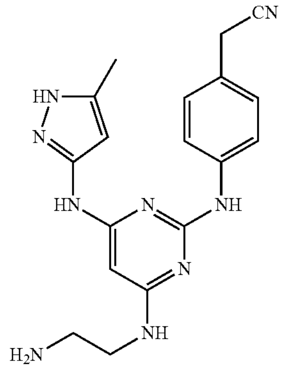

1-7

+

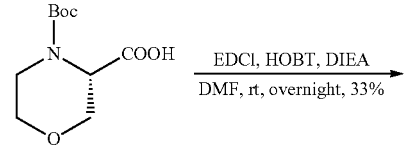

2-1

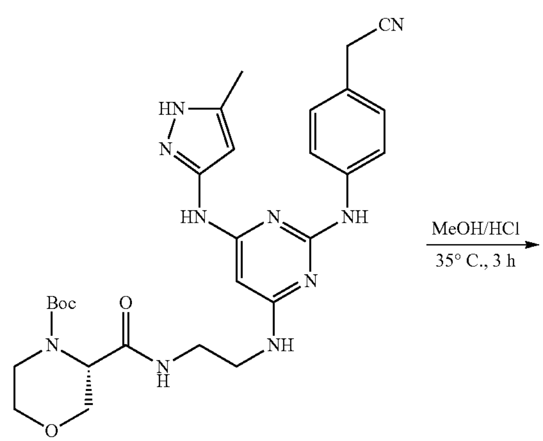

2-2

-continued

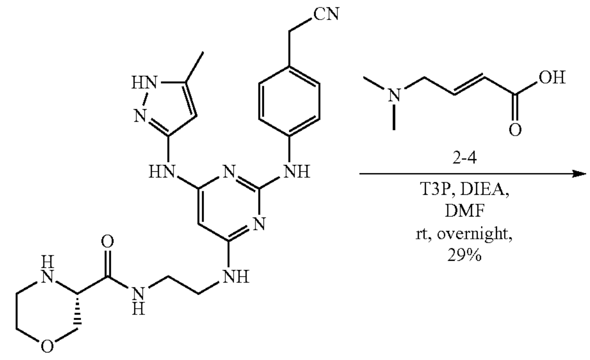

2-3

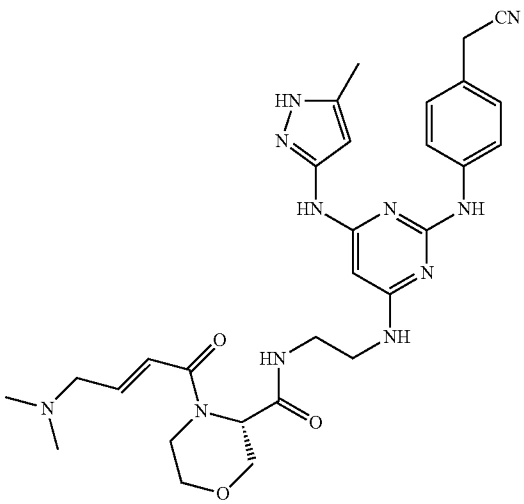

compound 2

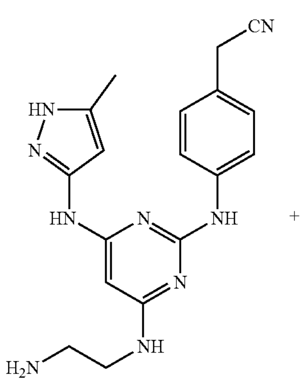

1-7

-continued

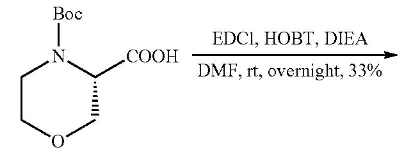

2-1

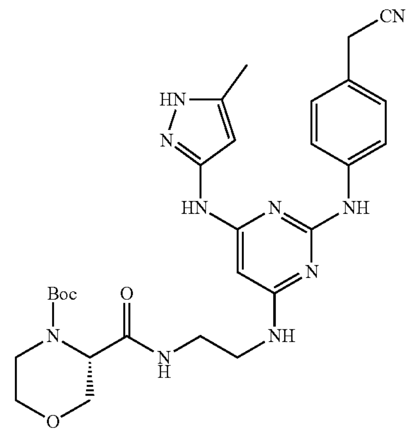

2-2

Synthesis of compound 1-7 is shown in Example 1. To the mixture of compound 1-7 (200 mg, 0.55 mmol, 1.0 eq), 1-Ethyl-3-(3-dimethylaminopropyl)carbodiimide hydrochloride (159 mg, 0.83 mmol, 1.5 eq), 1-Hydroxybenzotriazole (149 mg, 1.1 mmol, 2.0 eq) and N,N-diisopropylethylamine (213 mg, 1.65 mmol, 3.0 eq) in dimethylformamide (10 mL) was added compound 2-1 (127 mg, 0.55 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified by column chromatography on a silica gel (dichloromethane:methanol, 10:1) to give compound 2-2 (105 mg, 33%) as white solid. TLC: dichloromethane:methanol=10:1, UV 254 nm; $R_f$ (compound 2-2)=0.1

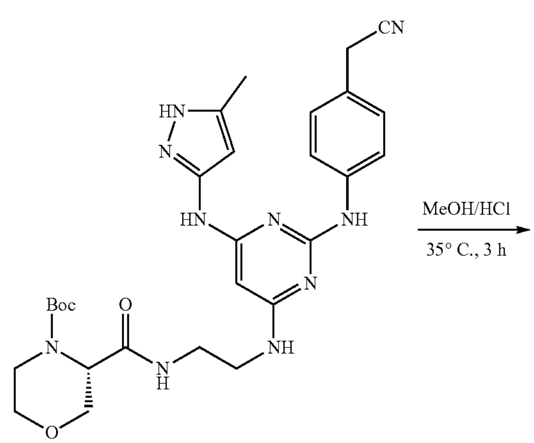

2-2

-continued

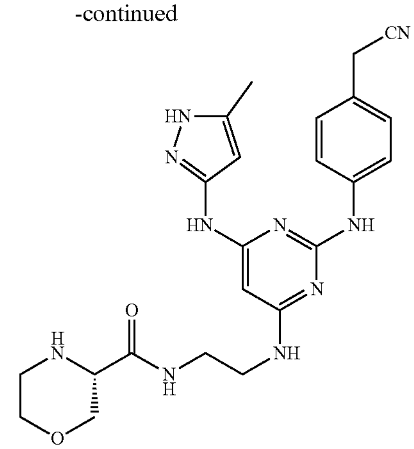

2-3

To a solution of compound 2-2 (105 mg, 0.18 mmol, 1.0 eq) in methanol (10 mL) was added hydrochloric acid/methanol (4 N, 5 mL) and then the mixture was stirred at 35° C. for 3 h. LCMS analysis of the reaction mixture showed full conversion to the desired product. The residue was concentrated under reduced pressure to give compound 2-3 (110 mg, crude) as yellow solid.

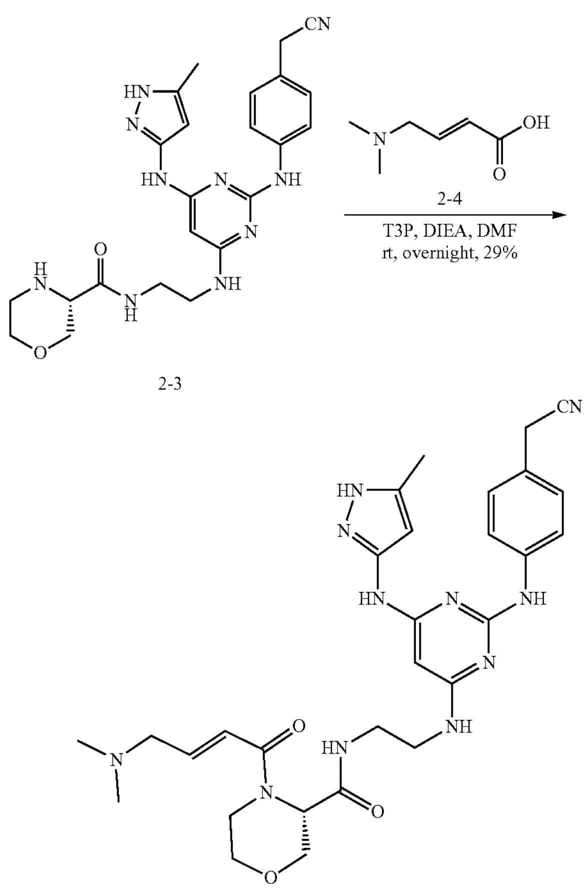

2-3 compound 2

To the mixture of compound 2-3 (110 mg, 0.23 mmol, 1.0 eq), Propylphosphonic anhydride (110 mg, 0.35 mmol, 1.5 eq) and N,N-diisopropylethylamine (89 mg, 0.69 mmol, 3.0 eq) in dimethylformamide (10 mL) was added compound 2-4 (30 mg, 0.23 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified via reverse phase column to afford compound 2 (39 mg, 29%) as white solid. LCMS: [M+1]=588 HNMR (400 MHz, DMSO): δ 10.47 (m, 1H), 9.85 (m, 1H), 8.20 (m, 2H), 7.63 (m, 2H), 7.35-7.33 (m, 2H), 6.86 (m, 1H), 6.60 (m, 1H), 5.70 (m, 1H), 4.75 (s, 1H), 4.00 (s, 3H), 3.88 (s, 2H), 3.78 (m, 3H), 3.75 (m, 3H), 3.49 (m, 4H), 3.13 (m, 4H). 7.75 (m, 8H) and 2.22 (s, 3H).

Example 3

Compound 3

Scheme 6. Synthesis of compound 3.

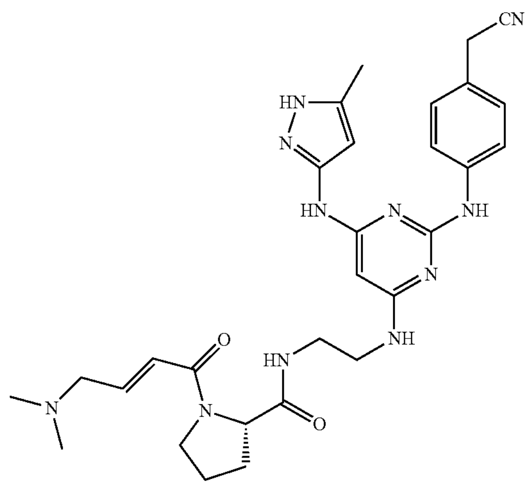

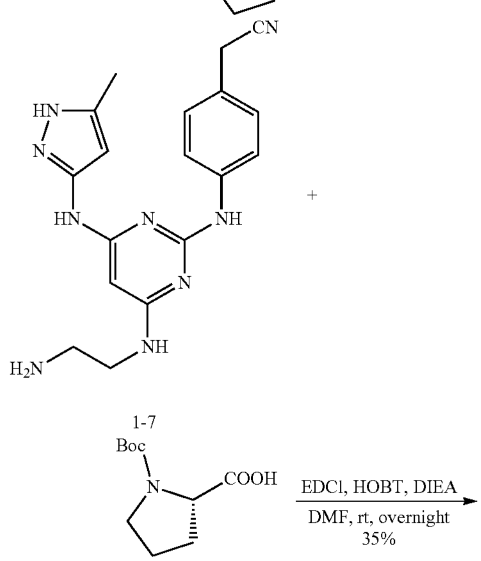

1-7

3-1

-continued

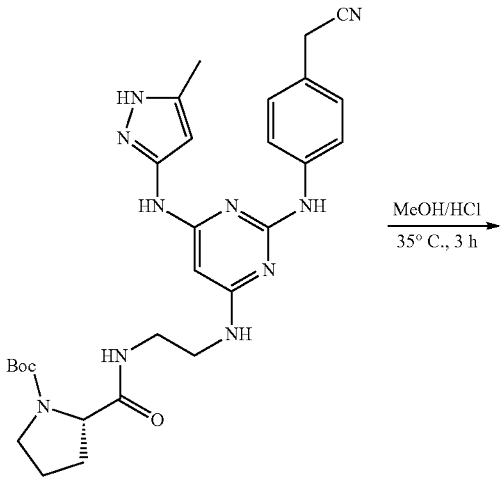

3-2

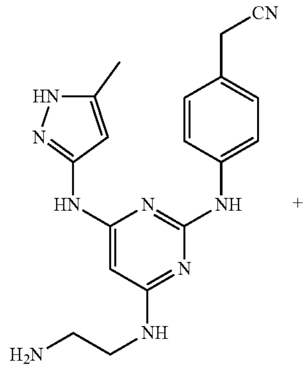

1-7

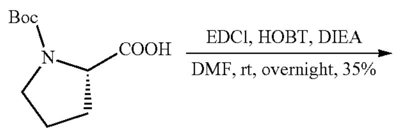

3-1

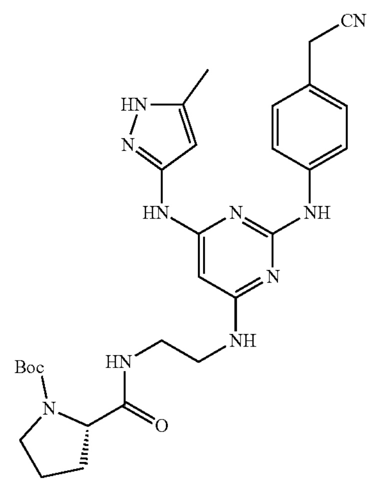

3-2

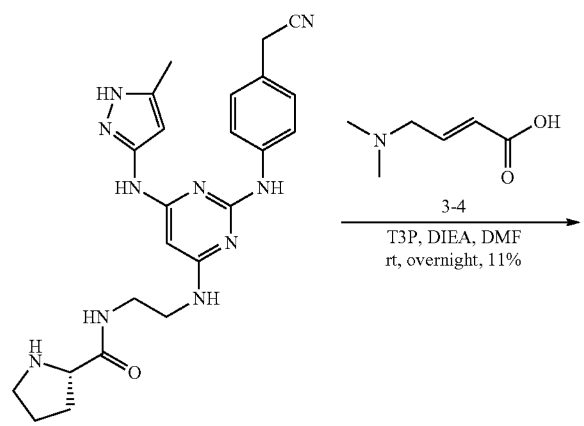

3-3

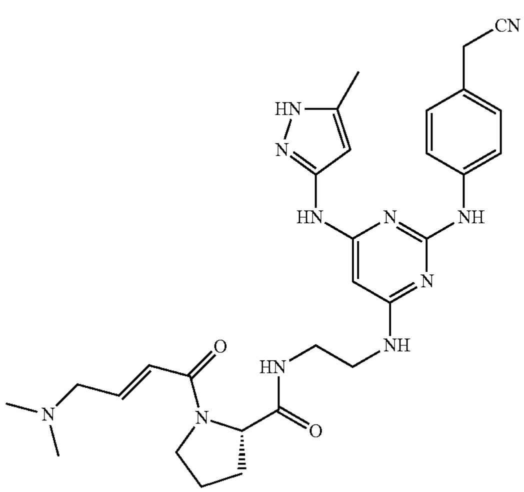

compound 3

Synthesis of compound 1-7 is shown in Example 1. To the mixture of compound 1-7 (130 mg, 0.36 mmol, 1.0 eq), 1-Ethyl-3-(3-dimethylaminopropyl)carbodiimide hydrochloride (103 mg, 0.54 mmol, 1.5 eq), 1-Hydroxybenzotriazole (97 mg, 0.72 mmol, 2.0 eq) and N,N-diisopropylethylamine (139 mg, 1.08 mmol, 3.0 eq) in dimethylformamide (10 mL) was added compound 3-1 (77 mg, 0.36 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified by column chromatography on a silica gel (dichloromethane:methanol, 10:1) to give compound 3-2 (70 mg, 35%) as white solid. TLC: dichloromethane:methanol=10:1, UV 254 nm; $R_f$ (compound 3-2)=0.3

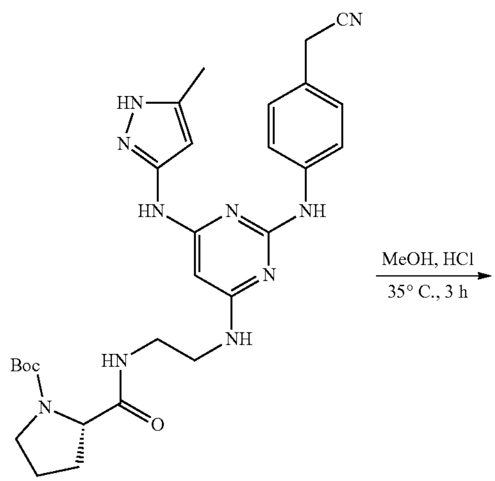

3-2

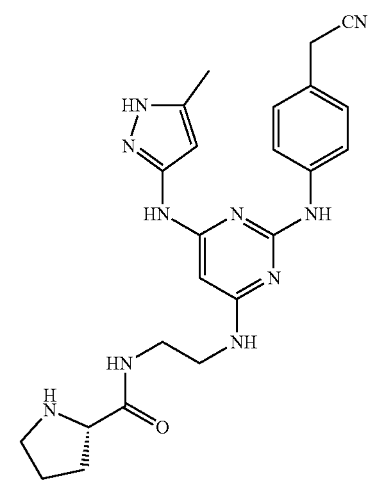

3-3

To a solution of compound 3-2 (70 mg, 0.12 mmol, 1.0 eq) in methanol (10 mL) was added hydrochloric acid/methanol (4 N, 5 mL) and then the mixture was stirred at 35° C. for 3 h. LCMS analysis of the reaction mixture showed full conversion to the desired product. The residue was concentrated under reduced pressure to give compound 3-3 (70 mg, crude) as yellow solid.

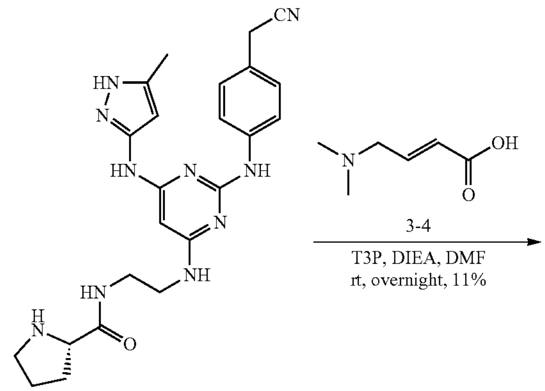

3-3

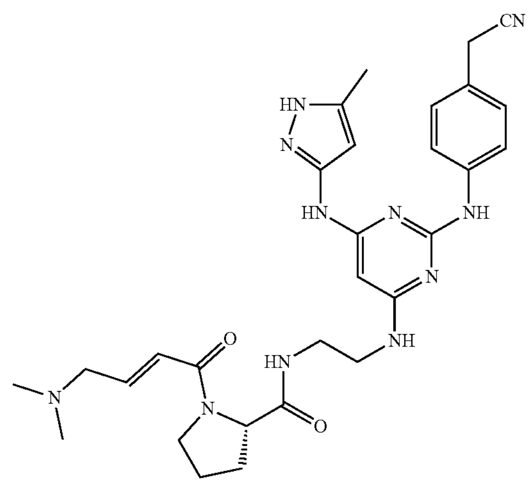

compound 3

To the mixture of compound 3-3 (70 mg, 0.15 mmol, 1.0 eq), 2-(7-Aza-1H-Benzotriazole-1-yl)-1,1,3,3-Tetramethyluronium Hexafluorophosphate (86 mg, 0.23 mmol, 1.5 eq) and N,N-diisopropylethylamine (48 mg, 0.37 mmol, 2.5 eq) in dimethylformamide (10 mL) was added compound 3-4 (89 mg, 20 mmol, 1.0 eq). The mixture was stirred at room temperature overnight under nitrogen atmosphere. TLC analysis of the reaction mixture showed full conversion to the desired product. Then the mixture was added water and extracted with ethyl acetate (3×10 mL). The organic layer was washed with brine. The residue was dried over sodium sulfate and concentrated under reduced pressure. The residue was purified via reverse phase column to afford compound 3 (9.0 mg, 11%) as yellow solid. LCMS: [M+1]=572 HNMR (400 MHz, DMSO): δ 8.30 (m, 1H), 7.63-7.61 (m, 2H), 7.41-7.39 (m, 2H), 6.79-6.68 (m. 2H), 5.74 (m, 1H), 4.74-4.39 (m, 1H), 3.93-3.80 (m, 4H), 3.74-3.46 (m, 8H), 2.99-2.68 (m, 6H), 2.27 (s, 3H) and 2.22-1.94 (m, 6H).

Example 4
(2S)—N-[2-[[2-[4-(cyanomethyl)anilino]-6-[(5-cyclobutyl-1H-pyrazol-3-yl)amino]pyrimidin-4-yl]amino]ethyl]-2-[methyl(prop-2-enoyl)amino]propanamide (Compound 4)
Scheme 7. Synthesis of compound 4.
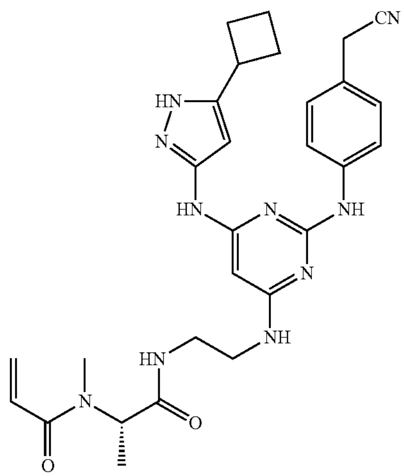
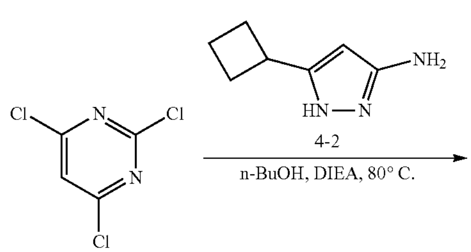
4-1
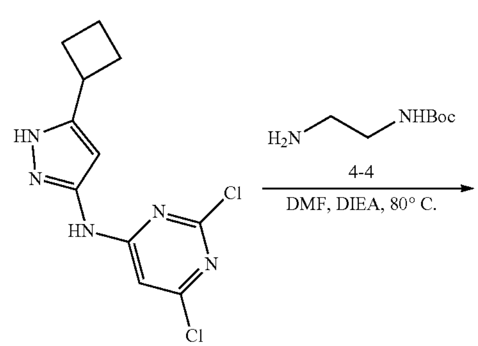
4-3
-continued
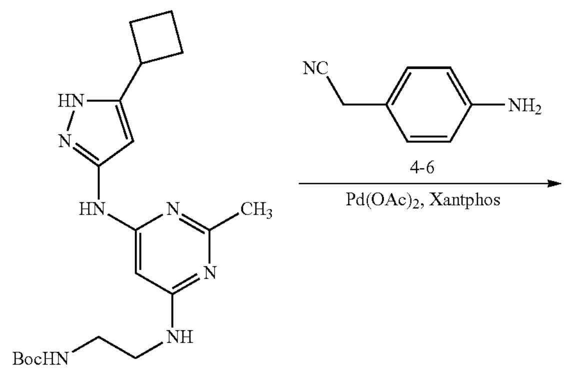
4-5
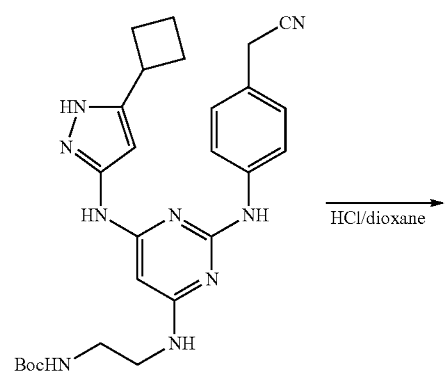
4-7
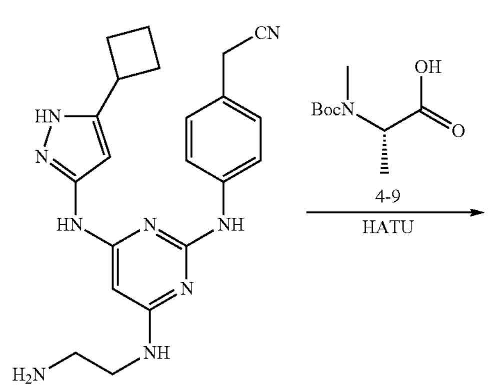
4-8

-continued

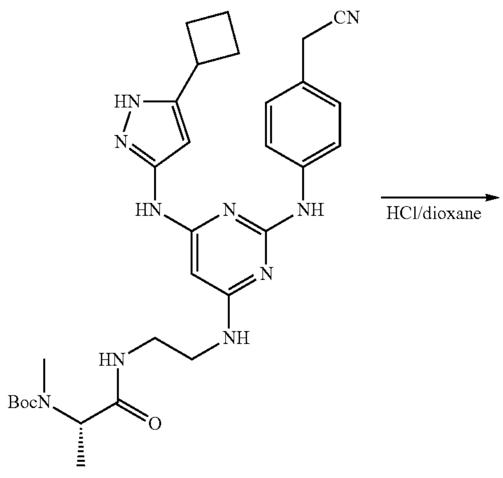

4-10

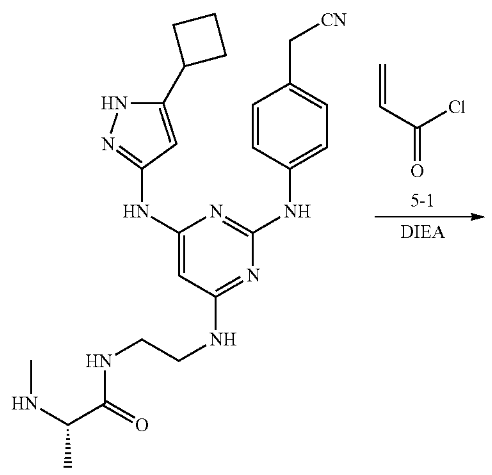

4-11

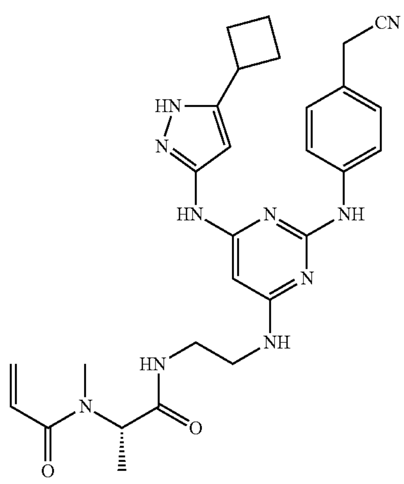

compound 4

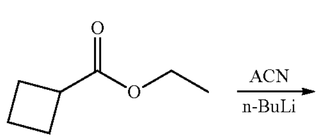

4-13

-continued

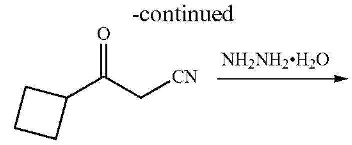

4-14

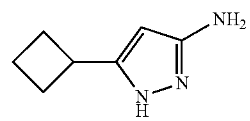

4-2

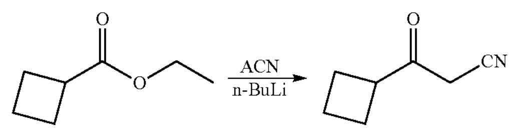

4-13

4-14

To a solution of MeCN (6.41 g, 156.04 mmol, 8.21 mL) in THF (200 mL) was added n-BuLi (2.5 M in hexane, 62.4 mL) stirred at −78° C. for 0.5 h. After that a solution of ethyl cyclobutanecarboxylate (10 g, 78.02 mmol, 10.78 mL) in THF (200 mL) added into the mixture and stirred at −78° C. for 0.5° C. Then the mixture was warmed to −45° C. and stirred for 2 h. The mixture was quenched by addition of $H_2O$ (50 mL) at 25° C., and then diluted with $H_2O$ (100 mL) and extracted with EtOAc (80×3). The combined organic layers were washed with brine (100 mL), dried over $Na_2SO_4$, filtered and concentrated under reduced pressure to afford 3-cyclobutyl-3-oxo-propanenitrile (10 g, crude) as yellow oil, which would be used directly in the next step. IE NMR (400 MHz, DMSO-$d_6$): δ=3.6 (s, 2H), 2.98-2.96 (m, 1H), 2.90-2.89 (m, 1H), 2.8 (s, 2H), 2.72-2.70 (m, 2H), 2.55-2.52 (m, 2H).

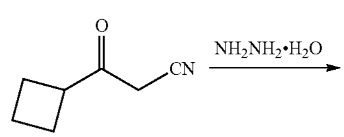

4-14

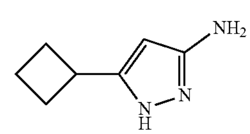

4-2

To a solution of 3-cyclobutyl-3-oxo-propanenitrile (9.5 g, 77.14 mmol) in EtOH (10 mL) was added $NH_2NH_2 \cdot H_2O$ (4.25 g, 84.85 mmol, 4.12 mL). The mixture was stirred at 75° C. for 12 h. The mixture was quenched by addition of $H_2O$ (50 mL) at 25° C., and then diluted with $H_2O$ (100 mL) and extracted with EtOAc (100×3). The combined organic layers were washed with brine (100 mL), dried over $Na_2SO_4$, filtered and concentrated under reduced pressure. The residue was purified by flash silica gel chromatography (ISCO®; 80 g SepaFlash® Silica Flash Column, Eluent of 0~10% DCM/MEOH @ 50 mL/min) to afford 5-cyclobutyl-1H-pyrazol-3-amine (4.7 g, 30.83 mmol, 40% yield, 90% purity) as yellow oil. $^1$H NMR (400 MHz, $CDCl_3$): δ=5.94-5.48 (m, 2H), 5.60 (s, 1H), 3.43-3.32 (m, 1H), 2.32-2.21 (m, 2H), 2.14-2.03 (m, 2H), 2.01-1.78 (m, 2H).

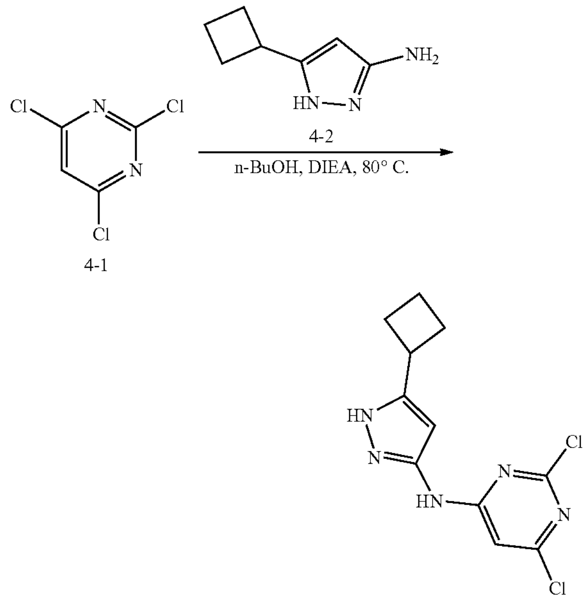

4-2

4-1

4-3

To a solution of 2,4,6-trichloropyrimidine (3 g, 16.36 mmol) in butan-1-ol (30 mL) was added DIPEA (6.34 g, 49.07 mmol) and 5-cyclobutyl-1H-pyrazol-3-amine (2.24 g, 16.36 mmol). The mixture was stirred at 80° C. for 1 h. The mixture was quenched by addition of $H_2O$ (50 mL) at 25° C., and then diluted with $H_2O$ (100 mL) and extracted with EtOAc (100×3). The combined organic layers were washed with brine (50 mL), dried over $Na_2SO_4$, filtered and concentrated under reduced pressure. The residue was purified by flash silica gel chromatography (ISCO®; 20 g Sepa-Flash® Silica Flash Column, Eluent of 0100% Ethyl acetate/Petroleum ether gradient @ 50 mL/min) to afford 2,6-dichloro-N-(5-cyclobutyl-1H-pyrazol-3-yl)pyrimidin-4-amine (3 g, 9.50 mmol, 58% yield, 90% purity) as a light yellow solid. $^1$H NMR (400 MHz, DMSO-$d_6$): δ=12.34 (s, 1H), 10.80-10.62 (m, 1H), 7.81 (s, 1H), 5.86 (s, 1H), 3.56-3.52 (m, 1H), 2.33-2.30 (m, 2H), 2.18-2.12 (m, 2H), 2.02-1.97 (m, 1H), 1.89484 (m, 1H).

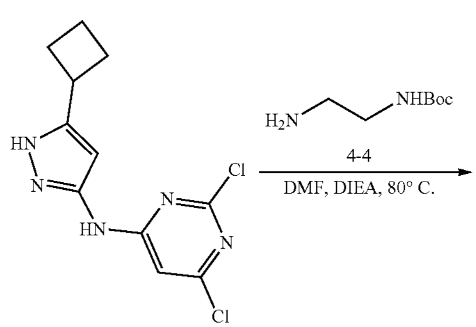

4-4

4-3

-continued

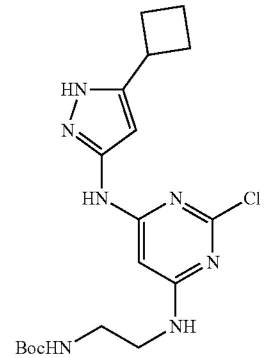

4-5

To a solution of 2,6-dichloro-N-(5-cyclobutyl-1H-pyrazol-3-yl)pyrimidin-4-amine (3 g, 10.56 mmol) in DMSO (20 mL) was added DIPEA (4.09 g, 31.67 mmol) and tert-butyl N-(2-aminoethyl)carbamate (2.03 g, 12.67 mmol). The mixture was stirred at 80° C. for 5 h. The mixture was quenched by addition of $H_2O$ (50 mL) at 25° C., and then diluted with $H_2O$ (50 mL) and extracted with EtOAc (100×3). The combined organic layers were washed with brine (50 mL), dried over $Na_2SO_4$, filtered and concentrated under reduced pressure. The residue was purified by flash silica gel chromatography (ISCO®; 20 g SepaFlash® Silica Flash Column, Eluent of 0~40% Ethyl acetate/Petroleum ether gradient a 50 mL/min) to afford tert-butyl N-[2-[[2-chloro-6-[(5-cyclobutyl-1H-pyrazol-3-yl)amino]pyrimidin-4-yl]amino]ethyl]carbamate (2.6 g, 5.74 mmol, 54% yield, 90% purity) as a light yellow solid. $^1$H NMR (400 MHz, DMSO-$d_6$): δ=12.01 (s, 1H), 9.62 (s, 1H), 7.25-7.01 (m, 1H), 6.94-6.77 (m, 1H), 6.40 (s, 2H), 3.54-3.41 (m, 1H), 3.31 (s, 2H), 3.11 (d, J=5.2 Hz, 2H), 2.32-2.22 (m, 2H), 2.20-2.07 (m, 2H), 1.98-1.91 (m, 1H), 1.89-1.81 (m, 1H), 1.38 (s, 9H).

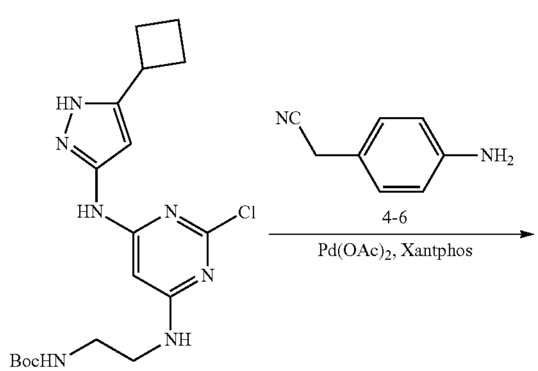

4-6

-continued

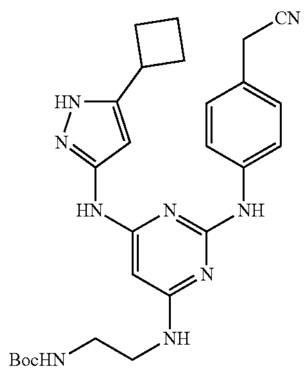

4-7

A mixture of tert-butyl N-[2-[[2-chloro-6-[(5-cyclobutyl-1H-pyrazol-3-yl)amino]pyrimidin-4-yl]amino]ethyl]carbamate (2.6 g, 6.37 mmol), 2-(4-aminophenyl)acetonitrile (1.01 g, 7.65 mmol), $Pd(OAc)_2$ (143 mg, 0.637 mmol), [2-(2-diphenylphosphanylphenoxy)phenyl]-diphenyl-phosphane (687 mg, 1.27 mmol) and $Cs_2CO_3$ (2.08 g, 6.37 mmol) in dioxane (20 mL) was degassed and purged with $N_2$ for 3 times, and then the mixture was stirred at 100° C. for 12 hr under $N_2$ atmosphere. The mixture was quenched by addition of $H_2O$ (50 mL) at 25° C., and then diluted with $H_2O$ (50 mL) and extracted with EtOAc (50×3). The combined organic layers were washed with brine (50 mL), dried over $Na_2SO_4$, filtered and concentrated under reduced pressure. The residue was purified by flash silica gel chromatography (ISCO®; 20 g SepaFlash® Silica Flash Column, Eluent of 0~10% DCM/MeOH @ 50 mL/min) to afford tert-butyl N-[2-[[2-[4-(cyanomethyl)anilino]-6-[(5-cyclobutyl-1H-pyrazol-3-yl)amino]pyrimidin-4-yl]amino]ethyl]carbamate (2 g, 2.78 mmol, 44% yield, 70% purity) as a brown solid. $^1H$ NMR (400 MHz, DMSO-$d_6$): δ=12.07-11.74 (m, 1H), 9.15-8.74 (m, 2H), 7.73 (d, J=8.4 Hz, 2H), 7.24 (d, J=8.4 Hz, 2H), 6.91 (s, 1H), 6.38-6.21 (m, 1H), 6.04-5.84 (m, 1H), 5.80 (s, 1H), 3.96 (s, 2H), 3.55-3.45 (m, 2H), 3.38-3.35 (m, 1H), 3.25-3.15 (m, 3H), 2.31 (d, J=8.0 Hz, 2H), 2.21-2.15 (m, 2H), 2.01-1.95 (m, 1H), 1.92-1.86 (m, 1H). 1.43 (s, 9H).

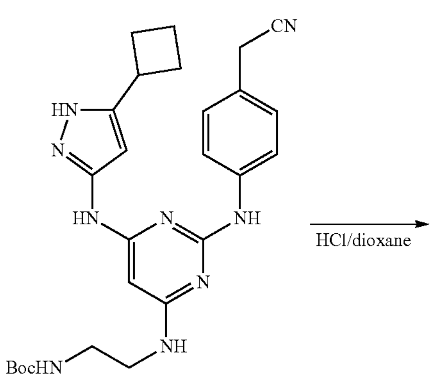

4-7

-continued

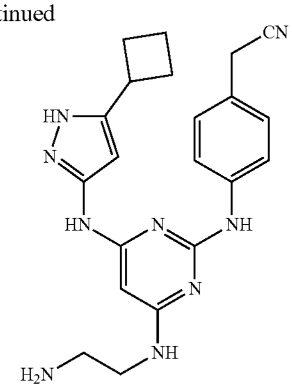

4-8

A solution of tert-butyl N-[2-[[2-[4-(cyanomethyl)anilino]-6-[(5-cyclobutyl-1H-pyrazol-3-yl)amino]pyrimidin-4-yl]amino]ethyl]carbamate (2 g, 3.97 mmol) in HCl/dioxane (4 M, 30 mL) was stirred at 25° C. for 0.5 hr. The mixture was concentrated under reduced pressure to afford 2-[4-[[4-(2-aminoethylamino)-6-[(5-cyclobutyl-1H-pyrazol-3-yl)amino]pyrimidin-2-yl]amino]phenyl]acetonitrile (1.7 g, crude) as a light yellow solid, which would be used directly in the next step.

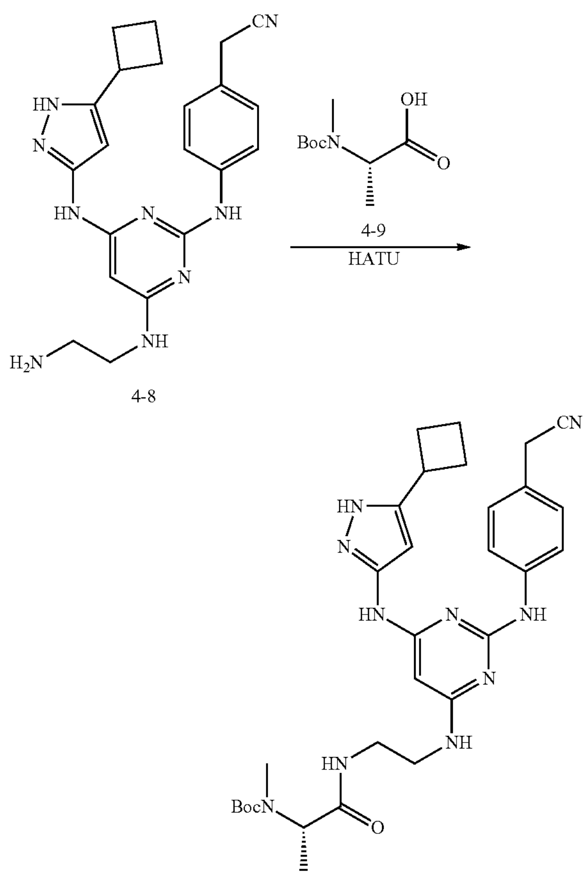

4-10

To a solution of 2-[4-[[4-(2-aminoethylamino)-6-[(5-cyclobutyl-1H-pyrazol-3-yl)amino]pyrimidin-2-yl]amino]phenyl]acetonitrile (700 mg, 1.73 mmol) in DMF (5 mL)

was added DIPEA (673 mg, 5.20 mmol) and HATU (792 mg, 2.08 mmol) and (2S)-2-[tert-butoxycarbonyl(methyl)amino]propanoic acid (211 mg, 1.04 mmol). The mixture was stirred at 0° C. for 0.5 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to afford tert-butyl N-[(1S)-2-[2-[[2-[4-(cyanomethyl)anilino]-6-[(5-cyclobutyl-1H-pyrazol-3-yl)amino]pyrimidin-4-yl]amino]ethylamino]-1-methyl-2-oxo-ethyl]-N-methyl-carbamate (1.2 g, crude) and as a light yellow solid.

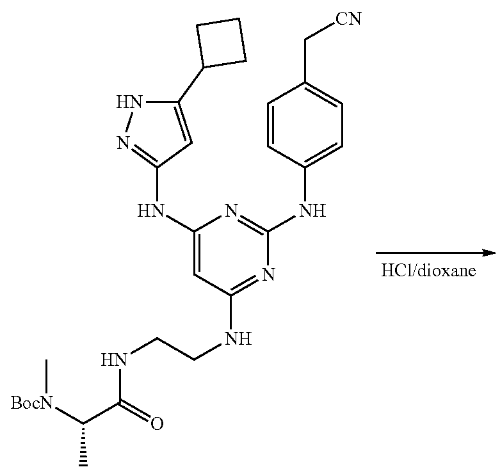

4-10

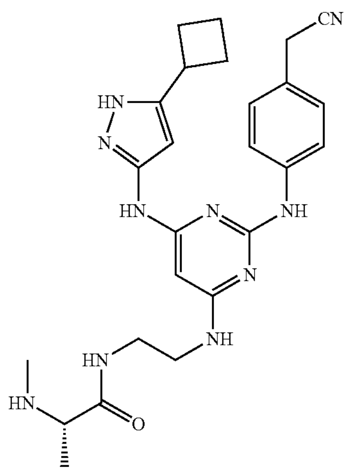

4-11

A solution of tert-butyl N-[(1S)-2-[2-[[2-[4-(cyanomethyl)anilino]-6-[(5-cyclobutyl-1H-pyrazol-3-yl)amino]pyrimidin-4-yl]amino]ethylamino]-1-methyl-2-oxo-ethyl]-N-methyl-carbamate (1.2 g, 2.04 mmol) in HCl/dioxane (4 M, 50 mL) was stirred at 25° C. for 0.5 hr. The mixture was concentrated under reduced pressure to afford (2S)—N-[2-[[2-[4-(cyanomethyl)anilino]-6-[(5-cyclobutyl-1H-pyrazol-3-yl)amino]pyrimidin-4-yl]amino]ethyl]-2-(methylamino)propanamide (1 g, crude) as a yellow solid, which was used directly in the next step.

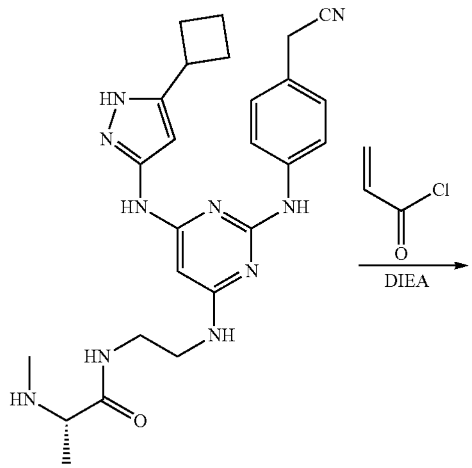

4-11

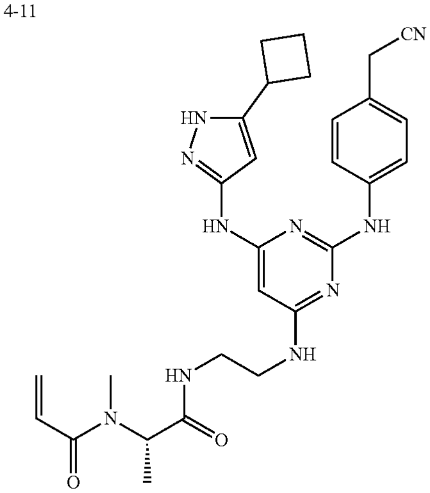

compound 4

Synthesis of (2S)—N-[2-[[2-[4-(cyanomethyl)anilino]-6-[(5-cyclobutyl-1H-pyrazol-3-yl)amino]pyrimidin-4-yl]amino]ethyl]-2-(methylamino)propanamide (4-11) is shown in Example 4. To a solution of 4-11 (100 mg, 0.205 mmol) in DCM (10 mL) and DIPEA (61 mg, 0.47 mmol) was added prop-2-enoyl chloride (22 mg, 0.245 mmol) 0° C. The mixture was stirred at 0° C. for 1 hr. The mixture was quenched by addition of $H_2O$ (50 mL) at 25° C., and then diluted with $H_2O$ (50 mL) and extracted with DCM (50 mL×3). The combined organic layers were washed with brine (50 mL), dried over $Na_2SO_4$, filtered and concentrated under reduced pressure. The residue was purified by prep-HPLC (water (0.04% $NH_3 \cdot H_2O$+10 mM $NH_4HCO_3$)-ACN) to afford (2S)—N-[2-[[2-[4-(cyanomethyl)anilino]-6-[(5-cyclobutyl-1H-pyrazol-3-yl)amino]pyrimidin-4-yl]amino]ethyl]-2-[methyl(prop-2-enoyl)amino]propanamide (22 mg, 0.04 mmol, 20% yield, 98.9% purity) as a white solid. LCMS: $t_R$=1.920 min in 10-80AB_4 min_220 &254_Shimadzu.1 cm, MS (ESI) m/z=543.5 $[M+H]^+$. $^1H$ NMR (400 MHz, DMSO-$d_6$): δ=11.80 (s, 1H), 8.95-8.67 (m, 2H), 8.12-7.87 (m, 1H), 7.67 (d, J=8.4 Hz, 2H), 7.19 (d, J=8.4 Hz, 2H), 6.76-6.68 (m, 1H), 6.31 (s, 1H), 6.20-6.04 (m, 2H), 5.92 (s, 1H), 5.71-5.61 (m, 1H), 5.03-4.59 (m, 1H), 3.92 (s, 2H), 3.51-3.42 (m, 2H), 3.33-3.31 (m, 2H), 3.29 (s, 1H), 2.93-2.76 (m, 3H), 2.27 (J=8.4 Hz, 2H), 2.12 (m, J=2.4, 9.2 Hz, 2H), 1.99-1.93 (m, 1H), 1.88-1.82 (m, 1H), 1.27-1.21

(m, 3H). Chiral SFC: $t_R$=4.652 min (Instrument column: Chiralpak AS-3 100×4.6 mm I.D., 3 um, Mobile phase: A: $CO_2$ B: ethanol (0.05% DEA), Gradient: from 5% to 40% of B in 4.5 min and hold 40% for 2.5 min, then 5% of B for 1 min; Flow rate: 2.8 mL/min Column temperature: 40° C.; UV detection: 220 nm), ee %=100%. $[\alpha]_D^{20}$=−31.0 (c=0.10, MeOH).

Example 5

N-[(1S)-2-[2-[[2-[4-(cyanomethyl)anilino]-6-[(5-cyclobutyl-1H-pyrazol-3-yl)amino]pyrimidin-4-yl]amino]ethylamino]-1-methyl-2-oxo-ethyl]-N-methyl-but-2-ynamide (Compound 5)

Scheme 8. Synthesis of compound 5.

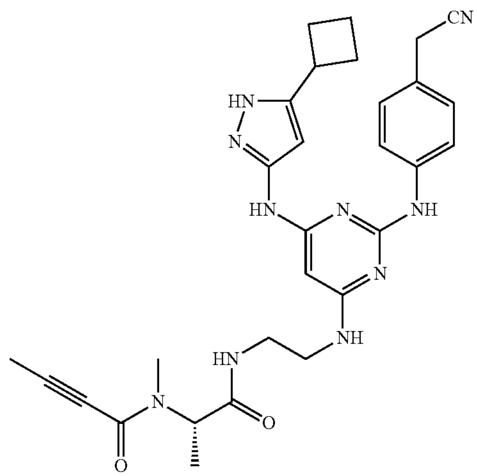

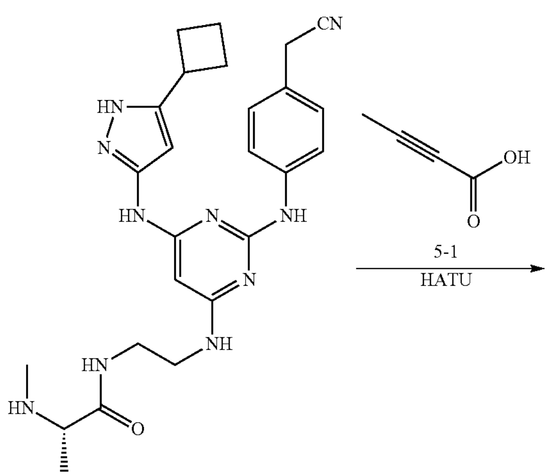

4-11

-continued

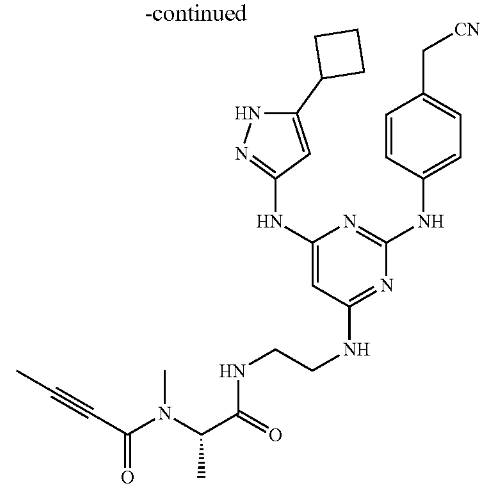

Compound 5

To a solution of (2S)—N-[2-[[2-[4-(cyanomethyl)anilino]-6-[(5-cyclobutyl-1H-pyrazol-3-yl)amino]pyrimidin-4-yl]amino]ethyl]-2-(methyl amino)propanamide (100 mg, 0.205 mmol) in DMF (10 mL) was added HATU (93 mg, 0.246 mmol), DIPEA (80 mg, 0.614 mmol) and but-2-ynoic acid (21 mg, 0.246 mmol). The mixture was stirred at 25° C. for 1 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by prep-HPLC (column: Waters Xbridge 150*25 mm*5 um; mobile phase: [water (0.04% $NH_3 \cdot H_2O$+10 mM $NH_4HCO_3$)-ACN]; B %: 25%-55%, 8 min) to afford N-[(1S)-2-[2-[[2-[4-(cyanomethyl)anilino]-6-[(5-cyclobutyl-1H-pyrazol-3-yl)amino]pyrimidin-4-yl]amino]ethylamino]-1-methyl-2-oxo-ethyl]-N-methyl-but- 2-ynamide (27.3 mg, 0.049 mmol, 24% yield, 98.62% purity) as a light yellow solid. LCMS: $t_R$=1.971 min in 10-80AB_4 min_220 &254_Shimadzu.1 cm, MS (ESI) m/z=555.5 $[M+H]^+$. $^1H$ NMR (400 MHz, DMSO-$d_6$): δ=11.80 (s, 1H), 8.93-8.71 (m, 2H), 8.08-7.95 (m, 1H), 7.68 (d. J=8.4 Hz, 2H). 7.19 (d, J=8.0 Hz, 2H), 6.40-6.06 (m, 2H), 5.91 (s, 1H), 4.93-4.86 (m, 1H), 3.92 (s, 2H), 3.50-3.40 (m, 2H), 3.31 (s. 2H), 3.27 (d, J=5.6 Hz, 1H), 3.05 (s, 3H), 2.27 (d. J=8.4 Hz, 2H), 2.16-2.11 (m, 2H), 2.01 (d, J=14.4 Hz, 3H), 1.96-1.91 (m, 1H), 1.84 (d, J=9.6 Hz, 1H), 1.33-1.23 (m, 3H). Chiral SFC: $t_R$=5.335 min (Instrument column: Chiralpak AD-3 100×4.6 mm I.D., Sum; Mobile phase: 40% of iso-propanol (0.05% DEA) in $CO_2$; Flow rate: 2.8 mL/min, Column temperature: 40° C.; UV detection: 220 nm), ee %=98.86%. $[\alpha]_D^{20}$=−17.0 (c=−108, MeOH).

Example 6

(2S)—N-[2-[[6-[(5-cyclobutylthiazol-2-yl)amino]-2-ethyl-pyrimidin-4-yl]amino]ethyl]-2-[methyl(prop-2-enoyl)amino]propanamide (Compound 6)

Scheme 9. Synthesis of compound 6.

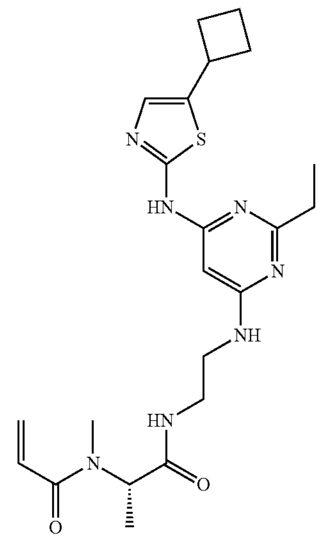

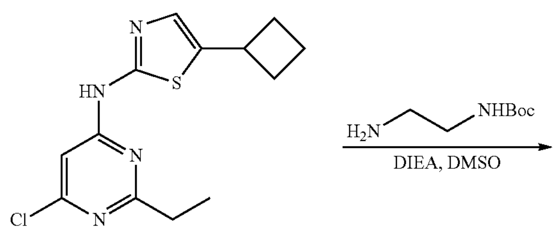

6-1

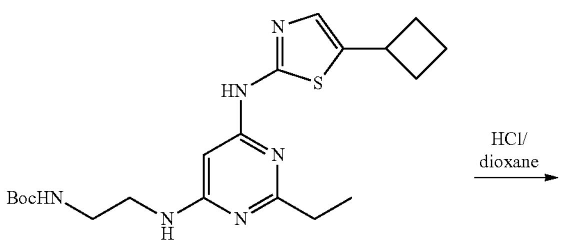

6-2

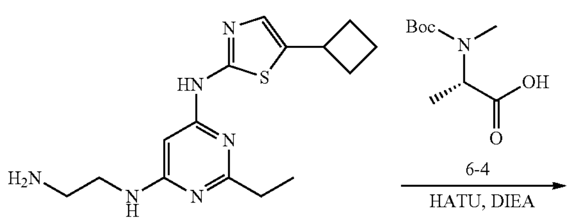

6-4

6-3

-continued

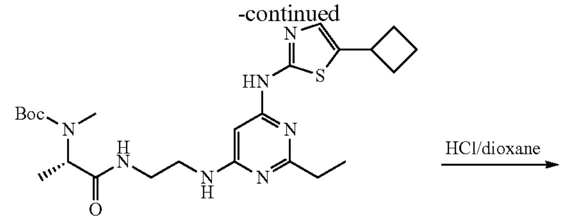

6-5

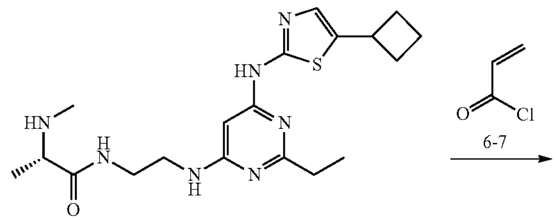

6-7

6-6

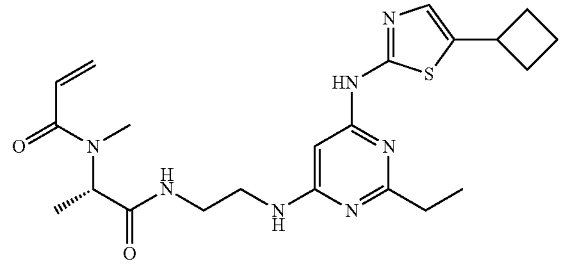

compound 6

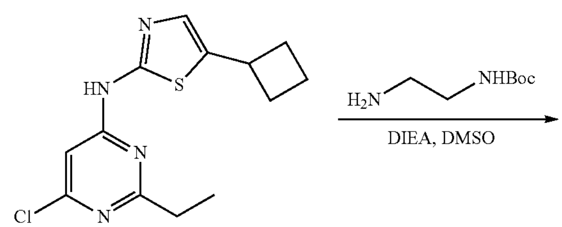

6-1

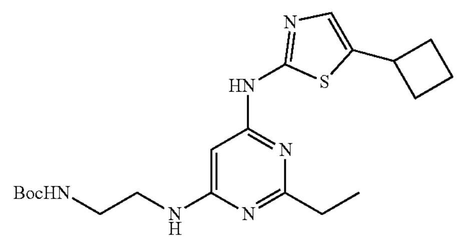

6-2

To a solution of N-(6-chloro-2-ethyl-pyrimidin-4-yl)-5-cyclobutyl-thiazol-2-amine (1.3 g, 4.41 mmol) and tert-butyl N-(2-aminoethyl)carbamate (5 g, 31.21 mmol) in DMSO (30 mL) was added DIPEA (1.71 g, 13.23 mmol). The mixture was stirred at 80° C. for 24 hr. The mixture was diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~50% Ethyl acetate/Petroleum ether gradient 60 mL/min) to afford tert-butyl N-[2-[[6-[(5-cyclobutylthiazol-2-yl)

amino]-2-ethyl-pyrimidin-4-yl]amino]ethyl]carbamate (1.5 g, 3.23 mmol, 73% yield, 90% purity) as a white solid, which would be used directly in the next step.

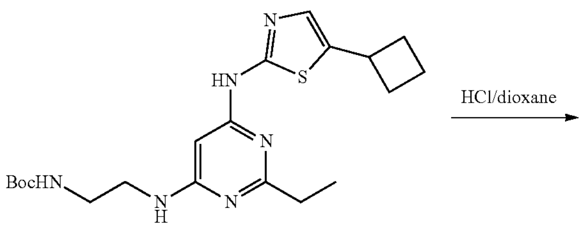

6-2

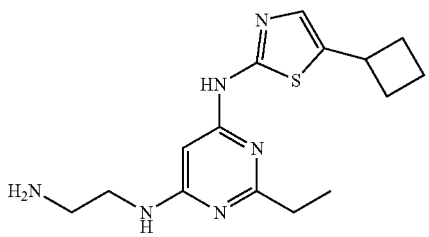

6-3

A solution of tert-butyl N-[2-[[6-[(5-cyclobutylthiazol-2-yl)amino]-2-ethyl-pyrimidin-4-yl]amino]ethyl]carbamate (1.5 g, 3.58 mmol) in HCl/dioxane (4 M, 20 mL) was stirred at 25° C. for 1 hr. The mixture was concentrated under reduced pressure to afford $N_6$-(2-aminoethyl)-$N_4$-(5-cyclobutylthiazol-2-yl)-2-ethyl-pyrimidine-4,6-diamine (2.8 g, crude) as a yellow solid, which would be used directly in the next step.

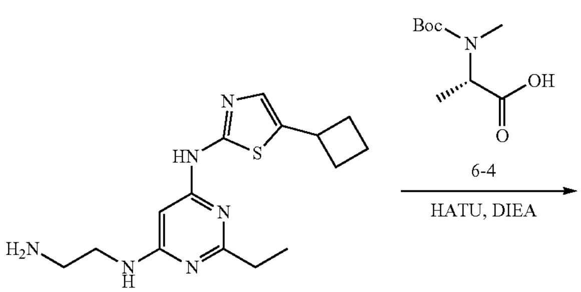

6-3

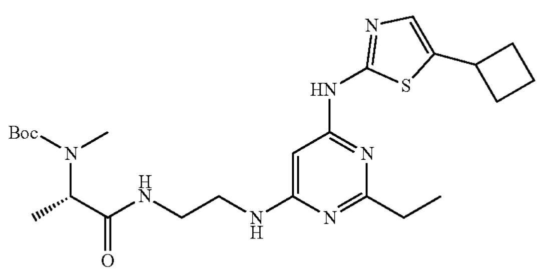

6-5

To a solution of $N_6$-(2-aminoethyl)-$N_4$-(5-cyclobutylthiazol-2-yl)-2-ethyl-pyrimidine-4,6-diamine (1.2 g, 1.51 mmol) in DMF (10 mL) was added HATU (689 mg, 1.81 mmol) and DIPEA (585 mg, 4.53 mmol) and (28)-2-[tert-butoxycarbonyl(methyl)amino]propanoic acid (368 mg, 1.81 mmol). The mixture was stirred at 25° C. for 2 hr. The mixture was diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~10% Ethyl acetate/Petroleum ether gradient 60 mL/min) to afford tert-butyl N-[(1S)-2-[2-[[6-[(5-cyclobutylthiazol-2-yl)amino]-2-ethyl-pyrimidin-4-yl]amino]ethyl amino]-1-methyl-2-oxo-ethyl]-N-methyl-carbamate (650 mg, 1.16 mmol, 77% yield) as a yellow solid.

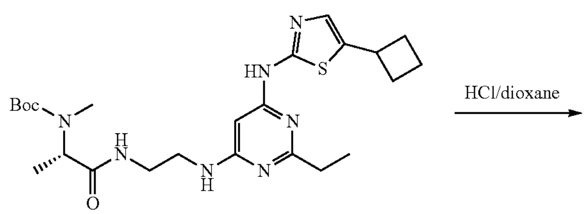

6-5

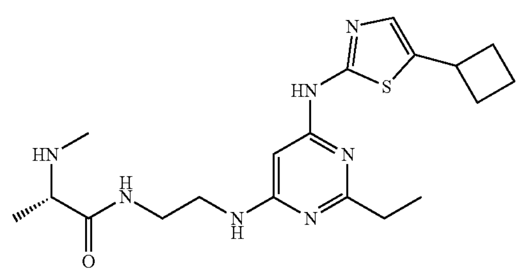

6-6

A solution of tert-butyl N-[(1S)-2-[2-[[6-[(5-cyclobutylthiazol-2-yl)amino]-2-ethyl-pyrimidin-4-yl]amino]ethylamino]-1-methyl-2-oxo-ethyl]-N-methyl-carbamate (650 mg, 1.29 mmol) in HCl/dioxane (4 M, 0.32 mL) was stirred at 25° C. for 1 hr. The mixture was concentrated under reduced pressure to afford (2S)—N-[2-[[6-[(5-cyclobutylthiazol-2-yl)amino]-2-ethyl-pyrimidin-4-yl]amino]ethyl]-2-(methylamino)propanamide (860 mg, crude) as a yellow oil, which would be used directly in the next step.

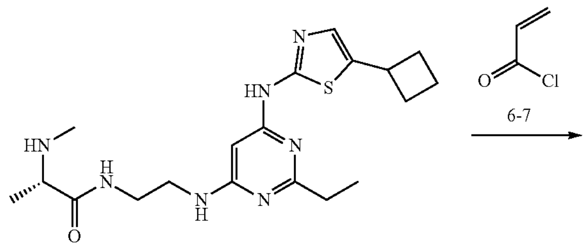

6-6

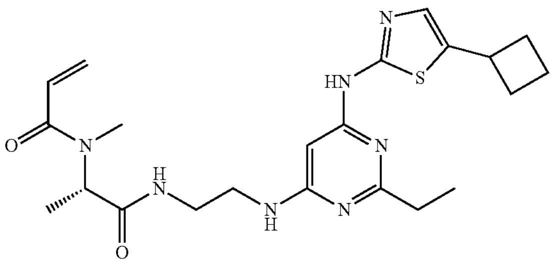

compound 6

To a solution of (2S)—N-[2-[[6-[(5-cyclobutylthiazol-2-yl)amino]-2-ethyl-pyrimidin-4-yl]amino]ethyl]-2-(methylamino)propanamide (350 mg, 0.52 mmol) in DCM (10 mL) was added DIPEA (135 mg, 1.04 mmol) and prop-2-enoyl chloride (47 mg, 0.52 mmol) at 0° C. The mixture was stirred at 0° C. for 1 hr. The mixture was diluted with $H_2O$ (50 mL) and extracted with DCM (50 mL×3). The combined organic layers were washed with brine (50 mL), dried over $Na_2SO_4$, filtered and concentrated under reduced pressure to give a residue. After that the residue was purified by flash silica gel chromatography (ISCO®; 20 g SepaFlash® Silica Flash Column, Eluent of 0~10% DCM/MeOH @ 40 mL/min) to afford (2S)—N-[2-[[6-[(5-cyclobutylthiazol-2-yl)amino]-2-ethyl-pyrimidin-4-yl]amino]ethyl]-2-[methyl (prop-2-enoyl)amino]propanamide (18.8 mg, 0.04 mmol, 7% yield, 96.5% purity) as a white solid. LCMS: $t_R$=2.197 min in 10-80AB_4 min_220 &254_Shimadzu.1 cm, MS (ESI) m/z=458.2 $[M+H]^+$. $^1$H NMR (400 MHz, DMSO-$d_6$): δ=10.88 (s, 1H), 8.23-7.92 (m, 1H), 7.17-6.96 (m, 2H), 6.80-6.76 (m, 1H), 6.24-6.11 (m, 1H), 5.89 (s, 1H), 5.80-5.67 (m, 1H), 5.08-4.65 (m, 1H), 3.73-3.64 (m, 1H), 3.36-3.26 (m, 4H), 2.98-2.79 (m, 3H), 2.68 (q, J=7.6 Hz, 2H), 2.42-2.36 (m, 2H), 2.16-2.08 (m, 2H), 2.05-1.97 (m, 1H), 1.94-1.85 (m, 1H), 1.36-1.33 (m, 3H), 1.29 (t, J=7.2 Hz, 3H). Chiral SFC: $t_R$=2.953 min (Instrument column: Chiralpak AS-3 100×4.6 mm I.D., 3 um, Mobile phase: A: $CO_2$ B: ethanol (0.05% DEA) Gradient: from 5% to 40% of B in 4.5 min and hold 40% for 2.5 min, then 5% of B for 1 min, Flow rate: 2.8 mL/min, Column temperature: 40° C., UV detection: 220 nm), ee %=96.90%. $[\alpha]_D^{20}$=−123.0 (c=−108, MeOH).

Example 7

(2S)—N-[2-[6-[(5-cyclobutylthiazol-2-yl)amino]-2-ethyl-pyrimidin-4-yl]oxyethyl]-2-[methyl(prop-2-enoyl)amino]propanamide (Compound 7)

Scheme 10. Synthesis of compound 7.

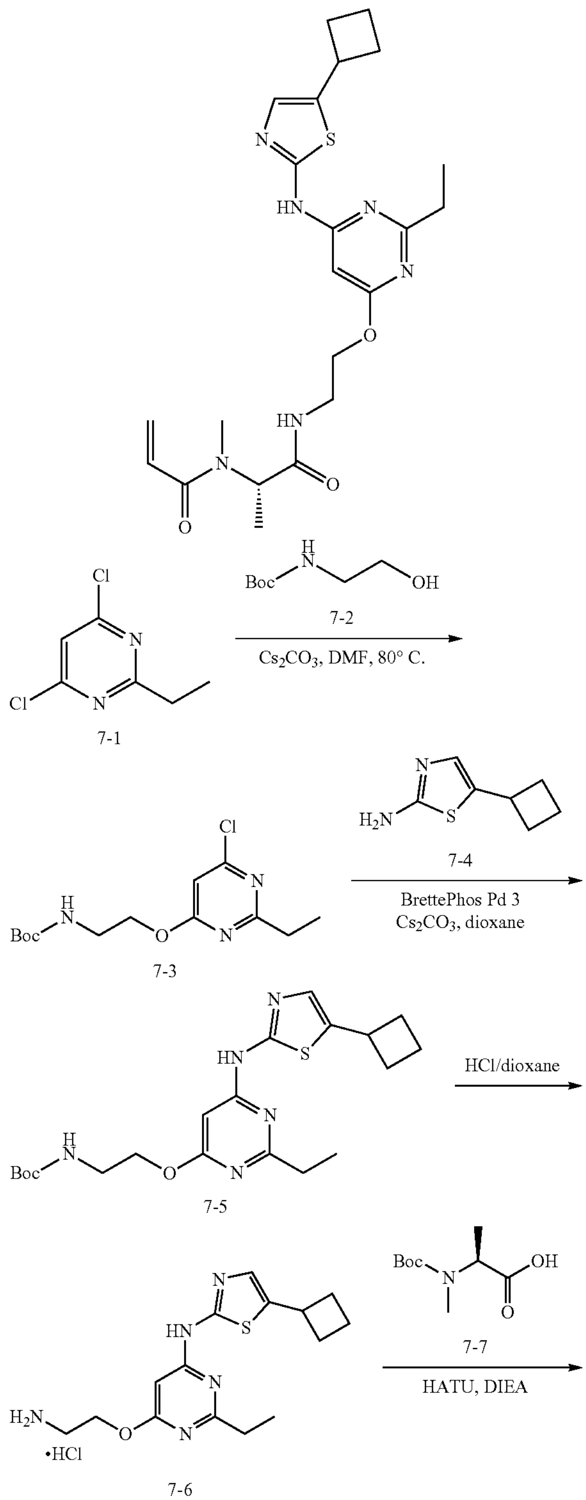

-continued

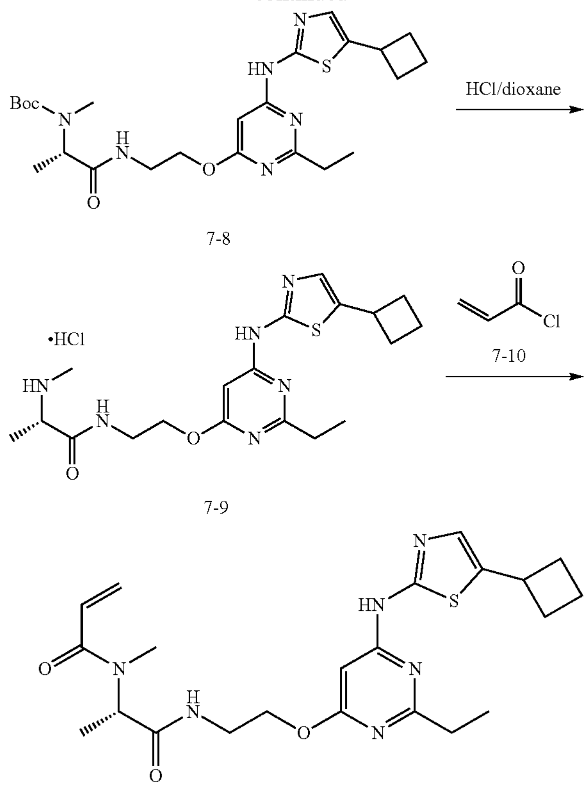

7-8

7-9 compound 7

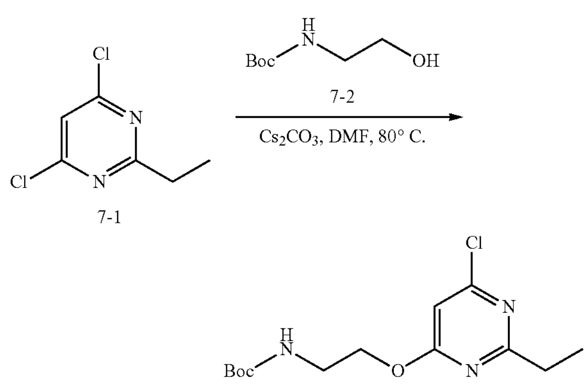

7-1

7-3

To a solution of 4,6-dichloro-2-ethyl-pyrimidine (1 g, 5.65 mmol) in DMF (10 mL) was added $Cs_2CO_3$ (2.76 g, 8.47 mmol) and tert-butyl N-(2-hydroxyethyl)carbamate (911 mg, 5.65 mmol). The mixture was stirred at 80° C. for 2.5 hr. The mixture was diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~20% Ethyl acetate/Petroleum ether gradient 40 mL/min) to afford tert-butyl N-[2-(6-chloro-2-ethyl-pyrimidin-4-yl)oxyethyl]carbamate (600 mg, 1.99 mmol, 35% yield) as a colorless oil.

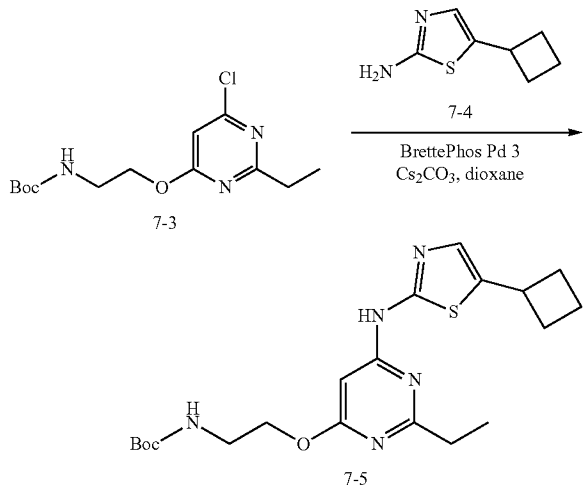

7-3

7-5

A mixture of tert-butyl N-[2-(6-chloro-2-ethyl-pyrimidin-4-yl)oxyethyl]carbamate (500 mg, 0.994 mmol), 5-cyclobutylthiazol-2-amine (230 mg, 1.49 mmol), [2-(2-aminophenyl)phenyl]-methylsulfonyloxy-palladium; dicyclohexyl-[3,6-dimethoxy-2-(2,4,6-triisopropylphenyl)phenyl]phosphane (180 mg, 0.20 mmol), $Cs_2CO_3$ (645 mg, 1.99 mmol) in dioxane (2 mL) was degassed and purged with $N_2$ for 3 times, and then the mixture was stirred at 80° C. for 1 hr under $N_2$ atmosphere. The mixture was diluted with $H_2O$ (50 mL) and extracted with EtOAc (50 mL×3). The combined organic layers were washed with brine (50 mL), dried over $Na_2SO_4$, filtered and concentrated under reduced pressure. The residue was purified by flash silica gel chromatography (ISCO®; 40 g SepaFlash® Silica Flash Column, Eluent of 0~30% Ethyl acetate/Petroleum ether gradient @ 100 mL/min) to afford tert-butyl N-[2-[6-[(5-cyclobutylthiazol-2-yl)amino]2-ethyl-pyrimidin-4-yl]oxy-ethyl]carbamate (300 mg, 0.715 mmol, 72% yield) as a yellow oil.

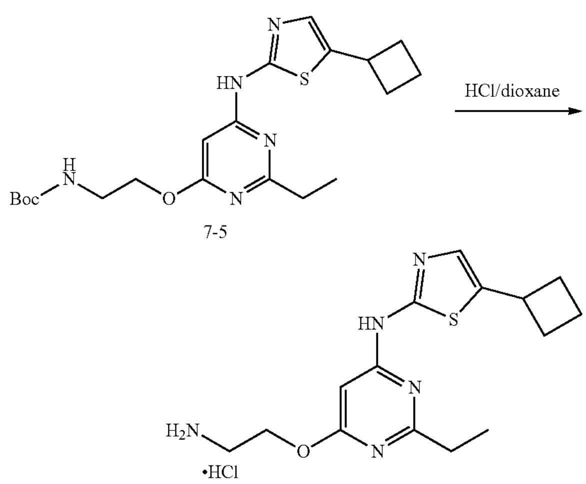

7-5

7-6

A solution of tert-butyl N-[2-[6-[(5-cyclobutylthiazol-2-yl)amino]-2-ethyl-pyrimidin-4-yl]oxyethyl]carbamate (300 mg, 0.715 mmol) in HCl/dioxane (4 M, 10 mL) was stirred at 25° C. for 0.5 hr. The mixture was concentrated under reduced pressure to afford N—[ 6-(2-aminoethoxy)-2-ethyl-pyrimidin-4-yl]-5-cyclobutyl-thiazol-2-amine (220 mg, crude) as a yellow oil, which would be used directly in the next step.

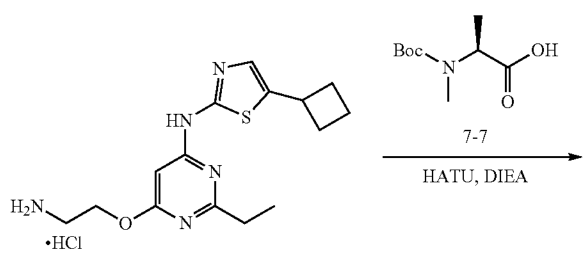

7-6

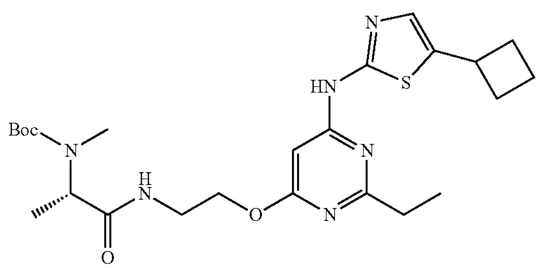

7-8

To a solution of N-[6-(2-aminoethoxy)-2-ethyl-pyrimidin-4-yl]-5-cyclobutyl-thiazol-2-amine (220 mg, 0.689 mmol) in DMF (10 mL) was added HATU (314 mg, 0.826 mmol), DIEA (267 mg, 2.07 mmol) and (2S)-2-[tert-butoxycarbonyl(methyl)amino]propanoic acid (154 mg, 0.758 mmol). The mixture was stirred at 25° C. for 2 hr. The mixture was diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~10% DCM/MeOH @ 40 mL/min) to afford tert-butyl N-[(1S)-2-[2-[6-[(5-cyclobutylthiazol-2-yl)amino]-2-ethyl-pyrimidin-4-yl]oxyethylamino]-1-methyl-2-oxo-ethyl]-N-methyl-carbamate (300 mg, 0.59 mmol, 86% yield) as a white solid.

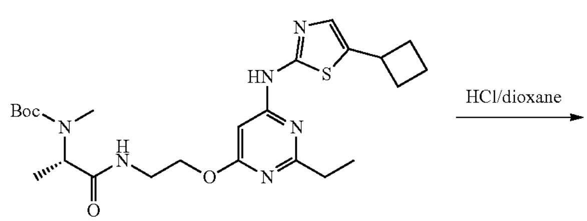

7-8

-continued

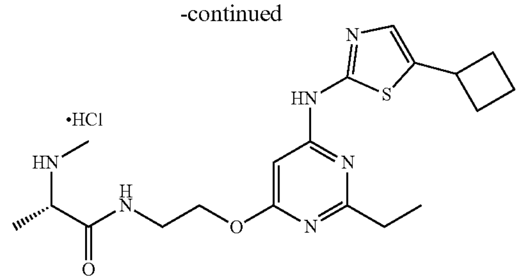

7-9

A solution of tert-butyl N-[(1S)-2-[2-[6-[(5-cyclobutylthiazol-2-yl)amino]-2-ethyl-pyrimidin-4-yl]oxyethylamino]-1-methyl-2-oxo-ethyl]-N-methyl-carbamate (300 mg, 0.59 mmol) in HCl/dioxane (4 M, 3 mL) was stirred at 25° C. for 0.5 hr. The mixture was concentrated under reduced pressure to afford (2S)—N-[2-[6-[(5-cyclobutylthiazol-2-yl)amino]-2-ethyl-pyrimidin-4-yl]oxyethyl]-2-(methylamino)propanamide (420 mg, crude) as a yellow oil, which would be used directly in the next step.

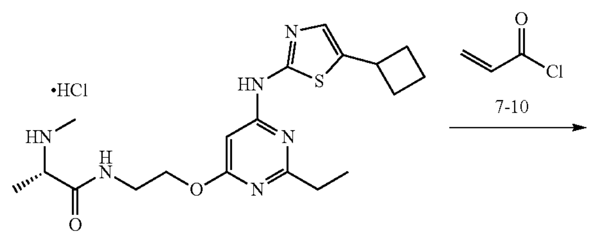

7-9

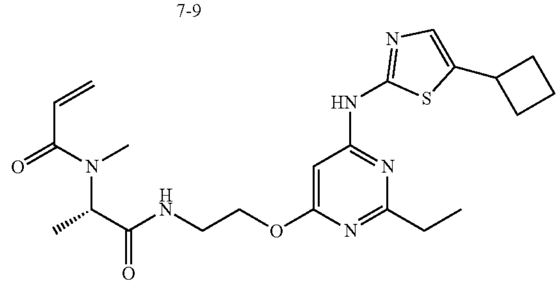

compound 7

To a solution of (2S)—N-[2-[6-[(5-cyclobutylthiazol-2-yl)amino]-2-ethyl-pyrimidin-4-yl]oxyethyl]-2-(methylamino)propanamide (420 mg, 0.59 mmol) in $CH_2Cl_2$ (10 mL) was added DIEA (153 mg, 1.18 mmol) and prop-2-enoyl chloride (54 mg, 0.59 mmol) at 0° C. The mixture was stirred at 0° C. for 1 hr. The mixture was diluted with $H_2O$ (50 mL) and extracted with $CH_2Cl_2$ (50 mL×3). The combined organic layers were washed with brine (50 mL), dried over $Na_2SO_4$, filtered and concentrated under reduced pressure to give a residue. After that the residue was purified by preparative HPLC (water (0.04% $NH_3 \cdot H_2O$+10 mM $NH_4HCO_3$)-ACN) to afford (2S)—N-[2-[6-[(5-cyclobutylthiazol-2-yl)amino]-2-ethyl-pyrimidin-4-yl]oxyethyl]-2-[methyl(prop-2-enoyl)amino]propanamide (29.2 mg, 0.06 mmol, 10% yield, 96% purity) as a white solid. LCMS: $t_R$=2.214 min in 10-80AB_4 min_220&254_Shimadzu.1 cm, MS (ESI) m/z=459.2 $[M+H]^+$. $^1$H NMR (400 MHz, MeOD): δ=7.04 (d, J=1.2 Hz, 1H), 6.79-6.61 (m, 1H), 6.28-6.16 (m, 1H), 6.14 (s, 1H), 5.79-5.67 (m, 1H), 5.11 (d, J=7.2 Hz, 1H), 4.46-4.35 (m, 2H), 3.75-3.50 (m, 3H), 3.06-2.88 (m, 3H), 2.83 (q, J=7.6 Hz, 2H), 2.48-2.38 (m, 2H), 2.25-2.14 (m, 2H), 2.13-2.02 (m, 1H), 2.01-1.89 (m, 1H), 1.45-1.34 (m, 6H), Chiral SFC: $t_R$=2.711 min (Instrument column: Chiralpak AS-3 100×4.6 mm I.D., 3 um, Mobile phase: A: $CO_2$, B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., UV Detection: 220 nm), ee %=100%. $[\alpha]_D^{20}$=−161 (c=−108, MeOH).

Example 8

(E)-N-[(1S)-2-[2-[[6-[(5-cyclobutylthiazol-2-yl)amino]-2-ethyl-pyrimidin-4-yl]amino]ethylamino]-1-methyl-2-oxo-ethyl]-4-(dimethylamino)-N-methyl-but-2-enamide (Compound 8)

Scheme 11. Synthesis of compound 8.

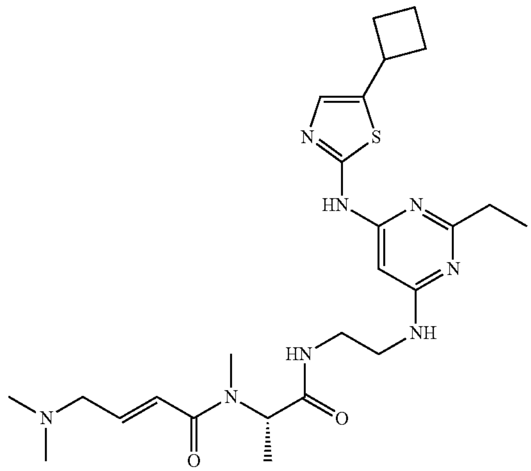

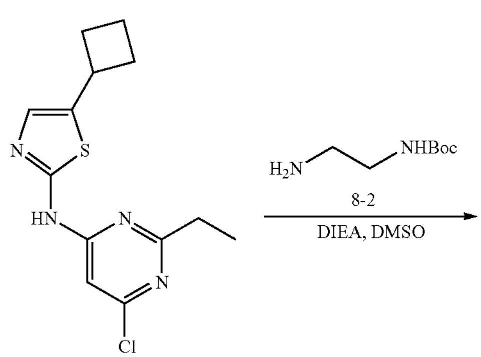

8-1

-continued

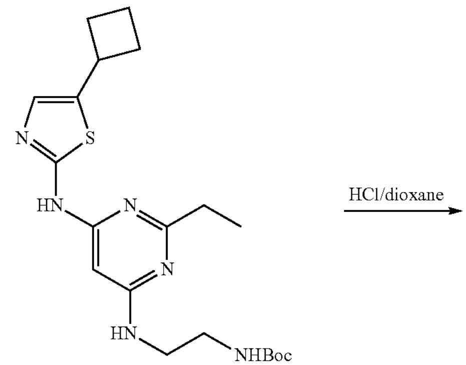

8-3

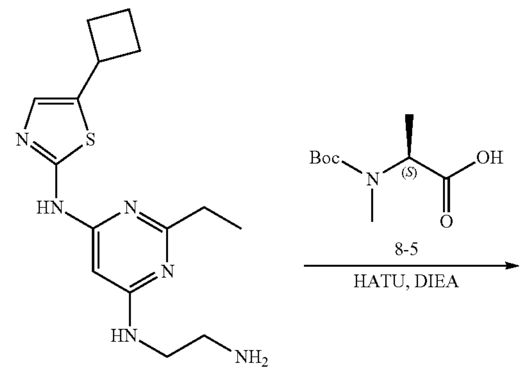

8-4

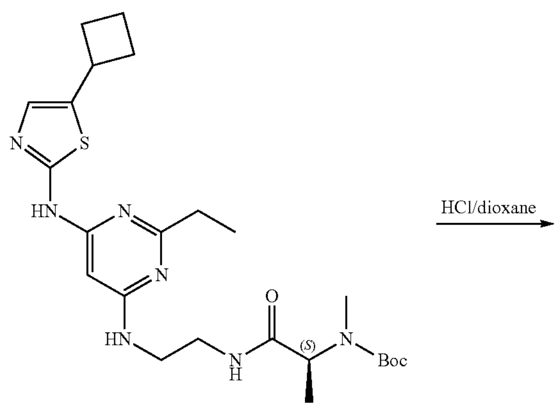

8-6

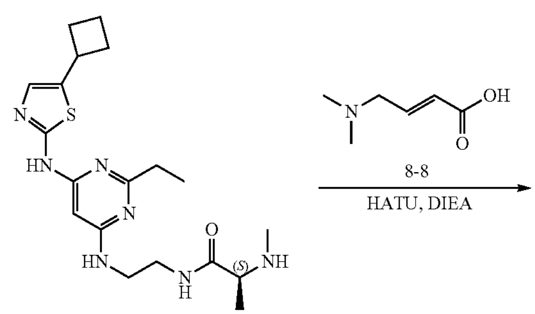

8-7

-continued

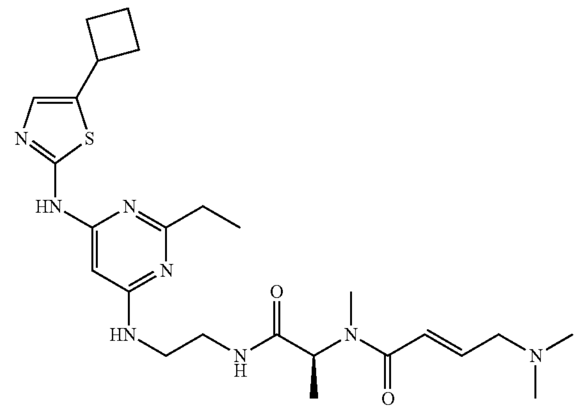

compound 8

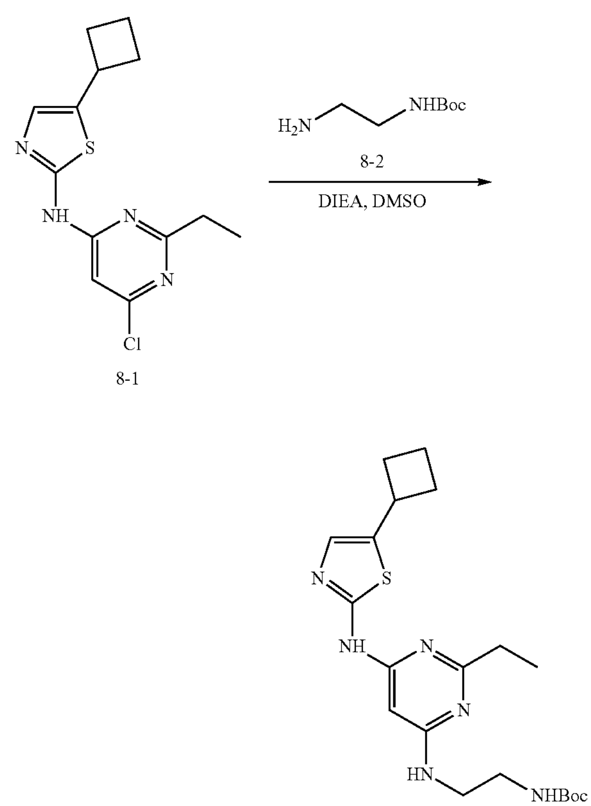

8-1

8-3

To a solution of N-(6-chloro-2-ethyl-pyrimidin-4-yl)-5-cyclobutyl-thiazol-2-amine (500 mg, 1.70 mmol) in DMSO (10 mL) was added DIEA (657 mg, 5.09 mmol) and tert-butyl N-(2-aminoethyl)carbamate (1.36 g, 8.48 mmol). The mixture was stirred at 80° C. for 12 hours. The mixture was poured into water (60 mL) and filtered, the filter cake was collected, dried to afford tert-butyl N-[2-[[6-[(5-cyclobutylthiazol-2-yl)amino]-2-ethyl-pyrimidin-4-yl]amino]ethyl]carbamate (800 mg, 91% yield) as a brown solid. LCMS: $t_R$=1.070 min in 10-80AB_2 min_220&254_Shimadzu.1 cm, MS (ESI) m/z=419.1 $[M+H]^+$.

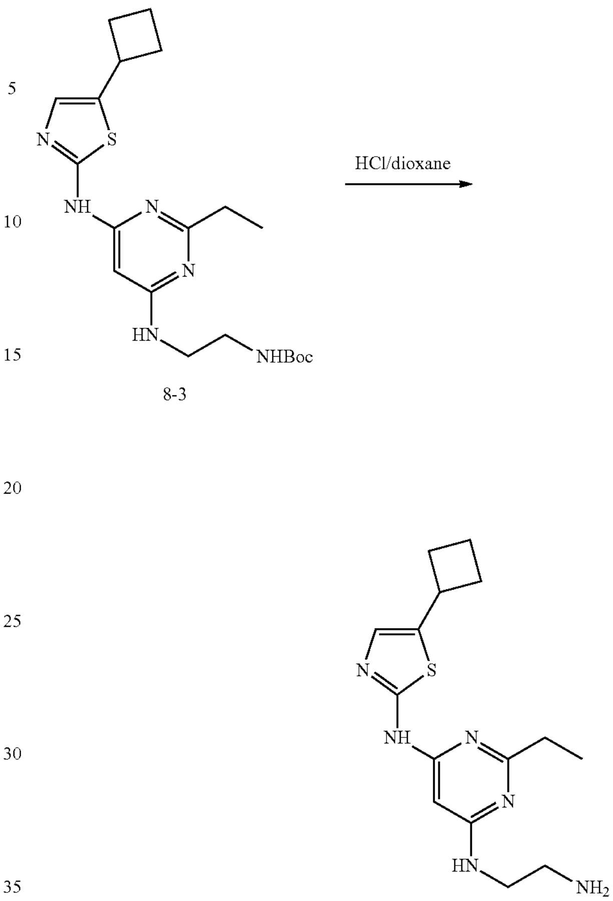

8-3

8-4

A solution of tert-butyl N-[2-[[6-[5-cyclobutylthiazol-2-yl)amino]-2-ethyl-pyrimidin-4-yl]amino]ethyl]carbamate (800 mg, 1.55 mmol) in HCl/dioxane (20 mL, 4 M) was stirred at 25° C. for 0.5 hour. The mixture was concentrated under reduced pressure to afford $N_4$-(2-aminoethyl)-$N_6$-(5-cyclobutylthiazol-2-yl)-2-ethyl-pyrimidine-4,6-diamine (800 mg, 97% yield) as a brown solid. LCMS: $t_R$=0.886 min in 10-80 AB_2 min_220&254_Shimadzu.1 cm, MS (ESI) m/z=318.9 $[M+H]^+$.

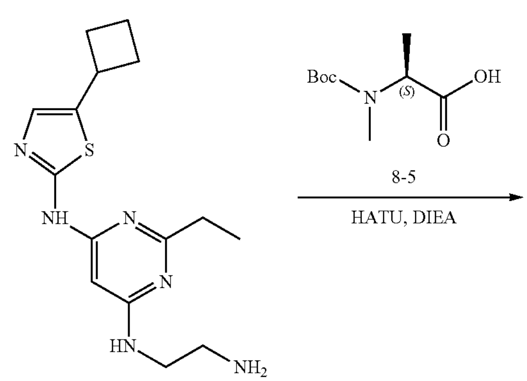

8-4

-continued

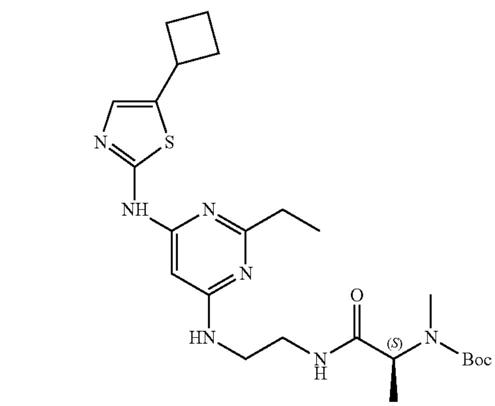

8-6

To a solution of $N_4$-(2-aminoethyl)-$N_6$-(5-cyclobutylthiazol-2-yl)-2-ethyl-pyrimidine-4,6-diamine (800 mg, 2.51 mmol) in DMF (10 mL) was added HATU (1.15 g, 3.01 mmol), (2S)-2-[tert-butoxycarbonyl(methyl)amino]propanoic acid (612 mg, 3.01 mmol) and DIEA (974 mg, 7.54 mmol). The mixture was stirred at 25° C. for 2 hours. The mixture was extracted with EtOAc (60 mL×3). The combined organic layers were washed with $H_2O$ (60 mL×3), dried over $Na_2SO_4$, filtered and concentrated under reduced pressure. The residue was purified by flash silica gel chromatography (ISCO®; 12 g SepaFlash® Silica Flash Column, Eluent of 0-10% Methanol/Dichloromethane @ 40 mL/min) to afford tert-butyl N-[(1S)-2-[2-[[6-[(5-cyclobutylthiazol-2-yl)amino]-2-ethyl-pyrimidin-4-yl]amino]ethylamino]-1-methyl-2-oxo-ethyl]-N-methyl-carbamate (600 mg, 47% yield) as a yellow solid. LCMS: $t_R$=0.884 min in 5-95 AB_1.5 min_220 &254_Shimadzu.1 cm, MS (ESI) m/z=504.2 $[M+H]^+$.

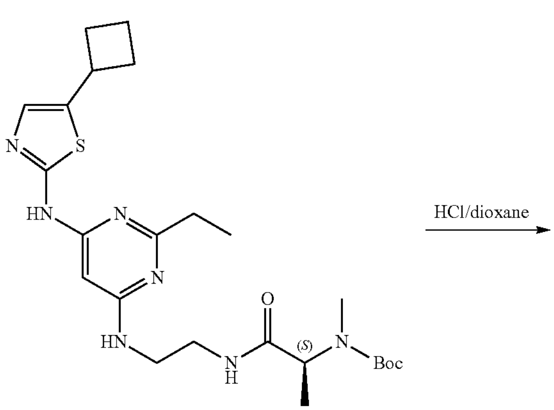

8-6

-continued

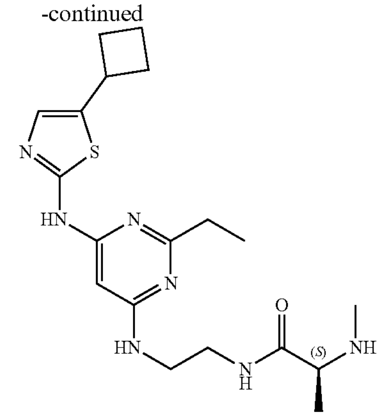

8-7

A solution of tert-butyl N-[(1S)-2-[2-[[6-[(5-cyclobutylthiazol-2-yl)amino]-2-ethyl-pyrimidin-4-yl]amino]ethylamino]-1-methyl-2-oxo-ethyl]-N-methyl-carbamate (600 mg, 1.19 mmol) in HCl/dioxane (20 mL, 4 M) was stirred at 25° C. for 0.5 hour. The mixture was concentrated under reduced pressure to afford (2S)—N-[2-[[6-[(5-cyclobutylthiazol-2-yl)amino]-2-ethyl-pyrimidin-4-yl]amino]ethyl]-2-(methylamino)propanamide (600 mg, 100% yield) as a yellow solid. LCMS: $t_R$=0.882 min in 10-80 AB_2 min_220 &254_Shimadzu.1 cm, MS (ESI) m/z=404.0 $[M+H]^+$.

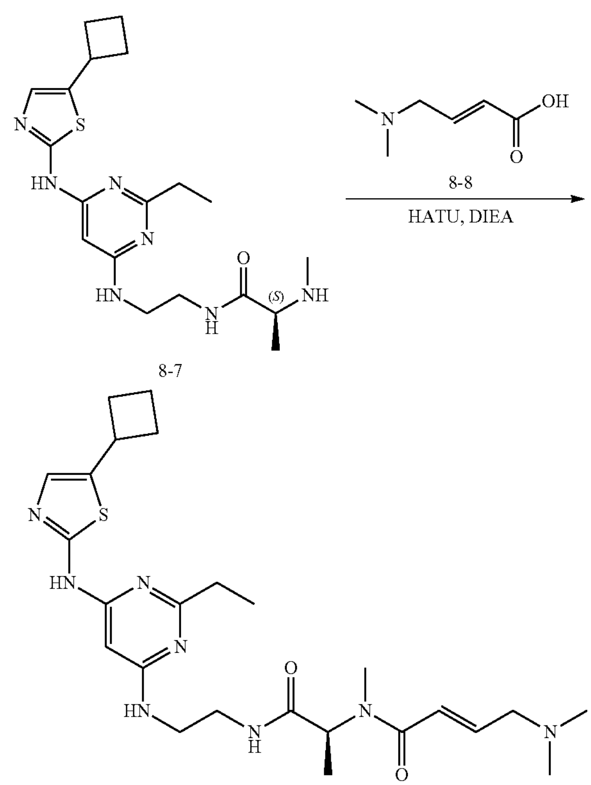

compound 8

To a solution of (2S)—N-[2-[[6-[(5-cyclobutylthiazol-2-yl)amino]-2-ethyl-pyrimidin-4-yl]amino]ethyl]-2-(methylamino)propanamide (150 mg, 0.371 mmol) in DMF (10 mL)

was added DIEA (144 mg, 1.12 mmol), HATU (169 mg, 0.446 mmol) and (E)-4-(dimethylamino)but-2-enoic acid (52 mg, 0.408 mmol). The mixture was stirred at 25° C. for 2 hours. The mixture was concentrated under reduced pressure. The residue was purified by preparative HPLC (Colum: Phenomenex Gemini-NX C18 75*30 mm*3 um; water (0.04% HCl)-ACN; B % from 30 to 60; Gradient Time: 8 min; Flow rate: 25 mL/min) to afford (E)-N—[ (1S)-2-[2-[[6-[(5-cyclobutylthiazol-2-yl)amino]-2-ethyl-pyrimidin-4-yl]amino]ethyl amino]-1-methyl-2-oxo-ethyl]-4-(dimethylamino)-N-methyl-but-2-enamide (14 mg, 7% yield, 96.56% purity) as a white solid. LCMS: $t_R$=1.180 min in 10-80 AB_4 min_E_Shimadzu.1 cm, MS (ESI) m/z=515.3 $[M+H]^+$. $^1H$ NMR (400 MHz. MeOD-$d_4$): δ=6.99 (s, 1H), 6.83-6.69 (m, 1H), 6.56-6.45 (m, 1H), 5.86 (s, 1H), 5.06-5.01 (m, 1H), 3.71-3.63 (m, 1H), 3.50-3.44 (m, 3H), 3.40-3.33 (m, 1H), 3.15-3.07 (m, 2H), 3.02-2.87 (m, 2H), 2.74-2.68 (m, 3H), 2.46-2.38 (m, 2H), 2.26 (s, 4H), 2.23-2.14 (m, 4H), 2.09-2.02 (m, 1H), 2.00-1.90 (m, 1H), 1.44-1.36 (m, 6H).

Example 9

(2S)—N-[2-[[2-methyl-6-[(5-phenylthiazol-2-yl)amino]pyrimidin-4-yl]amino]ethyl]-2-[methyl(prop-2-enoyl)amino]propanamide (Compound 9)

Scheme 12. Synthesis of compound 9.

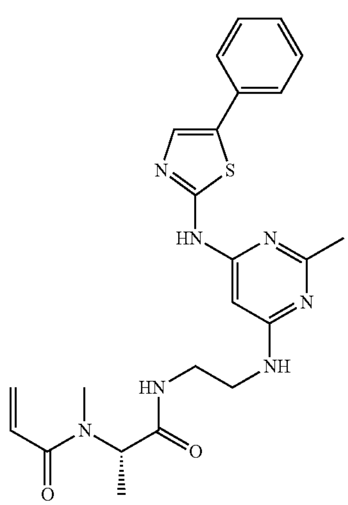

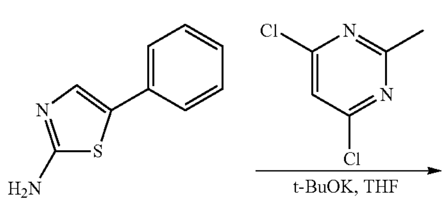

9-1

-continued

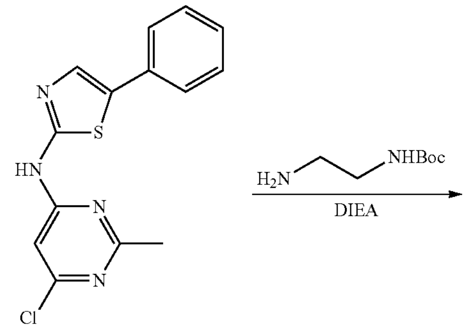

9-2

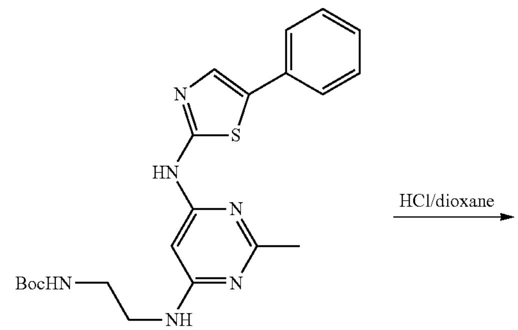

9-3

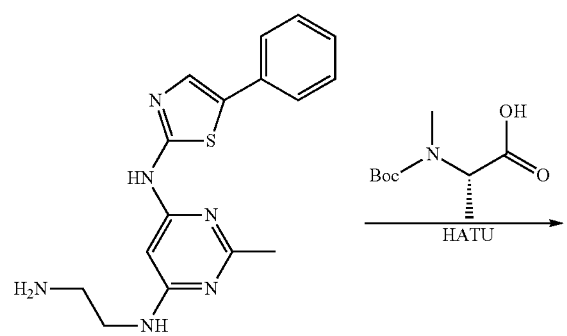

9-4

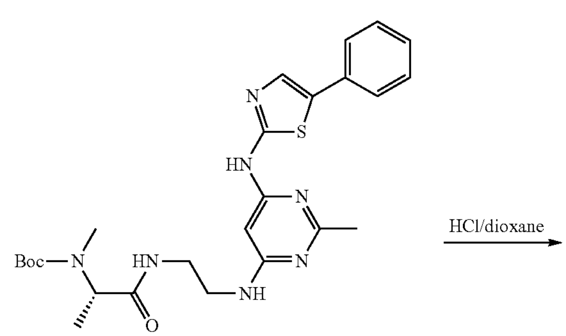

9-5

-continued

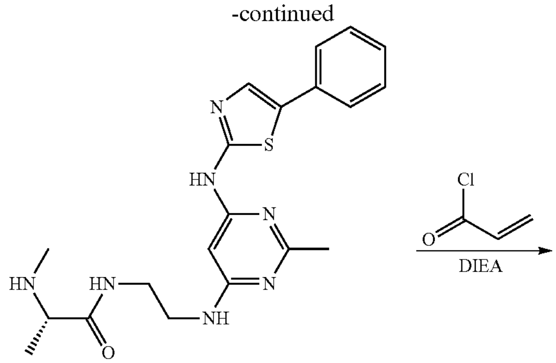

9-6

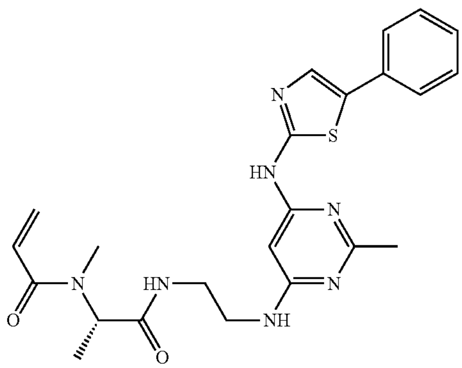

compound 9

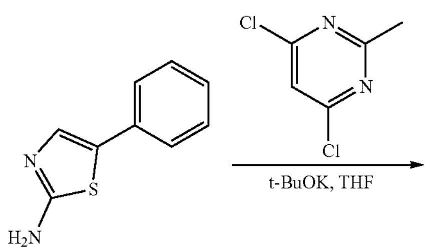

9-1

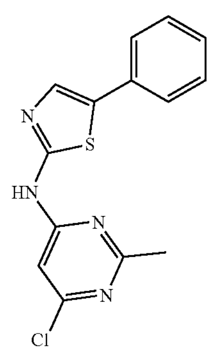

9-2

To a solution of 4,6-dichloro-2-methyl-pyrimidine (930 mg, 5.71 mmol) and 5-phenylthiazol-2-amine (914 mg, 5.19 mmol) in THF (50 mL) was added t-BuOK (1.16 g, 10.37 mmol) at 0° C. The mixture was stirred at 25° C. for 12 hours. The mixture was quenched by addition of $H_2O$ (20 mL) at 0° C., and then extracted with EtOAc (30 mL×2). The combined organic layers were dried over $Na_2SO_4$, filtered and concentrated under reduced pressure to give a residue.

The residue was purified by flash silica gel chromatography (Biotage 4 g Silica Flash Column; Eluent of gradient 0-50% ethyl acetate in petroleum ether @ 20 mL/min) to afford N-(6-chloro-2-methyl-pyrimidin-4-yl)-5-phenyl-thiazol-2-amine (1.5 g, 62% yield, 97% purity) as a light yellow solid. LCMS: $t_R$=3.158 min in 0-60AB_4 min_220 &254_Shimadzu.1 cm, MS (ESI) m/z=303.1 $[M+H]^+$. $^1H$ NMR (400 MHz, DMSO-$d_6$): δ=7.80 (s, 1H), 7.58 (d, J=7.6 Hz, 2H), 7.38 (t, J=8.0 Hz, 1H), 7.24 (t, J=7.6 Hz, 2H). 6.74 (s. 1M. 1.79 (s. 3M.

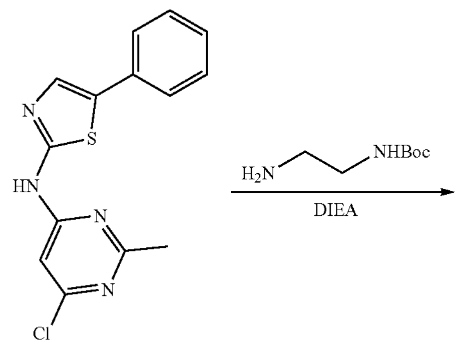

9-2

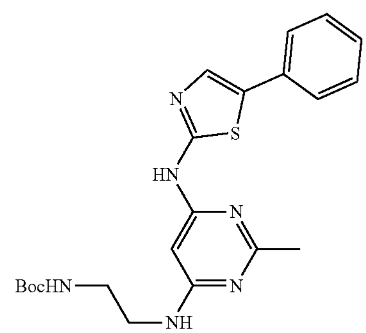

9-3

A mixture of N-(6-chloro-2-methyl-pyrimidin-4-yl)-5-phenyl-thiazol-2-amine (1.5 g, 4.95 mmol), tert-butyl N-(2-aminoethyl)carbamate (2.38 g, 14.86 mmol), DIPEA (1.28 g, 9.91 mmol) in DMSO (30 mL) was stirred at 100° C. for 12 hours. The mixture was quenched by addition of $H_2O$ (50 mL), and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. The residue was purified by flash silica gel chromatography (Biotage 12 g Silica Flash Column; Eluent of gradient 0-50% ethyl acetate in petroleum ether @ 60 mL/min) to afford tert-butyl N-[2-[[2-methyl-6-[(5-phenylthiazol-2-yl)amino]pyrimidin-4-yl]amino]ethyl]carbamate (1.5 g, 71% yield) as a yellow solid. LCMS: $t_R$=2.129 min in 10-80AB_4 min_220 &254_Shimadzu.1 cm, MS (ESI) m/z=427.3 $[M+H]^+$.

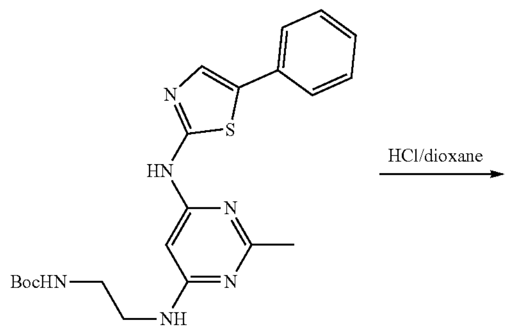

9-3

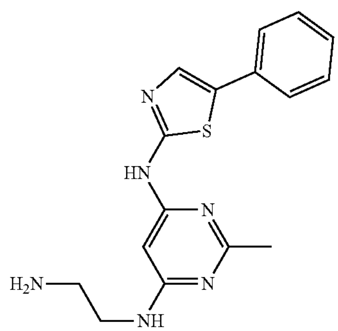

9-4

A solution of tert-butyl N-[2-[[2-methyl-6-[(5-phenylthiazol-2-yl)amino]pyrimidin-4-yl]amino]ethyl]carbamate (500 mg, 1.17 mmol) in HCl/dioxane (30 mL, 4 M) was stirred at 25° C. for 0.5 hour. The mixture was concentrated under reduced pressure to afford N4-(2-aminoethyl)-2-methyl-N6-(5-phenylthiazol-2-yl)pyrimidine-4,6-diamine (425 mg, 99% yield, HCl salt) as a light yellow solid. LCMS: $t_R$=0.892 min in 10-80AB_2 min_220 &254_Shimadzu.1 cm, MS (ESI) m/z=327.2[M+H]$^+$.

-continued

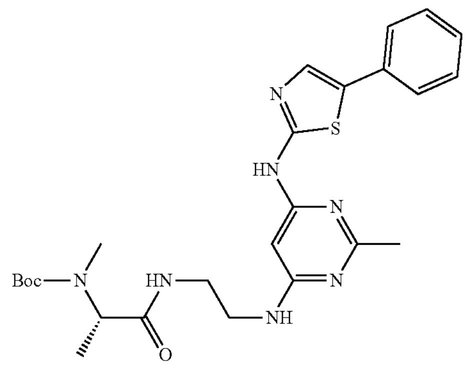

9-5

To a solution of N4-(2-aminoethyl)-2-methyl-N6-(5-phenylthiazol-2-yl)pyrimidine-4,6-diamine (380 mg, 1.05 mmol, HCl salt) in DMF (20 mL) was added HATU (477 mg, 1.26 mmol) and DIPEA (406 mg, 3.14 mmol) and (2S)-2-[tert-butoxycarbonyl(methyl)amino]propanoic acid (234 mg, 1.15 mmol). The mixture was stirred at 25° C. for 1 hour. The mixture was partitioned between $H_2O$ (10 mL) and EtOAc (20 mL). The organic phase was separated, washed with $H_2O$ (20 mL×5), dried over $Na_2SO_4$, filtered and concentrated under reduced pressure to give a residue. The residue was purified by flash silica gel chromatography (Biotage 12 g Silica Flash Column; Eluent of gradient 0-50% ethyl acetate in petroleum ether @ 40 mL/min) to afford tert-butyl N-methyl-N-[(1S)-1-methyl-2-[2-[[2-methyl-6-[(5-phenylthiazol-2-yl)amino]pyrimidin-4-yl]amino]ethylamino]-2-oxo-ethyl]carbamate (392 mg, 73% yield) as a light yellow solid. LCMS: $t_R$=1.108 min in 10-80AB_2 min_220 &254_Shimadzu.1 cm, MS (ESI) m/z=512.4[M+H]$^+$.

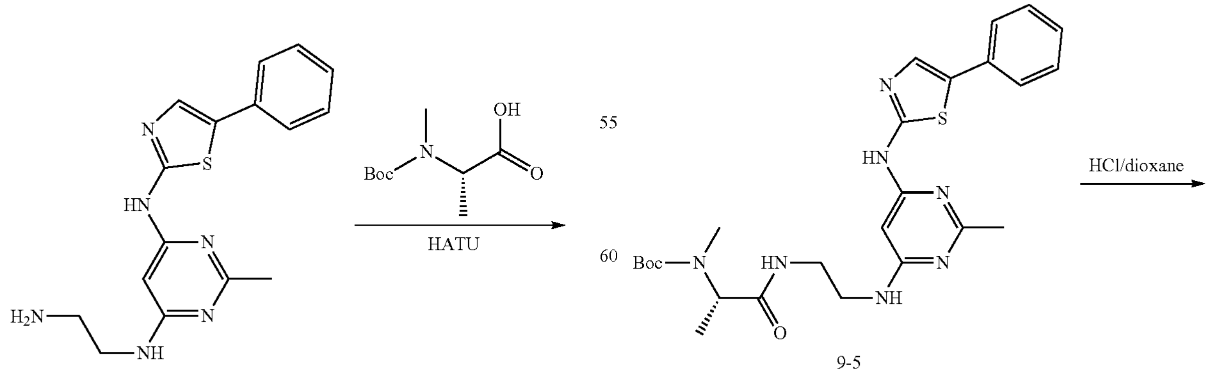

9-4

9-5

-continued

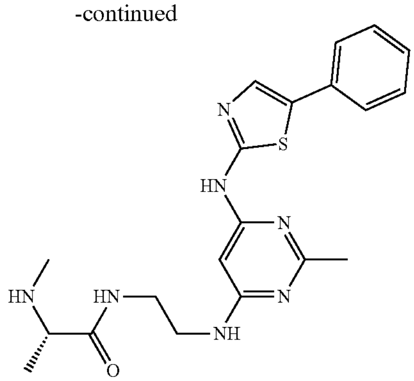

9-6

To a solution of tert-butyl N-methyl-N-[(1S)-1-methyl-2-[2-[[2-methyl-6-[(5-phenylthiazol-2-yl)amino]pyrimidin-4-yl]amino]ethyl amino]-2-oxo-ethyl]carbamate (392 mg, 0.77 mmol) in dioxane (20 mL) was added HCl/dioxane (20 mL, 4 M). The mixture was stirred at 25° C. for 2 hour. The mixture was concentrated under reduced pressure to afford (2S)-2-(methyl amino)-N-[2-[[2-methyl-6-[(5-phenylthiazol-2-yl)amino]pyrimidin-4-yl]amino]ethyl]propanamide (460 mg, crude) as a yellow solid. LCMS: $t_R$=0.913 mM in 10-80AB_2 min_220 &254_Shimadzu.1 cm, MS (ESI) m/z=412.3[M+H]$^+$.

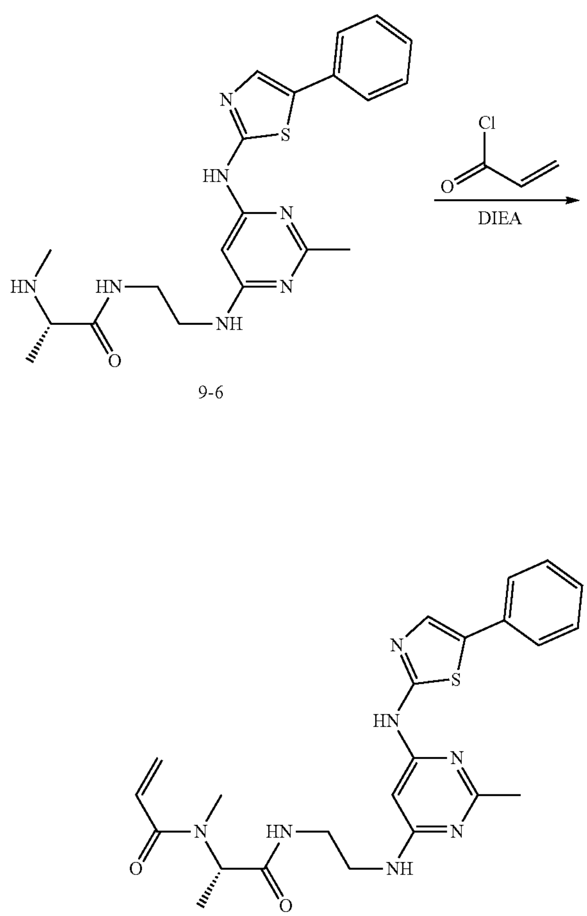

9-6 compound 9

To a solution of (2.5)-2-(methylamino)-N-[2-[[2-methyl-6-[(5-phenylthiazol-2-yl)amino]pyrimidin-4-yl]amino] ethyl]propanamide (200 mg, 0.49 mmol) in DCM (10 mL) and DIPEA (188 mg, 1.46 mmol) was added prop-2-enoyl chloride (39 mg, 0.44 mmol). The mixture was stirred at 0° C. for 1 hour. The mixture was quenched by addition of $H_2O$ (15 mL) at 25° C., and then extracted with DCM (50 mL×3). The combined organic layers were washed with sat. aq. NaCl (50 mL), dried over $Na_2SO_4$, filtered and concentrated under reduced pressure to give a residue. The residue was purified by preparative HPLC (Column: Agela DuraShell C18 150×25 mm×5 um: water (0.04% $NH_3$, $H_2O$+10 mM $NH_4HCO_3$)-ACN; B % from 25 to 55; Gradient time: 8 min; Flow rate: 25 mL/min) to afford (2S)—N-[2-[[2-methyl-6-[(5-phenylthiazol-2-yl)amino]pyrimidin-4-yl]amino]ethyl]-2-[methyl(prop-2-enoyl)amino]propanamide (60 mg, 27% yield) as a white solid. LCMS: $t_R$=1.959 mM in 10-80AB_4 min_220 &254_Shimadzu.1 cm, MS (ESI) m/z=466.3 [M+H]$^+$. $^1$H NMR (400 MHz, DMSO-$d_6$): δ=8.08-7.89 (m, 1H), 7.74 (s. 1H), 7.57 (d, J=7.2 Hz, 2H), 7.39 (t, J=8.0 Hz, 2H), 7.25 (t, J=7.6 Hz, 1H), 7.07 (s, 1H), 6.77-6.70 (m, 1H), 6.16-6.04 (m, 2H), 5.86 (s, 1H), 5.71-5.61 (m, 1H), 5.02-4.97 (m, 1H), 3.25-3.21 (m, 4H), 2.91 & 2.74 (s, 3H), 2.38 (s, 3H), 1.29-1.22 (m, 3H). Chiral SFC: $t_R$=4.349 mM (Instrument column: Chiralcel OD-3 100×4.6 mm I.D., 3 um Mobile phase: A: $CO_2$ B: ethanol (0.05% DEA), Gradient: from 5% to 40% of B in 4.5 mM and hold 40% for 2.5 mM, then 5% of B for 1 mM, Flow rate: 2.8 mL/min, Column temperature: 40° C.; UV detection: 220 nm), ee %=98.126%. $[\alpha]_D^{20}$=−15.0 (c=0.10, MeOH).

Example 10

(2S)—N-[2-[[2-methyl-6-[(5-phenylthiazol-2-yl) amino]pyrimidin-4-yl]amino]ethyl]-2-[methyl(propanoyl)amino]propanamide (Compound 10)

Scheme 13. Synthesis of compound 10.

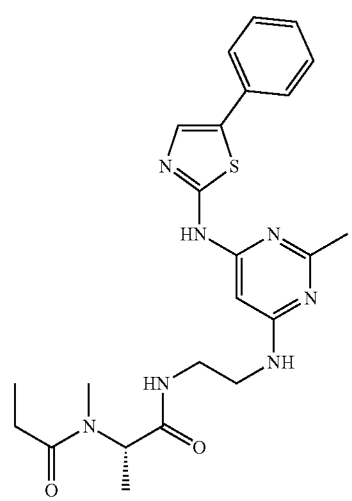

-continued

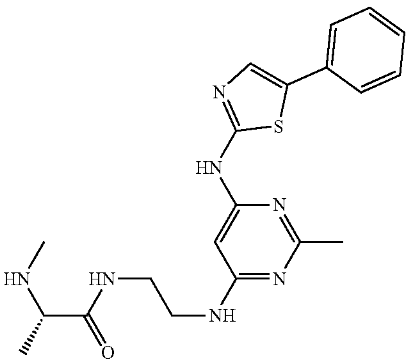

11-7

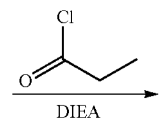

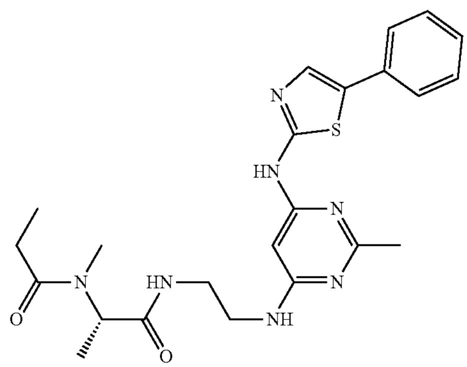

compound 10

Synthesis of (2S)-2-(methylamino)-N-[2-[[2-methyl-6-[(5-phenylthiazol-2-yl)amino]pyrimidin-4-yl]amino]ethyl]propanamide (11-7) is shown in Example 11. To a solution of 11-7 (300 mg, 0.67 mmol, HCl salt) in DMF (5 mL) was added propanoyl chloride (61 mg, 0.67 mmol) and DIPEA (173 mg, 1.34 mmol). The mixture was stirred at 25° C. for 2 hours. The mixture was quenched by addition of $H_2O$ (5 mL) at 25° C., and then diluted with $H_2O$ (10 mL) and extracted with EtOAc (50 mL×3). The combined organic layers were washed with sat. aq. NaCl (50 mL), dried over $Na_2SO_4$, filtered and concentrated under reduced pressure to give a residue. The residue was purified by preparative HPLC (Column: Agela DuraShell C18 150×25 mm×5 um: water (0.04% $NH_3 \cdot H_2O$+10 mM $NH_4HCO_3$)-ACN; B % from 35 to 65; Gradient time: 8 min; Flow rate: 25 mL/min) to afford (2S)—N-[2-[[2-methyl-6-[(5-phenylthiazol-2-yl)amino]pyrimidin-4-yl]amino]ethyl]-2-[methyl(propanoyl)amino]propanamide (46 mg, 14% yield, 96% purity) as a white solid. LCMS: $t_R$=1.946 min in 10-80AB_4 min_220&254 Shimadzu.1 cm, MS (ESI) m/z=468.4 $[M+H]^+$. $^1H$ NMR (400 MHz, DMSO-$d_6$): δ=11.08 (s, 1H), 8.01 &7.77 (s, 1H), 7.73 (s, 1H), 7.57 (d, J=7.6 Hz, 2H), 7.39 (t, J=8.0 Hz, 2H), 7.25 (t, J=7.6 Hz, 1H), 7.05 (s, 1H), 5.85 (s, 1H), 5.00-4.92 (m, 1H), 3.27-3.22 (m, 4H), 2.78 & 2.65 (s, 3H), 2.34 (s, 3H), 2.32-2.28 (m, 2H), 1.27-1.17 (m, 3H), 1.00-0.95 (m, 3H). Chiral SFC: $t_R$=4.373 min (Instrument column: Chiralcel OD-3 100×4.6 mm I.D., 3 um, Mobile phase: A: $CO_2$, B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., UV detection: 220 nm), ee %=96.476%. $[\alpha]_D^{20}$=−7.0 (c=0.10, MeOH).

Example 11

(E)-4-(dimethylamino)-N-methyl-N-[(1S)-1-methyl-2-[2-[[2-methyl-6-[5-phenylthiazol-2-yl)amino]pyrimidin-4-yl]amino]ethylamino]-2-oxo-ethyl]but-2-enamide (Compound 11)

Scheme 14. Synthesis of compound 11.

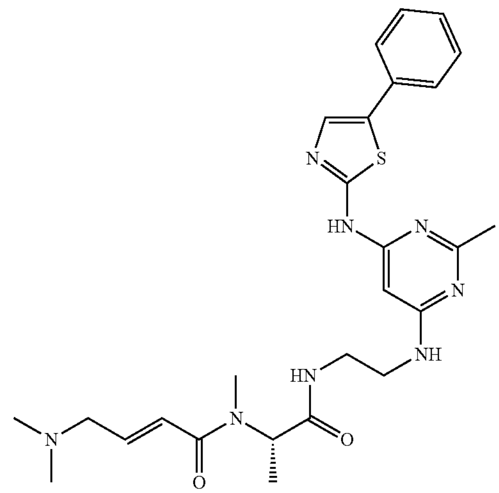

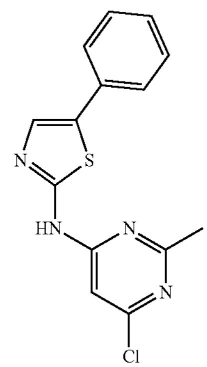

11-1

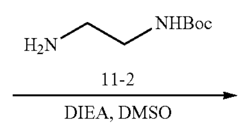

11-2

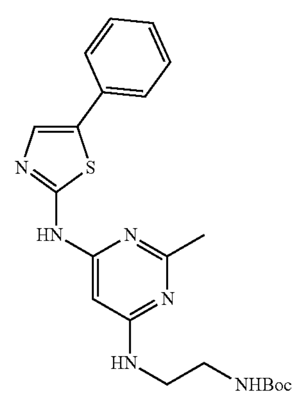

11-3

-continued

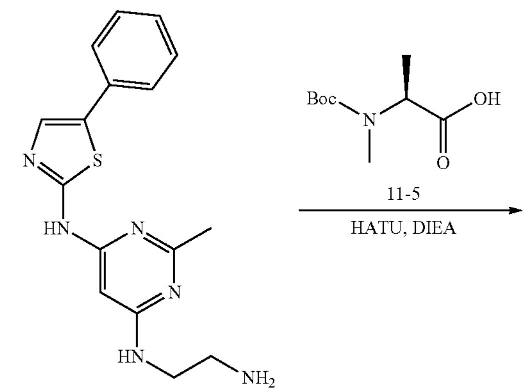

11-4

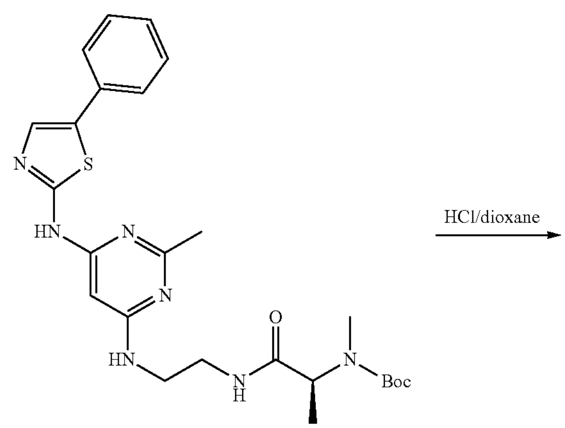

11-6

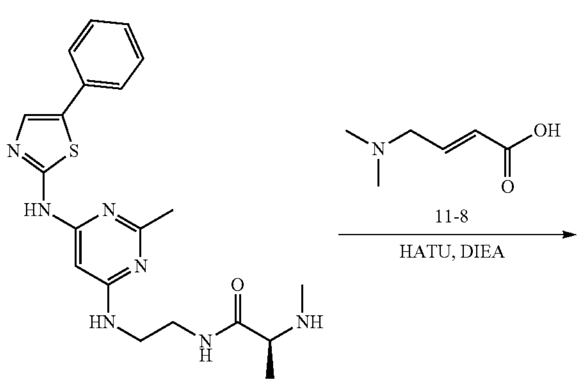

11-7

-continued

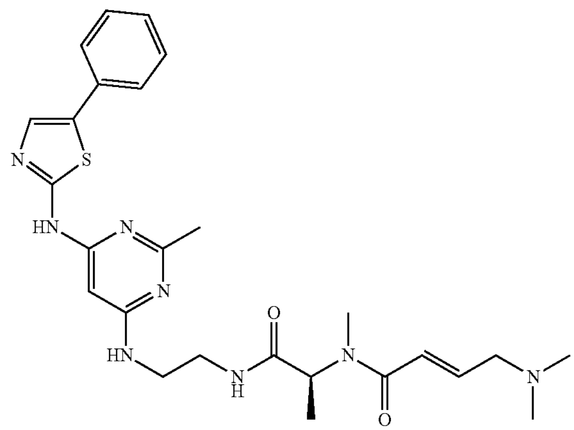

compound 11

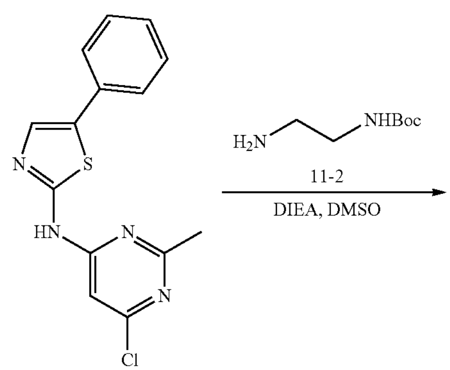

11-1

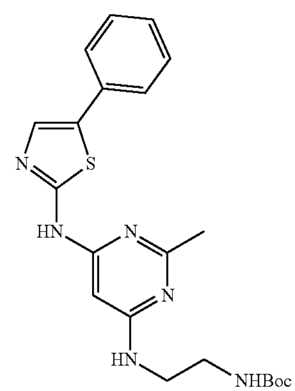

11-3

To a solution of N-(6-chloro-2-methyl-pyrimidin-4-yl)-5-phenyl-thiazol-2-amine (500 mg, 1.65 mmol) in DMSO (10 mL) was added DIEA (640 mg, 4.95 mmol) and tert-butyl N-(2-aminoethyl)carbamate (2.65 g, 16.51 mmol). The mixture was stirred at 90° C. for 12 hours. The mixture was poured into water (60 mL) and filtered, the filter cake was collected, dried to afford tert-butyl N-[2-[[2-methyl-6-[(5-phenylthiazol-2-yl)amino]pyrimidin-4-yl]amino]ethyl]carbamate (2.5 g, 99% yield) as a brown solid. LCMS: $t_R$=1.050 min in 10-80AB_2 min_220 &254_Shimadzu.1 cm, MS (ESI) m/z=427.0 $[M+H]^+$.

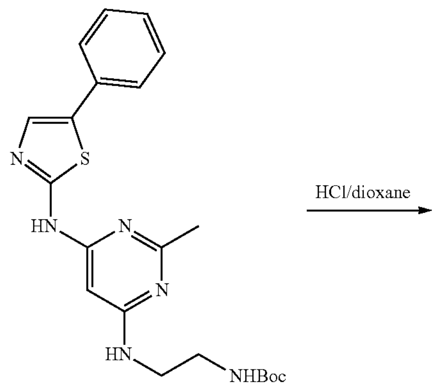

11-3

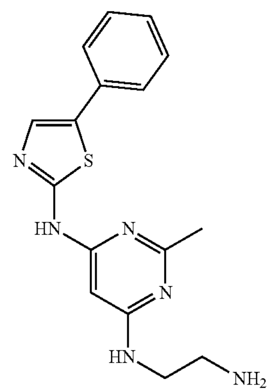

11-4

A solution of tert-butyl N-[2-[[2-methyl-6-[(5-phenylthiazol-2-yl)amino]pyrimidin-4-yl]amino]ethyl]carbamate (1 g. 0.914 mmol) in HCl/dioxane (30 mL, 4 M) was stirred at 25° C. for 0.5 hour. The mixture was concentrated under reduced pressure to afford $N_4$-(2-aminoethyl)-2-methyl-$N_6$-(5-phenylthiazol-2-yl)pyrimidine-4,6-diamine (480 mg. 97% yield) as a brown solid. LCMS: $t_R$=0.875 min in 10-80 AB_2 min_220 &254_Shimadzu.1 cm, MS (ESI)=326.9 $[M+H]^+$.

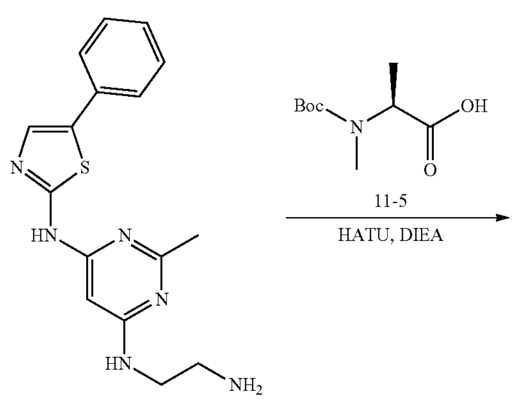

11-4

-continued

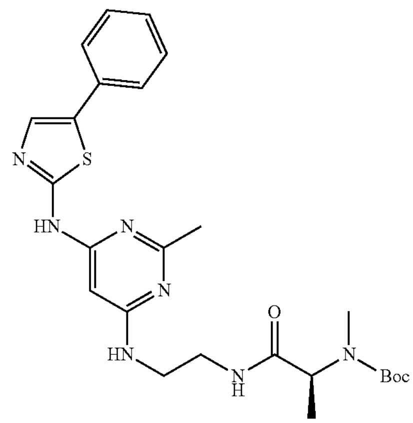

11-6

To a solution of $N_4$-(2-aminoethyl)-2-methyl-$N_6$-(5-phenylthiazol-2-yl)pyrimidine-4,6-diamine (480 mg, 1.47 mmol) in DMF (10 mL) was added HATU (670 mg, 1.76 mmol), (2S)-2-[tert-butoxycarbonyl(methyl)amino]propanoic acid (358 mg, 1.76 mmol) and DIEA (570 mg, 4.41 mmol). The mixture was stirred at 25° C. for 2 hours. The mixture was extracted with EtOAc (60 mL×3). The combined organic layers were washed with $H_2O$ (60 mL×3), dried over $Na_2SO_4$, filtered and concentrated under reduced pressure. The residue was purified by flash silica gel chromatography (ISCOR; 12 g SepaFlash® Silica Flash Column. Eluent of 0-10% Methanol/Dichloromethane @ 40 mL/min) to afford tert-butyl N-methyl-N-[(1S)-1-methyl-2-[2-[[2-methyl-6-[(5-phenylthiazol-2-yl)amino]pyrimidin-4-yl]amino]ethylamino]-2-oxo-ethyl]carbamate (360 mg, 48% yield) as a yellow solid. LCMS: $t_R$=0.871 min in 5-95 AB_1.5 min_220 &254_Shimadzu.1 cm, MS (ESI) m/z=512.2 $[M+H]^+$.

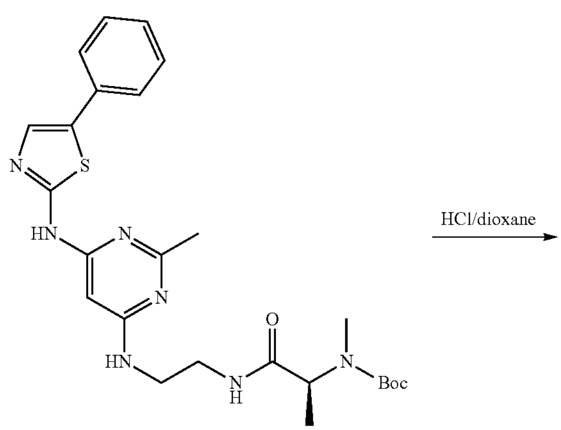

11-6

-continued

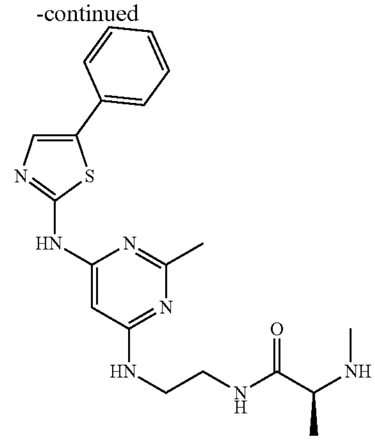

11-7

A solution of tert-butyl N-methyl-N-[(1S)-1-methyl-2-[2-[[2-methyl-6-[(5-phenylthiazol-2-yl)amino]pyrimidin-4-yl]amino]ethyl amino]-2-oxo-ethyl]carbamate (360 mg, 0.703 mmol) in HO/dioxane (20 mL, 4 M) was stirred at 25° C. for 0.5 hr. The mixture was concentrated under reduced pressure to give (2S)-2-(methylamino)-N-[2-[[2-methyl-6-[(5-phenylthiazol-2-yl)amino]pyrimidin-4-yl]amino]ethyl]propanamide (363 mg, 99% yield) as a yellow solid. LCMS: $t_R$=0.867 min in 0-60 AB_2 min_220 &254_Shimadzu.1 cm, MS (ESI) m/z=412.0 $[M+H]^+$.

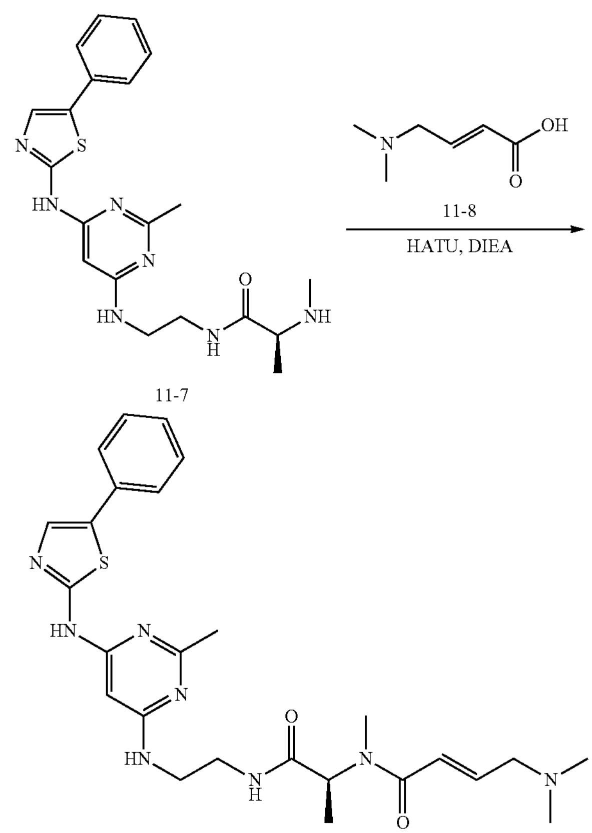

11-7 compound 11

To a solution of (2S)-2-(methylamino)-N-[2-[[2-methyl-6-[(5-phenylthiazol-2-yl)amino]pyrimidin-4-yl]amino]ethyl]propanamide (150 mg, 0.364 mmol) in DMF (10 mL) was added HATU (166 mg, 0.437 mmol), (E)-4-(dimethylamino)but-2-enoic acid (52 mg, 0.401 mmol) and DIEA (141 mg, 1.09 mmol). The mixture was stirred at 25° C. for 2 hours. The mixture was stirred at 25° C. for 0.5 hour. The mixture was concentrated under reduced pressure. The residue was purified by preparative HPLC (Colum: Xtimate C18 75*30 mm*3 um; water (0.04% HCl)-ACN; B % from 30 to 60; Gradient Time: 8 min; Flow rate: 25 mL/min) to afford (E)-4-(dimethylamino)-N-methyl-N-[(1S)-1-methyl-2-[2-[[2-methyl-6-[(5-phenylthiazol-2-yl)amino]pyrimidin-4-yl]amino]ethylamino]-2-oxo-ethyl]but-2-enamide (17.9 mg, 9% yield, 98.49% purity) as a white solid. LCMS: $t_R$=1.121 min in 0-60 AB_4 min_E_Shimadzu.1 cm, MS (ESI) m/z=523.2 $[M+H]^+$. $^1$H NMR (400 MHz, MeOD-$d_4$): δ=7.59-7.57 (m, 3H), 7.39 (t, J=36 Hz, 2H), 7.28 (t, J=36 Hz, 1H), 6.83-6.79 (m, 1H), 6.57-6.53 (m, 1H), 5.91 (s, 1H), 5.05-5.03 (m, 1H), 3.48-3.45 (m, 3H), 3.40-3.36 (m, 1H), 3.15-3.08 (m, 2H), 3.02-2.88 (m, 3H), 2.47 (s, 3H), 2.26-2.24 (m, 6H), 1.45-1.36 (m, 3H).

Example 12

(2S)—N-[2-[[2-methyl-6-[(5-phenylthiazol-2-yl)amino]-4-pyridyl]oxy]ethyl]-2-[methyl(prop-2-enoyl)amino]propanamide (Compound 12)

Scheme 15. Synthesis of compound 12.

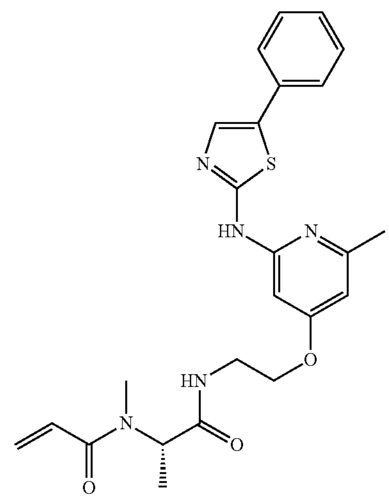

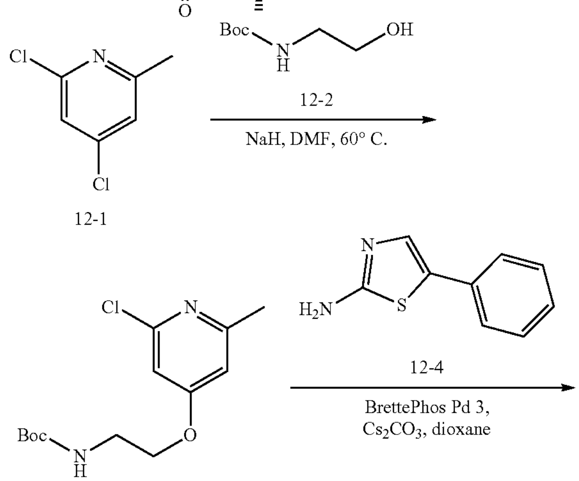

12-1

12-3

-continued
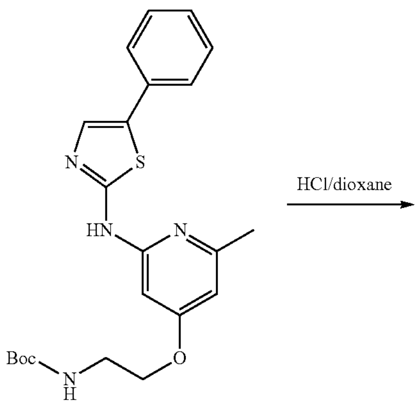
12-5
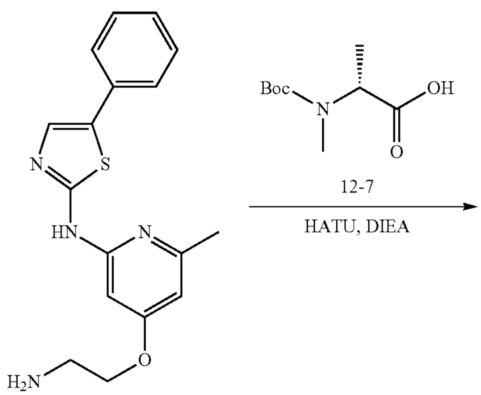
12-6
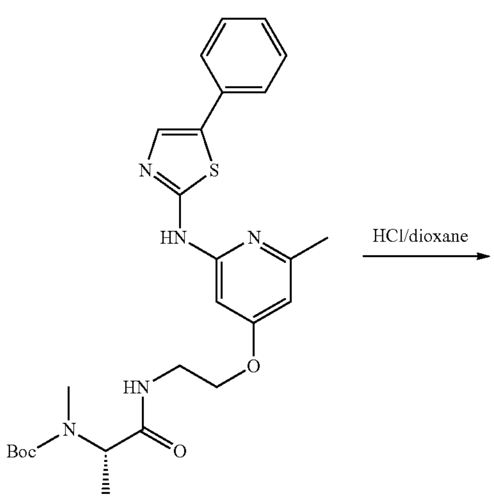
12-8
-continued
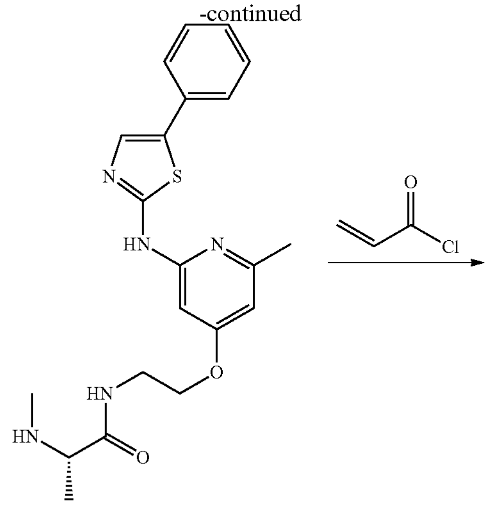
12-9
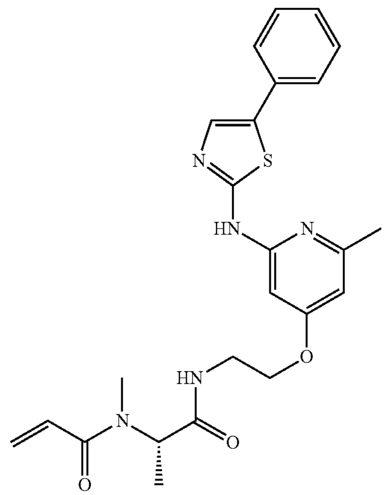
compound 12
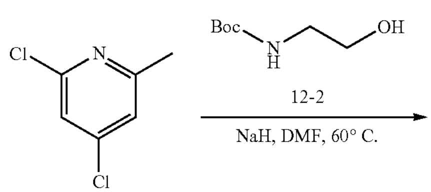
12-1
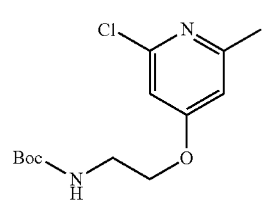
12-3
To a solution of tert-butyl N-(2-hydroxyethyl)carbamate (2.29 g, 14.20 mmol) in DMF (30 mL) was added NaH (681 mg, 17.04 mmol, 60% purity) and stirred at 0° C. for 0.5 hr. After that 2,4-dichloro-6-methyl-pyridine (2.3 g, 14.20 mmol) was added into the reaction mixture, and stirred at 25° C. for 5 hr. The mixture was quenched by addition $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0-30% Ethyl acetate/Petroleum ether gradient @ 40 mL/min) to afford tert-butyl N-[2-[(2-chloro-6-methyl-4-pyridyl)oxy]ethyl]carbamate (700 mg, 2.44 mmol, 17% yield) as a yellow oil.

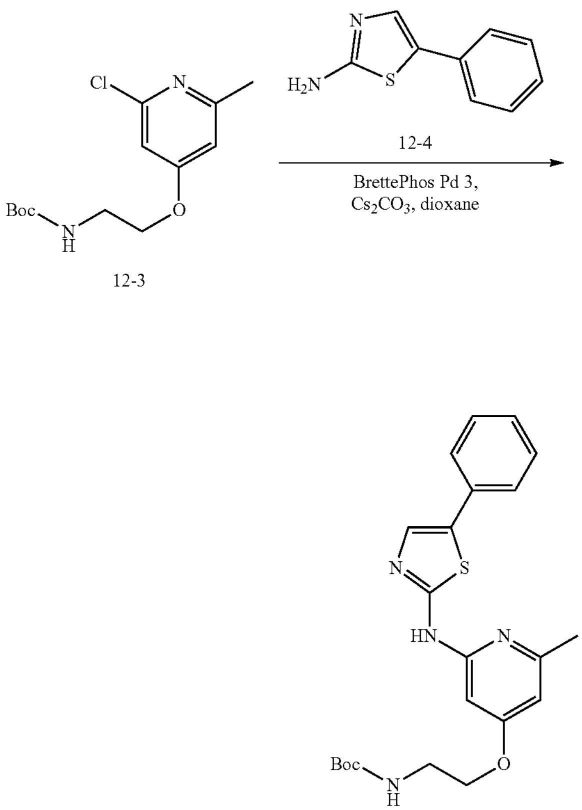

12-3
12-4
12-5

A mixture of tert-butyl N-[2-[(2-chloro-6-methyl-4-pyridyl)oxy]ethyl]carbamate (700 mg, 2.44 mmol), 5-phenylthiazol-2-amine (473 mg, 2.69 mmol), [2-(2-aminophenyl)phenyl]-methylsulfonyloxy-palladium; dicyclohexyl-[3,6-dimethoxy-2-(2,4,6-triisopropylphenyl)phenyl]phosphane (443 mg, 0.488 mmol), $Cs_2CO_3$ (1.59 g, 4.88 mmol) in dioxane (20 mL) was degassed and purged with $N_2$ for 3 times, and then the mixture was stirred at 80° C. for 12 hr under $N_2$ atmosphere. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 20 g SepaFlash® Silica Flash Column, Eluent of 0-50% Ethyl acetate/Petroleum ether gradient @ 60 mL/min) to afford tert-butyl N-[2-[[2-methyl-6-[(5-phenylthiazol-2-yl)amino]-4-pyridyl]oxy]ethyl]carbamate (587 mg, 1.38 mmol, 56% yield) as a brown solid.

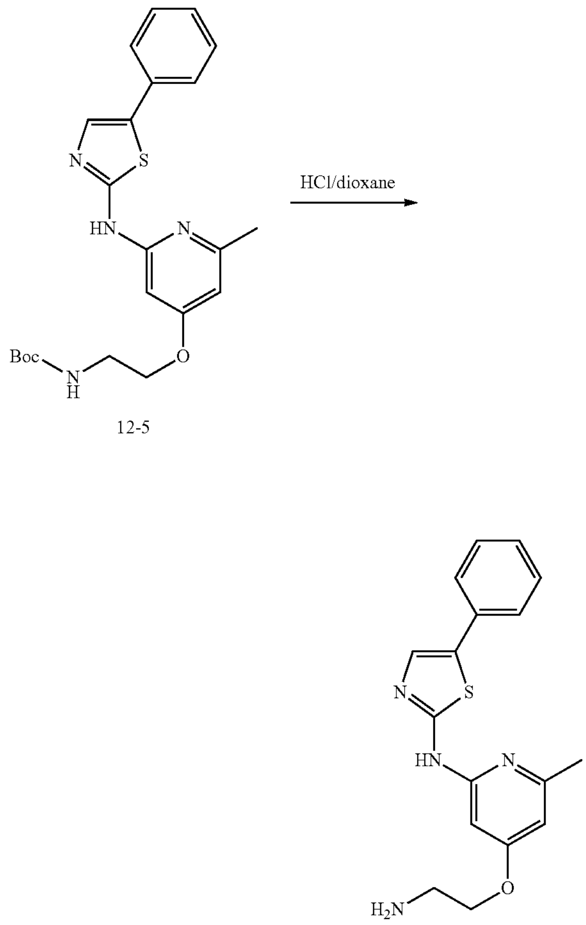

12-5
12-6

A solution of tert-butyl N-[2-[[2-methyl-6-[(5-phenylthiazol-2-yl)amino]-4-pyridyl]oxy]ethyl]carbamate (587 mg, 1.38 mmol) in HCl/dioxane (4 M, 0.34 mL) was stirred at 25° C. for 0.5 hr. The mixture was concentrated under reduced pressure to afford N-[4-(2-aminoethoxy)-6-methyl-2-pyridyl]-5-phenyl-thiazol-2-amine (700 mg, crude, HCl salt) as a yellow solid, which would be used directly in the next step.

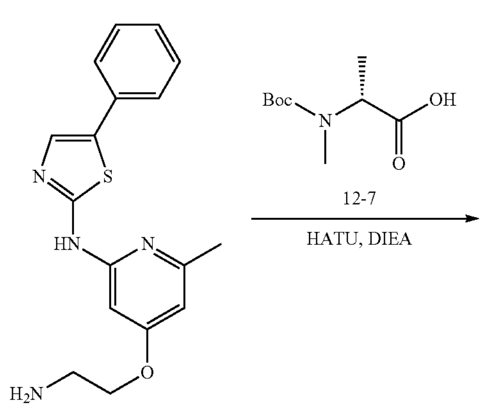

12-7
12-6

-continued

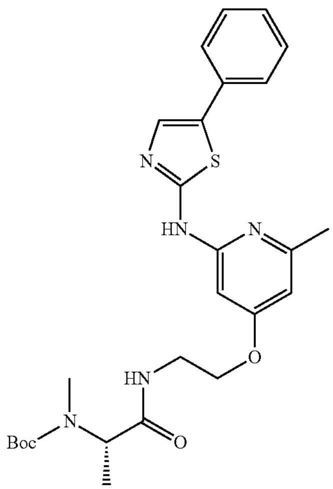

12-8

To a solution of N-[4-(2-aminoethoxy)-6-methyl-2-pyridyl]-5-phenyl-thiazol-2-amine (0.7 g, 1.35 mmol) in DMF (20 mL) was added HATU (616 mg, 1.62 mmol) and DIPEA (524 mg, 4.05 mmol) and (2R)-2-[tert-butoxycarbonyl(methyl)amino]propanoic acid (274 mg, 1.35 mmol). The mixture was stirred at 25° C. for 2 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~70% Ethyl acetate/Petroleum ether gradient @ 40 mL/min) to afford tert-butyl N-methyl-N-[(1S)-1-methyl-2-[2-[[2-methyl-6-[(5-phenylthiazol-2-yl)amino]-4-pyridyl]oxy]ethyl amino]-2-oxo-ethyl]carbamate (550 mg, 1.07 mmol, 80% yield) as a yellow solid.

-continued

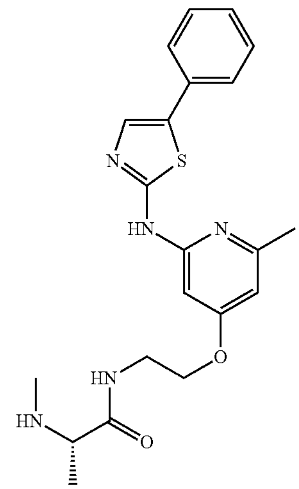

12-9

A solution of tert-butyl N-methyl-N-[(1S)-1-methyl-2-[2-[[2-methyl-6-[(5-phenylthiazol-2-yl)amino]-4-pyridyl]oxy]ethylamino]-2-oxo-ethyl]carbamate (550 mg, 1.07 mmol) in HCl/dioxane (4 M, 10 mL) was stirred at 25° C. for 0.5 hr. The mixture was concentrated under reduced pressure to afford (2S)-2-(methylamino)-N-[2-[[2-methyl-6-[(5-phenylthiazol-2-yl)amino]-4-pyridyl]oxy]ethyl]propanamide (690 mg, crude, HCl salt) as a yellow solid, which would be used directly in the next step.

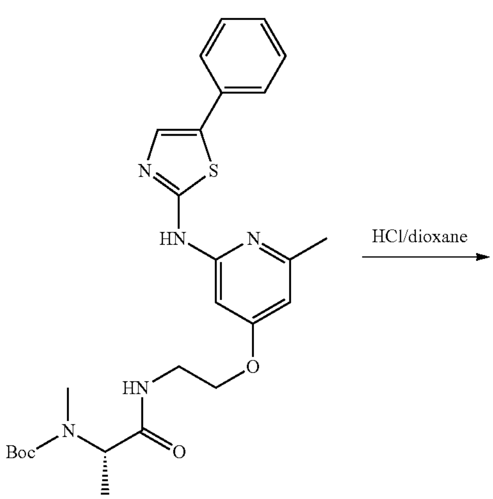

12-8

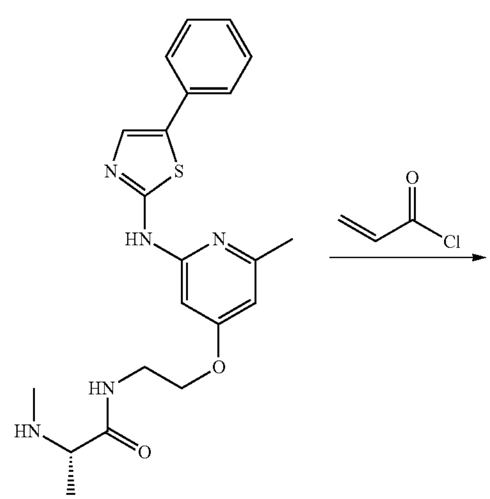

12-9

-continued

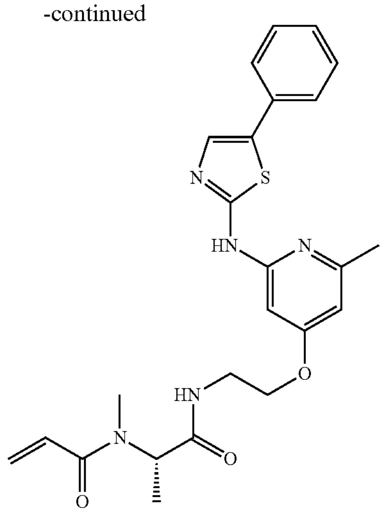

compound 12

To a solution of (2S)-2-(methylamino)-N-[2-[[2-methyl-6-[(5-phenylthiazol-2-yl)amino]-4-pyridyl]oxy]ethyl]propanamide (390 mg, 0.654 mmol) in $CH_2Cl_2$ (10 mL) was added DIPEA (254 mg, 1.96 mmol) and prop-2-enoyl chloride (59 mg, 0.654 mmol). The mixture was stirred at 0° C. for 0.5 hr. The mixture was quenched by addition of $H_2O$ (50 mL) at 25° C., and then diluted with $H_2O$ (50 mL) and extracted with DCM (50 mL×3). The combined organic layers were washed with brine (50 mL), dried over $Na_2SO_4$, filtered and concentrated under reduced pressure to give a residue. After that the residue was purified by flash silica gel chromatography (ISCOR; 12 g SepaFlash® Silica Flash Column, Eluent of 0~10% DCM/MeOH @ 40 mL/min) to afford (2S)—N-[2-[[2-methyl-6-[(5-phenylthiazol-2-yl)amino]-4-pyridyl]oxy]ethyl]-2-[methyl(prop-2-enoyl)amino]propanamide (75.6 mg, 0.159 mmol, 24% yield, 98% purity) as a white solid. LCMS: $t_R$=1.562 min in 10-80AB_4 min_220 &254_Shimadzu.1 cm, MS (ESI) m/z=466.2 $[M+H]^+$. $^1$H NMR (400 MHz, DMSO-$d_6$): δ=11.13 (s, 1H), 8.32-8.01 (m, 1H), 7.78-7.73 (m, 1H), 7.58 (d, J=7.2 Hz, 2H), 7.40 (t, J=7.6 Hz, 2H), 7.28-7.22 (m, 1H), 6.79-6.68 (m, 1H), 6.46 (s, 1H), 6.40 (d, J=1.6 Hz, 1H), 6.18-6.04 (m, 1H), 5.74-5.59 (m, 1H), 5.06-4.61 (m, 1H), 4.10-4.01 (m, 2H), 3.53-3.41 (m, 2H), 2.94-2.75 (m, 3H), 2.44 (s, 3H), 1.30-1.23 (m, 3H). Chiral SFC: $t_R$=4.609 min (Instrument column: Chiralcel OD-3 100×4.6 mm I.D., 3 um Mobile phase: A: $CO_2$ B: ethanol (0.05% DEA) Gradient: from 5% to 40% of B in 4.5 min and hold 40% for 2.5 min, then 5% of B for 1 min, Flow rate: 2.8 mL/min, Column temperature: 40° C., detection: 220 nm), ee %=100%. $[\alpha]_D^{20}$=−76.0 (c=0.10, MeOH).

Example 13

(2S)—N-[2-[2-methyl-6-[(5-phenylthiazol-2-yl)amino]pyrimidin-4-yl]oxy ethyl]-2-[methyl(prop-2-enoyl)amino]propanamide (Compound 13)

Scheme 16. Synthesis of compound 13.

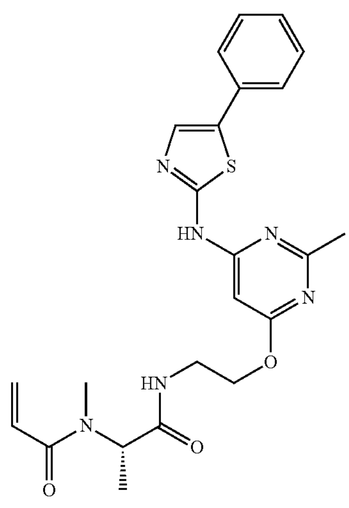

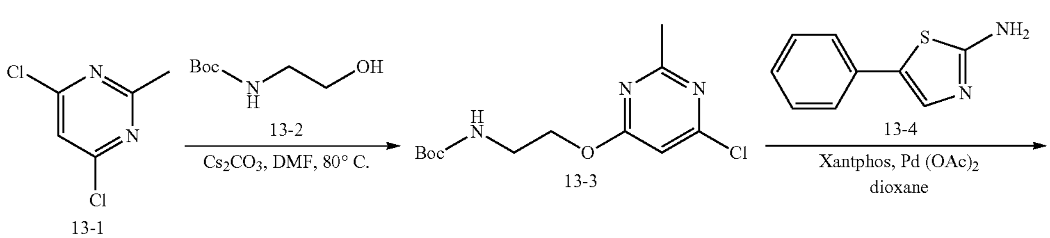

-continued

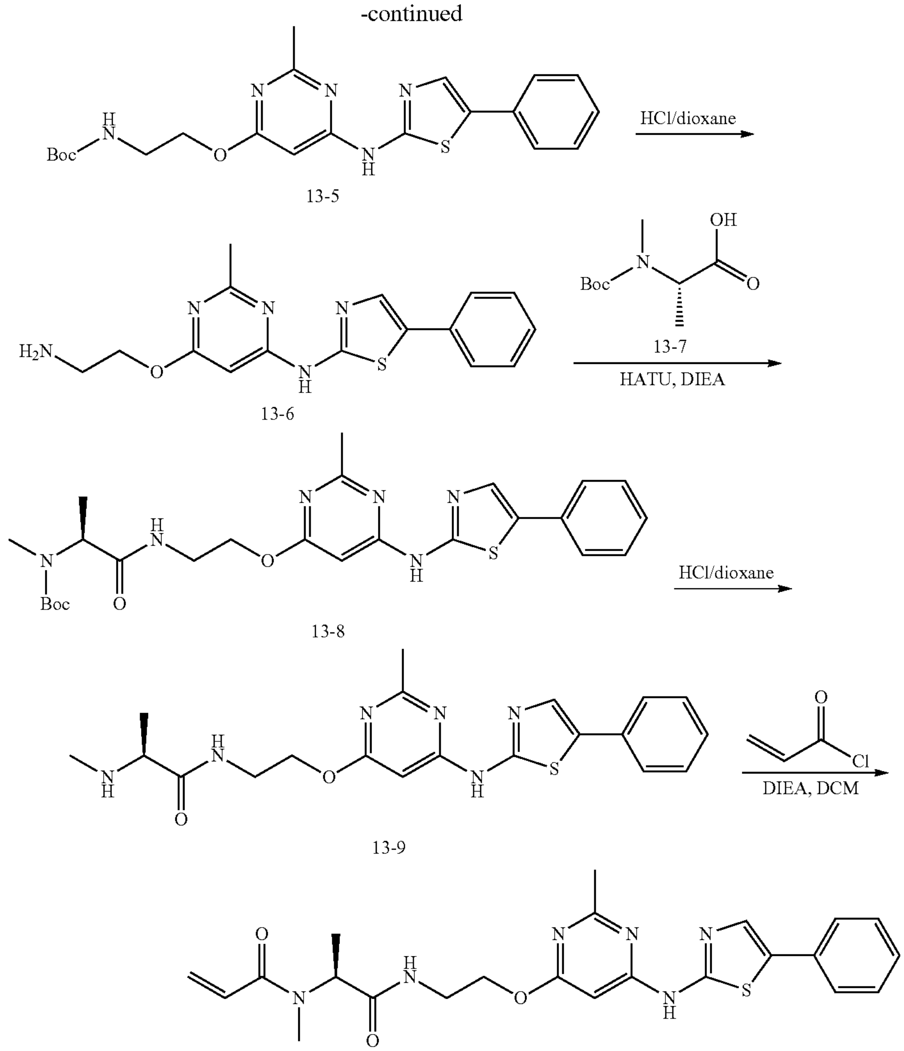

13-5

13-6

13-8

13-9 compound 13

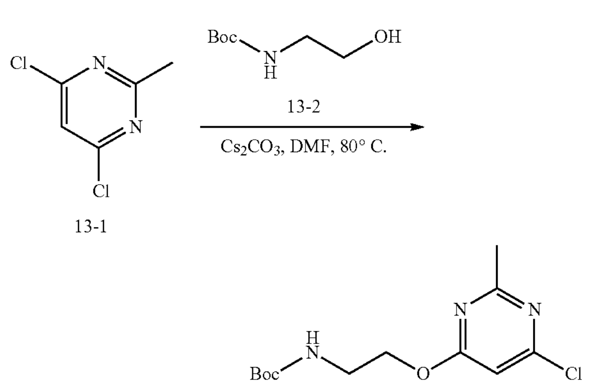

13-1

13-2

13-3

To a solution of 4,6-dichloro-2-methyl-pyrimidine (5 g, 30.67 mmol) in DMF (80 mL) was added $Cs_2CO_3$ (14.99 g, 46.01 mmol) and tert-butyl N-(2-hydroxyethyl)carbamate (4.94 g, 30.67 mmol). The mixture was stirred at 80° C. for 2 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 20 g SepaFlash® Silica Flash Column, Eluent of 0~40% Ethyl acetate/Petroleum ether gradient 40 mL/min) to afford tert-butyl N-[2-(6-chloro-2-methyl-pyrimidin-4-yl)oxyethyl]carbamate (4 g, 13.90 mmol, 45% yield) as a yellow oil. $^1H$ NMR (400 MHz, DMSO-$d_6$): δ=6.99 (m, J=5.2 Hz, 1H), 6.89 (s, 1H), 4.33 (m, J=5.6 Hz, 2H), 3.29 (m, J=5.6 Hz, 2H), 2.50 (s, 3H), 1.36 (s, 9H).

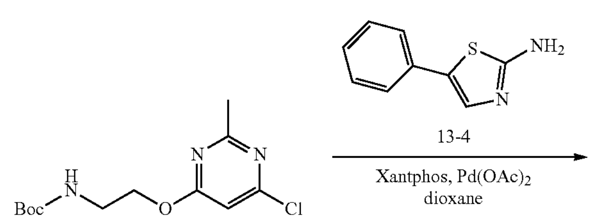

13-3

-continued

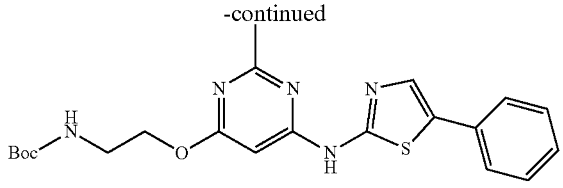

13-5

A mixture of tert-butyl N-[2-(6-chloro-2-methyl-pyrimidin-4-yl)oxyethyl]carbamate (1.2 g, 4.17 mmol), 5-phenylthiazol-2-amine (808 mg, 4.59 mmol), Xantphos (483 mg, 0.834 mmol), $Pd(OAc)_2$ (94 mg, 0.417 mmol) and $K_2CO_3$ (865 mg, 6.26 mmol) in dioxane (30 mL) was degassed and purged with $N_2$ for 3 times, and then the mixture was stirred at 80° C. for 2 hr under $N_2$ atmosphere. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 20 g SepaFlash® Silica Flash Column, Eluent of 0~40% Ethyl acetate/Petroleum ether gradient @, 60 mL/min) to afford tert-butyl N-[2-[2-methyl-6-[(5-phenylthiazol-2-yl)amino]pyrimidin-4-yl]oxyethyl]carbamate (0.8 g, 1.87 mmol, 45% yield) as a yellow solid.

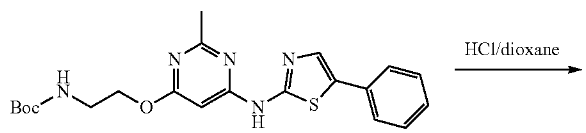

13-5

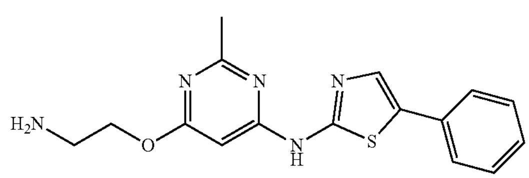

13-6

A solution of tert-butyl N-[2-[2-methyl-6-[(5-phenylthiazol-2-yl)amino]pyrimidin-4-yl]oxyethyl]carbamate (0.8 g, 1.87 mmol) in HCl/dioxane (4 M, 20 mL) was stirred at 25° C. for 0.5 hr. The mixture was concentrated under reduced pressure to remove solvent. The residue was diluted with $H_2O$ (50 mL) and adjusted the pH to 8~9 by addition of aq. $NaHCO_3$, then extracted with DCM (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~10% DCM/MeOH cv 40 mL/min) to afford N-[6-(2-aminoethoxy)-2-methyl-pyrimidin-4-yl]-5-phenyl-thiazol-2-amine (580 mg, 1.77 mmol, 95% yield) as a yellow solid.

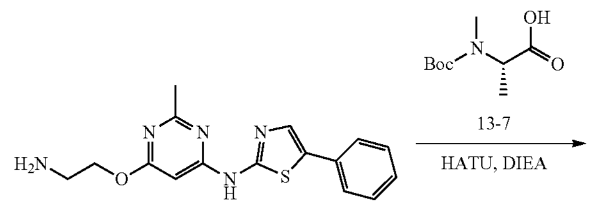

13-6

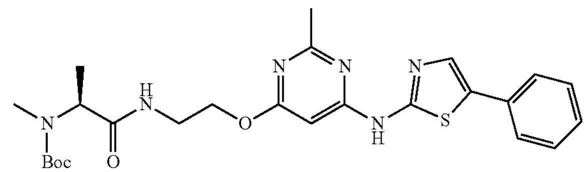

13-8

To a solution of N-[6-(2-aminoethoxy)-2-methyl-pyrimidin-4-yl]-5-phenyl-thiazol-2-amine (580 mg, 1.77 mmol) in DMF (10 mL) was added HATU (808 mg, 2.13 mmol), DIEA (687 mg, 5.31 mmol) and (2S)-2-[tert-butoxycarbonyl(methyl)amino]propanoic acid (396 mg, 1.95 mmol). The mixture was stirred at 25° C. for 2 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0~10% DCM/MEOH @ 40 mL/min) to afford tert-butyl N-methyl-N-[(1S)-1-methyl-2-[2-[2-methyl-6-[(5-phenylthiazol-2-yl)amino]pyrimidin-4-yl]oxy ethyl amino]-2-oxo-ethyl]carbamate (350 mg, 0.683 mmol, 38% yield) as a yellow solid.

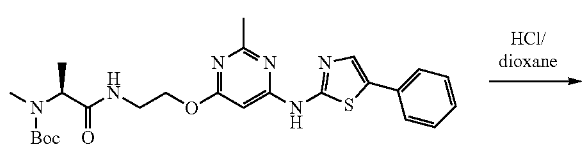

13-8

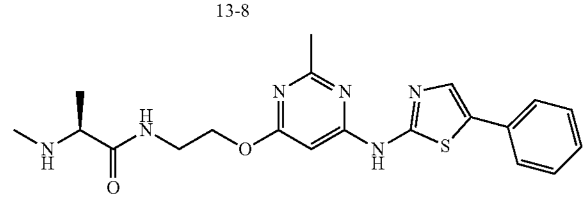

13-9

A solution of tert-butyl N-methyl-N-[(1S)-1-methyl-2-[2-[2-methyl-6-[(5-phenylthiazol-2-yl)amino]pyrimidin-4-yl]oxyethylamino]-2-oxo-ethyl]carbamate (350 mg, 0.683 mmol) in HCl/dioxane (4 M, 20 mL) was stirred at 25° C. for 0.5 hr. The mixture was concentrated under reduced pressure to afford (2S)-2-(methylamino)-N-[2-[2-methyl-6-[(5-phenylthiazol-2-yl)amino]pyrimidin-4-yl]oxyethyl]propanamide (367 mg, 0.676 mmol, 99% yield, 76% purity) as a yellow solid, which would be used directly in the next step.

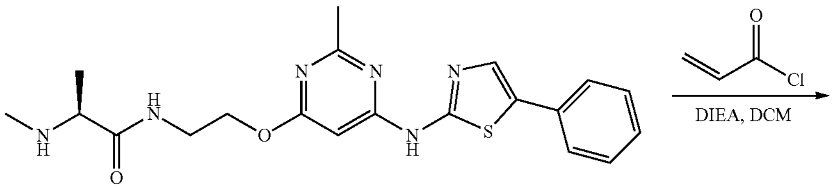

13-9

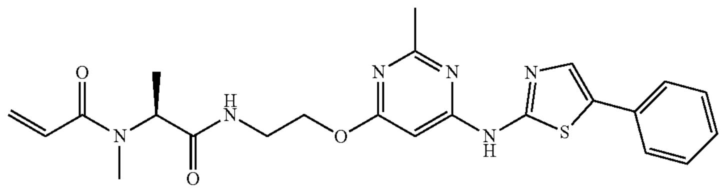

compound 13

To a solution of (2S)-2-(methylamino)-N-[2-[2-methyl-6-[(5-phenylthiazol-2-yl)amino]pyrimidin-4-yl]oxyethyl]propanamide (367 mg, 0.676 mmol) in $CH_2Cl_2$ (20 mL) was added DIEA (262 mg, 2.03 mmol) and prop-2-enoyl chloride (61 mg, 0.676 mmol) at 0° C. The mixture was stirred at 0° C. for 0.5 hr. The mixture was quenched by addition of $H_2O$ (50 mL) at 25° C., and then diluted with $H_2O$ (50 mL) and extracted with DCM (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0-10% methanol in dichloromethane @ 40 mL/min) to afford (2S)—N-[2-[2-methyl-6-[(5-phenylthiazol-2-yl)amino]pyrimidin-4-yl]oxy ethyl]-2-[methyl (prop-2-enoyl)amino]propanamide (53.3 mg, 113.10 umol, 17% yield, 99% purity) as a white solid. LCMS: $t_R$=1.980 min in 10-80AB_4 min_220 &254_Shimadzu.1 cm, MS (ESI) m/z=467.2 $[M+H]^+$. $^1H$ NMR (400 MHz, DMSO) δ=11.53 (s, 1H), 8.29-8.01 (m, 1H), 7.87-7.78 (m, 1H), 7.61 (d, J=7.2 Hz, 2H), 7.41 (d, J=7.6 Hz, 2H), 7.33-7.24 (m, 1H), 6.79-6.66 (m, 1H), 6.22 (s, 1H), 6.16-6.03 (m, 1H), 5.74-5.57 (m, 1H), 5.06-4.59 (m, 1H), 4.36-4.26 (m, 2H), 3.53-3.38 (m, 2H), 2.93-2.74 (m, 3H), 2.53 (s, 3H), 1.29-1.21 (m, 3H). Chiral SFC: $t_R$=4.609 min (Instrument column: Chiralcel OD-3 100×4.6 mm I.D., 3 um Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., detection: 220 nm), ee %=98.63%. $[\alpha]_D^{20}$=−239.0 (c=0.10, MeOH).

Example 14

(3S)—N-[2-[2-methyl-6-[(5-phenylthiazol-2-yl)amino]pyrimidin-4-yl]oxyethyl]-4-prop-2-enoyl-morpholine-3-carboxamide (Compound 14)

Scheme 17. Synthesis of compound 14.

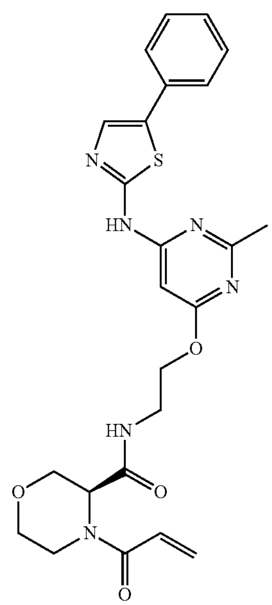

-continued

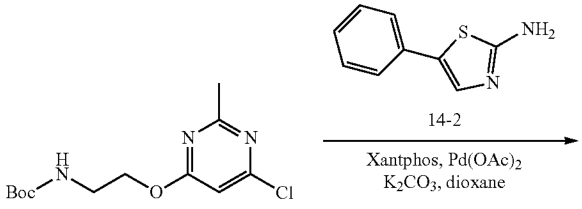

14-1

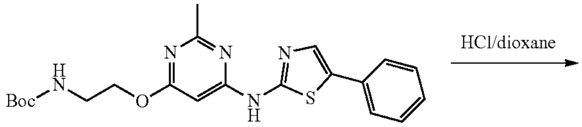

14-3

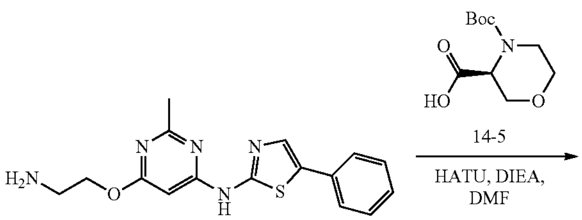

14-4

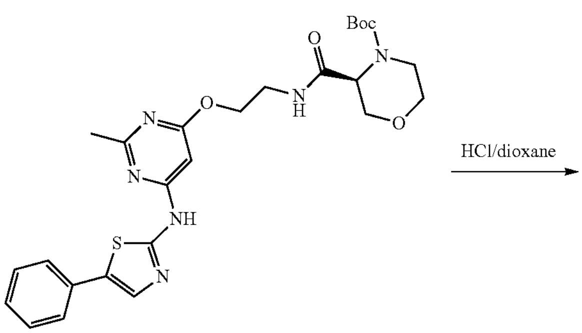

14-6

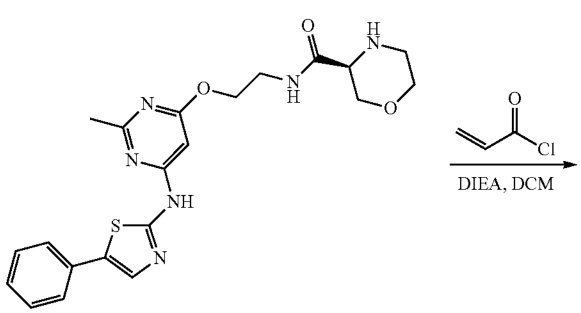

14-7

-continued

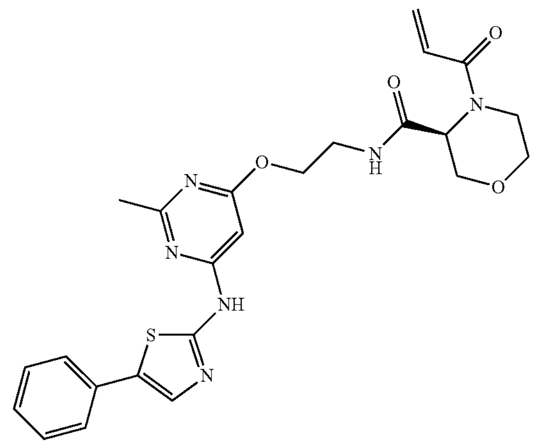

compound 14

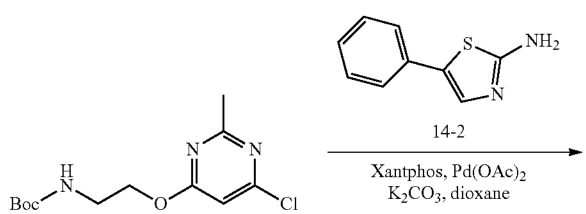

14-1

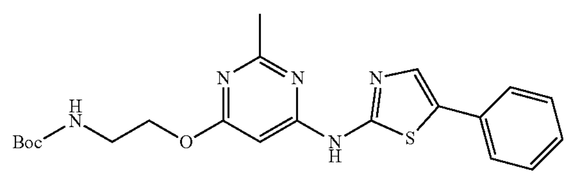

14-3

A mixture of tert-butyl N-[2-(6-chloro-2-methyl-pyrimidin-4-yl)oxyethyl]carbamate (3 g, 10.43 mmol), 5-phenylthiazol-2-amine (2.02 g, 11.47 mmol), Xantphos (1.21 g, 2.09 mmol), $Pd(OAc)_2$ (234 mg, 1.04 mmol) and $K_2CO_3$ (2.16 g, 15.64 mmol) in dioxane (50 mL) was degassed and purged with $N_2$ for 3 times, and then the mixture was stirred at 80° C. for 2 hours under $N_2$ atmosphere. The mixture was cooled to ambient temperature, and then was added water (20 mL) and extracted with ethyl acetate (50 mL×3). The organic layers were concentrated and the residue was purified by flash column chromatography on silica gel (ethyl acetate in petroleum ether from 0% to 40%) to afford tert-butyl N-[2-[2-methyl-6-[(5-phenylthiazol-2-yl)amino]pyrimidin-4-yl]oxy ethyl]carbamate (2.33 g, 48% yield) as a yellow solid.

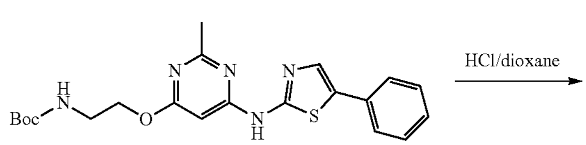

14-3

-continued

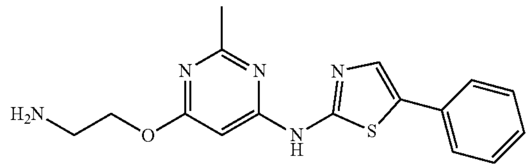

14-4

A solution of tert-butyl N-[2-[2-methyl-6-[(5-phenylthiazol-2-yl)amino]pyrimidin-4-yl]oxyethyl]carbamate (2.33 g, 5.45 mmol) in HCl/dioxane (4 M, 30 mL) was stirred at 20° C. for 0.5 hour. The mixture was concentrated under reduced pressure to remove solvent. The residue was diluted with $H_2O$ (20 mL) and adjusted the pH to 8~9 by addition of aq. $NaHCO_3$, then filtered. The filter cake was dried to afford N-[6-(2-aminoethoxy)-2-methyl-pyrimidin-4-yl]-5-phenyl-thiazol-2-amine (1.5 g, 84% yield) as a yellow solid. $^1H$ NMR (400 MHz, DMSO-$d_6$): δ=7.80 (s, 1H), 7.62-7.59 (m, 2H), 7.40 (t, J=7.6 Hz, 3H), 6.24 (s, 1H), 4.26-4.20 (m, 2H), 3.30 (s, 2H), 2.88 (t, J=5.6 Hz, 2H), 2.52 (s, 3H).

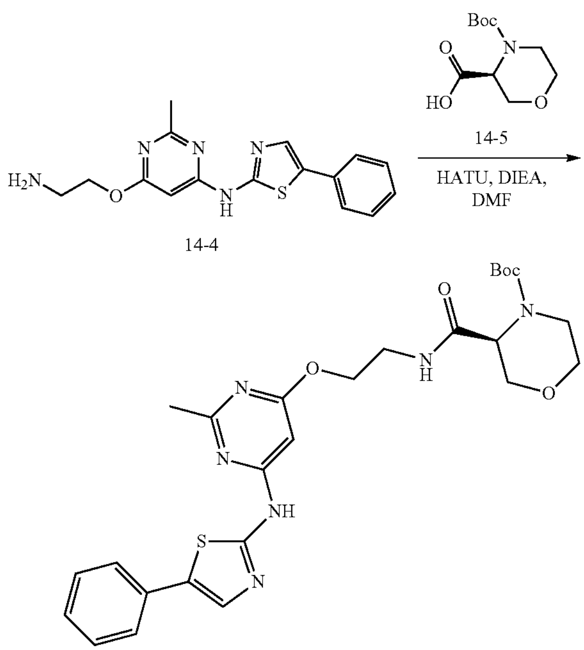

14-4

14-5

14-6

A solution of (3S)-4-tert-butoxycarbonylmorpholine-3-carboxylic acid (311 mg, 1.34 mmol), HATU (557 mg, 1.47 mmol) and DIEA (474 mg, 3.67 mmol) in DMF (6 mL) was stirred for 0.5 hour, and then added N-[6-(2-aminoethoxy)-2-methyl-pyrimidin-4-yl]-5-phenyl-thiazol-2-amine (400 mg, 1.22 mmol). The mixture was stirred at 25° C. for 2 hours. The mixture was quenched by addition of water (10 mL) at 25° C., and then extracted with ethyl acetate (15 mL×3). The organic layers were concentrated and purified by flash column chromatography on silica gel (methanol in dichloromethane from 0% to 3%) to afford tert-butyl (3S)-3-[2-[2-methyl-6-[(5-phenylthiazol-2-yl)amino]pyrimidin-4-yl]oxy ethyl carbamoyl]morpholine-4-carboxylate (827 mg, 87% purity) as a yellow solid.

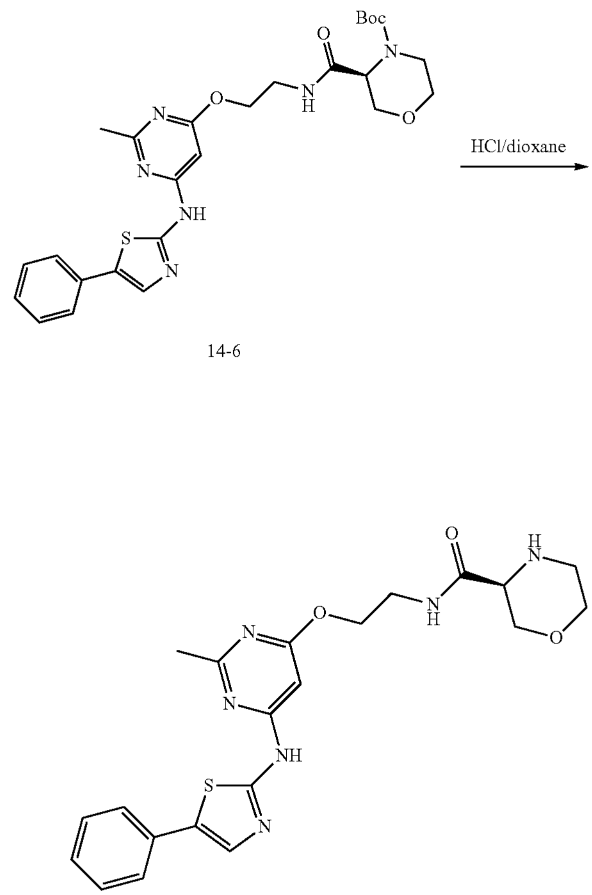

14-6

14-7

A solution of tert-butyl (3S)-3-[2-[2-methyl-6-[(5-phenylthiazol-2-yl)amino]pyrimidin-4-yl]oxyethylcarbamoyl]morpholine-4-carboxylate (827 mg, 1.33 mmol) in HCl/dioxane (4 M, 20 mL) was stirred at 25° C. for 1 hour. The mixture was concentrated in vacuo. The residue was dissolved in methanol (10 mL) and adjusted to pH=8 by addition of saturated aqueous $NaHCO_3$. The precipitation was filtered, dried to afford (3S)—N-[2-[2-methyl-6-[(5-phenylthiazol-2-yl)amino]pyrimidin-4-yl]oxy ethyl]morpholine-3-carboxamide (400 mg, 65% yield) as a yellow solid.

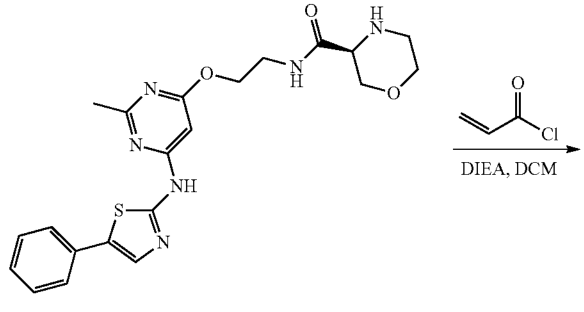

14-7

-continued

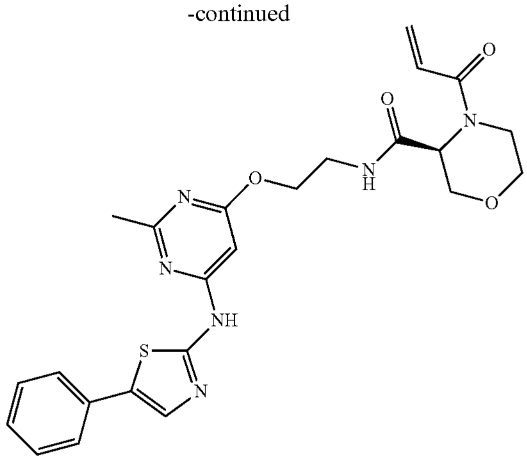

compound 14

To a solution of (3S)—N-[2-[2-methyl-6-[(5-phenylthiazol-2-yl)amino]pyrimidin-4-yl]oxyethyl]morpholine-3-carboxamide (100 mg, 0.23 mmol) in DCM (2 mL) was added TEA (46 mg, 0.45 mmol) and prop-2-enoyl chloride (21 mg, 0.23 mmol) at 0° C. The mixture was stirred at 25° C. for 0.5 hour. The mixture was concentrated in vacuo and purified by prep-HPLC (1_Welch Xtimate 75*40 mm*3 um; mobile phase: [water (0.225% FA)-ACN]; B %: 35%-65%, 10 min) to afford (3S)—N-[2-[2-methyl-6-[(5-phenylthiazol-2-yl)amine]pyrimidin-4-yl]oxyethyl]-4-prop-2-enoyl-morpholine-3-carboxamide (11.1 mg, 10% yield) as a yellow solid. LCMS: $t_R$=1.674 min in 10-80 AB_4 min_220 &254_Shimadzu.1 cm, MS (ESI) m/z=495.3 $[M+H]^+$. $^1H$ NMR (400 MHz, DMSO-$d_6$): δ=11.52 (s, 1H), 8.25-8.13 (m, 1H), 7.81 (s, 1H), 7.60 (d, J=7.2 Hz, 2H), 7.41 (t, J=7.6 Hz, 2H), 7.31-7.25 (m, 1H), 6.91-6.44 (m, 1H), 6.61-6.43 (m, 1H), 6.30-6.01 (m, 2H), 5.79-5.58 (m, 1H), 4.84-4.48 (m, 1H), 4.38-4.10 (m, 4H), 3.85-3.76 (m, 1H), 3.63-3.39 (m, 5H), 2.53 (s, 3H). Chiral SFC: $t_R$=5.225 min, Column: (S,S)-Whelk-0-3 50 um*4.6 mm I.D., 1.8 um, Mobile phase: A: $CO_2$ B: ethanol (0.05% DEA), Gradient: from 5% to 40% of B in 4 min and hold 40% for 2.5 min, then 5% of B for 1 min, Flow rate: 2.5 mL/min, Column temp.: 35° C., ABPR: 1500 psi. Acq Method: Whelk0_3_EtOH_DEA_5_40_25 ML. ee %=96.46%.

Example 15

(2S)-4-methyl-N-[2-[2-methyl-6-[(5-phenylthiazol-2-yl)amino]pyrimidin-4-yl]oxyethyl]-1-prop-2-enoyl-piperazine-2-carboxamide (Compound 15)

Scheme 18. Synthesis of compound 15.

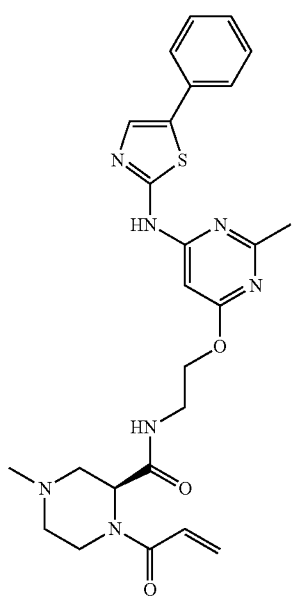

-continued
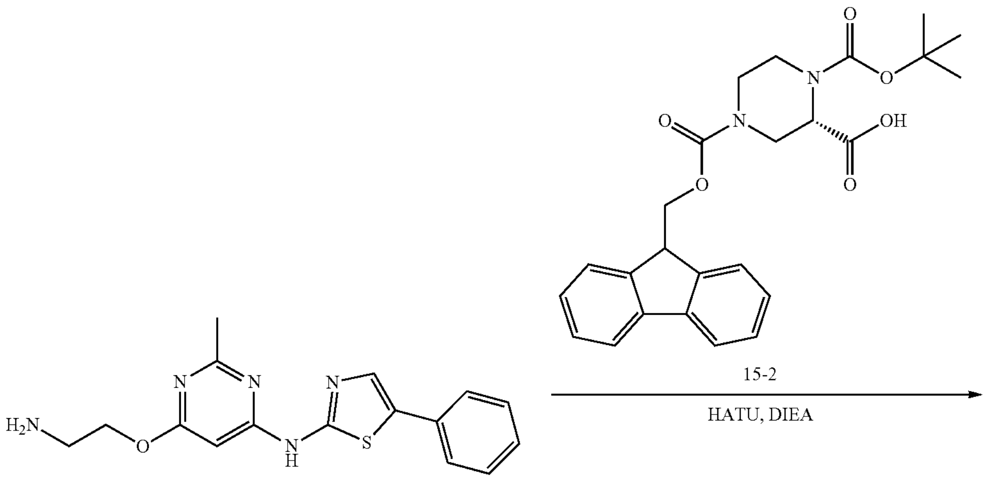
15-1
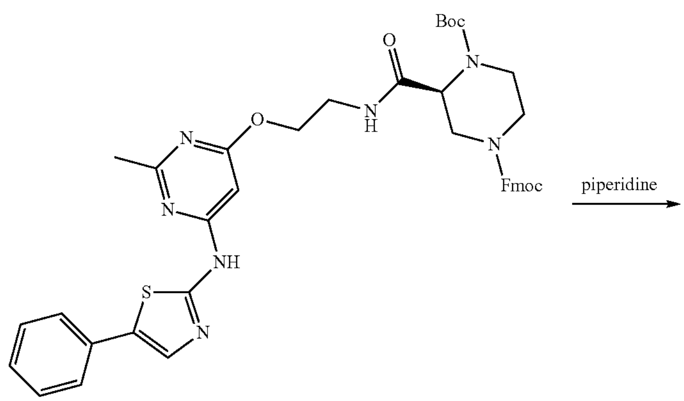
15-3
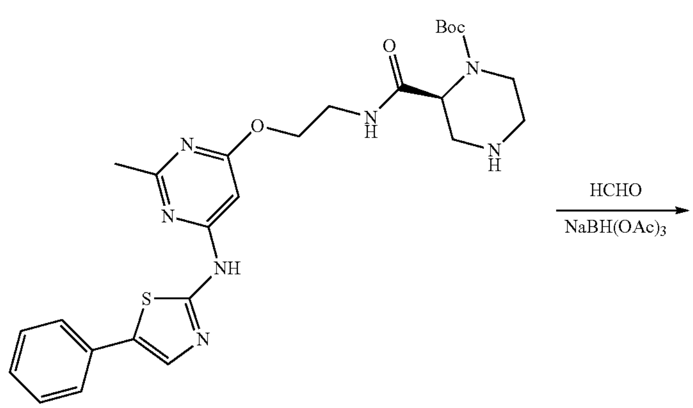
15-4

-continued
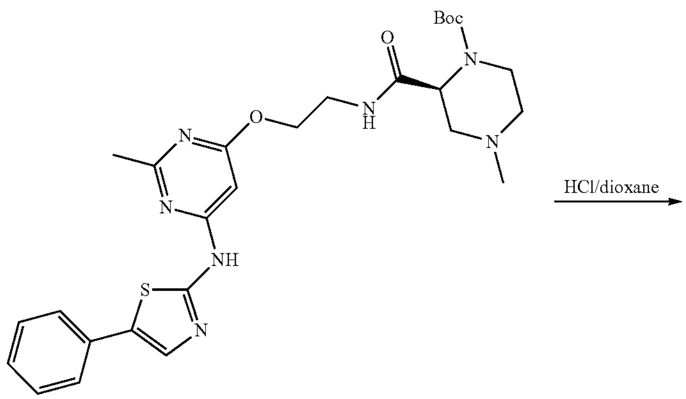
15-5
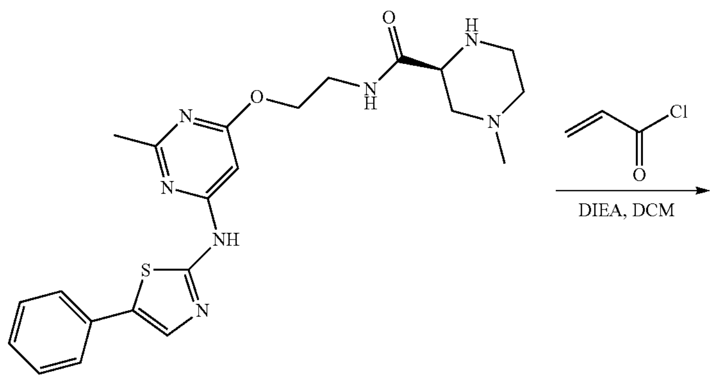
15-6
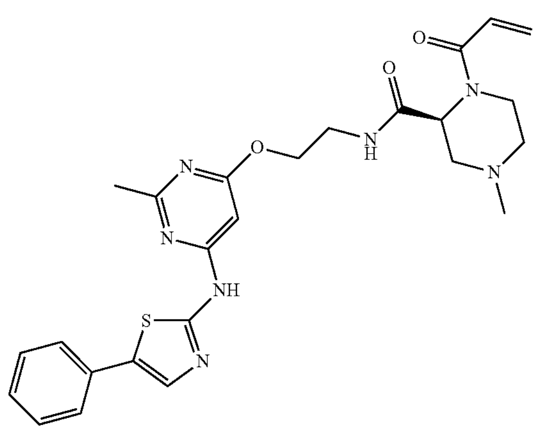
compound 15

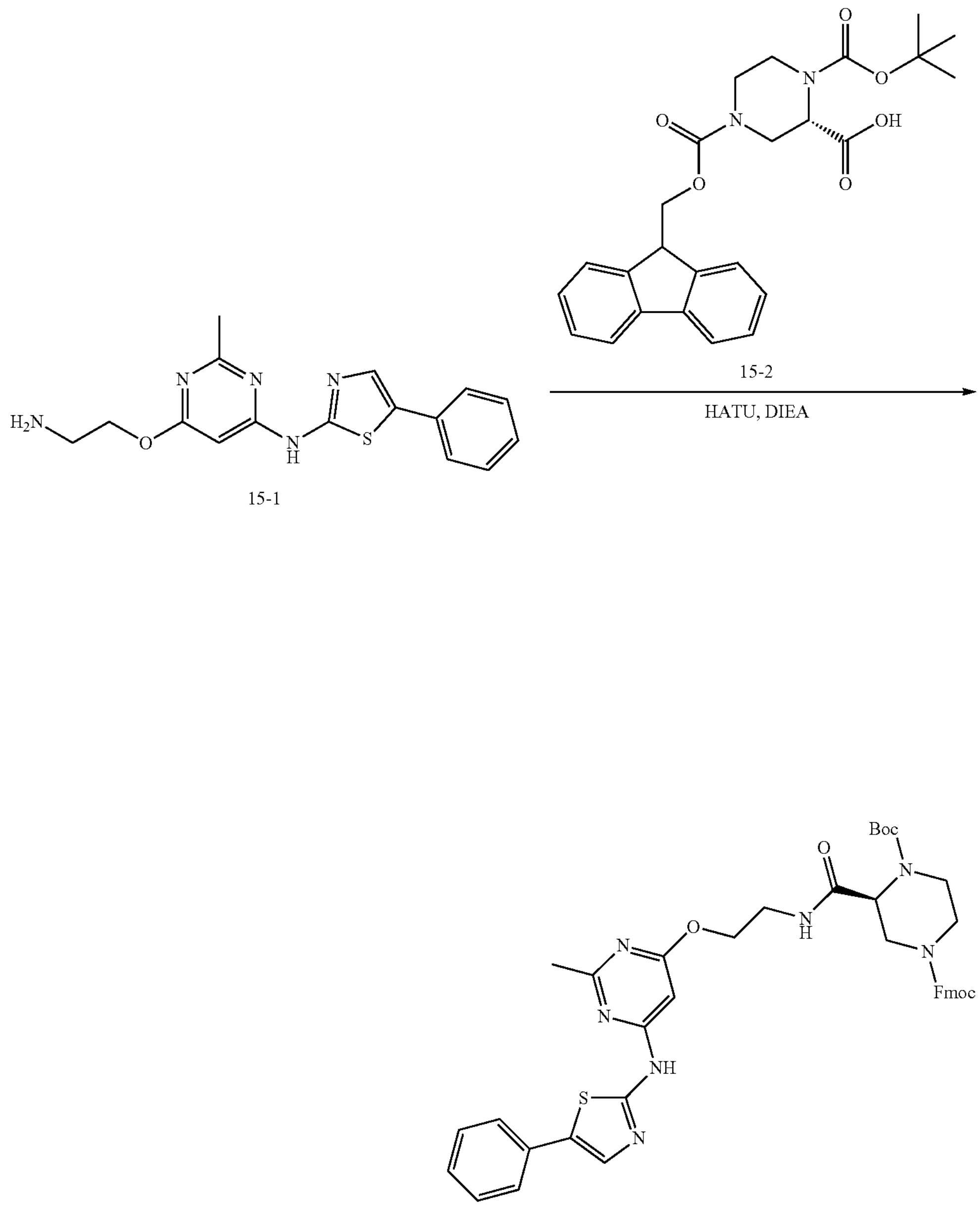

15-2

15-1

15-3

To a solution of (2S)-1-tert-butoxycarbonyl-4-(9H-fluoren-9-ylmethoxycarbonyl)piperazine-2-carboxylic acid (580 mg, 1.28 mmol) in DMF (6 mL) was added HATU (557 mg, 1.47 mmol) and DIEA (316 mg, 2.44 mmol). 0.5 hour later, N-[6-(2-aminoethoxy)-2-methyl-pyrimidin-4-yl]-5-phenyl-thiazol-2-amine (400 mg, 1.22 mmol) was added. The mixture was stirred at 25° C. for 2 hours. The mixture was concentrated in vacuo to give a residue, which was purified by flash column chromatography on silica gel (ethyl acetate in petroleum ether from 0% to 63%) to afford 01-led-butyl 04-(9H-fluoren-9-ylmethyl) (2S)-2-[2-[2-methyl-6-[(5-phenylthiazol-2-yl)amino]pyrimidin-4-yl]oxyethylcarbamoyl] piperazine-1,4-dicarboxylate (740 mg, 76% yield) as a yellow solid.

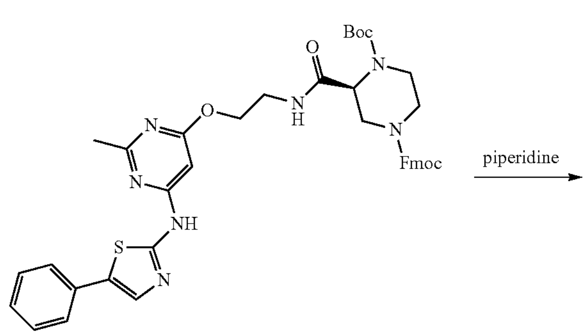

15-3

-continued

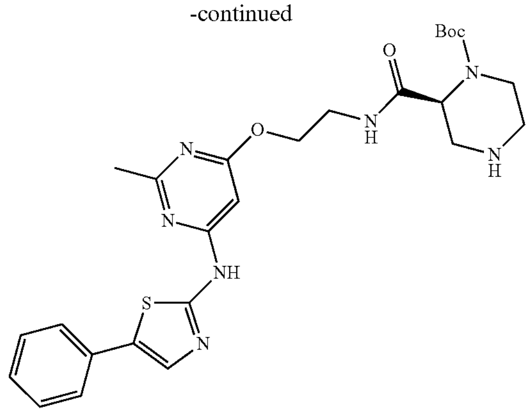

15-4

To a solution of $O_1$-tert-butyl $O_4$-(9H-fluoren-9-ylmethyl) (2S)-2-[2-[2-methyl-6-[(5-phenylthiazol-2-yl)amino]pyrimidin-4-yl]oxy ethylcarbamoyl]piperazine-1,4-dicarboxylate (740 mg, 0.97 mmol) in MeCN (10 mL) was added piperazine (2.18 g, 25.25 mmol). The mixture was stirred at 25° C. for 0.5 hour. The mixture was concentrated in vacuo to give a residue, which was purified by flash column chromatography on silica gel (methanol in dichloromethane from 0% to 3%, addition of 0.1% ammonia (v/v)) to afford tert-butyl (2S)-2-[2-[2-methyl-6-[(5-phenylthiazol-2-yl)amino]pyrimidin-4-yl]oxyethylcarbamoyl]piperazine-1-carboxylate (440 mg, 82% yield) as a yellow solid.

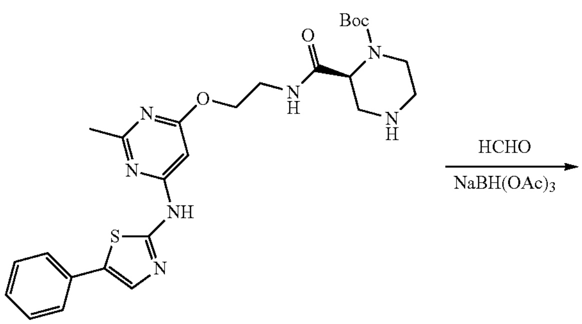

15-4

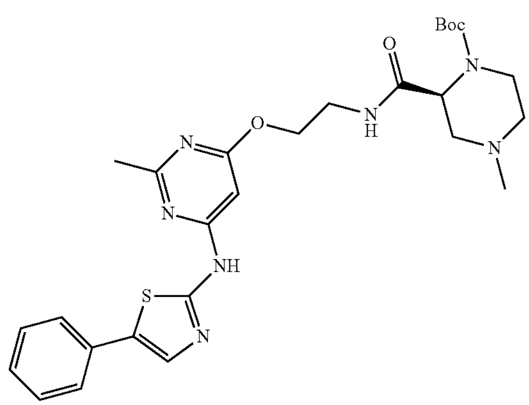

15-5

To a solution of tert-butyl (2S)-2-[2-[2-methyl-6-[(5-phenylthiazol-2-yl)amino]pyrimidin-4-yl]oxy ethyl carbamoyl] piperazine-1-carboxylate (420 mg, 0.78 mmol) in MeOH (10 mL) was added HCHO (35 mg, 1.17 mmol), $NaBH_3CN$ (73 mg, 1.17 mmol) and AcOH (117 mg, 1.95 mmol). The mixture was stirred at 25° C. for 2 hours. The mixture was filtered, the filtrate was concentrated in vacuo to afford tert-butyl (2S)-4-methyl-2-[2-[2-methyl-6-[(5-phenylthiazol-2-yl)amino]pyrimidin-4-yl]oxyethylcarbamoyl]piperazine-1-carboxylate (640 mg, crude) as a brown gum.

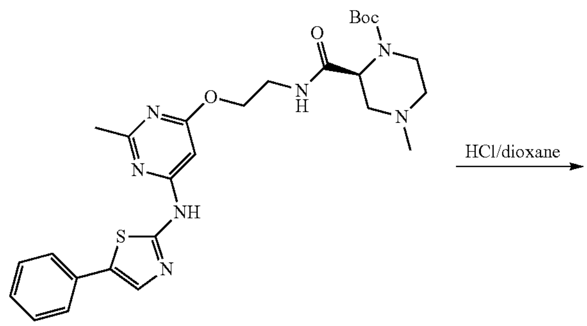

15-5

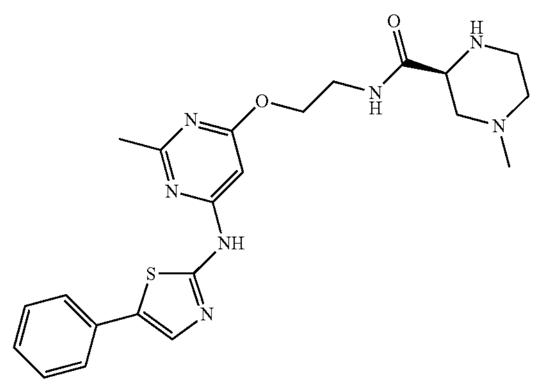

15-6

A solution of tert-butyl (2S)-4-methyl-2-[2-[2-methyl-6-[(5-phenylthiazol-2-yl)amino]pyrimidin-4-yl]oxy ethyl carbamoyl]piperazine-1-carboxylate (640 mg, 1.16 mmol) in HCl/dioxane (4 M, 20 mL) was stirred at 25° C. for 1 hour. The mixture was added water (20 mL), adjusted to pH=8 with $NaHCO_3$, and then extracted with ethyl acetate (30 mL×3). The organic layer was concentrated to afford (2S)-4-methyl-N-[2-[2-methyl-6-[(5-phenylthiazol-2-yl)amino]pyrimidin-4-yl]oxyethyl]piperazine-2-carboxamide (305 mg, 58% yield) as a yellow solid.

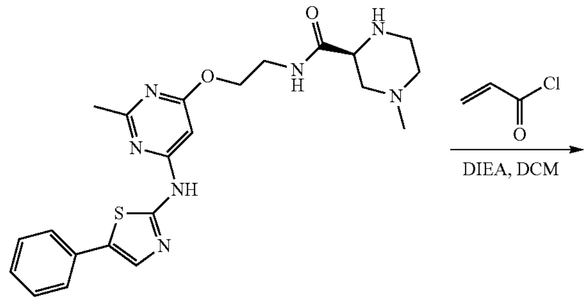

15-6

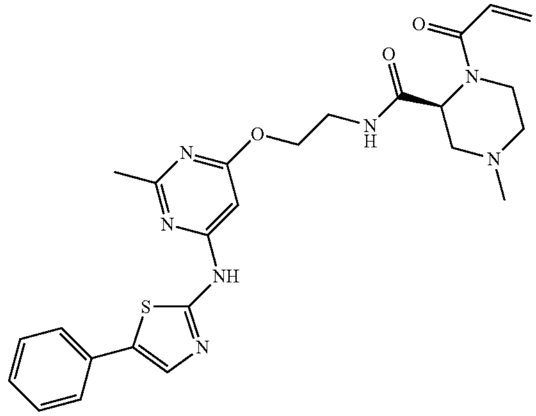

compound 15

To a solution of (2S)-4-methyl-N-[2-[2-methyl-6-[(5-phenylthiazol-2-yl)amino]pyrimidin-4-yl]oxyethyl]piperazine-2-carboxamide (100 mg, 0.22 mmol) in DCM (2 mL) was added DIEA (57 mg, 0.44 mmol) and prop-2-enoyl chloride (20 mg, 0.22 mmol) at 0° C. The mixture was stirred at 0° C. for 0.2 hr. The mixture was filtered and then filtrate was concentrated in vacuo to give the residue. Which was purified by prep-HPLC (column: Phenomenex Gemini-NX C18 75*30 mm*3 um; mobile phase: [water (0.04% $NH_3 \cdot H_2O$+10 mM $NH_4HCO_3$)-ACN]; B %: 27%-53%, 9 min) to give (2S)-4-methyl-N-[2-[2-methyl-6-[(5-phenylthiazol-2-yl)amino]pyrimidin-4-yl]oxy ethyl]-1-prop-2-enoyl-piperazine-2-carboxamide (14.1 mg, 12% yield) as a white solid. LCMS: $t_R$=1.991 min in 10-80CD_4 min_Pos_220 &254_Shimadzu.1 cm, MS (ESI) m/z=508.3 [M−H]+. $^1$H NMR (400 MHz, $CDCl_3$): δ=11.02 (s, 1H), 7.75-7.50 (m, 3H), 7.41 (t, J=7.2 Hz, 2H), 7.35-7.32 (m, 1H), 6.78-6.45 (m, 1H), 6.31 (d, J=3.6 Hz, 1H), 6.05 (s, 1H), 5.71 (d, J=10.8 Hz, 1H), 5.23 (s, 1H), 4.63-4.32 (m, 3H), 3.81-3.61 (m, 2H), 3.53-3.38 (m, 1H), 3.35-2.92 (m, 1H), 2.75 (d, J=10.8 Hz, 1H), 2.59 (d, J=3.6 Hz, 3H), 2.25 (d, J=14.4 Hz, 3H), 2.12-2.01 (m, 3H). Chiral SFC: $t_R$=4.859 min, Column: (S,S)-Whelk-0-3 50 um*4.6 mm I.D., 1.8 um, Mobile phase: A: $CO_2$ B: ethanol (0.05% DEA), Gradient: from 5% to 40% of B in 4 min and hold 40% for 2.5 min, then 5% of B for 1 min, Flow rate: 2.8 mL/min, Column temp.: 35° C., ABPR: 1500 psi. Acq Method: Whelk0_3_EtOH_DEA_5_40_28ML. ee %=98.86%. $[\alpha]_D^{20}$=−44.0 (c=0.05, MeOH).

Example 16

N-methyl-N-[(1S)-1-methyl-2-[2-[2-methyl-6-[(5-phenylthiazol-2-yl)amino]pyrimidin-4-yl]oxyethylamino]-2-oxoethyl]but-2-enamide (Compound 16)

Scheme 19. Synthesis of compound 16.

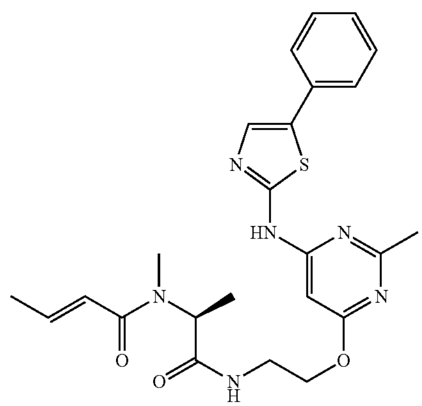

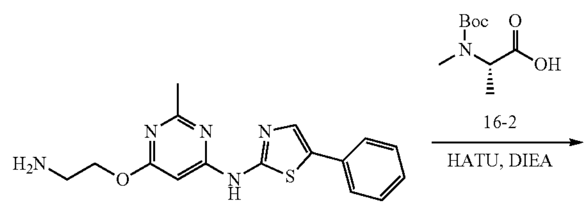

16-1

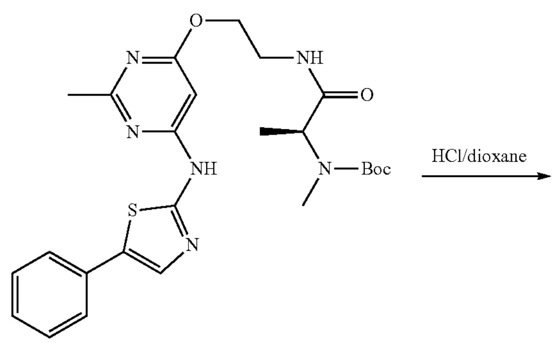

16-3

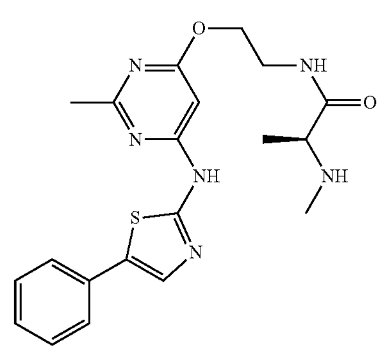

16-4

-continued

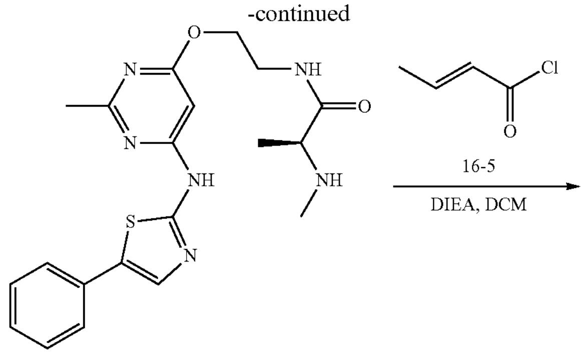

16-4

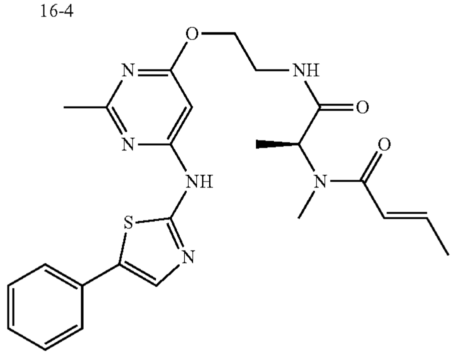

compound 16

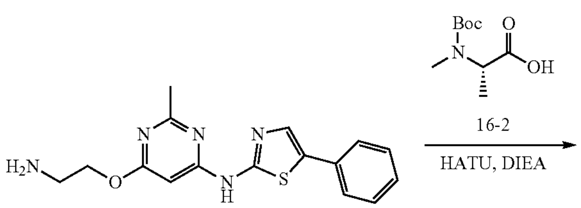

16-1

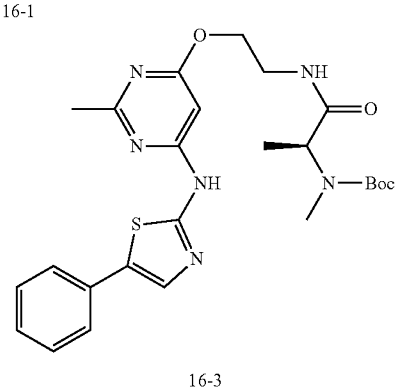

16-3

A solution of (2S)-2-[tert-butoxycarbonyl(methyl)amino] propanoic acid (273 mg, L34 mmol), HATU (557 mg, 1.47 mmol) and DIEA (474 mg, 3.67 mmol) in DMF (6 mL) was stirred for 0.5 hour, and then added N-[6-(2-aminoethoxy)-2-methyl-pyrimidin-4-yl]-5-phenyl-thiazol-2-amine (400 mg, 1.22 mmol). The mixture was stirred at 25° C. for 2 hours. The mixture was quenched by addition of water (10 mL) at 25° C., and then extracted with ethyl acetate (15 mL×3). The organic layers were concentrated and purified by flash column chromatography on silica gel (methanol in dichloromethane from 0% to 3%) to afford tert-butyl N-methyl-N—[ (1S)-1-methyl-2-[2-[2-methyl-6-[(5-phenyl thiazol-2-yl)amino]pyrimidin-4-yl]oxyethylamino]-2-oxo-ethyl]carbamate (920 mg, 79% purity) as a yellow solid.

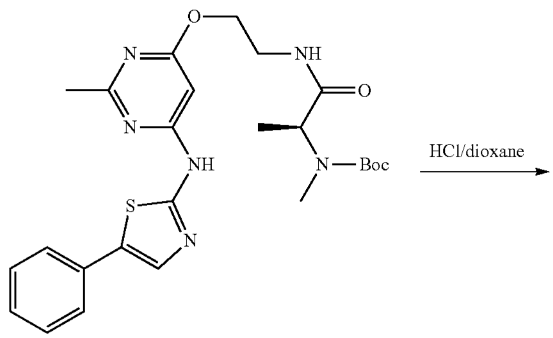

16-3

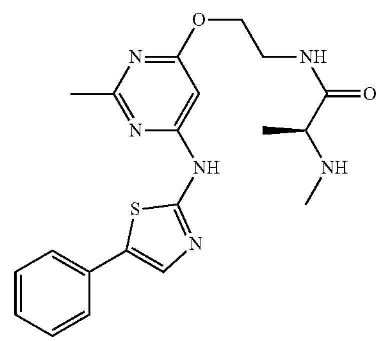

16-4

A solution of tert-butyl N-methyl-N-[(1S)-1-methyl-2-[2-[2-methyl-6-[(5-phenylthiazol-2-yl)amino]pyrimidin-4-yl] oxy ethyl amino]-2-oxo-ethyl]carbamate (920 mg, 1.42 mmol) in HCl/dioxane (4 M, 20 mL) was stirred at 25° C. for 1 hour. The mixture was concentrated in vacuo to give a residue, and then the residue was dissolved in methanol (10 mL) and added adjusted to pH=8 by addition of saturated aqueous $NaHCO_3$. The precipitation was filtered, dried to afford (2S)-2-(methylamino)-N-[2-[2-methyl-6-[(5-phenylthiazol-2-yl)amino]pyrimidin-4-yl]oxyethyl]propanamide (425 mg, 57% yield) as a yellow solid.

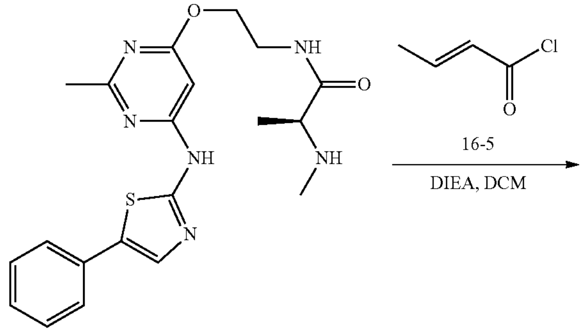

16-4

-continued

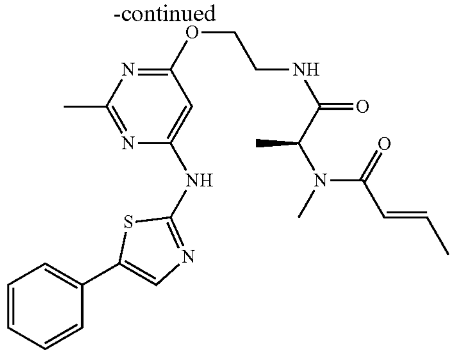

compound 16

To a solution of (2S)-2-(methylamino)-N-[2-[2-methyl-6-[(5-phenylthiazol-2-yl)amino]pyrimidin-4-yl]oxyethyl]propanamide (100 mg, 0.24 mmol) in DCM (2 mL) was added TEA (49 mg, 0.48 mmol) and but-2-enoyl chloride (29 mg, 0.27 mmol) at 0° C. The mixture was stirred at 25° C. for 0.5 hour. The mixture was concentrated in vacuo to give a residue, which was purified by prep-HPLC (Welch Ximate 75*40 mm*3 um; mobile phase: [water (0.225% FA)-ACN]; B %: 40%-70%, 10 min) to afford N-methyl-N-[(1S)-1-methyl-2-[2-[2-methyl-6-[(5-phenylthiazol-2-yl)amino]pyrimidin-4-yl]oxyethylamino]-2-oxoethyl]but-2-enamide (16.6 mg, 13% yield) as a yellow solid. LCMS: $t_R$=1.1.832 min in 10-80 AB_4 min_220 &254_Shimadzu.1 cm, MS (ESI) m/z=481.3 [M+H]$^+$. $^1$H NMR (400 MHz, DMSO-$d_6$): δ=11.51 (s, 1H), 8.24-7.92 (m, 1H), 7.81 (s, 1H), 7.61 (d, J=7.6 Hz, 2H), 7.41 (t, J=8.0 Hz, 2H), 7.28 (t, J=7.2 Hz, 1H), 6.76-6.56 (m, 1H), 6.46-6.34 (m, 1H), 6.20 (s, 1H), 5.97-5.80 (m, 1H), 5.11-4.95 (m, 1H), 4.39-4.21 (m, 2H), 3.52-3.36 (m, 2H), 3.32-3.29 (m, 1H), 3.22-3.08 (m, 1H), 2.90-2.65 (m, 3H), 2.53 (s, 3H), 2.15-1.75 (s, 2H), 1.29-1.14 (m, 3H).

Example 17

(2S)-2-[methyl(prop-2-enoyl)amino]-N-[2-[[2-methyl-6-[[5-(4-pyridyl)thiazol-2-yl]amino]pyrimidin-4-yl]amino]ethyl]propanamide (Compound 17)

Scheme 20. Synthesis of compound 17.

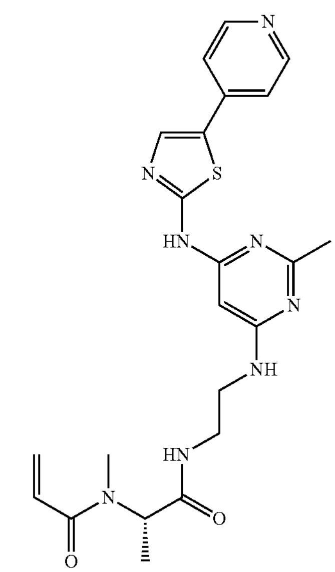

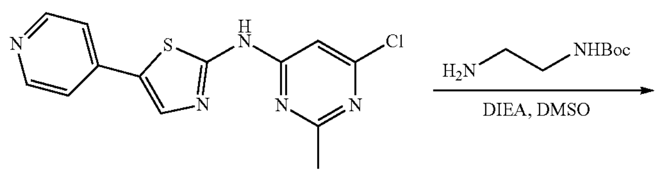

17-1

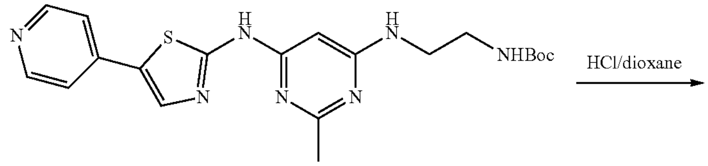

17-2

-continued

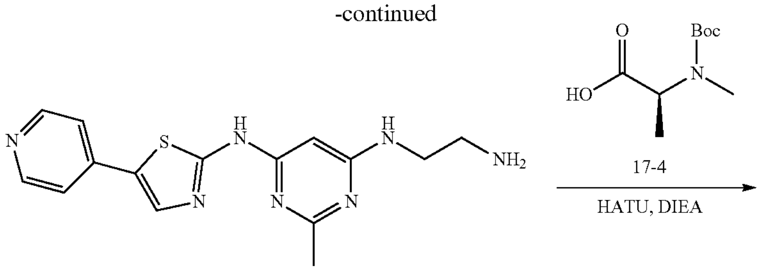

17-3

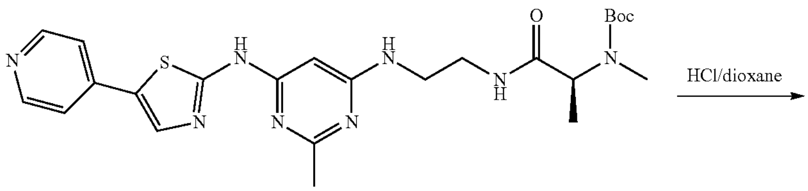

17-5

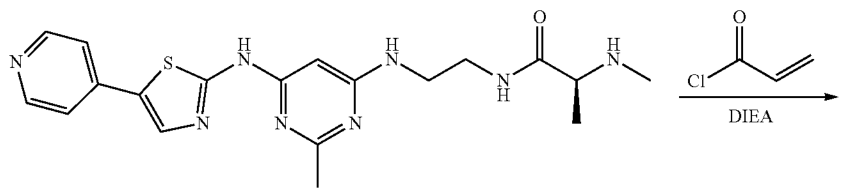

17-6

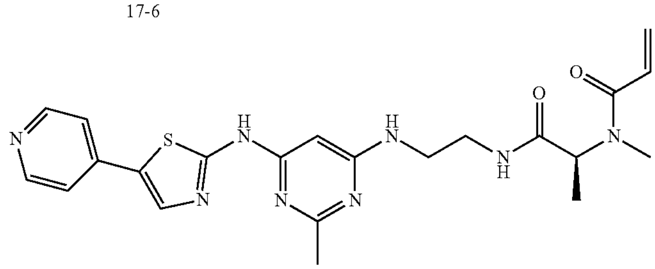

compound 17

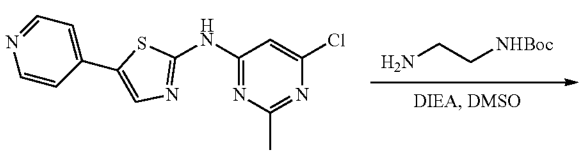

17-1

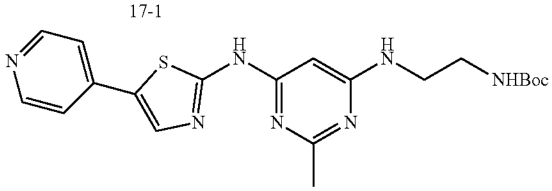

17-2

To a solution of N-(6-chloro-2-methyl-pyrimidin-4-yl)-5-(4-pyridyl)thiazol-2-amine (4.5 g, 14.81 mmol) in DMSO (5 mL) was added DIPEA (1.91 g, 14.81 mmol) and tert-butyl N-(2-aminoethyl)carbamate (4.75 g, 29.63 mmol). The mixture was stirred at 80° C. for 12 hr. The mixture was quenched by addition of $H_2O$ (50 mL) at 25° C., and then diluted with $H_2O$ (50 mL) and extracted with EtOAc (50×3). The combined organic layers were washed with brine (50 mL), dried over $Na_2SO_4$, filtered and concentrated. The residue was purified by flash silica gel chromatography (ISCO®; 12 g SepaFlash® Silica Flash Column, Eluent of 0-70% Ethylacetate/Petroleum ether gradient @ 60 mL/min) to afford tert-butyl N-[2-[[2-methyl-6-[[5-(4-pyridyl)thiazol-2-yl]amino]pyrimidin-4-yl]amino]ethyl]carbamate (4 g, 9.36 mmol, 63% yield) as a yellow solid.

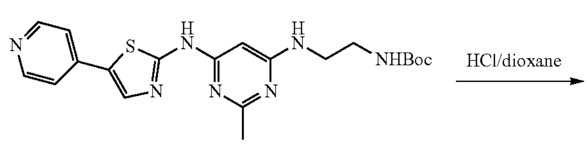

17-2

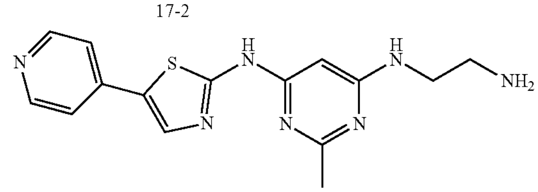

17-3

A solution of tert-butyl N-[2-[[2-methyl-6-[[5-(4-pyridyl)thiazol-2-yl]amino]pyrimidin-4-yl]amino]ethyl]carbamate (4 g, 9.36 mmol) in HCl/dioxane (4 M, 20 mL) was stirred at 25° C. for 0.5 hr. The mixture was concentrated under reduced pressure to afford $N_6$-(2-aminoethyl)-2-methyl-N4-[5-(4-pyridyl)thiazol-2-yl]pyrimidine-4,6-diamine (3 g, 9.16 mmol, 98% yield) as a brown solid, which was used directly in the next step.

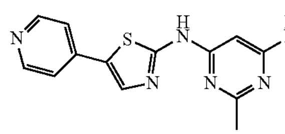

17-3

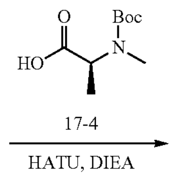

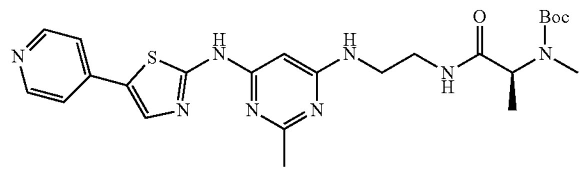

17-5

To a solution of N6-(2-aminoethyl)-2-methyl-$N_4$-[5-(4-pyridyl)thiazol-2-yl]pyrimidine-4,6-diamine (2 g, 6.11 mmol) in DMF (50 mL) was added DIPEA (2.37 g, 18.33 mmol), HATU (2.79 g, 7.33 mmol) and (2S)-2-[tert-butoxycarbonyl(methyl)amino]propanoic acid (1.37 g, 6.72 mmol). The mixture was stirred at 25° C. for 2 hr. The mixture was quenched by addition of $H_2O$ (50 mL) at 25° C., and then diluted with $H_2O$ (50 mL) and extracted with EtOAc (50×3). The combined organic layers were washed with brine (50 mL), dried over $Na_2SO_4$, filtered and concentrated. The residue was purified by flash silica gel chromatography (ISCO®; 20 g SepaFlash® Silica Flash Column, Eluent of 0-70% Ethyl acetate/Petroleum ether gradient @ 80 mL/min) afford tert-butyl N-methyl-N-[(1S)-1-methyl-2-[2-[[2-methyl-6-[[5-(4-pyridyl)thiazol-2-yl]amino]pyrimidin-4-yl]amino]ethyl amino]-2-oxo-ethyl]carbamate (3 g, 5.85 mmol, 95% yield) as a brown solid.

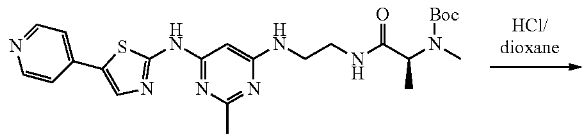

17-5

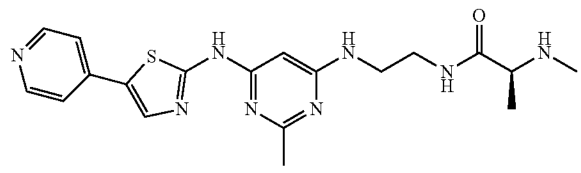

17-6

To a solution of tert-butyl N-methyl-N-[(1S)-1-methyl-2-[2-[[2-methyl-6-[[5-(4-pyridyl)thiazol-2-yl]amino]pyrimidin-4-yl]amino]ethylamino]-2-oxo-ethyl]carbamate (4 g, 7.80 mmol) in HCl/dioxane (4 M, 50 mL) was stirred at 25° C. for 0.5 hr. The mixture was concentrated under reduced pressure to afford (2S)-2-(methylamino)-N-[2-[[2-methyl-6-[[5-(4-pyridyl)thiazol-2-yl]amino]pyrimidin-4-yl]amino]ethyl]propanamide (2.4 g, 5.82 mmol, 74% yield) as a light yellow solid, which was used directly in the next step.

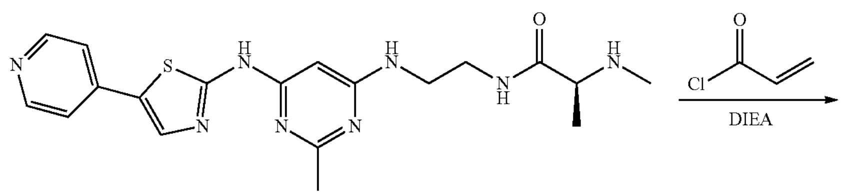

17-6

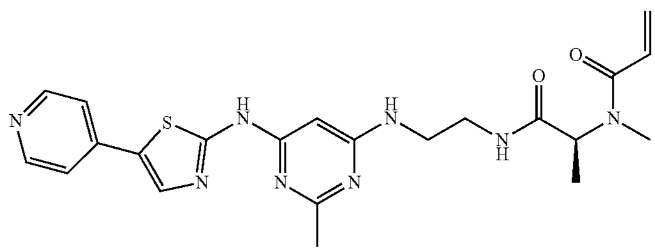

compound 17

To a solution of (2S)-2-(methylamino)-N-[2-[[2-methyl-6-[[5-(4-pyridyl)thiazol-2-yl]amino]pyrimidin-4-yl]amino]ethyl]propanamide (200 mg, 0.48 mmol) in DCM (10 mL) was added DIPEA (188 mg, 1.45 mmol) and prop-2-enoyl chloride (44 mg, 0.48 mmol). The mixture was stirred at 0° C. for 0.5 hr. The mixture was quenched by addition of $H_2O$ (50 mL) at 25° C., and then diluted with $H_2O$ (50 mL) and extracted with EtOAc (50×3). The combined organic layers were washed with brine (50 mL), dried over $Na_2SO_4$, filtered and concentrated. The residue was purified by preparative HPLC (water (0.04% $NH_3 \cdot H_2O$+10 mM $NH_4HCO_3$)-ACN) to afford (2S)-2-[methyl(prop-2-enoyl)amino]-N-[2-[[2-methyl-6-[[5-(4-pyridyl)thiazol-2-yl]amino]pyrimidin-4-yl]amino]ethyl]propanamide (1.8 mg, 0.0037 mmol, 0.8% yield, 96.0% purity) as a light yellow solid, LCMS: $t_R$=1.806 mm in 10-80AB_4 min_220 &254_Shimadzu.1 cm, MS (ESI) m/z=467.2 $[M+H]^+$. $^1H$ NMR (400 MHz, MeOD) δ=8.50-8.43 (m, 2H), 7.93 (s, 1H), 7.64-7.54 (m, 2H), 6.77-6.59 (m, 1H), 6.30-6.13 (m, 1H), 5.89 (s, 1H), 5.80-5.66 (m, 1H), 5.00-4.98 (m, 1H), 3.45-3.36 (m, 4H), 3.05-2.86 (m, 3H), 2.47 (s, 3H), 1.43-1.35 (m, 3H). Chiral SFC: $t_R$=3.727 min (Instrument column: Chiralpak AS-3 100×4.6 mm I.D., 3 um Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., detection: 220 nm), ee %=98.14%. $[\alpha]_D^{20}$=−25.0 (c=0.1, MeOH).

Example 18

N-methyl-N-[(1S)-1-methyl-2-[2-[[2-methyl-6-[[5-(4-pyridyl)thiazol-2-yl]amino]pyrimidin-4-yl]amino]ethylamino]-2-oxo-ethyl]but-2-ynamide (Compound 18)

Scheme 21. Synthesis of compound 18.

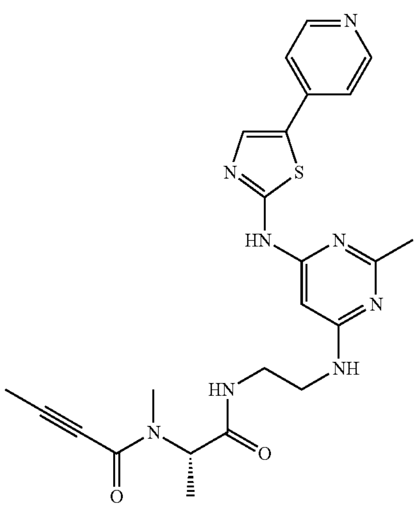

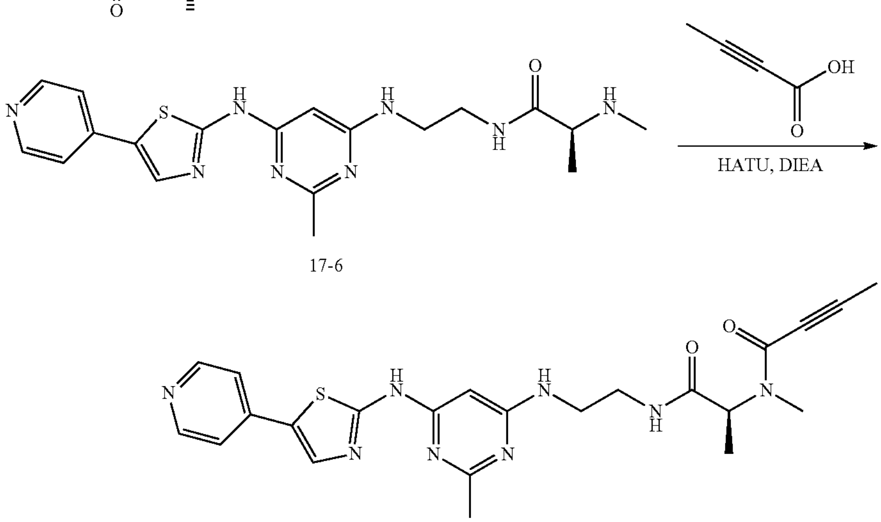

17-6 compound 18

Synthesis of (2S)-2-(methylamino)-N-[2-[[2-methyl-6-[[5-(4-pyridyl)thiazol-2-yl]amino]pyrimidin-4-yl]amino]ethyl]propanamide (17-6) is shown in Example 17. To a solution of (2S)-2-(methylamino)-N-[2-[[2-methyl-6-[[5-(4-pyridyl)thiazol-2-yl]amino]pyrimidin-4-yl]amino]ethyl]propanamide (17-6, 300 mg, 0.73 mmol) in DMF (15 mL) was added HATU (332 mg, 0.87 mmol), DIPEA (282 mg, 2.18 mmol) and but-2-ynoic acid (73 mg, 0.87 mmol). The mixture was stirred at 25° C. for 2 hr. The mixture was quenched by addition of $H_2O$ (50 mL) at 25° C., and then diluted with $H_2O$ (50 mL) and extracted with EtOAc (50×3). The combined organic layers were washed with brine (50 mL), dried over $Na_2SO_4$, filtered and concentrated. The residue was purified by preparative HPLC (water (0.04% $NH_3 \cdot H_2O$+10 mM $NH_4HCO_3$)-ACN) to afford N-methyl-N-[(1S)-1-methyl-2-[2-[[2-methyl-6-[[5-(4-pyridyl)thiazol-2-yl]amino]pyrimidin-4-yl]amino]ethyl amino]-2-oxo-ethyl]but-2-ynamide (42.1 mg, 0.088 mmol, 12% yield, 99.5% purity) as a light yellow solid. LCMS: $t_R$=1.468 mM in 10-80AB_4 min_220 &254_Shimadzu.1 cm, MS (ESI) m/z=479.2 $[M+H]^+$. $^1H$ NMR (400 MHz, DMSO-$d_6$) δ=11.32 (s, 1H), 8.55-8.47 (m, 2H), 8.10-7.92 (m, 2H), 7.59-7.52 (m, 2H), 7.13 (s, 1H), 5.87 (s, 1H), 4.94-4.80 (m, 1H), 3.29-3.23 (m, 4H), 2.75-2.74 (m, 1H), 3.04-2.71 (m, 2H), 2.44-2.31 (m, 3H), 2.01 (d, J=14.8 Hz, 3H), 1.36-1.21 (m, 3H). Chiral SFC: $t_R$=4.717 min (Instrument column: Chiralcel OD-3 100$_i$Å4.6 mm I.D., 3 um Mobile phase: A: $CO_2$ B: ethanol (0.05% DEA), Gradient: from 5% to 40% of B in 4 min and hold 40% for 2.5 min, then 5% of B for 1.5 min, Flow rate: 2.8 mL/min, Column temperature: 40° C., detection: 220 nm), ee %=99.74%.

Example 19

(2S)—N-[2-[methyl-[2-methyl-6-[[5-(4-pyridyl)thiazol-2-yl]amino]pyrimidin-4-yl]amino]ethyl]-2-[methyl(prop-2-enoyl)amino]propanamide (Compound 19)

Scheme 22. Synthesis of compound 19.

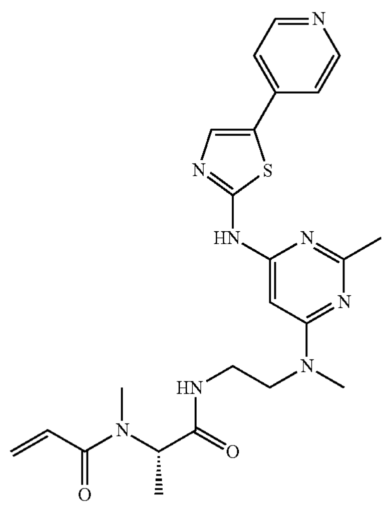

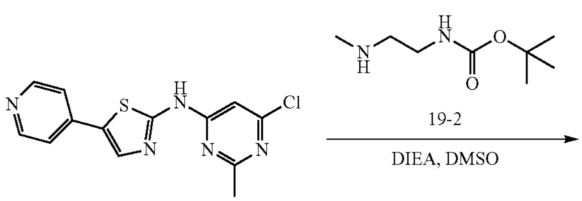

19-1

19-2

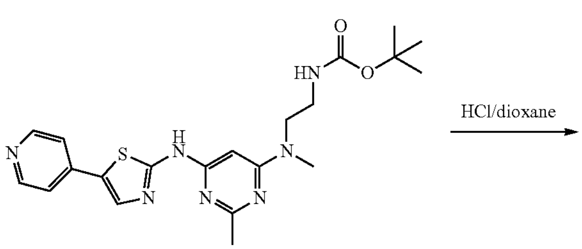

19-3

-continued

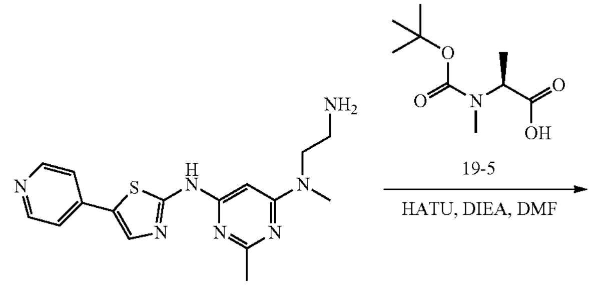

19-4

19-5

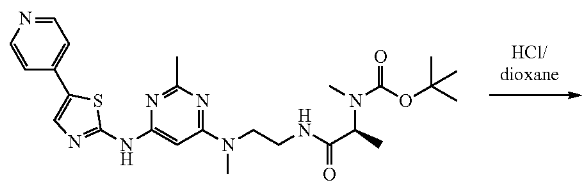

19-6

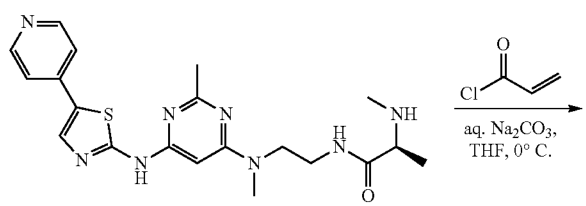

19-7

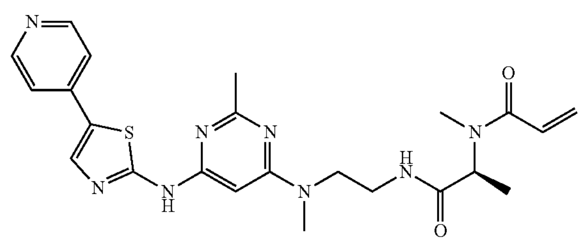

compound 19

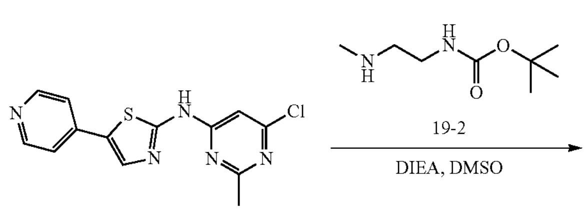

19-1

19-2

-continued

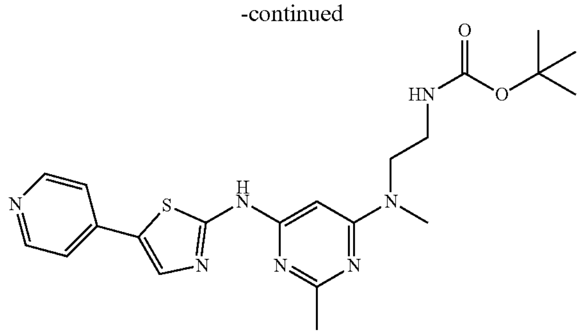

19-3

To a solution of N-(6-chloro-2-methyl-pyrimidin-4-yl)-5-(4-pyridyl)thiazol-2-amine (300 mg, 0.99 mmol) in DMSO (10 mL) was added DIEA (766 mg, 5.93 mmol) and tert-butyl N-[2-(methylamino)ethyl]carbamate (860 mg, 4.94 mmol). The mixture was stirred at 80° C. for 2 h. To the mixture was added water (20 mL), and then extracted with ethyl acetate (20 mL×3). The organic phase was separated, concentrated and purified by flash column chromatography on silica gel (methanol in dichloromethane from 0% to 5%) to afford tat-butyl N-[2-[methyl-[2-methyl-6-[[5-(4-pyridyl)thiazol-2-yl]amino]pyrimidin-4-yl]amino]ethyl]carbamate (420 mg, 68% yield) as a yellow solid.

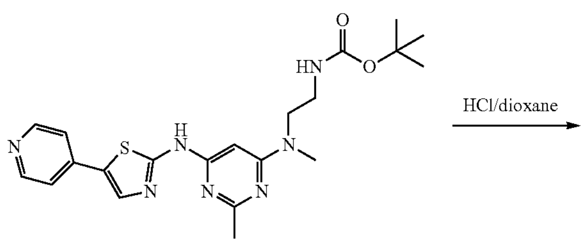

19-3

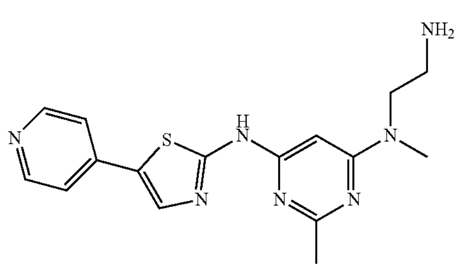

19-4

To a solution of tert-butyl N-[2-[methyl-[2-methyl-6-[[5-(4-pyridyl)thiazol-2-yl]amino]pyrimidin-4-yl]amino]ethyl]carbamate (420 mg, 0.95 mmol) in DCM (2 mL) was added HCl/dioxane (10 mL, 4 M). The mixture was stirred at 25° C. for 1 h. The mixture was concentrated under reduced pressure to afford N$_4$-(2-aminoethyl)-N$_{4,2}$-dimethyl-N$_6$-[5-(4-pyridyl)thiazol-2-yl]pyrimidine-4,6-diamine (498 mg, crude) as a yellow solid which was used directly in the next step without further purification.

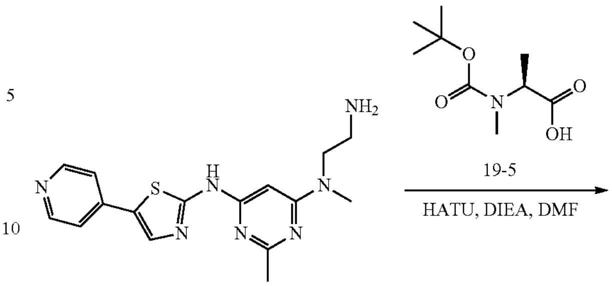

19-4

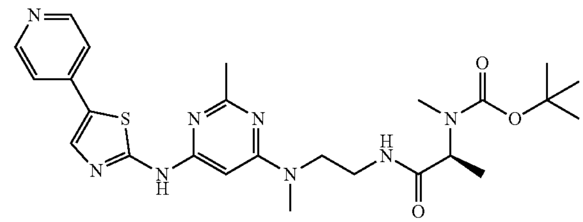

19-6

To a solution of (2S)-2-[tert-butoxycarbonyl(methyl)amino]propanoic acid (249 mg, 1.22 mmol) in DMF (7 mL) was added HATU (532 mg, 1.40 mmol), DIEA (301 mg, 2.33 mmol) and N4-(2-aminoethyl)-N4,2-dimethyl-N6-[5-(4-pyridyl)thiazol-2-yl]pyrimidine-4,6-diamine (398 mg, 1.17 mmol), The mixture was stirred at 50° C. for 1 h. The mixture was concentrated under reduced pressure. The residue was purified by flash column chromatography on silica gel (methanol in dichloromethane from 0% to 7%) to afford the product of tert-butyl N-methyl-N-[(1S)-1-methyl-2-[2-[methyl-[2-methyl-6-[[5-(4 -pyridyl)thiazol-2-yl]amino]pyrimidin-4-yl]amino]ethylamino]-2-oxo-ethyl]carbamate (175 mg, 24% yield) as a yellow oil.

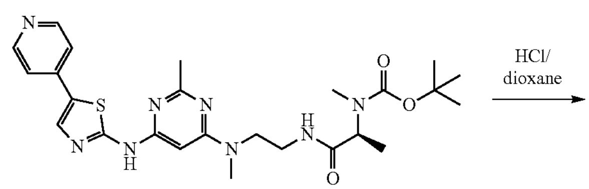

19-6

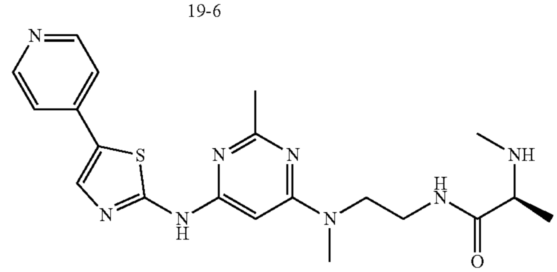

19-7

To a solution of tert-butyl N-methyl-N-[(1S)-1-methyl-2-[2-[methyl-[2-methyl-6-[[5-(4-pyridyl)thiazol-2-yl]amino]pyrimidin-4-yl]amino]ethyl amino]-2-oxo-ethyl]carbamate (175 mg, 0.33 mmol) in DCM (2 mL) was added 4M HCl/dioxane (10 mL). The mixture was stirred at 25° C. for 1 h. The mixture was concentrated to afford (2S)-2-(methylamino)-N-[2-[methyl-[2-methyl-6-[[5-(4-pyridyl)thiazol- 2-yl]amino]pyrimidin-4-yl]amino]ethyl]propanamide (211 mg, crude) as a yellow solid which was used directly in the next step without further purification.

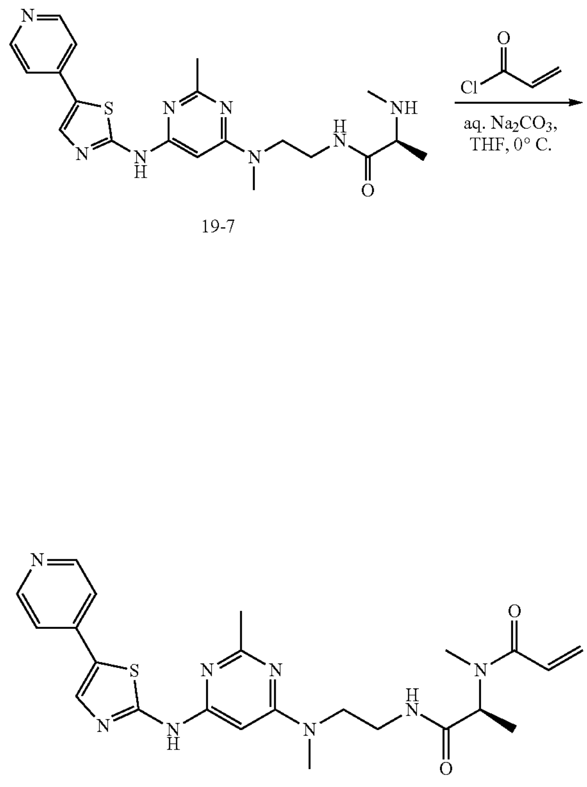

19-7 compound 19

To a solution of (2S)-2-(methylamino)-N-[2-[methyl-[2-methyl-6-[[5-(4-pyridyl)thiazol-2-yl]amino]pyrimidin-4-yl]amino]ethyl]propanamide (171 mg, 0.40 mmol) in $H_2O$ (5 mL) and THF (5 mL) was added $Na_2CO_3$ (127 mg, 1.20 mmol), then prop-2-enoyl chloride (36 mg, 0.40 mmol) was added at 0° C. The mixture was stirred at 25° C. for 0.5 h. The mixture was extracted with ethyl acetate (30 mL×3). The organic layers were concentrated and the residue was purified by prep-HPLC (column: Phenomenex Gemini-NX C18 75*30 mm*3 um; mobile phase: water (0.04% $NH_3 \cdot H_2O$+10 mM $NH_4HCO_3$)-ACN; B %: 15-55%, 14 min); Flow Rate; 25 mL/min) to afford (2S)—N-[2-[methyl-[2-methyl-6-[[5-(4-pyridyl)thiazol-2-yl]amino]pyrimidin-4-yl]amino]ethyl]-2-[methyl(prop-2-enoyl)amino]propanamide (3.3 mg, 2% yield) as a yellow solid. LCMS: $t_R$=0.718 min in 10-80 AB_4 min_220 &254_Shimadzu.1 cm, MS (ESI) m/z=481.3 $[M+H]^+$. $^1$H NMR (400 MHz, $CDCl_3$): δ=8.58 (d, J=4.0 Hz, 2H), 7.78 (s, 1H), 7.42 (d, J=4.0 Hz, 2H), 7.01 (s, 1H), 6.54-6.30 (m, 2H), 5.82-5.72 (m, 2H), 5.14-5.09 (m, 1H), 3.87-3.70 (m, 2H), 3.56-3.42 (m, 2H), 3.02 (s, 3H), 2.95 (s, 3H), 2.52 (s, 3H), 1.33 (d, J=8.0 Hz, 3H). Chiral SFC: $t_R$=4.239 min Column: Chiralpak ND-3 100 um*4.6 mm, I.D., 3 um, Mobile phase: 40% of iso-propanol (0.05% DEA) in $CO_2$, Flow rate: 2.8 mL/min, Column temp.: 35° C., ABPR: 1500 psi. Acq Method: ND_3_IPA_DEA_40_28ML. ee %=96.54%. $[\alpha]_D^{20}$=−13.3 (c=0.03, MeOH).

Example 20

(2S)-2-[methyl(prop-2-enoyl)amino]-N-[(3S)-1-[2-methyl-6-[[5-(4-pyridyl)thiazol-2-yl]amino]pyrimidin-4-yl]pyrrolidin-3-yl]propanamide (Compound 20)

Scheme 23. Synthesis of compound 20.

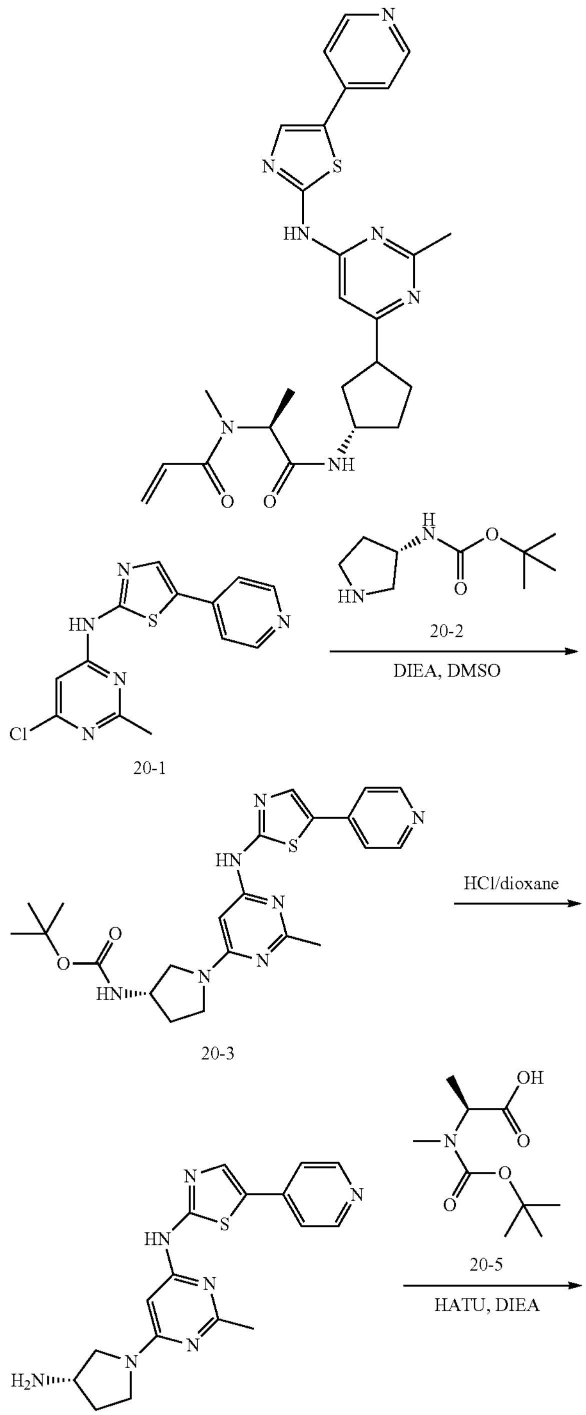

20-1

20-2

20-3

20-4

20-5

-continued

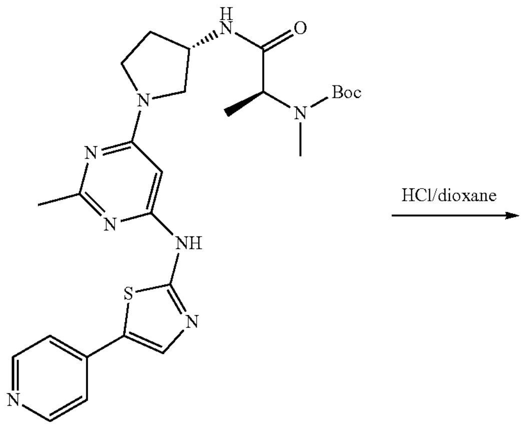

20-6

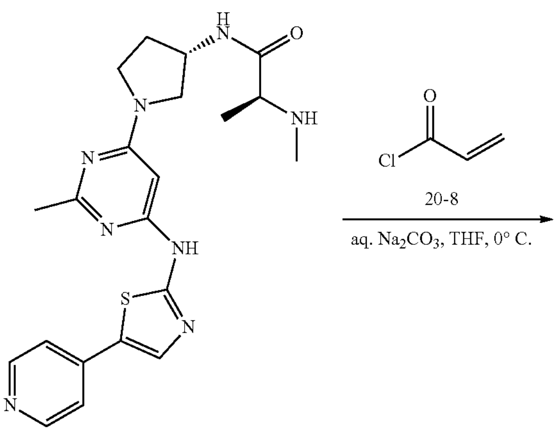

20-8

20-7

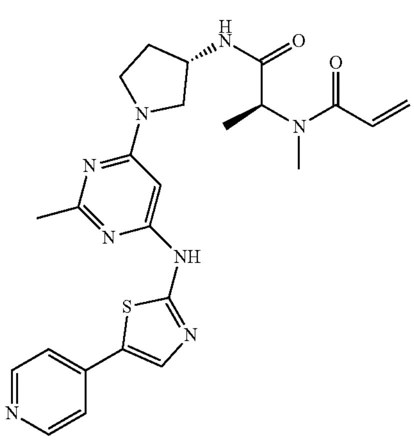

compound 20

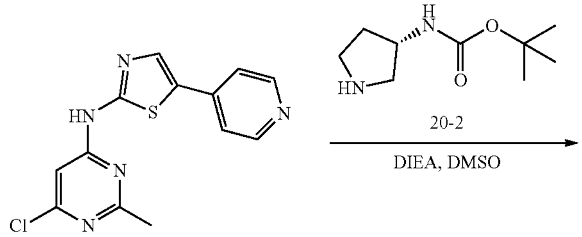

20-2

20-1

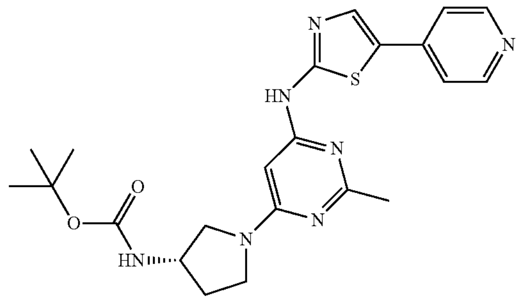

20-3

A mixture of N-(6-chloro-2-methyl-pyrimidin-4-yl)-5-(4-pyridyl)thiazol-2-amine (1.26 g, 4.15 mmol), tert-butyl N-[(3S)-pyrrolidin-3-yl]carbamate (927 mg, 4.98 mmol), DIEA (643 mg, 4.98 mmol) in DMSO (50 mL) was stirred at 80° C. for 2 h. The mixture was added water (30 mL), and then extracted with ethyl acetate (20 mL×3). The combined organic phase was washed with brine (20 mL), dried over anhydrous sodium sulfate, filtered and concentrated in vacuo. The residue was purified by flash column chromatography on silica gel (ethyl acetate in petroleum ether from 0% to 100%) to afford tert-butyl N-[(3S)-1-[2-methyl-6-[[5-(4-pyridyl)thiazol-2-yl]amino]pyrimidin-4-yl]pyrrolidin-3-yl]carbamate (1.61 g, 68% yield) as a yellow solid.

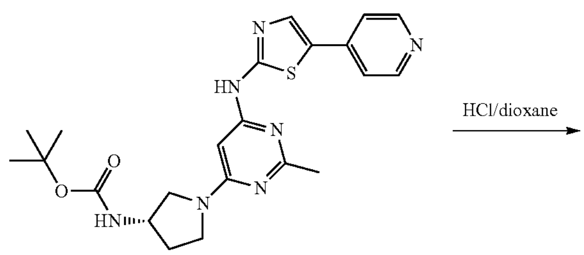

20-3

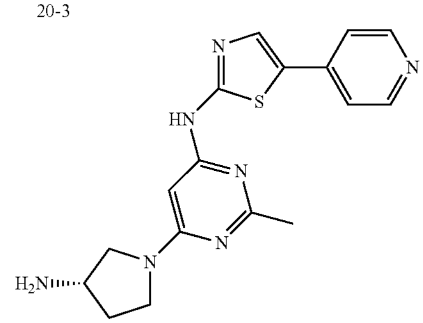

20-4

To a solution of tert-butyl N-[(3S)-1-[2-methyl-6-[[5-(4-pyridyl)thiazol-2-yl]amino]pyrimidin-4-yl]pyrrolidin-3-yl]

carbamate (1.51 g, 3.33 mmol) in DCM (15 mL) and was added 4M HCl/dioxane (50 mL). The mixture was stirred at 25° C. for 1 h. The mixture was concentrated under reduced pressure to afford N-[6-[(3S)-3-aminopyrrolidin-1-yl]-2-methyl-pyrimidin-4-yl]-5-(4-pyridyl)thiazol-2-amine (1.91 g, crude) as a yellow solid.

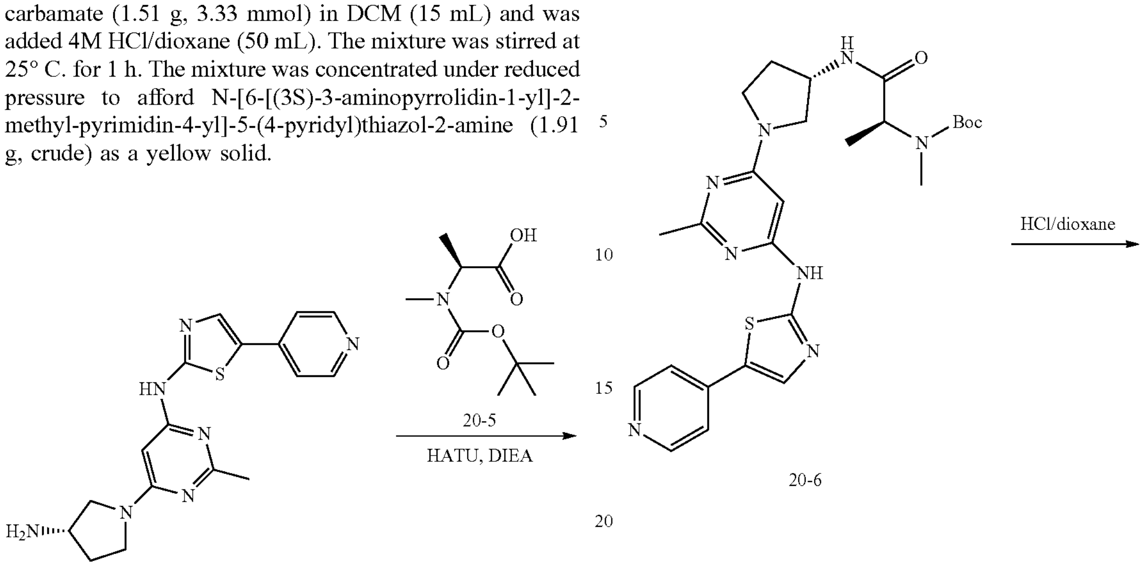

20-4

20-5

20-6

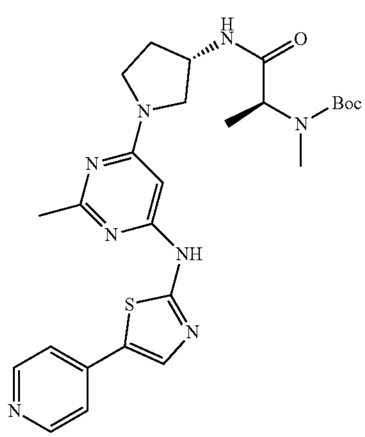

20-6

To a solution of (2S)-2-[tert-butoxycarbonyl(methyl)amino]propanoic acid (604 mg, 2.97 mmol) in DMF (20 mL) was added HATU (1.29 g, 3.40 mmol), DIEA (731 mg, 5.66 mmol) and N-[6-[(3S)-3-aminopyrrolidin-1-yl]-2-methyl-pyrimidin-4-yl]-5-(4-pyridyl)thiazol-2-amine (1 g, 2.83 mmol). The mixture was stirred at 25° C. for 1 h. The mixture was concentrated under reduced pressure and the residue was purified by flash column chromatography on silica gel (methanol in dichloromethane from 0% to 10%) to afford tert-butyl N-methyl-N-[(1S)-1-methyl-2-[[(3S)-1-[2-methyl-6-[[5-(4-pyridyl)thiazol-2-yl]amino]pyrimidin-4-yl]pyrrolidin-3-yl]amino]-2-oxo-ethyl]carbamate (1.14 g, 60% yield) as a yellow solid.

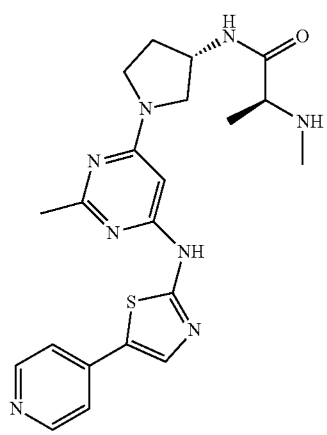

20-7

To a solution of tert-butyl N-methyl-N-[(1S)-1-methyl-2-[[(3S)-1-[2-methyl-6-[[5-(4-pyridyl)thiazol-2-yl]amino]pyrimidin-4-yl]pyrrolidin-3-yl]amino]-2-oxo-ethyl]carbamate (1.14 g, 2.11 mmol) in DCM (3 mL) was added HCl/dioxane (4 M, 30 mL). The mixture was stirred at 25° C. for 1 h. The mixture was concentrated under reduced pressure to afford (2S)-2-(methylamino)-N-[(3S)-1-[2-methyl-6-[[5-(4-pyridyl)thiazol-2-yl]amino]pyrimidin-4-yl]pyrrolidin-3-yl]propanamide (1.51 g, crude) as a yellow solid.

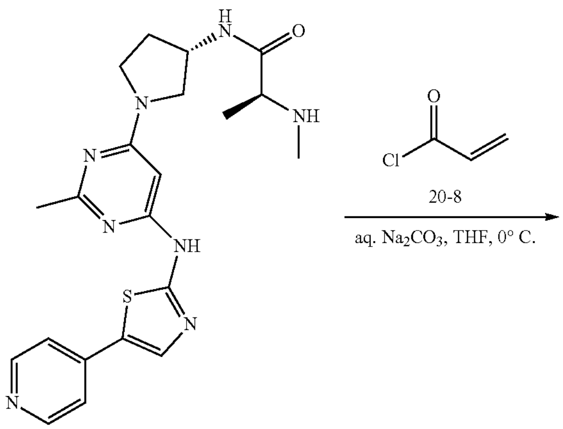

20-7

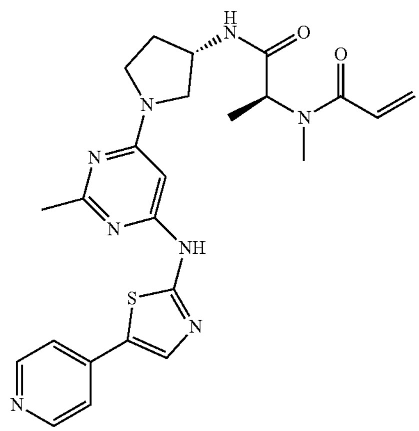

compound 20

To a solution of (2S)-2-(methylamino)-N-[(3S)-1-[2-methyl-6-[[5-(4-pyridyl)thiazol-2-yl]amino]pyrimidin-4-yl]pyrrolidin-3-yl]propanamide (150 mg, 0.34 mmol) in THF (2 mL) and $H_2O$ (2 mL) was added $Na_2CO_3$ (109 mg, 1.03 mmol). Then prop-2-enoyl chloride (31 mg, 0.34 mmol) was added at 0° C. The mixture was stirred at 25° C. for 0.5 h. The mixture was extracted with ethyl acetate (30 mL×3). The organic layers were concentrated and the residue was purified by prep-HPLC (column: Phenomenex Gemini-NX C18 75*30 mm*3 um; mobile phase: water (0.05% $NH_3 \cdot H_2O$+10 mM $NH_4HCO_3$)-ACN; B %: 35-55%, 10 min); Flow Rate: 25 mL/min) to afford (2S)-2-[methyl(prop-2-enoyl)amino]-N-[(3S)-1-[2-methyl-6-[[5-(4-pyridyl)thiazol-2-yl]amino]pyrimidin-4-yl]pyrrolidin-3-yl]propanamide (5.3 mg, 3% yield) as a yellow solid. LCMS: $t_R$=0.701 min in 10-80 AB_4 min_220 &254_Shimadzu.1 cm, MS (ESI) m/z=493.3 $[M+H]^+$. $^1H$ NMR (400 MHz, $CDCl_3$): =8.57 (d, J=4.0 Hz, 2H), 7.76 (s, 1H), 7.43 (d, J=8.0 Hz, 2H), 6.65-6.58 (m, 1H), 6.40-6.36 (m, 1H), 5.78-5.76 (m, 1H), 5.59 (s, 1H), 5.19-5.13 (m, 1H), 4.45 (s, 1H), 3.64-3.48 (m, 4H), 3.09 (s, 3H), 2.46 (s, 3H), 2.25-2.04 (m, 2H), 1.41 (d, J=4.0 Hz, 3H). Chiral SFC: $t_R$=5.238 min, Column: Chiral MD-3 100 um*4.6 mm I.D., 3 um, Mobile phase: A: $CO_2$ B: ethanol (0.05% DEA), Gradient: from 5% to 40% of B in 4 min and hold 40% for 2.5 min, then 5% of B for 1.5 min, Flow rate: 2.8 mL/min, Column temp.: 35° C., ABPR: 1500 psi. Acq Method: MD_3_EtOH_DEA_5_40_28ML_8 mM. ee %=98.32%. $[\alpha]_D^{20}$=−13.3 (c=0.03, MeOH).

Example 21

(2S)—N-[(3S)-1-[2-methyl-6-[[5-(4-pyridyl)thiazol-2-yl]amino]pyrimidin-4-yl]pyrrolidin-3-yl]-1-prop-2-enoyl-pyrrolidine-2-carboxamide (Compound 21)

Scheme 24. Synthesis of compound 21.

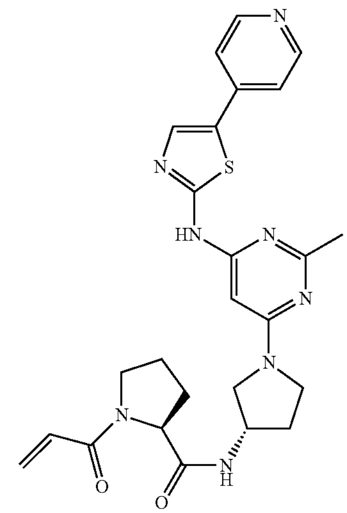

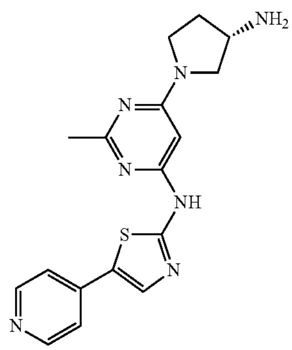

21-4

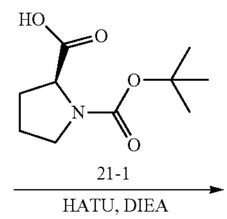

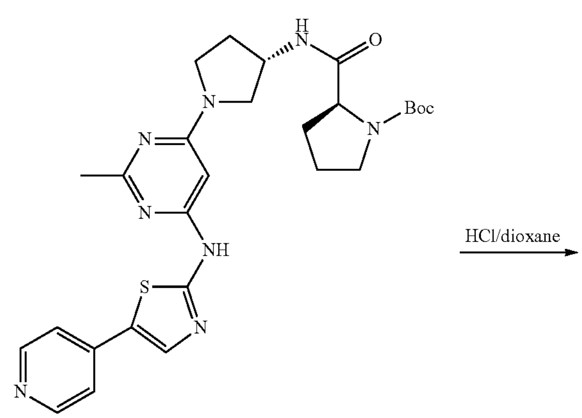

21-2

-continued

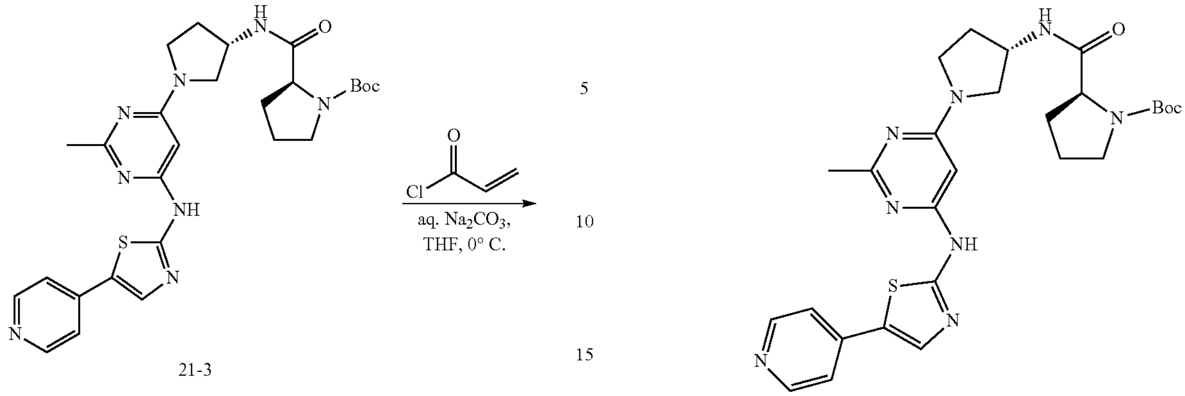

21-3

21-2

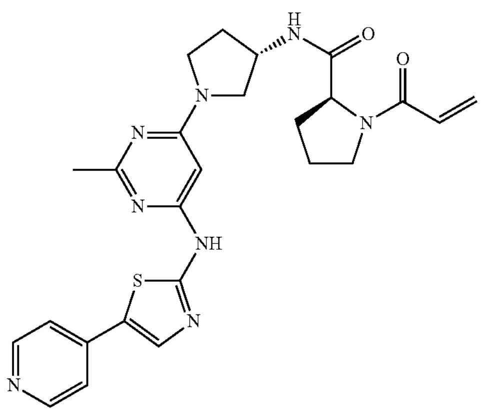

compound 21

Synthesis of N-[6-[(3S)-3-aminopyrrolidin-1-yl]-2-methyl-pyrimidin-4-yl]-5-(4-pyridyl)thiazol-2-amine (25-4) is shown in Example 16. To a solution of (2S)-1-tert-butoxycarbonylpyrrolidine-2-carboxylic acid (958 mg, 4.45 mmol) in DMF (20 mL) was added HATU (1.94 g, 5.09 mmol), DIEA (1.10 g, 8.48 mmol) and N-[6-[(3S)-3-aminopyrrolidin-1-yl]-2-methyl-pyrimidin-4-yl]-5-(4-pyridyl)thiazol-2-amine (1.5 g. 4.24 mmol). The mixture was stirred at 25° C. for 1 h. The mixture was concentrated under reduced pressure and the residue was purified by flash column chromatography on silica gel (methanol in dichloromethane from 0% to 10%) to afford the product of tert-butyl (2S)-2-[[(3S)-1-[2 -methyl-6-[[5-(4-pyridyl)thiazol-2-yl]amino]pyrimidin-4-yl]pyrrolidin-3-yl]carbamoyl]pyrrolidine-1-carboxylate (754 mg, 27% yield) as a yellow solid.

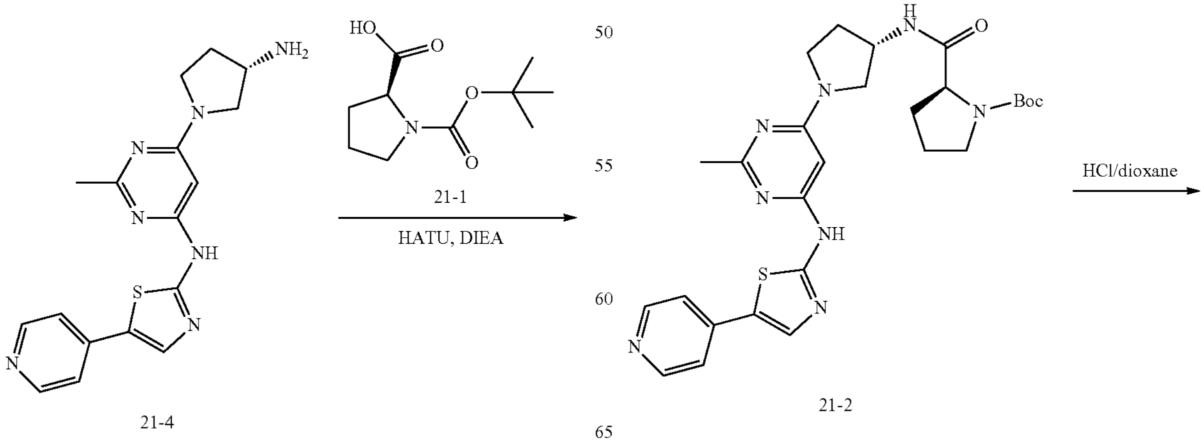

21-4

21-2

-continued

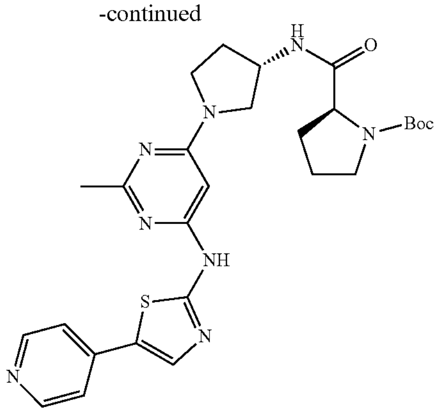

21-3

To a solution of tert-butyl (2S)-2-[[(3S)-1-[2-methyl-6-[[5-(4-pyridyl)thiazol-2-yl]amino]pyrimidin-4-yl]pyrrolidin-3-yl]carbamoyl]pyrrolidine-1-carboxylate (754 mg, 1.37 mmol) in DCM (2 mL) was added 4M HCl/dioxane (15 mL), The mixture was stirred at 25° C. for 1 h. The mixture was concentrated under reduced pressure to afford (2S)—N-[(3S)-1-[2-methyl-6-[[5-(4-pyridyl)thiazol-2-yl]amino]pyrimidin-4-yl]pyrrolidin-3-yl]pyrrolidine-2-carboxamide (939 mg, crude) as a yellow solid which was used directly in the next step without further purification.

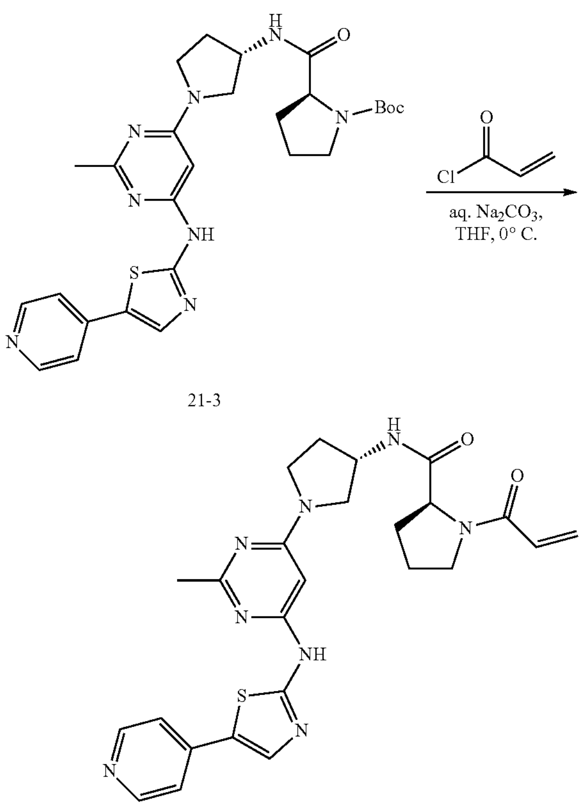

21-3 compound 21

To a solution of (2S)—N-[(3S)-1-[2-methyl-6-[[5-(4-pyridyl)thiazol-2-yl]amino]pyrimidin-4-yl]pyrrolidin-3-yl]pyrrolidine-2-carboxamide (150 mg, 0.33 mmol) in THF (2 mL) and $H_2O$ (2 mL) was added $Na_2CO_3$ (106 mg, 1.00 mmol). Then prop-2-enoyl chloride (30 mg, 0.33 mmol) was added at 0° C. The mixture was stirred at 25° C. for 0.5 h. The mixture was extracted with ethyl acetate (30 mL×3). The organic layers were concentrated and the residue was purified by prep-HPLC (column: Phenomenex Gemini-NX C18 75*30 mm*3 um; mobile phase: water (0.04% $NH_3 \cdot H_2O$+10 mM $NH_4HCO_3$)-ACN; B %: 14-44%, 12 min); Flow Rate: 25 mL/min) to afford (2S)—N-[(3S)-1-[2-methyl-6-[[5-(4-pyridyl)thiazol-2-yl]amino]pyrimidin-4-yl]pyrrolidin-3-yl]-1-prop-2-enoyl-pyrrolidine-2-carboxamide (10.2 mg, 6% yield) as a red solid. LCMS: $t_R$=2.319 min in 10-80CD_7 min_Pos_220&254_Shimadzu.1 cm, MS (ESI) m/z=505.2 $[M+H]^+$. $^1$H NMR (400 MHz, $CDCl_3$): δ=9.99 (s, 1H), 9.26 (s, 1H), 8.59 (d, J=4.0 Hz, 2H), 7.56 (s, 1H), 7.45 (d, J=4.0 Hz, 2H), 6.57-6.42 (m, 2H), 5.74 (d, J=12.0 Hz, 2H), 4.79 (s, 1H), 4.37 (s, 1H), 3.95-3.31 (m, 6H), 2.51-1.99 (m, 9H). Chiral SFC: $t_R$=5.238 min, Column: Chiralpak OJ-3 100 um*4.6 mm I.D., 3 um, Mobile phase: A: $CO_2$ B: ethanol (0.05% DEA), Gradient: from 5% to 40% of B in 4 min and hold 40% for 2.5 min, then 5% of B for 1.5 min, Flow rate: 2.8 mL/min, Column temp.: 35° C., ABPR: 1500 psi. Acq Method: OJ_3_EtOH_DEA_5_40_28ML_8 min. ee %=100%. $[\alpha]_D^{20}$=−36.7 (c=0.03, MeOH).

Example 22

(2S)—N-[2-[[2-methyl-6-[[5-(4-pyridyl)thiazol-2-yl]amino]pyrimidin-4-yl]amino]ethyl]-1-prop-2-enoyl-pyrrolidine-2-carboxamide (Compound 22)

Scheme 25. Synthesis of compound 22.

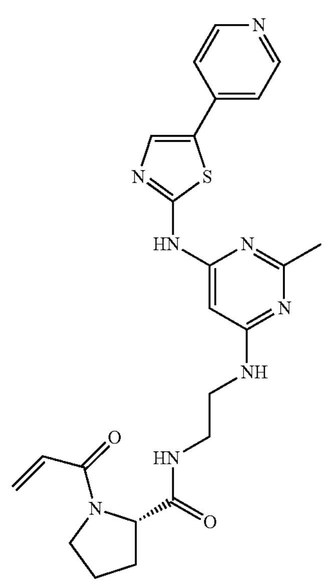

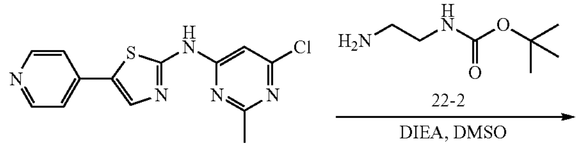

22-1

-continued

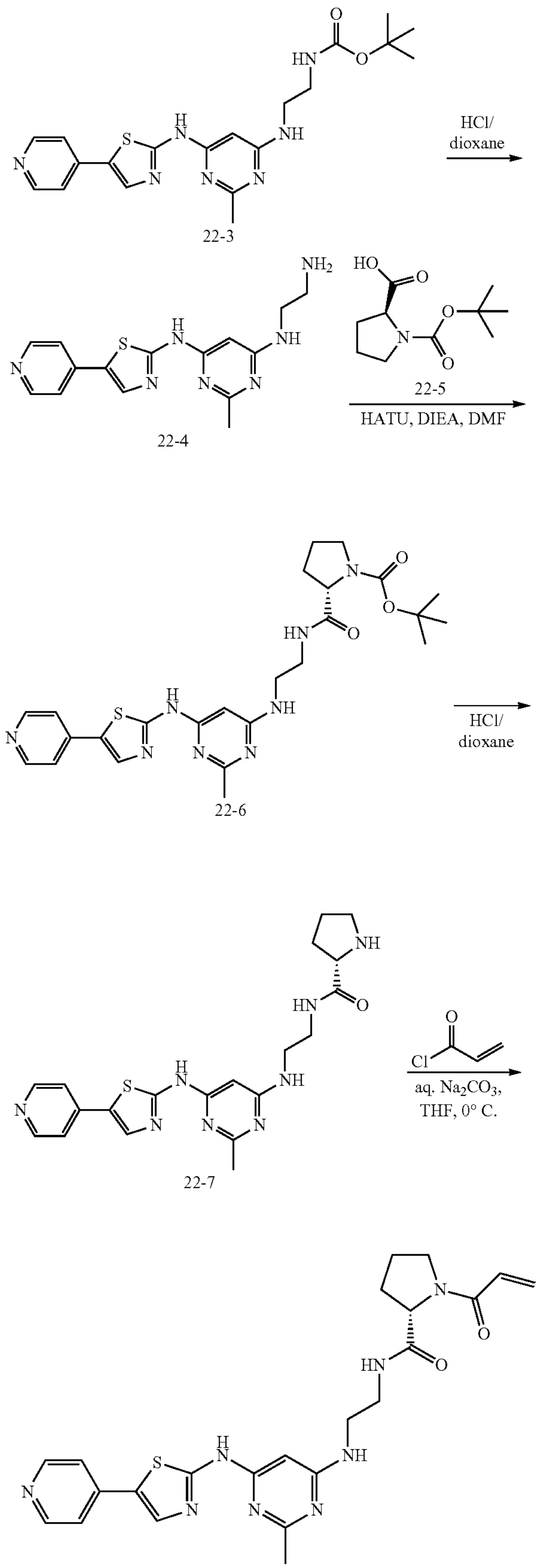

22-3

22-4

22-5

22-6

22-7 compound 22

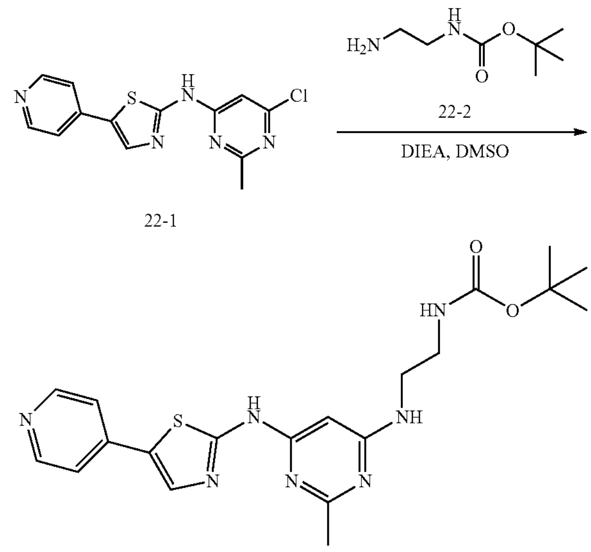

22-1

22-2

22-3

To a solution of N-(6-chloro-2-methyl-pyrimidin-4-yl)-5-(4-pyridyl)thiazol-2-amine (300 mg, 0.99 mmol) in DMSO (10 mL) was added DIEA (766 mg, 5.93 mmol) and tert-butyl N-(2-aminoethyl)carbamate (791 mg, 4.94 mmol). The mixture was stirred at 80° C. for 4 h. To the mixture was added water (20 mL), and then extracted with ethyl acetate (20 mL×3). The organic phase was separated, concentrated and purified by flash column chromatography on silica gel (methanol in dichloromethane from 0% to 5%) to afford the product of tert-butyl N-[2-[[2-methyl-6-[[5-(4-pyridyl)thiazol-2-yl]amino]pyrimidin-4-yl]amino]ethyl]carbamate (485 mg, 85% yield) as a yellow solid.

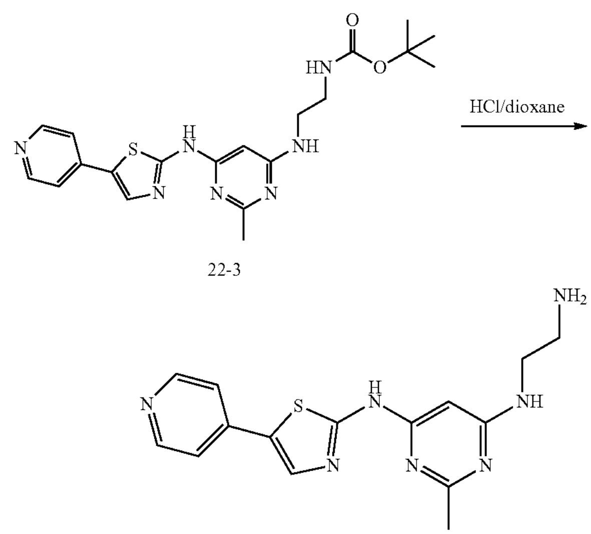

22-3

22-4

To a solution of tert-butyl N-[2-[[2-methyl-6-[[5-(4-pyridyl)thiazol-2-yl]amino]pyrimidin-4-yl]amino]ethyl]carbamate (485 mg, 1.13 mmol) in DCM (2 mL) was added HCl/dioxane (10 mL, 4 M). The mixture was stirred at 25° C. for 1 h. The mixture was concentrated under reduced pressure to afford $N_4$-(2-aminoethyl)-2-methyl-$N_6$-[5-(4- pyridyl)thiazol-2-yl]pyrimidine-4,6-diamine (471 mg, crude) as a yellow solid which was used directly in the next step without further purification.

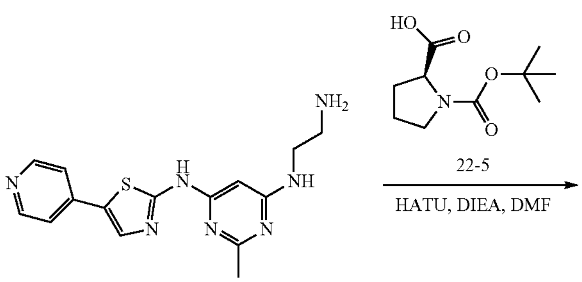

22-4

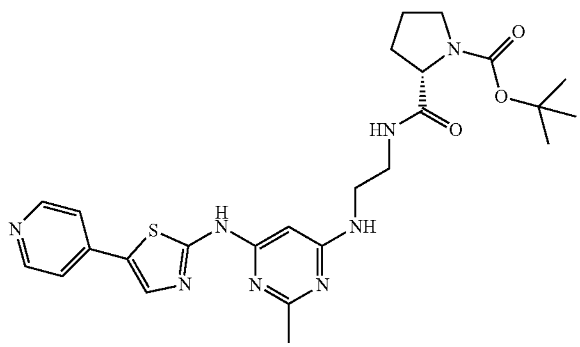

22-6

To a solution of (2S)-1-tert-butoxycarbonylpyrrolidine-2-carboxylic acid (188 mg, 0.87 mmol) in DMF (6 mL) was added HATU (379 mg, 1.00 mmol) and DIEA (215 mg, 1.66 mmol). Then $N_4$-(2-aminoethyl)-2-methyl-$N_6$-[5-(4-pyridyl)thiazol-2-yl]pyrimidine-4,6-diamine (272 mg, 0.83 mmol) was added. The mixture was stirred at 50° C. for 1 h. The mixture was concentrated under reduced pressure and the residue was purified by flash column chromatography on silica gel (methanol in dichloromethane from 0% to 8%, addition of 0.1% ammonia (v/v)) to afford the product of tert-butyl (2S)-2-[2-[[2-methyl-6-[[5-(4-pyridyl)thiazol-2-yl]amino]pyrimidin-4-yl]amino]ethyl carbamoyl]pyrrolidine-1-carboxylate (206 mg, 47% yield) as a yellow oil.

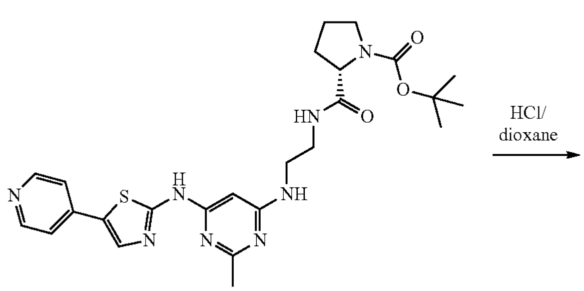

22-6

-continued

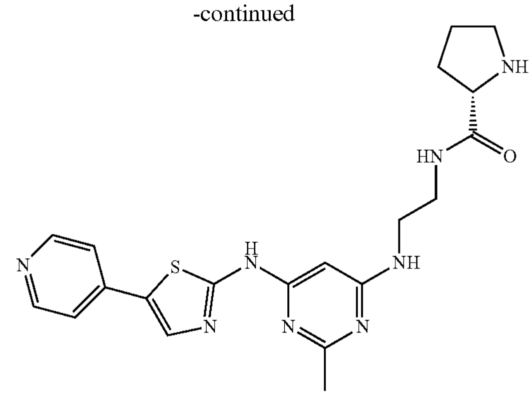

22-7

To a solution of tert-butyl (2S)-2-[2-[[2-methyl-6-[[5-(4-pyridyl)thiazol-2-yl]amino]pyrimidin-4-yl]amino]ethylcarbamoyl]pyrrolidine-1-carboxylate (206 mg, 0.39 mmol) in DCM (2 mL) was added 4 M HCl/dioxane (5 mL). The mixture was stirred at 25° C. for 1 h. The mixture was concentrated under reduced pressure to afford (2S)—N-[2-[[2-methyl-6-[[5-(4-pyridyl)thiazol-2-yl]amino]pyrimidin-4-yl]amino]ethyl]pyrrolidine-2-carboxamide (189 mg, crude) as a yellow solid which was used directly in the next step without further purification.

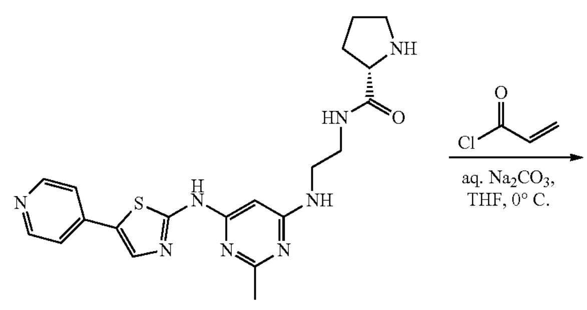

22-7

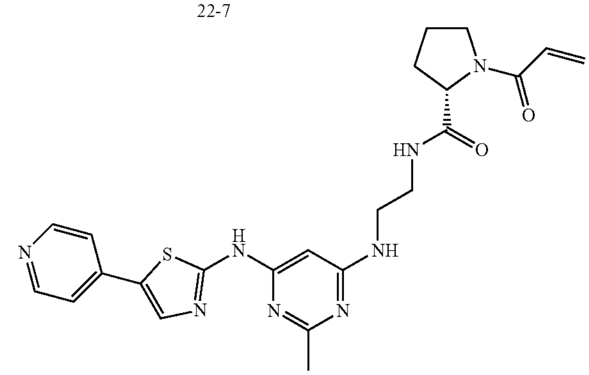

compound 22

To a solution of (2S)—N-[2-[[2-methyl-6-[[5-(4-pyridyl)thiazol-2-yl]amino]pyrimidin-4-yl]amino]ethyl]pyrrolidine-2-carboxamide (189 mg, 0.45 mmol) in THF (5 mL) and $H_2O$ (5 mL) was added $Na_2CO_3$ (142 mg, 1.34 mmol). Then prop-2-enoyl chloride (40 mg, 0.45 mmol) was added at 0° C. The mixture was stirred at 25° C. for 0.5 h. The mixture was extracted with ethyl acetate (30 mL×3). The organic layers were concentrated and the residue was purified by prep-HPLC (column: Phenomenex Gemini-NX C18 75*30 mm*3 um, mobile phase: water (0.04% $NH_3$, $H_2O$+10 mM $NH_4HCO_3$)-ACN; B %: 10-50%, 14 min); Flow Rate: 25 mL/min) to afford (2S)—N-[2-[[2-methyl-6-[[5-(4-pyridyl)thiazol-2-yl]amino]pyrimidin-4-yl]amino]ethyl]-1-prop-2-enoyl-pyrrolidine-2-carboxamide (16.9 mg, 8% yield) as a yellow solid. LCMS: $t_R$=0.636 min in 10-80 AB_4 min_220 &254_Shimadzu.1 cm, MS (ESI) m/z=479.3 $[M+H]^+$. $^1H$ NMR (400 MHz, $CDCl_3$): δ=10.05 (s, 1H), 8.56-8.54 (d, J=8.0 Hz, 2H), 7.78 (s, 1H), 7.57 (s, 1H), 7.42-7.41 (d, 4.0 Hz, 2H), 6.56-6.42 (m, 2H), 5.99 (s, 1H), 5.80-5.67 (m, 1H), 5.46 (s, 1H), 4.56-4.54 (m, 1H), 3.77-3.56 (m, 3H), 3.47-3.26 (m, 2H), 3.27-3.26 (m, 1H), 2.49 (s, 3H), 2.27-2.14 (m, 2H), 2.07-1.97 (m, 2H). Chiral SFC: $t_R$=3.100 min, Column: Chiral MJ-3 100 um*4.6 mm I.D., 3 um, Mobile phase: A: $CO_2$ B: ethanol (0.05% DEA), Gradient: from 5% to 40% of B in 4 min and hold 40% for 2.5 min, then 5% of B for 1.5 min, Flow rate: 2.8 mL/min, Column temp.: 35° C., ABPR: 1500 psi. Acq Method: MJ_3_EtOH_DEA_5_40_28 ML_8_min. ee %=100%. $[\alpha]_D^{20}$=−10.0 (c=0.06, MeOH).

Example 23

5-[(5-fluoro-2-oxo-indolin-3-ylidene)methyl]-4-methyl-N-[2-[[(2S)-2-[methyl(prop-2-enoyl)amino]propanoyl]amino]ethyl]-1H-pyrrole-3-carboxamide (Compound 23)

Scheme 26. Synthesis of compound 23.

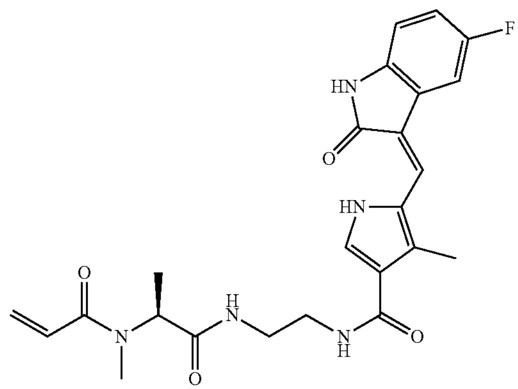

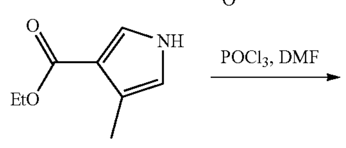

23-1

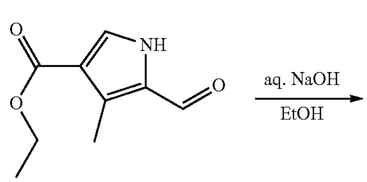

23-2

-continued

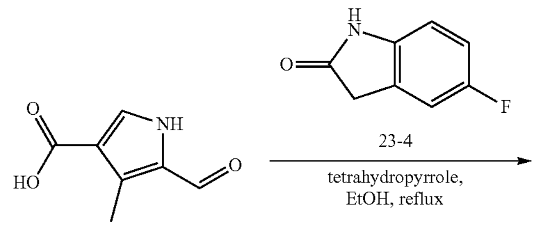

23-3

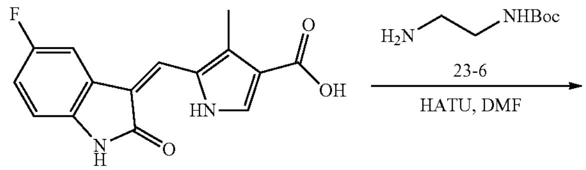

23-5

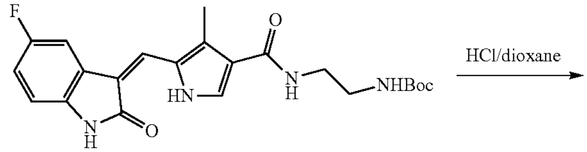

23-7

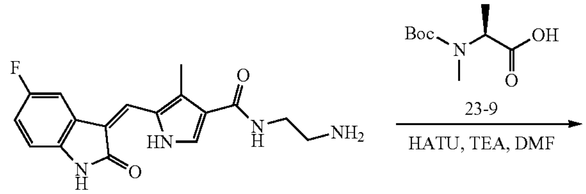

23-8

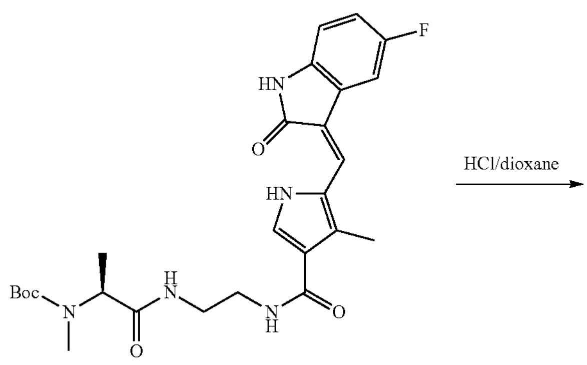

23-10

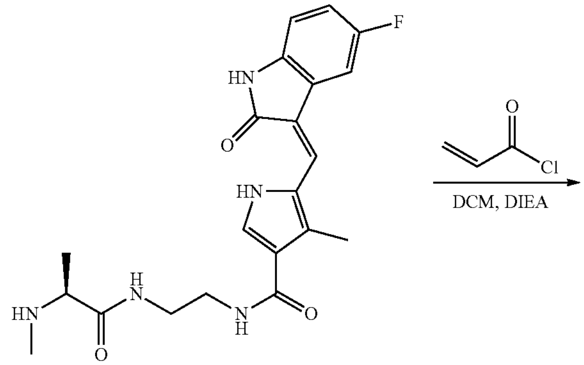

23-11

-continued

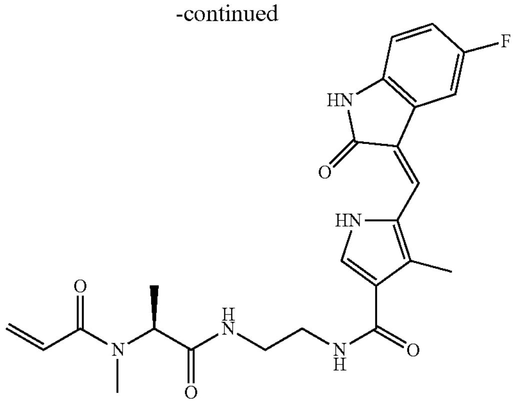

compound 23

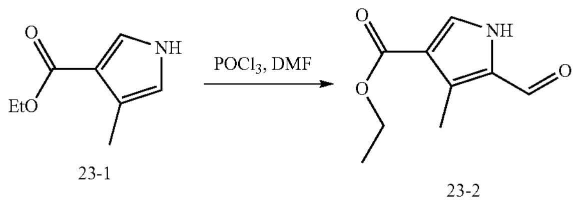

23-1 23-2

$POCl_3$ (16.82 g, 109.68 mmol) was added drop-wise to DMF (8.02 g, 109.68 mmol) at 0° C. The mixture was stirred at 25° C. for 1 h. A solution of ethyl 4-methyl-1H-pyrrole-3-carboxylate (4 g, 26.11 mmol) in DMF (50 mL) was added thereto at 0° C. Then the mixture was warmed to 25° C. and stirred for 1 h. The mixture was poured to ice (20 g). The pH of the mixture was adjusted to 7-8 by adding 2 M NaOH and a white solid was formed. The mixture was filtered and the filter cake was washed with water (2 mL×2) and concentrated under reduced pressure to afford ethyl 5-formyl-4-methyl-1H-pyrrole-3-carboxylate (4.2 g, 23.18 mmol, 89 yield) as a white solid, which would be used directly in the next step. $^1$H NMR (400 MHz, DMSO-$d_6$): δ=12.42 (s, 1H), 9.76 (s, 1H), 7.67 (d, J=3.6 Hz, 1H), 4.25 (q, J=7.2 Hz, 2H), 2.56 (s, 3H), 1.32 (t, J=7.2 Hz, 3H).

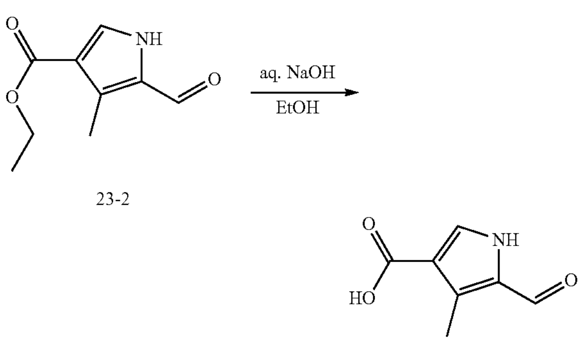

23-2

23-3

To a solution of ethyl 5-formyl-4-methyl-1H-pyrrole-3-carboxylate (4.2 g, 23.18 mmol) in EtOH (40 mL) and $H_2O$ (20 mL) was added NaOH (13.91 g, 347.7 mmol). The mixture was stirred at 100° C. for 12 h. The pH of the mixture was adjusted to 5-6 with 2 M HCl and the resulting mixture was filtered, the filter cake was washed with water (2 mL×2) and concentrated under reduced pressure to afford 5-formyl-4-methyl-1H-pyrrole-3-carboxylic acid (3.2 g, 20.90 mmol, 90% yield) as a brown solid, which would be used directly in the next step. $^1$H NMR (400 MHz, DMSO-$d_6$): δ=12.40 (s, 1H), 12.15 (brs, 1H), 9.70 (s, 1H), 7.58 (d, J=3.6 Hz, 1H), 2.50 (s, 3H).

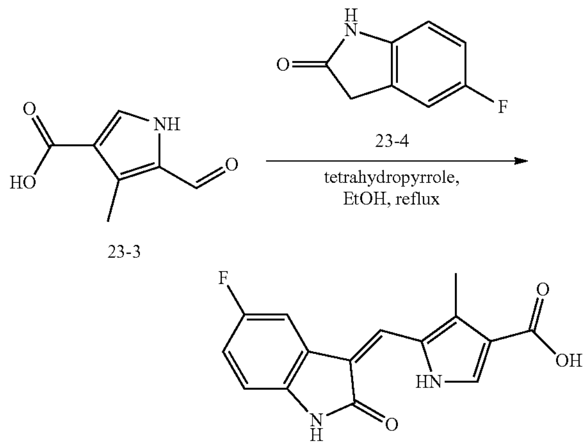

23-3

23-5

To a solution of 5-formyl-4-methyl-1H-pyrrole-3-carboxylic acid (0.5 g, 3.27 mmol) in EtOH (10 mL) was added tetrahydropyrrole (23 mg, 0.326 mmol) and 5-fluoroindolin-2-one (493 mg, 3.27 mmol). The mixture was stirred at 80° C. for 3 h. The mixture was filtered and the filtrate was concentrated under reduced pressure to afford 5-[(5-fluoro-2-oxo-indolin-3-ylidene)methyl]-4-methyl-1H-pyrrole-3-carboxylic acid (800 mg, 2.79 mmol, 85% yield) as a yellow solid, which would be used directly in the next step. $^1$H NMR (400 MHz, DMSO-$d_6$): δ=13.78 (s, 1H), 11.01 (s, 1H), 7.87-7.77 (m, 3H), 7.02-6.92 (m, 1H), 6.86 (dd, J=8.4 and 4.4 Hz, 1H), 2.56-2.53 (m, 3H).

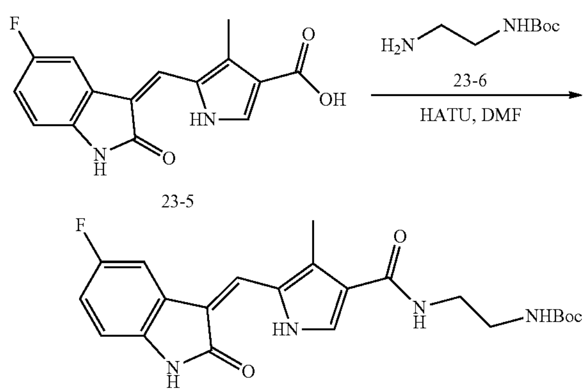

23-5

23-7

To a solution of 5-[(5-fluoro-2-oxo-indolin-3-ylidene) methyl]-4-methyl-1H-pyrrole-3-carboxylic acid (800 mg, 2.79 mmol) in DMF (20 mL) was added HATU (1.28 g, 3.35 mmol) and TEA (848 mg, 8.38 mmol) and tert-butyl N-(2-aminoethyl)carbamate (493 mg, 3.07 mmol). The mixture was stirred at 25° C. for 2 h. The mixture was quenched by addition of $H_2O$ (20 mL) at 25° C., and the mixture was extracted with EtOAc (30 mL×2), dried over $Na_2SO_4$, filtered and concentrated under reduced pressure to afford tert-butyl N-[2-[[5-[(5-fluoro-2-oxo-indolin-3-ylidene)methyl]-4-methyl-1H-pyrrole-3-carbonyl]amino]ethyl]carbamate (1 g, 2.33 mmol, 83% yield) as a yellow solid, which would be used directly in the next step.

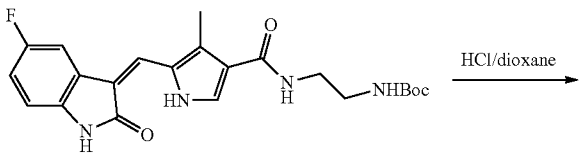

23-7

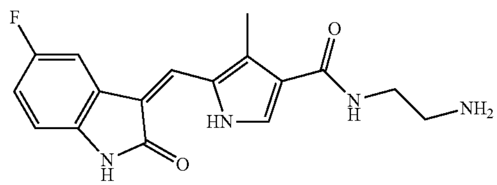

23-8

To a solution of tert-butyl N-[2-[[5-[(5-fluoro-2-oxo-indolin-3-ylidene)methyl]-4-methyl-1H-pyrrole-3-carbonyl]amino]ethyl]carbamate (1 g, 2.33 mmol) in HCl/dioxane (4 M, 20 mL). The mixture was stirred at 25° C. for 0.5 h. The mixture was concentrated under reduced pressure to afford N-(2-aminoethyl)-5-[(5-fluoro-2-oxo-indolin-3-ylidene)methyl]-4-methyl-1H-pyrrole-3-carboxamide (700 mg, 2.13 mmol, 91% yield) as a yellow solid, which would be used directly in the next step.

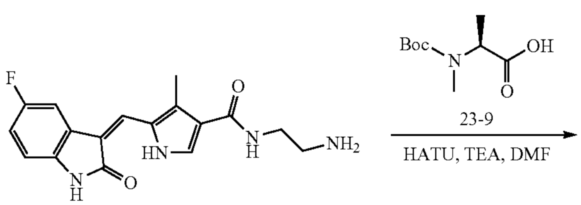

23-8

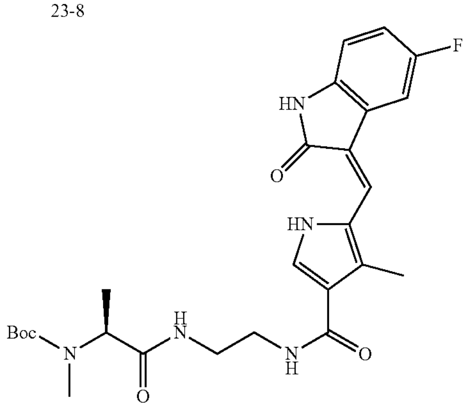

23-10

To a solution of N-(2-aminoethyl)-5-[(5-fluoro-2-oxo-indolin-3-ylidene)methyl]-4-methyl-1H-pyrrole-3-carboxamide (700 mg, 2.13 mmol) in DMF (10 mL) was added HATU (973 mg, 2.56 mmol), TEA (827 mg, 8.17 mmol) and (2S)-2-[tert-butoxycarbonyl)methyl)amino]propanoic acid (520 mg, 2.56 mmol). The mixture was stirred at 25° C. for 2 h. The mixture concentrated under reduced pressure and the residue was purified with flash column (PE: EtOAc=1:0 to 1:1) to afford tert-butyl N-[(1S)-2-[2-[[5-[(5-fluoro-2-oxo-indolin-3-ylidene)methyl]-4-methyl-1H-pyrrole-3-carbonyl]amino]ethyl amino]-1-methyl-2-oxo-ethyl]-N-methyl-carbamate (0.8 g, 1.56 mmol, 73% yield) as a yellow solid, which would be used directly in the next step. $^1H$ NMR (400 MHz, DMSO-$d_6$): δ=13.69 (s, 1H), 10.96 (s, 1H), 8.03-7.85 (m, 2H), 7.84-7.73 (m, 3H), 7.04-6.91 (m, 1H), 6.86 (dd, J=8.0 and 4.4 Hz, 1H), 4.65-4.16 (m, 1H), 3.29-3.21 (m, 4H), 2.74 (s, 3H), 2.54 (s, 3H), 1.38 (s, 9H), 1.24 (d, J=5.6 Hz, 3H).

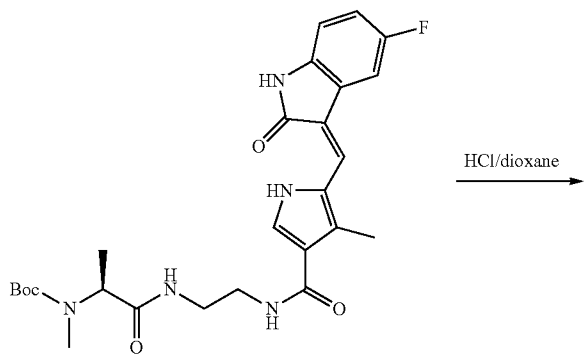

23-10

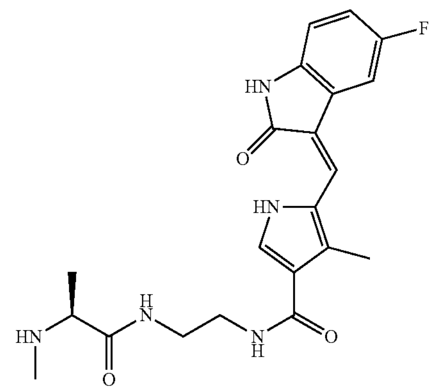

23-11

To a solution of tert-butyl N-[(1S)-2-[2-[[5-[(5-fluoro-2-oxo-indolin-3-ylidene)methyl]-4-methyl-1H-pyrrole-3-carbonyl]amino]ethyl amino]-1-methyl-2-oxo-ethyl]-N-methyl-carbamate (0.8 g, 1.56 mmol) in HCl/dioxane (4 M, 20 mL). The mixture was stirred at 25° C. for 0.5 hr. The mixture was concentrated under reduced pressure to afford 5-[5-fluoro-2-oxo-indolin-3-ylidene)methyl]-4-methyl-N-[2-[[(2S)-2 -(methylamino)propanoyl]amino]ethyl]-1H-pyrrole-3-carboxamide (0.6 g, 1.45 mmol, 93% yield) as a yellow solid, which would be used directly in the next step.

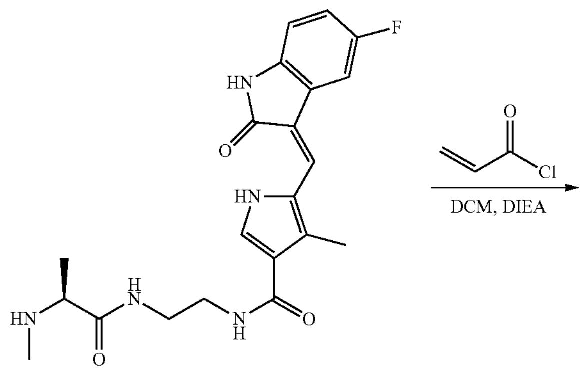

23-11

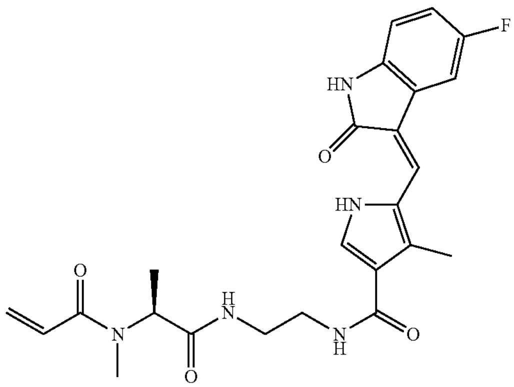

compound 23

To a solution of 5-[(5-fluoro-2-oxo-indolin-3-ylidene)methyl]-4-methyl-N-[2-[[(2S)-2-(methylamino)propanoyl]amino]ethyl]-1H-pyrrole-3-carboxamide (300 mg, 0.726 mmol) in DCM (10 mL) was added DIEA (188 mg, 1.45 mmol) and prop-2-enoyl chloride (66 mg, 0.726 mmol). The mixture was stirred at 0° C. for 1 h. The mixture was quenched by addition of $H_2O$ (50 mL) at 25° C., and then diluted with $H_2O$ (50 mL) and extracted with DCM (50×3). The combined organic layers were washed with brine (50 mL), dried over $Na_2SO_4$, filtered and concentrated under reduced pressure to give a residue. After that the residue was purified by preparative HPLC (water (0.04% $NH_3 \cdot H_2O$+10 mM $NH_4HCO_3$)-ACN) to afford product (130 mg, purity 85%) as a white solid, which was further separated by SFC (column: DAICEL CHIRALPAK AD (250 mm*50 mm, 10 um); mobile phase: [0.1% $NH_3 \cdot H_2O$ ETOH]; B %: 35%-35%, min) to afford 5-[(5-fluoro-2-oxo-indolin-3-ylidene)methyl]-4-methyl-N-[2-[[(2S)-2-[methyl(prop-2-enoyl)amino]propanoyl]amino]ethyl]-1H-pyrrole-3-carboxamide (11.8 mg, 0.025 mmol, 3% yield, 97.5% purity) as a yellow solid. LCMS: $t_R$=2.515 mM in 10-80AB_4 min_220 &254_Shimadzu.1 cm, MS (ESI) m/z=468.5 $[M+H]^+$. $^1H$ NMR (400 MHz, DMSO-$d_6$): δ=13.68 (s, 1H), 10.96 (s, 1H), 8.14-7.86 (m, 2H), 7.82-7.76 (m, 2H), 7.01-6.93 (m, 1H), 6.86 (dd, J=8.4 and 4.4 Hz, 1H), 6.79-6.68 (m, 1H), 6.18-6.02 (m, 1H), 5.74-5.59 (m, 1H), 5.04-4.56 (m, 1H), 3.25-3.20 (m, 4H), 2.94-2.75 (m, 3H), 2.53 (s, 3H), 1.33-1.22 (m, 3H). Chiral SFC: t 3.198 min (Instrument column: Chiralcel OJ-3 100×4.6 mm I.D., 3 um, Mobile phase: A: $CO_2$, B: ethanol (0.05% DEA), Gradient: from 5% to 40% of B in 4.5 min and hold 40% for 2.5 min, then 5% of B for 1 mM, Flow rate: 2.8 mL/min, Column temperature: 40° C., detection: 220 nm), ee %=97.22%. $[\alpha]_D^{20}$=−10.0 (c=0.1, MeOH).

Example 24

5-[(5-fluoro-2-oxo-indolin-3-ylidene)methyl]-4-methyl-N-[2-[[(2S)-2-[methyl(propanoyl)amino]propanoyl]amino]ethyl]-1H-pyrrole-3-carboxamide (Compound 24)

Scheme 27. Synthesis of compound 24.

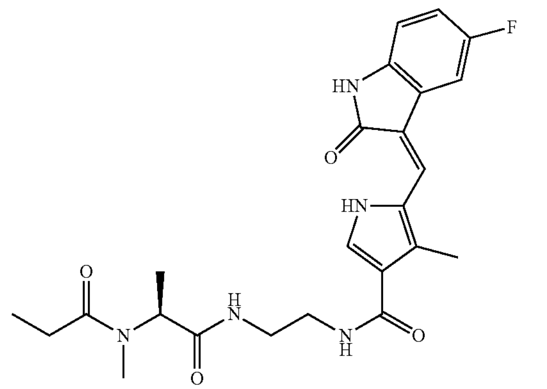

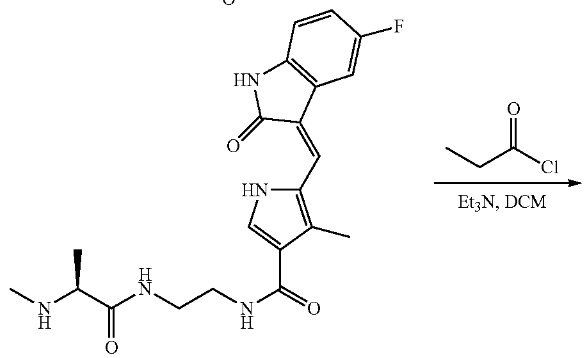

23-11

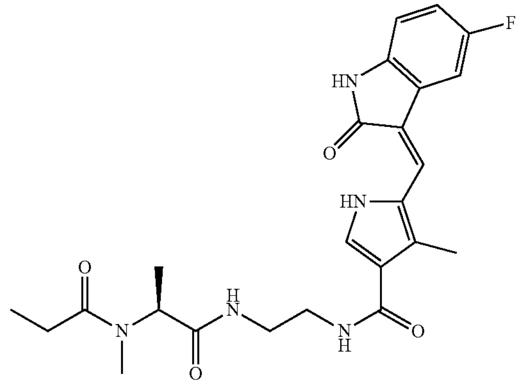

compound 24

Synthesis of 5-[(5-fluoro-2-oxo-indolin-3-ylidene)methyl]-4-methyl-N-[2-[[(2S)-2-(methylamino)propanoyl]amino]ethyl]-1H-pyrrole-3-carboxamide (23-11) is shown in Example 23. To a solution of 5-[(5-fluoro-2-oxo-indolin-3-ylidene)methyl]-4-methyl-N-[2-[[(2S)-2-(methylamino)propanoyl]amino]ethyl]-1H-pyrrole-3-carboxamide (23-11, 160 mg, 0.387 mmol) and $Et_3N$ (39 mg, 0.387 mmol) in DCM (20 mL) was added propanoyl chloride (71 mg, 0.774 mmol). The mixture was stirred at 25° C. for 1 hr. The mixture was quenched by water (5 mL), extracted with DCM (50 mL×3), then combined organic layers, dried over $Na_2SO_4$, filtered and concentrated. The residue was purified by silica gel chromatography (Biotage 12 g Silica Flash Column; Eluent of gradient 0-10% methanol in dichloromethane 30 mL/min) to afford 5-[(5-fluoro-2-oxo-indolin-3-ylidene)methyl]-4-methyl-N-[2-[[(2S)-2-[methyl(propanoyl)amino]propanoyl]amino]ethyl]-1H-pyrrole-3-carboxamide (25.2 mg, 13% yield) as yellow solid. LCMS: $t_R$=2.418 min in 0-60 AB_4 min_220 &254_Shimadzu.1 cm, MS (ESI) m/z=470.3 $[M+H]^+$. $^1H$ NMR (400 MHz, DMSO-$d_6$): δ=13.68 (s, 1H), 10.98 (s, 1H), 8.07-7.94 (m, 1H), 7.82-7.77 (m, 4H), 6.97-6.84 (m, 2H), 5.01-4.46 (m, 1H), 3.28-3.23 (m, 4H), 2.82, 2.67 (s, 3H), 2.67-2.54 (m, 3H), 2.36-2.32 (m, 2H), 1.29-1.19 (m, 3H), 1.00-0.96 (m, 3H). Chiral SFC: $t_R$=5.366 min (Instrument column: Chiralpak AD-3 100×4.6 mm I.D., 3 um, Mobile phase: A: $CO_2$, B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., detection: 220 nm), ee %=100%. $[\alpha]_D^{20}$=−36.0 (c=0.1, MeOH).

Example 25

5-[(5-fluoro-2-oxo-indolin-3-ylidene)methyl]-4-methyl-N-[2-[[(2S)-2-[methyl(propanoyl)amino]propanoyl]amino]ethyl]-1H-pyrrole-3-carboxamide (Compound 25)

Scheme 28. Synthesis of compound 25.

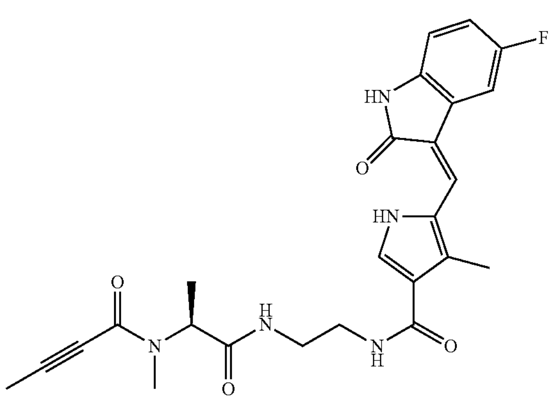

-continued

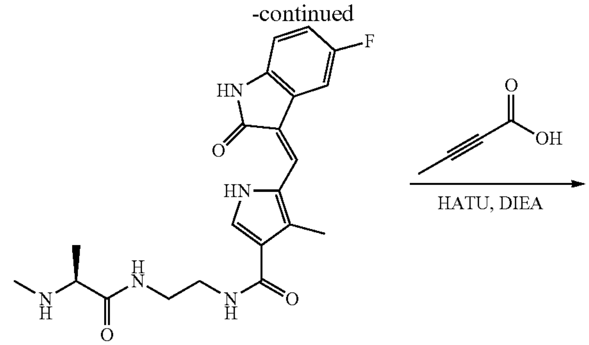

23-11

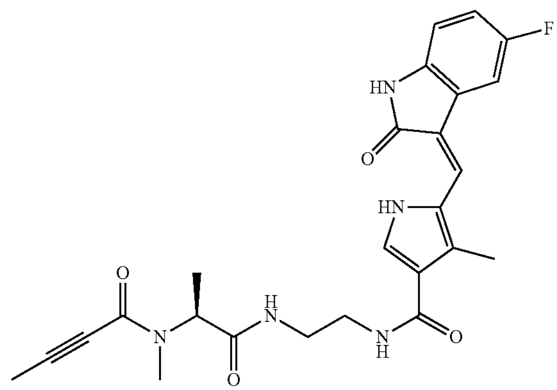

compound 25

Synthesis of 5-[(5-fluoro-2-oxo-indolin-3-ylidene)methyl]-4-methyl-N-[2-[[(2S)-2-(methylamino)propanoyl]amino]ethyl]-1H-pyrrole-3-carboxamide (23-11) is shown in Example 23. To a solution of 5-[(5-fluoro-2-oxo-indolin-3-ylidene)methyl]-4-methyl-N-[2-[[(2S)-2-(methylamino)propanoyl]amino]ethyl]-1H-pyrrole-3-carboxamide (23-11, 150 mg, 0.363 mmol) and HATU (166 mg, 0.435 mmol) and DIEA (141 mg, 1.09 mmol) in DMF (10 mL) was added but-2-ynoic acid (34 mg, 0.40 mmol). The mixture was stirred at 25° C. for 2 hrs. The mixture was diluted with water (20 mL), extracted with EtOAc (50 mL×3), then combined organic layers, washed with sat. aq. NaCl (20 mL×7), dried over $Na_2SO_4$, filtered and concentrated. The residue was purified by preparative HPLC (basic condition) to afford N-[2-[[(2S)-2-[but-2-ynoyl(methyl)amino]propanoyl]amino]ethyl]-5-[(5-fluoro-2-oxo-indolin-3-ylidene)methyl]-4-methyl-1H-pyrrole-3-carboxamide (67 mg, 38% yield) as yellow solid. LCMS: $t_R$=2.167 min in 10-80 AB_4 min_220&254_Shimadzu.1 cm, MS (ESI) m/z=480.2 $[M+H]^+$. $^1H$ NMR (400 MHz, DMSO-$d_6$): δ=13.68 (s, 1H), 10.97 (s, 1H), 7.99-7.81 (m, 2H), 7.81-7.75 (m, 3H), 6.96-6.86 (m, 2H), 4.92-4.80 (m, 1H), 3.35-3.20 (m, 4H), 3.04-2.72 (m, 3H), 2.01 (d, J=15.6 Hz, 3H), 1.34-1.23 (m, 3H). Chiral SFC: $t_R$=5.366 min (Instrument column: Chiralpak AD-3 100×4.6 mm I.D., 3 um, Mobile phase: A: $CO_2$, B: ethanol (0.05% DEA), Gradient: from 5% to 40% of B in 4.5 min and hold 40% for 2.5 min, then 5% of B for 1 min, Flow rate: 2.8 mL/min, Column temperature: 40° C., detection: 220 nm), ee %=99.28%. $[\alpha]_D^{20}$=−56.0 (c=0.1, MeOH).

Example 26

N-(2-((S)-2-((E)-4-(dimethylamino)-N-methylbut-2-enamido)propanamido)ethyl)-5-((Z)-(5-fluoro-2-oxoindolin-3-ylidene)methyl)-4-methyl-1H-pyrrole-3-carboxamide (Compound 26)

Scheme 29. Synthesis of compound 26.

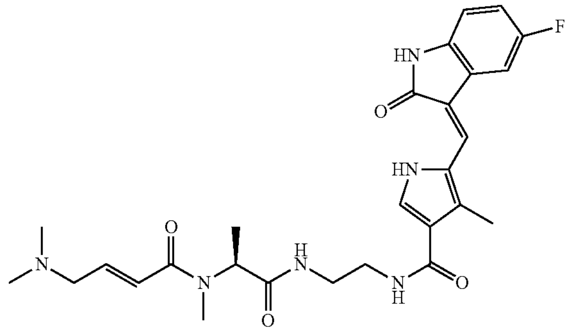

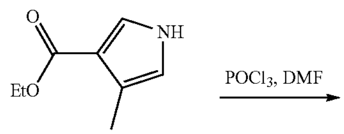

26-1

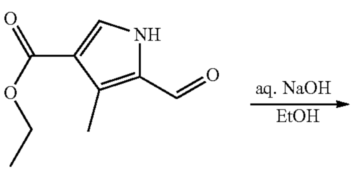

26-2

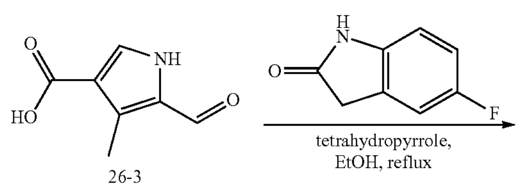

26-3

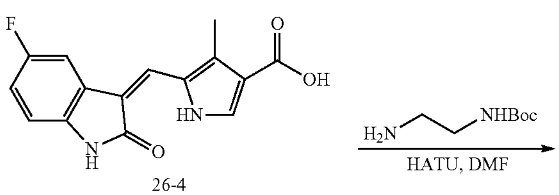

26-4

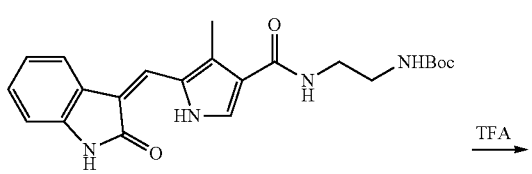

26-5

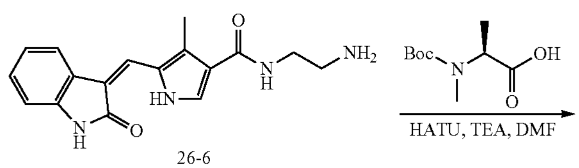

26-6

-continued

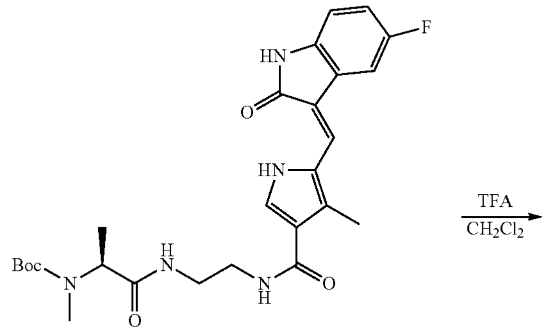

26-7

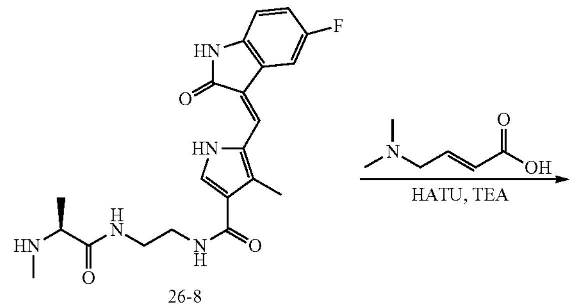

26-8

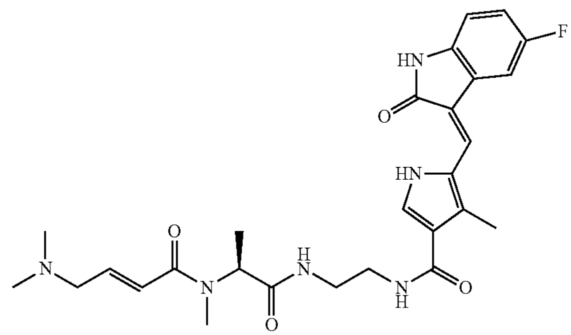

compound 26

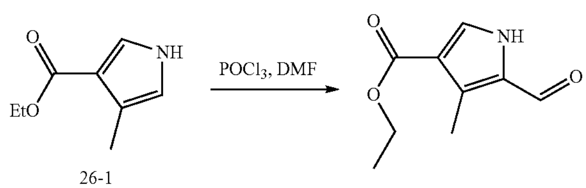

26-1

26-2

$POCl_3$ (2.12 g, 13.83 mmol) was added drop-wise to DMF (1.01 g, 13.84 mmol) at 0° C. The mixture was stirred at 15° C. for 1 hr. A solution of ethyl 4-methyl-1H-pyrrole-3-carboxylate (0.5 g, 3.26 mmol) in DMF (8 mL) was added thereto at 0° C. Then the mixture was warmed to 15° C. and stirred for 1 hr. The mixture was poured to ice (20 g). The pH of the mixture was adjusted to 7-8 by adding 2 M NaOH and a white solid was formed. The mixture was filtered and the filter cake was washed with water (2 mL×2). The filter cake was dried to afford ethyl 5-formyl-4-methyl-1H-pyrrole-3-carboxylate (523 mg, 94% purity, 83% yield) as white solid. LCMS: $t_R$=0.687 min in 5-95 AB_1.5 min_220 &254_Agil.1 cm, MS (ESI) m/z=182.1 $[M+H]^+$. HPLC: $t_R$=2.08 min in 10-80 AB_8 min. met (Ultimate C18 3 um, 3.0*50 mm). $^{1}$H NMR (400 MHz, $CDCl_3$): δ=9.78 (brs, 1H), 9.71 (s, 1H), 7.64 (s, 1H), 4.31 (q, J=7.2 Hz, 2H), 2.61 (s, 2H), 1.36 (t, J=7.2 Hz, 3H).

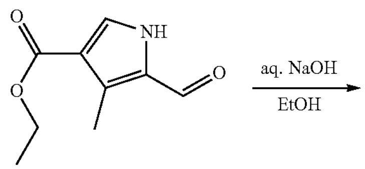

26-2

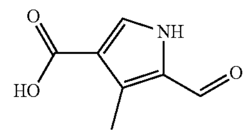

26-3

To a solution of ethyl 5-formyl-4-methyl-1H-pyrrole-3-carboxylate (400 mg, 2.21 mmol) in EtOH (5 mL) and $H_2O$ (3 mL) was added NaOH (106 mg, 2.65 mmol). Then the mixture was heated to 100° C. and stirred for 2 hr. Another batch NaOH (530 mg, 13.25 mmol) was added. The mixture was stirred at 100° C. for 2 hr. The pH of the mixture was adjusted to 5-6 with 2 N HCl and the resulting mixture was filtered. The filter cake was washed with water (2 mL×2). The filter cake was dried to afford 5-formyl-4-methyl-1H-pyrrole-3-carboxylic acid (284 mg, 84% yield) as white solid. LCMS: $t_R$=0.342 min in 5-95 AB_1.5 min_220 &254_Agilent.1 cm, MS (ESI) m/z=154.1 $[M+H]^+$. $^{1}$H NMR (400 MHz, DMSO-$d_6$): δ=12.26 (br s, 1H), 9.70 (s, 1H), 7.56 (s, 1H), 2.50 (s, 3H).

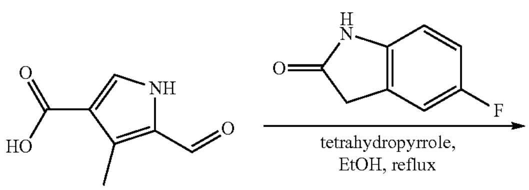

26-3

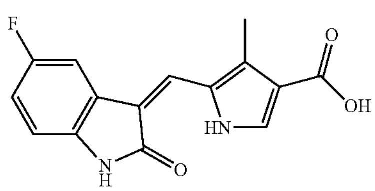

26-4

To a solution of 5-formyl-4-methyl-1H-pyrrole-3-carboxylic acid (280 mg, 1.83 mmol) in EtOH (5 mL) was added tetrahydropyrrole (13 mg, 0.183 mmol) and 5-fluoroindolin-2-one (276 mg, 1.83 mmol). Then the mixture was heated to 80° C. and stirred for 3 hr. The mixture was filtered and the filter cake was washed with EtOAc (2 mL×2). The filter cake was dried to give 5-[(Z)-(5-fluoro-2-oxo-indolin-3-ylidene) methyl]-4-methyl-1H-pyrrole-3-carboxylic acid (432 mg, 100% purity, 83% yield) as yellow solid. LCMS: $t_R$=0.823 min in 5-95 AB_1.5 min_220 &254_Agilent.1 cm, MS (ESI) m/z=287.1 $[M+H]^+$. $^{1}$H NMR (400 MHz, DMSO-$d_6$): δ=13.78 (s, 1H), 12.13 (brs, 1H), 11.01 (s, 1H), 7.86-7.78 (m, 3H), 7.00-6.92 (m, 1H), 6.85 (dd, J=8.4 and 4.4 Hz, 1H), 2.54 (s, 3H).

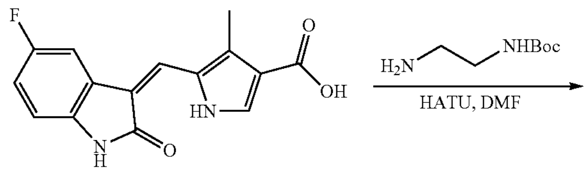

26-4

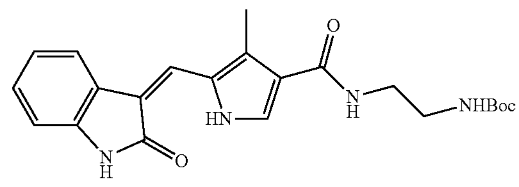

26-5

To a solution of 5-[(Z)-(5-fluoro-2-oxo-indolin-3-ylidene) methyl]-4-methyl-1H-pyrrole-3-carboxylic acid (390 mg, 1.36 mmol) in DMF (10 mL) was added HATU (622 mg, 1.63 mmol) and TEA (414 mg, 4.09 mmol). The mixture was stirred at 15° C. for 0.5 hr. tert-butyl N-(2-aminoethyl) carbamate (218 mg, 1.36 mmol) was added. The mixture was stirred at 15° C. for 2 hr. Water (20 mL) was added. The mixture was stirred at 20° C. for 10 min. The mixture was filtered and the filter cake was washed with EtOAc (3 mL×3). The filter cake was dried to afford tert-butyl N-[2-[[4-methyl-5-[(Z)-(2-oxoindolin-3-ylidene)methyl]-1H-pyrrole-3-carbonyl]amino]ethyl]carbamate (502 mg, crude) as yellow solid. $^{1}$H NMR (400 MHz, DMSO-$d_6$): δ=13.67 (brs, 1H), 10.96 (s, 1H), 7.95 (s, 1H), 7.90-7.84 (m, 1H), 7.83-7.75 (m, 3H), 6.99-6.92 (m, 1H), 6.91-6.82 (m, 2H), 3.23-3.20 (m, 2H), 3.08-3.04 (m, 2H), 2.53 (s, 3H), 1.38 (s, 9H).

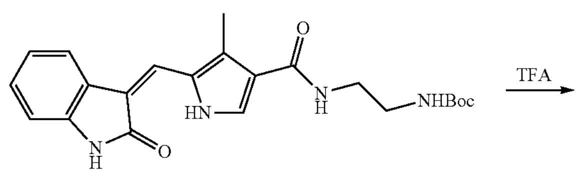

26-5

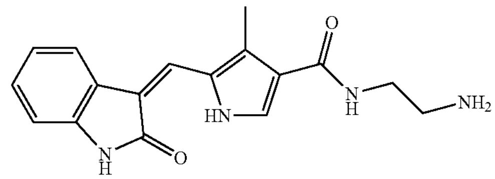

26-6

To a solution of tert-butyl N-[2-[[5-[(Z)-(5-fluoro-2-oxo-indolin-3-ylidene)methyl]-4-methyl-1H-pyrrole-3-carbonyl]amino]ethyl]carbamate (500 mg, 1.17 mmol) in DCM (6 mL) was added TFA (15.40 g, 135.06 mmol). The mixture was stirred at 20° C. for 1 hr. The solvent was removed under reduced pressure. The residue was triturated with EtOAc (20 mL) at 15° C. for 20 min. The mixture was filtered and the filter cake was washed with EtOAc (2 mL×2). The filter cake was dried to give N-(2-aminoethyl)-5-[(Z)-(5-fluoro-2-oxo-indolin-3-ylidene)methyl]-4-methyl-1H-pyrrole-3-carboxamide (510 mg, crude, TFA salt) as yellow solid.

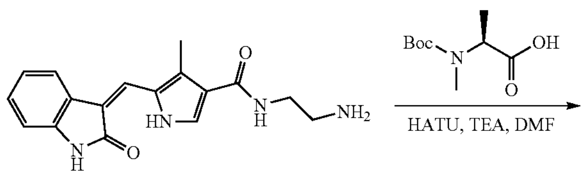

26-6

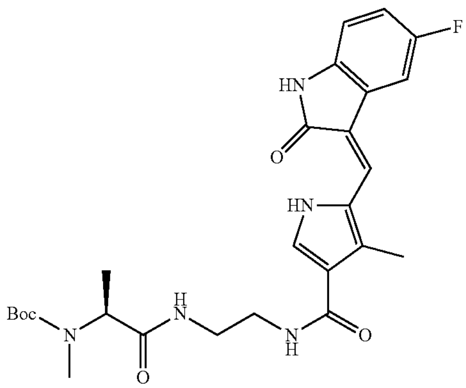

26-7

To a solution of (2S)-2-[tert-butoxycarbonyl(methyl)amino]propanoic acid (190 mg, 0.932 mmol) in DMF (9 mL) was added HATU (387 mg, 1.02 mmol), N-(2-aminoethyl)-5-[(Z)-(5-fluoro-2-oxo-indolin-3-ylidene)methyl]-4-methyl-1H-pyrrole-3-carboxamide (375 mg, 0.848 mmol) and TEA (343 mg, 3.39 mmol). The mixture was stirred at 20° C. for 2 hr. Water (20 mL) was added. The mixture was filtered and the filter cake was washed with EtOAc (5 mL×3). The filter cake was dried to give tert-butyl N-[(1S)-2-[2-[[5-[(Z)-(5-fluoro-2-oxo-indolin-3-ylidene)methyl]-4-methyl-1H-pyrrole-3-carbonyl]amino]ethyl amino]-1-methyl-2-oxo-ethyl]-N-methyl-carbamate (406 mg, crude) as yellow solid.

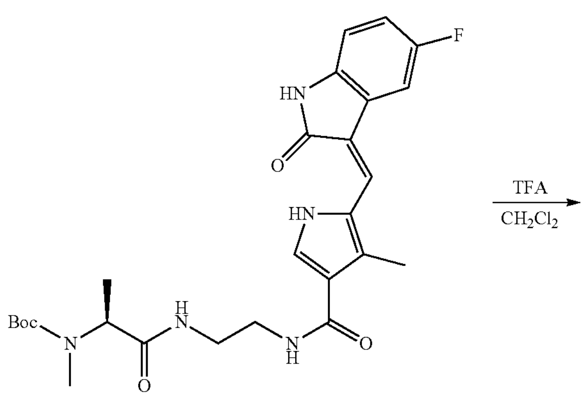

26-7

-continued

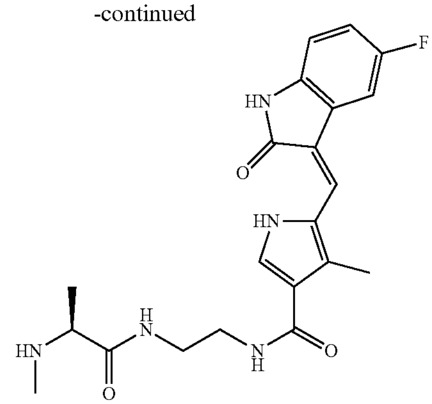

26-8

To a solution of tert-butyl N-[(1S)-2-[2-[[5-[(Z)-(5-fluoro-2-oxo-indolin-3-ylidene)methyl]-4-methyl-1H-pyrrole-3-carbonyl]amino]ethylamino]-1-methyl-2-oxo-ethyl]-N-methyl-carbamate (490 mg, 0.954 mmol) in DCM (4 mL) was added TFA (9.24 g, 81.04 mmol). The mixture was stirred at 20° C. for 2 hr. The solvent was removed under reduced pressure. The residue was diluted with EA (10 mL) and stirred at 15° C. for 0.5 h. The mixture was filtered and the filter cake was washed with EtOAc (5 mL×3). The filter cake was dried to give 5-[(Z)-(5-fluoro-2-oxo-indolin-3-ylidene)methyl]-4-methyl-N-[2-[[(2S)-2-(methylamino)propanoyl]amino]ethyl]-1H-pyrrole-3-carboxamide (453 mg, crude, TFA salt) as yellow solid. LCMS: $t_R$=1.255 min in 10-80 AB_2.0 min_220&254_Shimadzu.1 cm, MS (ESI) m/z=414.3 $[M+H]^+$.

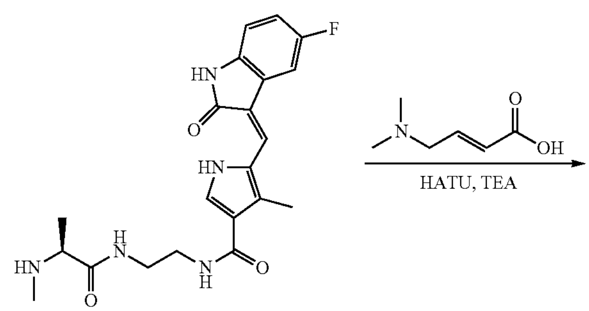

26-8

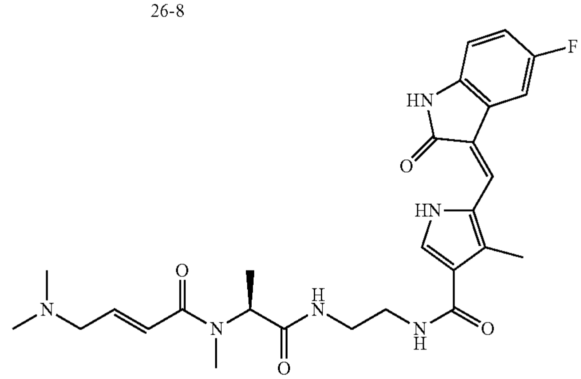

compound 26

To a solution of 4-(dimethylamino)but-2-enoic acid (54 mg, 0.417 mmol), 5-[(Z)-(5-fluoro-2-oxo-indolin-3-ylidene)

methyl]-4-methyl-N-[2-[[(2S)-2-(methylamino)propanoyl]amino]ethyl]-1H-pyrrole-3-carboxamide (200 mg, 0.379 mmol, TFA salt) and TEA (153 mg, 1.52 mmol) in DMF (3 mL) was added HATU (159 mg, 0.417 mmol). The mixture was stirred at 20° C. for 1 hr. The mixture was filtered and the residue was purified by preparative HPLC ((Column: Agela DuraShell C18 250*25 mm*10 um: water (0.04% $NH_3 \cdot H_2O$+10 mM $NH_4HCO_3$)-ACN; B % from 25 to 55; Gradient time: 8 mM; Flow rate: 25 mL/min) to afford N-(2-((S)-2-((E)-4-(dimethylamino)-N-methylbut-2-enamido)propanamido)ethyl)-5-((Z)-(5-fluoro-2-oxoindolin-3-ylidene)methyl)-4-methyl-1H-pyrrole- 3-carboxamide (19 mg, 92% purity, 9% yield) as yellow solid. LCMS: $t_R$=1.205 min in 10-80 AB_2 min_220&254_Shimadzu.1 cm, MS (ESI) m/z=525.4 $[M+H]^+$. $^1H$ NMR (400 MHz, $CD_3OD-d_4$): δ=7.66-7.63 (m, 2H), 7.48 (d, J=8.4 Hz, 1H), 6.95-6.84 (m, 2H), 6.82-6.70 (m, 1H), 6.62-6.51 (m, 1H), 5.05-4.94 (m, 1H), 3.55-3.38 (m, 4H), 3.15 (d, J=6.0 Hz, 1H), 3.07 (s, 3H), 3.01-2.88 (m, 1H), 2.57 (s, 3H), 2.26 (s, 6H), 1.46-1.39 (m, 3H). Chiral SFC: $t_R$=3.370 min (Instrument column: Chiralpak AS-3 100×4.6 mm I.D., 3 um; Mobile phase: A: $CO_2$ B: ethanol (0.05% DEA), Gradient: from 5% to 40% of B in 4.5 min and hold 40% for 2.5 min, then 5% of B for 1 min; Flow rate: 2.8 mL/min, Column temperature: 40° C.; UV detection: 220 nm), ee %=100%. $[\alpha]_D^{20}$=−42.0 (c=0.10, MeOH).

Example 27

(2S)—N-[[(6S)-2-[(5-fluoro-2-oxo-indolin-3-ylidene)methyl]-3-methyl-4,5,6,7-tetrahydro-1H-indol-6-yl]methyl]-2-[methyl(prop-2-enoyl)amino]propanamide (Compound 27) and (2S)—N-[[(6R)-2-[(5-fluoro-2-oxo-indolin-3-ylidene)methyl]-3-methyl-4,5,6,7-tetrahydro-1H-indol-6-yl]methyl]-2-[methyl(prop-2-enoyl)amino]propanamide (Compound 28)

Scheme 30. Synthesis of compounds 27 and 28.

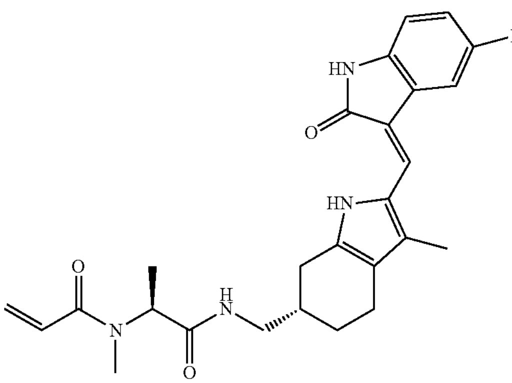

compound 27

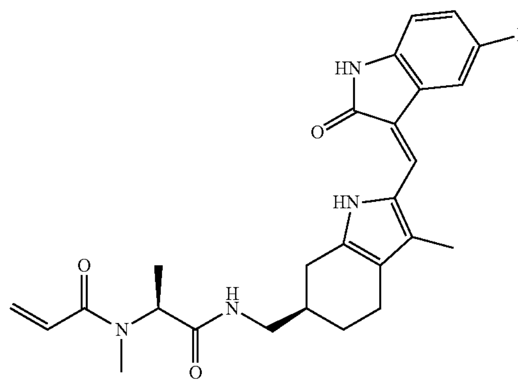

compound 28

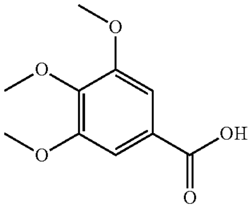

27-1

Na/$NH_3$

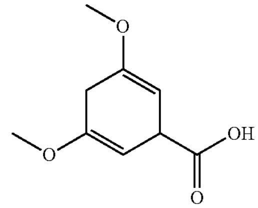

27-2

$LiAlH_4$

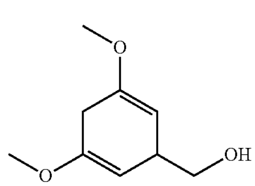

27-3

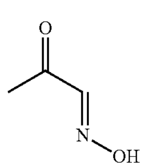

27-4

Zn, AcOH

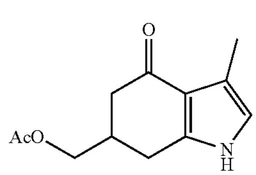

27-5

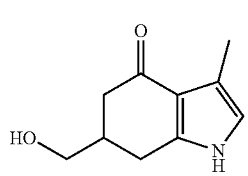

27-5A $NaBH_4$, iPrOH

80° C., overnight

-continued
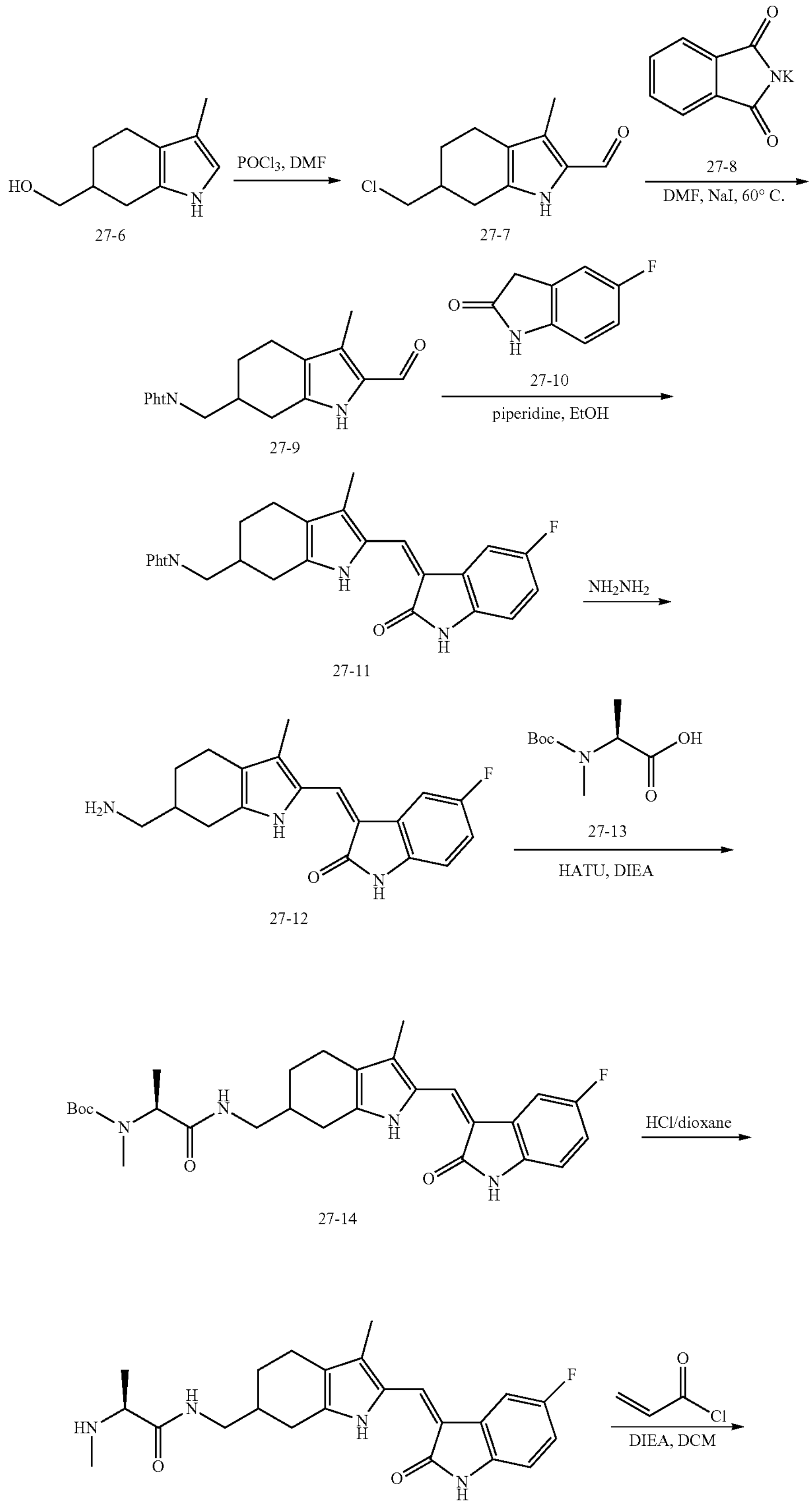
27-6
27-7
27-9
27-11
27-12
27-14
27-15

-continued

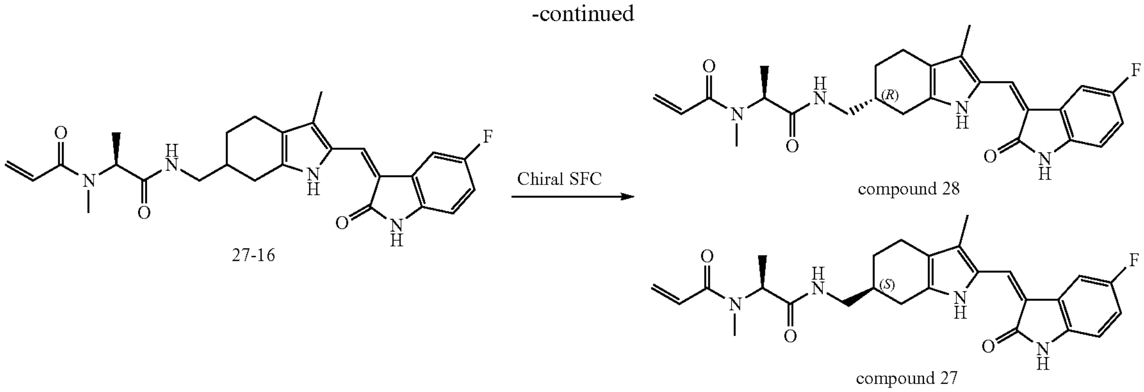

27-16 compound 28 compound 27

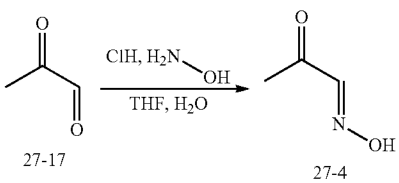

27-17

27-4

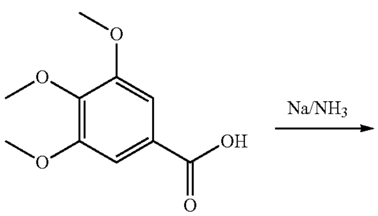

27-1

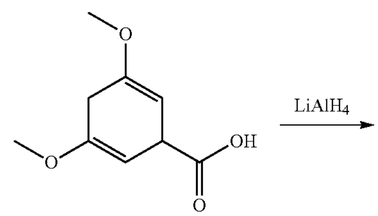

27-2

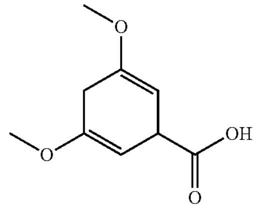

27-2

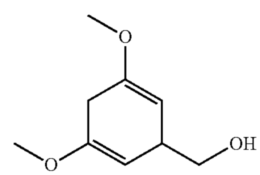

27-3

To a solution of 3,4,5-trimethoxybenzoic acid (25 g, 117.81 mmol) in MeOH (80 mL) and $NH_3$ (400 mL) was added Na (13.54 g, 0.589 mmol). The mixture was stirred at −78° C. for 3 hr. The mixture was quenched by addition of $NH_4Cl$ (10 g) at −60° C. and concentrated under reduced pressure to give a residue. The residue was dissolved in ice-water and solution was acidified with 2 M HCl until pH=4-5. The mixture was extracted with EtOAc (50 mL×3). The combined organic layers were washed with brine (50 mL), dried over $Na_2SO_4$, filtered and concentrated under reduced pressure to afford 3,5-dimethoxycyclohexa-2,5-diene-1-carboxylic acid (22 g, crude) as a white solid, which was used directly in the next step. $^1$H NMR (400 MHz, DMSO-$d_6$): δ=4.77 (d, J=3.6 Hz, 2H), 3.83-3.78 (m, 1H), 3.54-3.48 (m, 6H), 2.68 (d, J=7.2 Hz, 2H).

To a solution of 3,5-dimethoxycyclohexa-2,5-diene-1-carboxylic acid (22 g, 0.119 mmol) in THF (200 mL) was added $LiAlH_4$ (18.13 g, 0.478 mmol). The mixture was stirred at 0° C. for 2 hr. The mixture was quenched by addition of $H_2O$ (15 mL) at 25° C., 2 M NaOH (15 mL) and $H_2O$ (60 mL) successively. The resulting mixture was filtered, and the filtrate was concentrated under reduced pressure to afford (3,5-dimethoxycyclohexa-2,5-dien-1-yl) methanol (20 g, 118 mmol, 98% yield) as a colourless oil, which was used directly in the next step. $^1$H NMR (400 MHz, DMSO-$d_6$): δ=4.73-4.68 (m, 3H), 3.49 (s, 6H), 3.26 (t, J=6.0 Hz, 2H), 2.95 (m, J=3.2, 6.6 Hz, 1H), 2.69-2.63 (m, 2H).

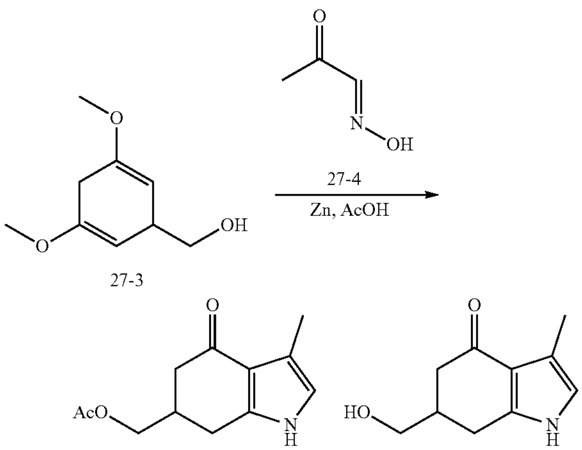

27-3

27-4

27-5

27-5A

To a solution of (3,5-dimethoxycyclohexa-2,5-dien-1-yl) methanol (8 g, 47.0 mmol) in AcOH (100 mL) and $H_2O$ (25 mL) was stirred at 100° C. for 15 min. Then remove from the heating bath and 2-oxopropanal oxime (4.91 g, 56.40 mmol) was added in portions over 15 mm with stirring. The mixture was heated to 50° C. and Zn (9.22 g, 141.01 mmol) was added in portions. The resulting mixture was 100° C. for 4 hr and then cooled to room temperature. The mixture was concentrated under reduced pressure to remove solvent. The residue was diluted with $H_2O$ (20 mL) and extracted with DCM (20 mL×3). The combined organic layers were dried $Na_2SO_4$, concentrated under reduced pressure to give a residue. After that the residue was purified by flash silica gel chromatography (ISCO®; 40 g SepaFlash® Silica Flash Column, Eluent of 0100% Ethylacetate/Petroleum ether gradient @ 80 mL/min) to afford (3-methyl-4-oxo-1,5,6,7-tetrahydroindol-6-yl)methyl acetate (800 mg, 3.62 mmol, 8% yield) and 6-(hydroxymethyl)-3-methyl-1,5,6,7-tetrahydroindol-4-one (2.5 g, 13.95 mmol, 30% yield) as yellow solid. $^1H$ NMR (400 MHz, DMSO-$d_6$): δ=11.00 (s, 1H), 6.47 (d, J=0.8 Hz, 1H), 4.07-3.98 (m, 2H), 2.83 (dd, J=4.0, 15.2 Hz, 1H), 2.59-2.53 (m, 1H), 2.49-2.42 (m, 1H), 2.35-2.21 (m, 2H), 2.13 (d, J=1.2 Hz, 3H), 2.04 (s, 3H). $^1H$ NMR (400 MHz, DMSO-$d_6$): δ=10.95 (s, 1H), 6.44 (d, J=0.8 Hz, 1H), 4.70-4.62 (m, 1H), 3.18 (d, J=5.2 Hz, 2H), 2.80 (dd, J=4.4, 15.8 Hz, 1H), 2.48-2.37 (m, 1H), 2.30-2.14 (m, 4H), 2.13 (d, J=1.2 Hz, 3H).

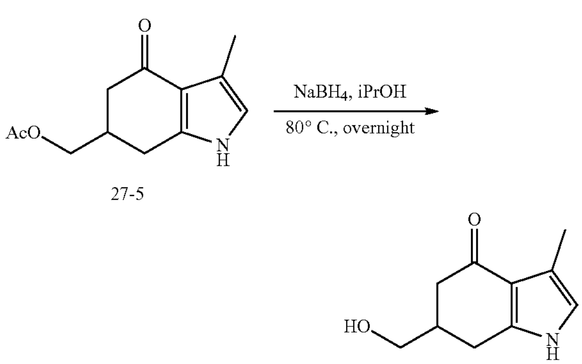

27-5

27-6

To a solution of 6-(hydroxymethyl)-3-methyl-1,5,6,7-tetrahydroindol-4-one (2.5 g, 13.95 mmol) in i-PrOH (50 mL) was added $NaBH_4$ (1.06 g, 27.90 mmol). The mixture was stirred at 80° C. for 12 hr. The mixture was quenched by addition of sat. $NH_4Cl$ (30 mL) at 20° C., and then extracted with EtOAc (30 mL×2). The combined organic layers were dried over $Na_2SO_4$, filtered and concentrated under reduced pressure to give a residue. After that the residue was purified by flash silica gel chromatography (ISCO®; 12 g SepaFlash® Silica Flash Column, Eluent of 0-70% Ethyl acetate/Petroleum ether gradient (4, 60 mL/min) to afford (3-methyl-4,5,6,7-tetrahydro-1H-indol-6-yl)methanol (1.3 g, 6.29 mmol, 35% yield, 80% purity) as a brown oil.

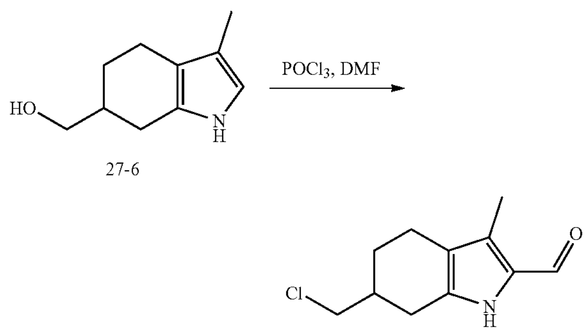

27-6

27-7

$POCl_3$ (557 mg, 3.63 mmol) was added dropwise to DMF (664 mg, 9.08 mmol) at 0° C. The mixture was stirred at 0° C. for 1 hour. Then a solution of (3-methyl-4,5,6,7-tetrahydro-1H-indol-6-yl)methanol (600 mg, 3.63 mmol) in DCE (10 mL) was added thereto at 0° C. dropwise. Then the mixture was stirred at 85° C. for another 4 hours. The mixture was cooled to 25° C. and quenched with sat. aq. NaOAc (20 mL), and stirred at 90° C. for 4 hours. The mixture was concentrated under reduced pressure and quenched with ice water and extracted with EtOAc (50 mL×3). The combined organic layers were washed with brine (50 mL), dried over $Na_2SO_4$, filtered and concentrated under reduced pressure to give a residue.

After that the residue was purified by flash silica gel chromatography (ISCO®; 4 g SepaFlash® Silica Flash Column, Eluent of 0-50% Ethyl acetate/Petroleum ether gradient @ 40 mL/min) to afford 6-(chloromethyl)-3-methyl-4,5,6,7-tetrahydro-1H-indole-2-carbaldehyde (300 mg, 1.42 mmol, 39% yield) as a brown solid.

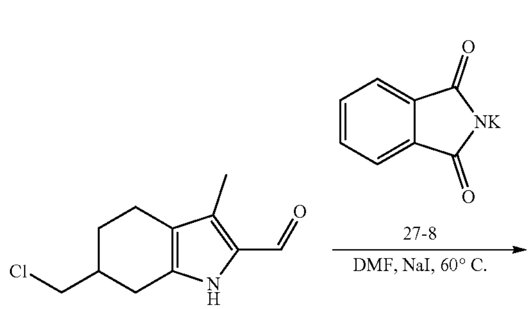

27-8

27-7

-continued

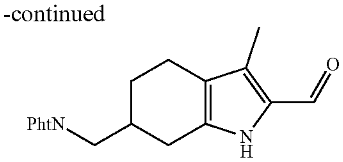

27-9

To a solution of 6-(chloromethyl)-3-methyl-4,5,6,7-tetrahydro-1H-indole-2-carbaldehyde (300 mg, 1.42 mmol) in DMF (5 mL) was added (1,3-dioxoisoindolin-2-yl)potassium (315 mg, 1.70 mmol) and NaI (425 mg, 2.83 mmol). The mixture was stirred at 90° C. for 12 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0-30% Ethyl acetate/Petroleum ether gradient @ 40 mL/min) to afford 6-[(1,3-dioxoisoindolin-2-yl)methyl]-3-methyl-4,5,6,7-tetrahydro-1H-indole-2-carbaldehyde (185 mg, 0.574 mmol, 40% yield) as a yellow solid.

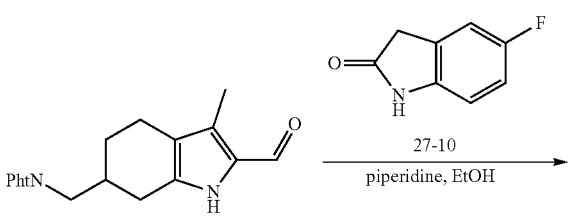

27-9

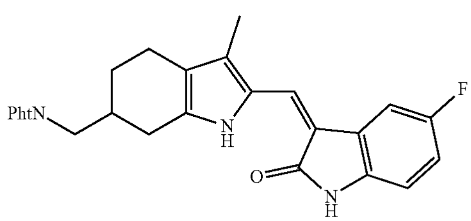

27-11

To a solution of 6-[(1,3-dioxoisoindolin-2-yl)methyl]-3-methyl-4,5,6,7-tetrahydro-1H-indole-2-carbaldehyde (185 mg, 0.574 mmol) in EtOH (5 mL) was added piperidine (5 mg, 0.057 mmol) and 5-fluoroindolin-2-one (104 mg, 0.689 mmol). The mixture was stirred at 80° C. for 12 hr. The mixture was stirred at 0° C. for 0.5 hr and the mixture was filtered, dried to afford 2-[[2-[(5-fluoro-2-oxo-indolin-3-ylidene)methyl]-3-methyl-4,5,6,7-tetrahydro-1H-indol-6-yl]methyl]isoindoline-1,3-dione (230 mg, 0.454 mmol, 79% yield, 90% purity) as a yellow solid, which was used directly in the next step.

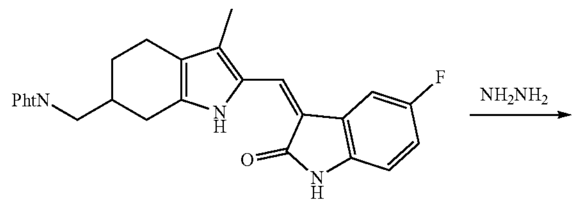

27-11

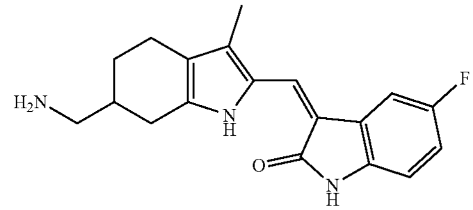

27-12

To a solution of 2-[[2-[(5-fluoro-2-oxo-indolin-3-ylidene)methyl]-3-methyl-4,5,6,7-tetrahydro-1H-indol-6-yl]methyl]isoindoline-1,3-dione (230 mg, 0.505 mmol) in EtOH (5 mL) was added $NH_2NH_2$ (34 mg, 1.01 mmol). The mixture was stirred at 25° C. for 12 hr. The mixture was filtered and the filtrate was concentrated under reduced pressure to afford 3-[[6-(aminomethyl)-3-methyl-4,5,6,7-tetrahydro-1H-indol-2-yl]methylene]-5-fluoro-indolin-2-one (150 mg, 0.461 mmol, 91% yield) as a yellow solid, which was used directly in the next step.

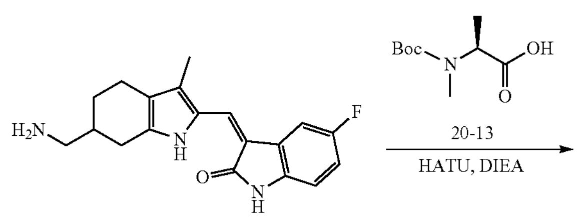

27-12

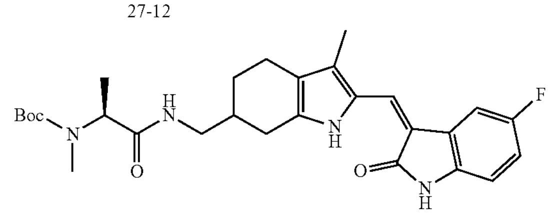

27-14

To a solution of 3-[[6-(aminomethyl)-3-methyl-4,5,6,7-tetrahydro-1H-indol-2-yl]methylene]-5-fluoro-indolin-2-one (120 mg, 0.369 mmol) in DMF (5 mL) was added HATU (168 mg, 0.443 mmol), DIEA (48 mg, 0.369 mmol) and (2S)-2-[tert-butoxycarbonyl(methyl)amino]propanoic acid (83 mg, 0.406 mmol). The mixture was stirred at 25° C. for 1 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0-50% Ethyl acetate/Petroleum ether gradient @ 40 mL/min) to afford tert-butyl N-[(1S)-2-[[2-

[(5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-carbamate (150 mg, 0.294 mmol, 80% yield) as a yellow solid.

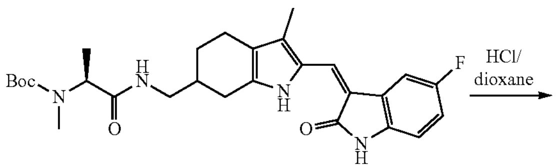

27-14

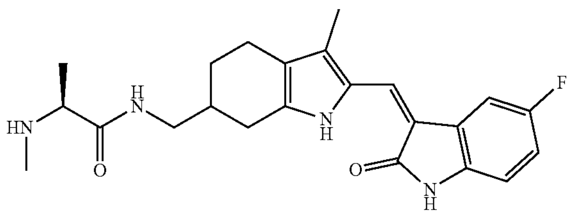

27-15

A solution of tert-butyl N-[(1S)-2-[[2-[5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-carbamate (150 mg, 0.294 mmol) in HCl/dioxane (4 M, 10 mL) was stirred at 25° C. for 0.5 hr. The mixture was concentrated under reduced pressure to afford (2S)—N-[[2-[(5-fluoro-2-oxo-indolin-3-ylidene)methyl]-3-methyl-4,5,6,7-tetrahydro-1H-indol-6-yl]methyl]-2-(methylamino)propanamide (220 mg, 0.29 mmol, 99% yield, 59% purity, HCl salt) as a yellow solid, which was used directly in the next step.

To a solution of (2S)—N-[[2-[(5-fluoro-2-oxo-indolin-3-ylidene)methyl]-3-methyl-4,5,6,7-tetrahydro-1H-indol-6-yl]methyl]-2-(methylamino)propanamide (220 mg, 0.290 mmol, HCl salt) in DCM (5 mL) was added DIEA (114 mg, 0.87 mmol) and prop-2-enoyl chloride (26 mg, 0.29 mmol). The mixture was stirred at 0° C. for 0.5 hr. The mixture was quenched by addition of $H_2O$ (50 mL) at 25° C., and then diluted with $H_2O$ (50 mL) and extracted with DCM (50 mL×3). The combined organic layers were washed with brine (50 mL), dried over $Na_2SO_4$, filtered and concentrated under reduced pressure to give a residue. After that the residue was purified by flash silica gel chromatography (ISCO®; 12 g SepaFlash® Silica Flash Column, Eluent of 0-10% Dichloromethane: Methanol @ 40 mL/min) to afford (2S)—N-[[2-[(5-fluoro-2-oxo-indolin-3-ylidene)methyl]-3-methyl-4,5,6,7-tetrahydro-1H-indol-6-yl]methyl]-2-[methyl(prop-2-enoyl)amino]propanamide (100 mg, 0.215 mmol, 74% yield) as a red solid.

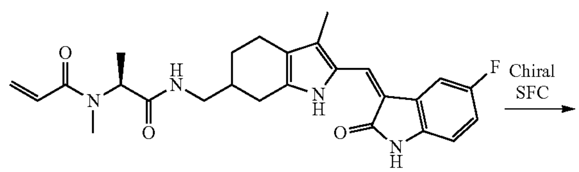

27-16

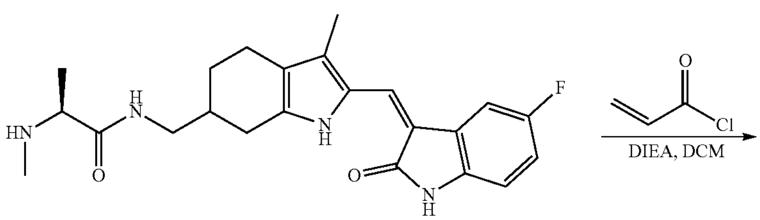

27-15

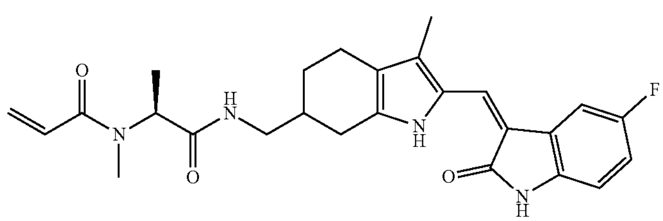

27-16

-continued

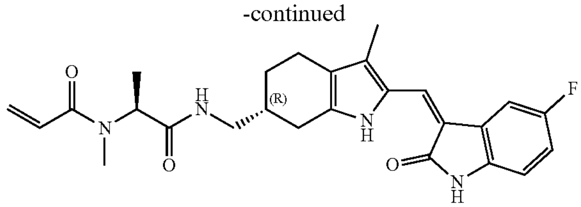

compound 28

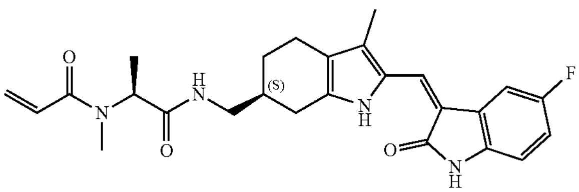

compound 27

The racemic product (100 mg) was purified by chiral SFC (Column: DAICEL CHIRALCEL OD (250 mm*30 mm, 10 um); Condition: 0.1% $NH_3{\cdot}H_2O$ ETOH) to give desired products as a yellow solid, which were further separated by prep-HPLC (Column: Phenomenex luna C18 100*40 mm*3 um; Condition: water (0.225% FA)-ACN) to afford (2S)—N-[[(6R)-2-[(5-fluoro-2-oxo-indolin-3-ylidene)methyl]-3-methyl-4,5,6,7-tetrahydro-1H-indol-6-yl]methyl]-2-[methyl(prop-2-enoyl)amino]propanamide (15.2 mg, 0.033 mmol, 16% yield, 100% purity) and (2S)—N-[[(6S)-2-[(5-fluoro-2-oxo-indolin-3-ylidene)methyl]-3-methyl- 4,5,6,7-tetrahydro-1H-indol-6-yl]methyl]-2-[methyl(prop-2-enoyl) amino]propanamide (15.7 mg, 0.034 mmol, 17% yield, 100% purity) as yellow solid. LCMS: $t_R$=2.319 min in 10-80AB_4 min_220 &254_Shimadzu.1 cm, MS (ESI) m/z=465.3 $[M+H]^+$. $^1$H NMR (400 MHz, DMSO-$d_6$): δ=13.35 (s, 1H), 10.77 (s, 1H), 8.35-7.81 (m, 1H), 7.72-7.65 (m, 2H), 6.90-6.74 (m, 3H), 6.19-6.07 (m, 1H), 5.75-5.65 (m, 1H), 5.06-4.59 (m, 1H), 3.16-3.07 (m, 2H), 3.00-2.80 (m, 3H), 2.75 (dd, J=4.8, 17.2 Hz, 1H), 2.40-2.32 (m, 2H), 2.23 (s, 3H), 1.99-1.81 (m, 2H), 1.47-1.15 (m, 5H). Chiral SFC: $t_R$=4.678 min (Column: Chiral MD-3 100×4.6 mm, I.D., 3 um, Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min, Column temperature: 40° C.), ee %=98.78%. LCMS: $t_R$=2.322 min in 10-80AB_4 min_220 &254_Shimadzu.1 cm, MS (ESI) m/z=465.3 $[M+H]^+$. $^1$H NMR (400 MHz, DMSO-$d_6$): δ=13.35 (s, 1H), 10.76 (s, 1H), 8.18-7.90 (m, 1H), 7.72-7.63 (m, 2H), 6.89-6.68 (m, 3H), 6.22-6.06 (m, 1H), 5.80-5.62 (m, 1H), 5.07-4.62 (m, 1H), 3.24-3.05 (m, 2H), 2.98-2.79 (m, 3H), 2.78-2.69 (m, 1H), 2.40-2.32 (m, 2H), 2.23 (s, 3H), 2.01-1.82 (m, 2H), 1.51-1.11 (m, 5H). Chiral SFC: $t_R$=5.030 min (Column: Chiral MD-3 100×4.6 mm, I.D., 3 um, Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min, Column temperature: 40° C.), ee %=100%.

Example 28

(E)-4-(dimethylamino)-N-[(1S)-2-[[(6R)-2-[(Z)-(5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-but-2-enamide (Compound 29) and (E)-4-(dimethylamino)-N-[(1S)-2-[[(6R)-2-[(Z)-(5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-but-2-enamide (Compound 30)

Scheme 31. Synthesis of compounds 29 and 30.

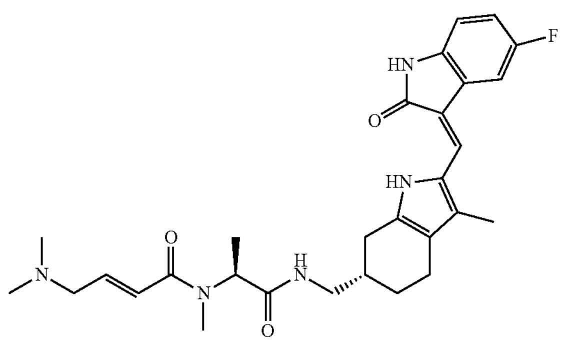

compound 29

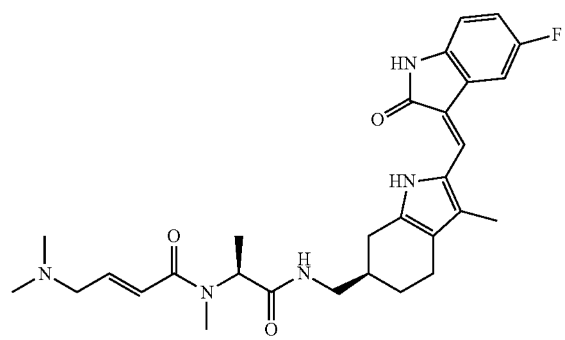

compound 30

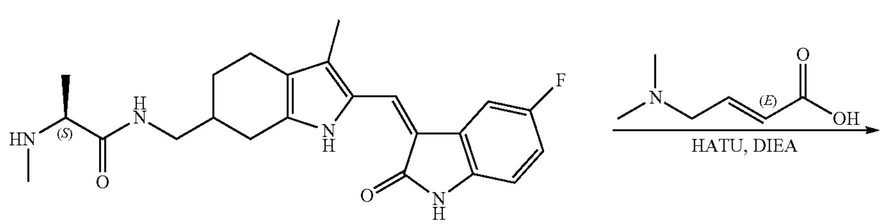

27-15

-continued

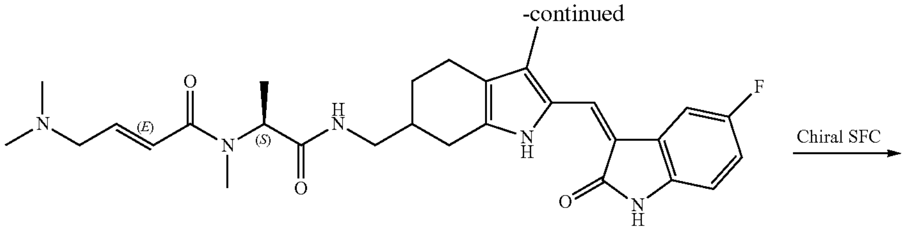

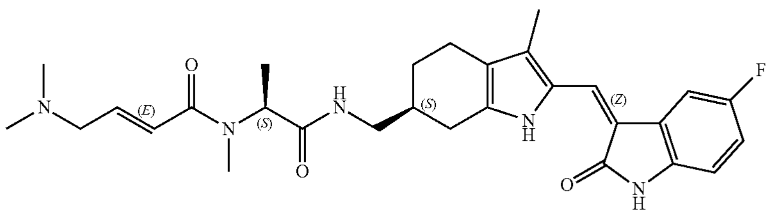

compound 29

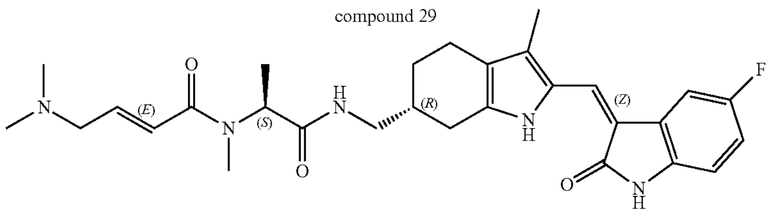

compound 30

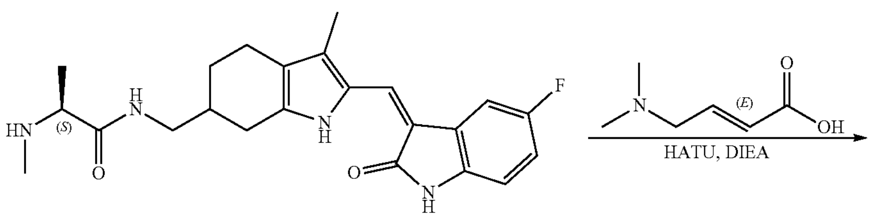

27-15

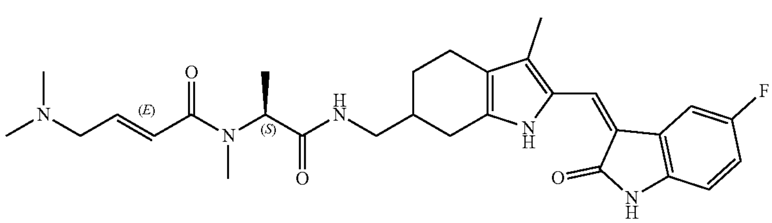

Synthesis of (2S)—N-[[(6S)-2-[(5-fluoro-2-oxo-indolin-3-ylidene)methyl]-3-methyl-4,5,6,7-tetrahydro-1H-indol-6-yl]methyl]-2-(methylamino)propanamide (27-15) is shown in Example 20. To a solution of (2S)—N-[[(6S)-2-[(5-fluoro-2-oxo-indolin-3-ylidene)methyl]-3-methyl-4,5,6,7-tetrahydro-1H-indol-6-yl]methyl]-2-(methylamino)propanamide (27-15, 280 mg, 0.501 mmol, HCl salt) and (E)-4-(dimethylamino)but-2-enoic acid (71 mg, 0.551 mmol) in DMF (5 mL) was added HATU (229 mg, 0.601 mmol) and DIEA (194 mg, 1.50 mmol). The mixture was stirred at 25° C. for 2 hr. The mixture was quenched by addition of $H_2O$ (50 mL) at 25° C., and then diluted with $H_2O$ (50 mL) and extracted with EtOAc (50 mL×3). The combined organic layers were washed with brine (50 mL), dried over $Na_2SO_4$, filtered and concentrated under reduced pressure to give a residue. After that the residue was purified by prep-HPLC (water (0.05% $NH_3 \cdot H_2O$+10 mM $NH_4HCO_3$)-ACN) to afford (E)-4-(dimethylamino)-N-((2S)-1-4(24(Z)-(5-fluoro-2-oxoindolin-3-ylidene)methyl)-3-methyl-4,5,6,7-tetrahydro-1H-indol-6-yl)methy 1)amino)-1-oxopropan-2-yl)-N-methylbut-2-enamide (40 mg, 0.073 mmol, 15% yield, 95% purity) as a yellow solid.

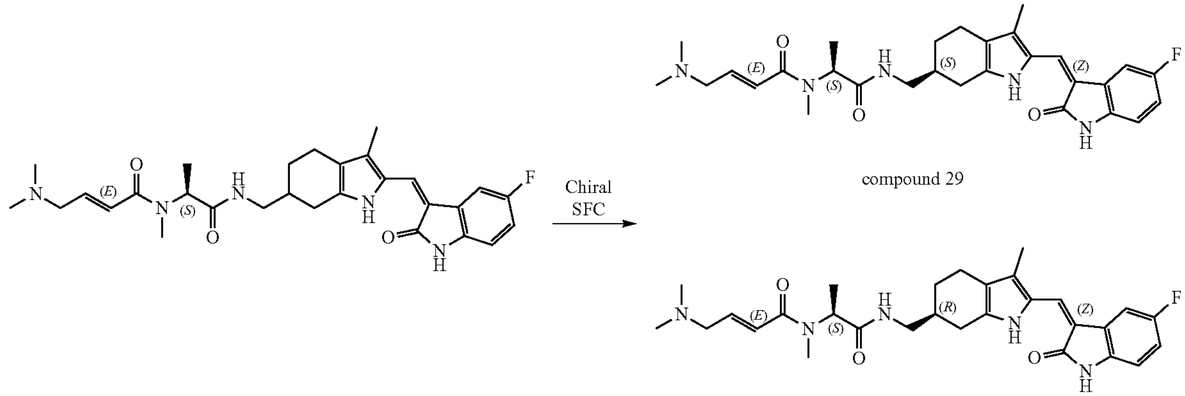

compound 29 compound 30

The racemic product (40 mg) was separated by chiral SFC (Column:Chiralcel OD-3 100×4.6 mm I.D., 3 um, Mobile phase: A: $CO_2$ B: ethanol (0.05% DEA), Gradient: from 5% to 40% of B in 4.5 min and hold 40% for 2.5 min, then 5% of B for 1 min, Flow rate: 2.8 mL/min) to afford (E)-4-(dimethylamino)-N-[(1S)-2-[[(6S)-2-[(Z)-(5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-but-2-enamide (9.6 mg, 0.018 mmol, 23% yield, 97.5% purity) as a yellow solid, and (E)-4-(dimethylamino)-N-[(1S)-2-[[(6R)-2-[(Z)-(5-fluoro-2-oxo-indolin-3-ylidene)methyl]-3-methyl-4,5,6,7-tetrahydro-1H-indol-6-yl]methylamino]-1-methyl-2-oxo-ethyl]-N-methyl-but-2-enamide (12.6 mg, 0.023 mmol, 31% yield, 96.9% purity) as a yellow solid. LCMS: $t_R$=1.818 min in 10-80AB_4 min_220 &254_Shimadzu.1 cm, MS (ESI) m/z=522.3 [M+H]t $^1$H NMR (400 MHz, methanol-$d_4$): δ=7.50 (s, 1H), 7.33 (dd, J=2.0, 9.2 Hz, 1H), 6.89-6.77 (m, 3H), 6.69-6.59 (m, 1H), 5.12-4.90 (m, 1H), 3.27-3.19 (m, 2H), 3.12-2.95 (m, 3H), 2.79 (dd, J=4.8, 17.2 Hz, 1H), 2.59 (d, J=15.6 Hz, 1H), 2.42-2.27 (m, 8H), 2.23 (s, 3H), 2.15-1.95 (m, 3H), 1.46-1.39 (m, 3H), 1.30 (s, 2H). Chiral SFC: $t_R$=4.355 min (Column: Chiralpak OD-3 100×4.6 mm I.D., 3 um, Mobile phase: A: $CO_2$ B: methanol (0.05% DEA), Gradient: from 5% to 40% of B in 4.5 min and hold 40% for 2.5 min, then 5% of B for 1 min, Flow rate: 2.8 mL/min, Column temperature: 40° C.), ee %=100%, $[\alpha]_D^{20}$=−138 (c=1.0, MeOH). LCMS: $t_R$=1.827 min in 10-80AB4 min_220 &254_Shimadzu.1 cm, MS (ESI) m/z=522.3 [M+H]t $^1$H NMR (400 MHz, methanol-$d_4$): δ=7.50 (s, 1H), 7.33 (dd, J=2.0, 9.2 Hz, 1H), 6.89-6.77 (m, 3H), 6.69-6.59 (m, 1H), 5.12-4.90 (m, 1H), 3.27-3.19 (m, 2H), 3.12-2.95 (m, 3H), 2.79 (dd, J=4, 8, 17.2 Hz, 1H), 2.59 (d, J=15.6 Hz, 1H), 2.42-2.27 (m, 8H), 2.23 (s, 3H), 2.15-1.95 (m, 3H), 1.46-1.39 (m, 3H), 1.30 (s, 2H). Chiral SFC: $t_R$=4.570 min (Column: Chiralpak OD-3 100×4.6 mm I.D., 3 um Mobile phase: A: $CO_2$ B: methanol (0.05% DEA), Gradient: from 5% to 40% of B in 4.5 min and hold 40% for 2.5 min, then 5% of B for 1 min, Flow rate: 2.8 mL/min, Column temperature: 40° C.), ee %=95.16%. $[\alpha]1)^{20}$=37 (c=1.0, MeOH).

Example 29

Characterization of the Kinase Inhibition Properties of the Disclosed Compounds Compounds' inhibition of recombinant kinases (FGR, FLT3, FMS, KIT, or RON) was measured using Caliper mobility shift assay, which is based on the difference in capillary electrophoresis mobility of a fluorescent-tagged peptide as a result of a phosphorylation by the kinase under study. Reactions were started by the addition of various concentrations of a compound (originally in DMSO solution) to a kinase solution in assay buffer followed by addition of a mixture of ATP and a fluorescent-tagged peptide substrate in assay buffer. Concentrations of the enzyme, ATP and the peptide were pre-optimized so that 15% substrate conversion to ensure initial velocity measurements. After incubation for 3 hours at room temperature, the kinase reaction was quenched by the addition of a concentrated EDTA solution before analysis on a LabChip EZ Reader II to yield percentage inhibition by comparing to the DMSO control.

Table 2 below summarizes the assay conditions for the characterization of the kinase inhibition properties of the disclosed compounds.

TABLE 2

Assay conditions to characterization difference kinase inhibition properties.

| Kinase | Enzyme Preparation (Vendor; Cat No.; Lot No.) | [Enzyme] (nM) | ATP Concentration (μM) | Assay Incubation Time (hr) |
|---|---|---|---|---|
| FMS | Invitrogen; PV3249;662393N | 0.25 | 100 | 3 |
| KIT | BPS; 40250;81027 | 0.9 | 400 | 17 |
| FLT-3 | ThermoFisher; PV3182;884910 | 0.1 | 95 | 3 |
| FGR | BPS;4022;110419 | 0.3 | 50 | 3 |
| RON | Invitrogen; PV4314;36889 | 0.4 | 20 | 3 |

TABLE 3 below summarizes the kinase inhibition properties of the disclosed compounds

| Compounds | FGR inhibition | FLT3 inhibition | FMS inhibition | KIT inhibition | RON inhibition |
|---|---|---|---|---|---|
| Compound 1 | ++ | +++ | +++ | +++ | + |
| Compound 2 | N/A | +++ | N/A | N/A | N/A |
| Compound 3 | N/A | +++ | N/A | +++ | N/A |
| Compound 4 | N/A | +++ | N/A | ++ | N/A |

TABLE 3-continued

| below summarizes the kinase inhibition properties of the disclosed compounds | | | | | |
|---|---|---|---|---|---|
| Compounds | FGR inhibition | FLT3 inhibition | FMS inhibition | KIT inhibition | RON inhibition |
| Compound 5 | N/A | +++ | N/A | ++ | N/A |
| Compound 6 | N/A | +++ | N/A | N/A | N/A |
| Compound 7 | N/A | +++ | N/A | N/A | N/A |
| Compound 8 | N/A | +++ | N/A | N/A | N/A |
| Compound 9 | N/A | +++ | N/A | +++ | N/A |
| Compound 10 | N/A | ++ | N/A | ++ | N/A |
| Compound 11 | N/A | +++ | N/A | N/A | N/A |
| Compound 12 | N/A | +++ | N/A | +++ | N/A |
| Compound 13 | N/A | +++ | N/A | +++ | N/A |
| Compound 14 | N/A | +++ | N/A | N/A | N/A |
| Compound 15 | N/A | +++ | N/A | N/A | N/A |
| Compound 16 | N/A | ++ | N/A | N/A | N/A |
| Compound 17 | N/A | +++ | N/A | +++ | N/A |
| Compound 18 | N/A | +++ | N/A | +++ | N/A |
| Compound 19 | N/A | +++ | N/A | N/A | N/A |
| Compound 20 | N/A | +++ | N/A | N/A | N/A |
| Compound 21 | N/A | +++ | N/A | N/A | N/A |
| Compound 22 | N/A | +++ | N/A | N/A | N/A |
| Compound 23 | N/A | +++ | N/A | N/A | N/A |
| Compound 24 | N/A | ++ | N/A | N/A | N/A |
| Compound 25 | N/A | +++ | N/A | N/A | N/A |
| Compound 26 | + | +++ | +++ | +++ | + |
| Compound 27 | N/A | +++ | N/A | N/A | N/A |
| Compound 28 | N/A | +++ | N/A | N/A | N/A |
| Compound 29 | N/A | +++ | N/A | N/A | N/A |
| Compound 30 | N/A | +++ | N/A | N/A | N/A |
| Compound 31 | N/A | +++ | N/A | N/A | N/A |

+++: less than 10 nmol/L
++: more than or equal to 10 nmol/L and less than 100 nmol/L
+: more than or equal to 100 nmol/L and less than 1000 nmol/L
−: more than or equal to 1000 nmol/L
N/A: not available Cell viability assay was performed based on the following brief procedures. Cells were plated at the density of 5K/well with volume of 1804 in 96-well white plate and clear bottom plates. 20 μL of veh. or compound was added at proper concentration to the well. The final volume is 200 μL, with final conc. of DMSO=0.1%, 11 points, triplicates. The cells were then treated at 37° C. in the TC incubator for 72 hr. Equal volume (200 μL) of CellTiter-Glo reagent (Promega) was added to the well and protect from light at room temperature for 15 min. The chemiluminicent was measured with EnSight (Perkin Elmer). GraphPad Prism non-linear regression, Log[inhibitor] response with four parameters were used to calculate $GI_{50}$. Table 4 below shows the FLT3 cell-based assay results.

TABLE 4

| The tyrosine kinase inhibitor compounds in cell viability assays in the present disclosure. | | | |
|---|---|---|---|
| Compounds | MV4-11 $GI_{50}$ | Kasumi-1 $GI_{50}$ (nM) | THP-1 $GI_{50}$ |
| Compound 1 | +++ | + | − |
| Compound 2 | ++ | + | − |
| Compound 3 | ++ | − | − |
| Compound 4 | +++ | + | + |
| Compound 5 | +++ | − | − |
| Compound 6 | +++ | +++ | ++ |
| Compound 7 | +++ | +++ | + |
| Compound 8 | +++ | + | − |
| Compound 9 | +++ | +++ | − |
| Compound 10 | +++ | ++ | − |
| Compound 11 | +++ | +++ | − |
| Compound 12 | +++ | +++ | − |
| Compound 13 | +++ | +++ | − |

TABLE 4-continued

| The tyrosine kinase inhibitor compounds in cell viability assays in the present disclosure. | | | |
|---|---|---|---|
| Compounds | MV4-11 $GI_{50}$ | Kasumi-1 $GI_{50}$ (nM) | THP-1 $GI_{50}$ |
| Compound 17 | +++ | +++ | − |
| Compound 18 | +++ | +++ | − |
| Compound 23 | +++ | N/A | − |
| Compound 24 | ++ | N/A | = |
| Compound 25 | +++ | N/A | − |
| Compound 26 | +++ | N/A | − |
| Compound 27 | +++ | N/A | − |
| Compound 28 | +++ | N/A | − |
| Compound 29 | +++ | N/A | − |
| Compound 30 | +++ | N/A | − |

+++: less than 10 nmol/L
++: more than or equal to 10 nmol/L and less than 100 nmol/L
+: more than or equal to 100 nmol/L and less than 1000 nmol/L
−: more than or equal to 1000 nmol/L
N/A: not available Those skilled in the art will recognize, or be able to ascertain, using no more than routine experimentation, numerous equivalents to the specific composition and procedures described herein. Such equivalents are considered to be within the scope of this disclosure, and are covered by the following claims.

What is claimed is:

1. A compound according to Formula (IV)

Formula (IV)

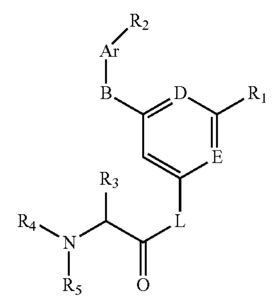

or an optically pure stereoisomer, pharmaceutically acceptable salt, or solvate thereof, wherein B is $—NR_6—$;

D is N;

E is N;

L is $—O(CH_2)_{1-5}O—$, $—O(CH_2)_{1-5}NR_6—$, $—NR_6(CH_2)_{1-5}NR_6—$, $—CONR_6(CH_2)_{1-5}NR_6—$, $—NR_6CO(CH_2)_{1-5}NR_6—$, $(CH_2)_{1-5}NR_6—$, $—(CH_2)_{1-5}O—$, $—(CH_2)_{1-5}OCO—$, $—(CH_2)_{1-5}CONR_6—$,

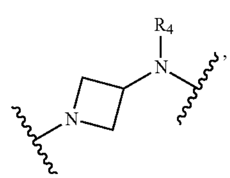, 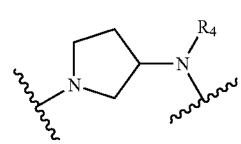, or

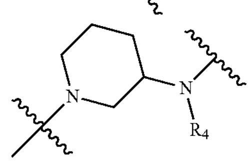, each of which is optionally substituted by one, two, three, or four $R_7$;

Ar is selected from the group consisting of

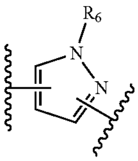

and

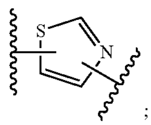

;

$R_1$ is H, F, Cl, Br, OH, $N_3$, $NO_2$, $CF_3$, CN, methyl, ethyl, propyl, isopropyl, or $-G-Ar_1$, wherein G is —CO—, —COO—, —$CONR_6$—, —$NR_6$—, —$(CH_2)_{1-5}$—, —O—, —OPO—, —$OPO_2$—, —S—, —SO—, or —$SO_2$—, $Ar_1$ is phenyl,

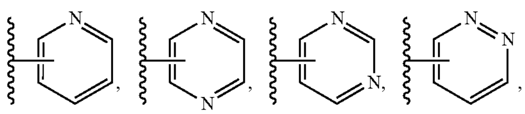

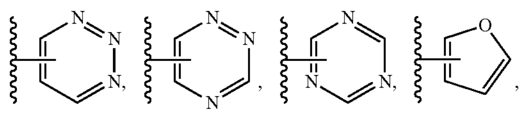

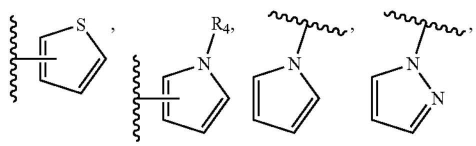

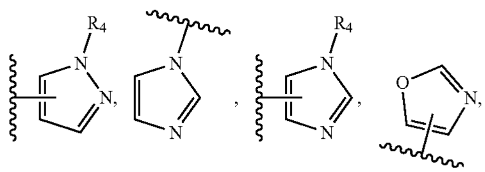

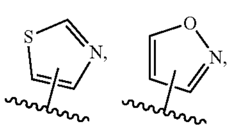

each of which is optionally substituted by F, Br, Cl, $CF_3$, CN, $N_3$, $NH_2$, $NO_2$, OH, $OCH_3$, methyl, $CH_2CN$, ethyl, propyl, isopropyl, or cyclopropyl;

$R_2$ is selected from the group consisting of H, F, Br, Cl, $CF_3$, CN, $N_3$, $NH_2$, $NO_2$, OH, $OCH_3$, methyl, ethyl, propyl, isopropyl,

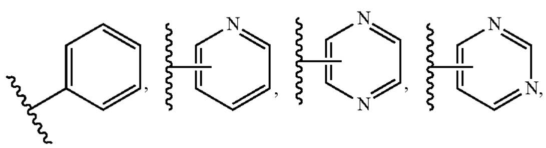

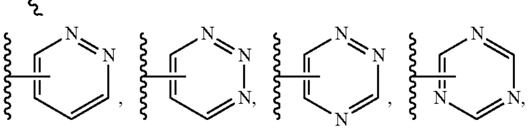

-continued

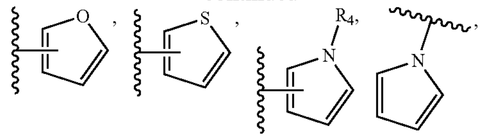

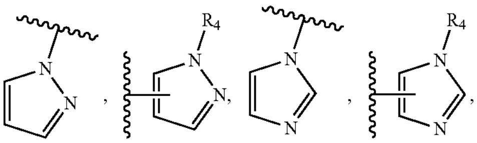

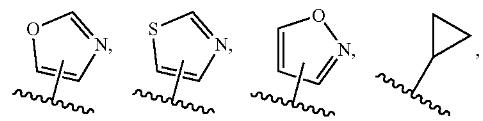

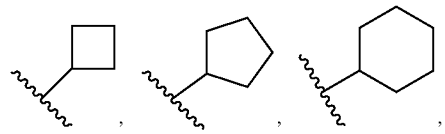

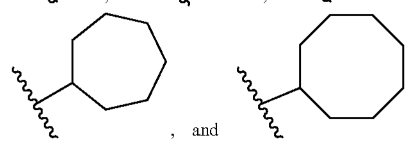

each of which is optionally substituted by one, two, three, or four $R_7$;

$R_3$ is H, methyl, ethyl, propyl, isopropyl, butyl, isobutyl, or tert-butyl, each of which can be substituted by one, two, three, or four $R_7$;

$R_4$ is selected from the group consisting of H, methyl, ethyl, propyl, and isopropyl;

or $R_3$ and $R_4$ together form

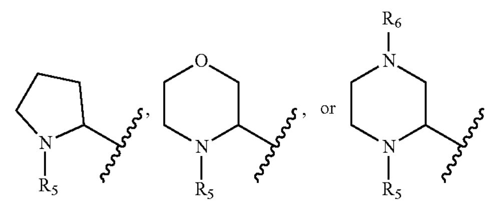

$R_5$ is selected from the group consisting of $CO(CH_2)_{0-5}CH_3$, $CONR_6$ $(CH_2)_{0-5}CH_3$, COO $(CH_2)_{0-5}CH_3$, $SO_2$ $(CH_2)_{0-5}CH_3$, $CO(CH_2)_{0-5}CH{=}CH_2$, $CONR_6$ $(CH_2)_{0-5}CH{=}CH_2$, COO $(CH_2)_{0-5}CH{=}CH_2$, $SO_2$ $(CH_2)_{0-5}CH{=}CH_2$, $CO(CH_2)_{0-5}CH{=}CHCH_3$, COO $(CH_2)_{0-5}CH{=}CHCH_3$, $CONR_6$ $(CH_2)_{0-5}CH{=}CHCH_3$, $SO_2$ $(CH_2)_{0-5}CH{=}CHCH_3$, $CO(CH_2)_{0-5}C{\equiv}CH$, COO $(CH_2)_{0-5}C{\equiv}CH$, $CONR_6(CH_2)_{0-5}C{\equiv}CH$, $SO_2$ $(CH_2)_{0-5}C{\equiv}CH$, $CO(CH_2)_{0-5}C{\equiv}CCH_3$, COO $(CH_2)_{0-5}CCCH_3$, $CONR_6$ $(CH_2)_{0-5}CCCH_3$, and $SO_2$ $(CH_2)_{0-5}C{=}CCH_3$, each of which is optionally substituted by one, two, three, or four $R_7$;

each $R_6$ is H; and each $R_7$ is independently H, methyl, ethyl, propyl, isopropyl, cyclopropyl, cyclobutyl, F, Br, Cl, $CF_3$, $NO_2$, OH, $OCH_3$, CN, or amino group unsubstituted or substituted with methyl, ethyl, or propyl.

2. The compound of claim 1, wherein $R_5$ is selected from the group consisting of

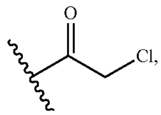, 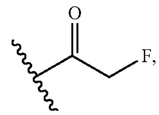, 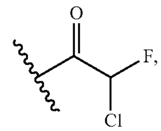,

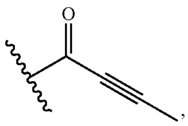, 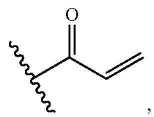, 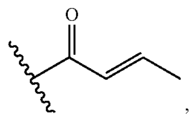,

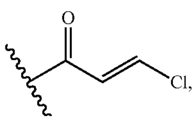, 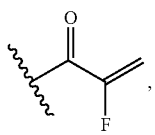, 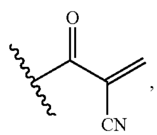, and

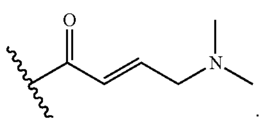.

3. The compound of claim 1, wherein the compound exhibits covalent inhibition of macrophage colony-stimulating factor 1 receptor (FMS), mast/stem cell growth factor receptor Kit (KIT), FMS like tyrosine kinase 3 (FLT-3), feline Gardner-Rasheed sarcoma viral oncogene homolog (FGR), or macrophage-stimulating protein receptor (RON).

4. A pharmaceutical formulation, comprising the compound according to claim 1 and a pharmaceutically acceptable carrier.

5. A method for treating a myeloid cancer in a subject comprising administering the compound according to claim 1.

6. The method of claim 5, wherein the myeloid cancer is selected from Acute Myeloid Leukemia (AML), Chronic Myelogenous Leukemia (CML), Myelodysplasia/Myelodysplastic Syndromes (MDS), Multiple Myeloma (MM), and Chronic Myeloproliferative Disorders.

7. The method of claim 5, further comprising administering a chemotherapeutic agent.

8. The method of claim 7, wherein the compound is administered prior to, simultaneously with or following the administration of the chemotherapeutic agent.

9. A method of inhibiting FMS, KIT, FLT-3, FGR, or RON activity comprising contacting a cell with the compound according to claim 1.

10. The method of claim 9, wherein the cell is a myeloid cancer cell.

11. The method of claim 10, wherein the myeloid cancer cell is selected from Acute Myeloid Leukemia (AML), Chronic Myelogenous Leukemia (CML), Myelodysplasia/Myelodysplastic Syndromes (MDS), Multiple Myeloma (MM), and Chronic Myeloproliferative Disorder cells.

12. The compound of claim 1, wherein the compound is selected from the group consisting of

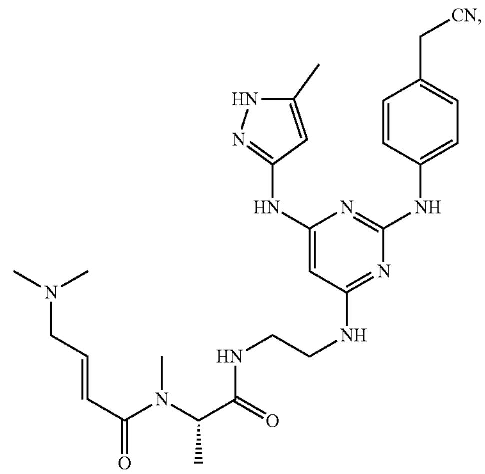,

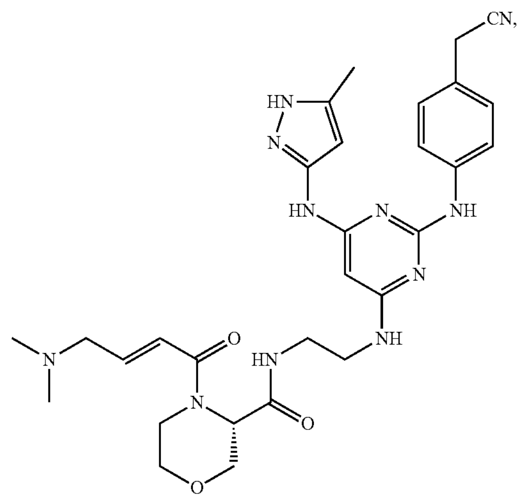,

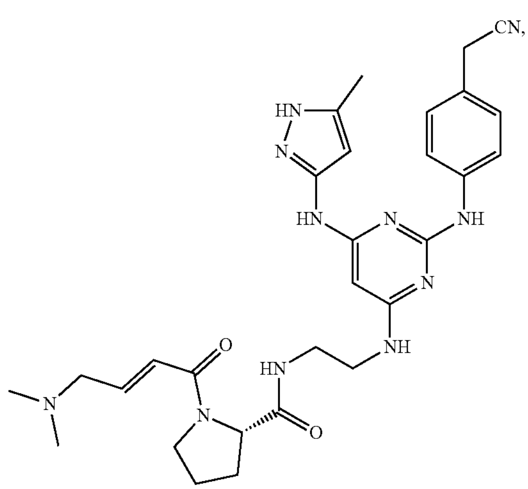,

-continued
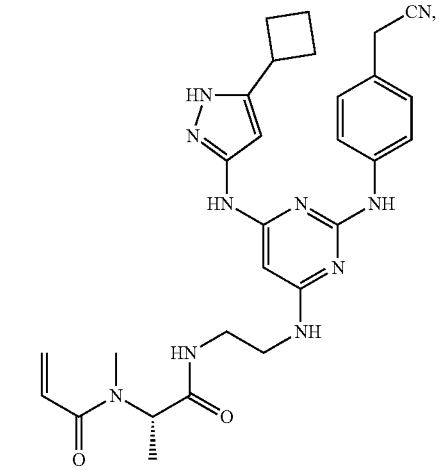
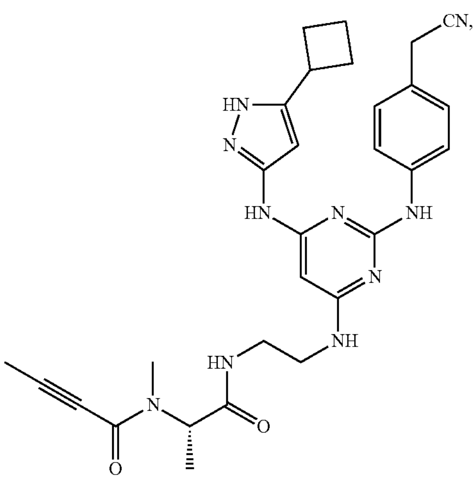
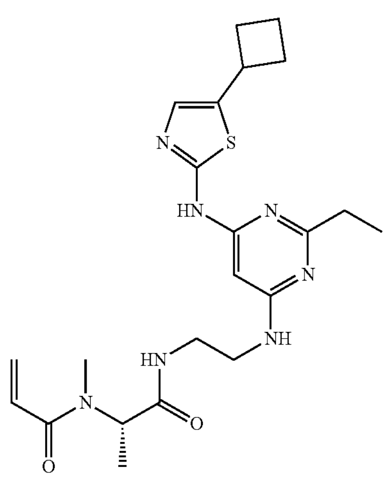
,
-continued
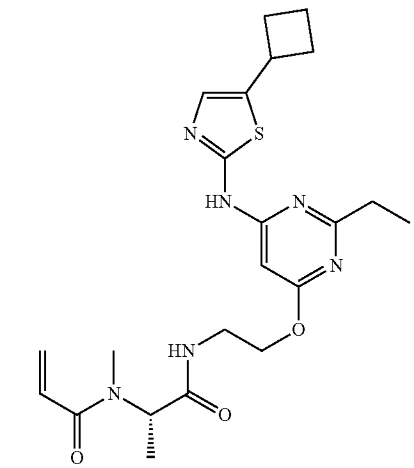
,
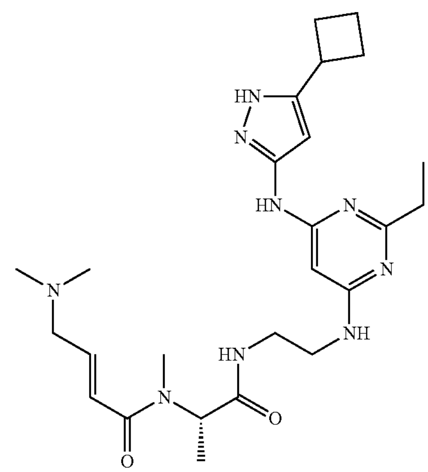
,
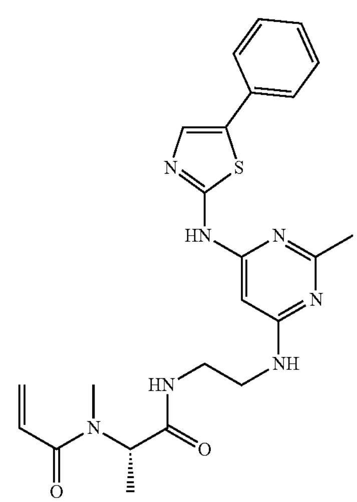
, -continued
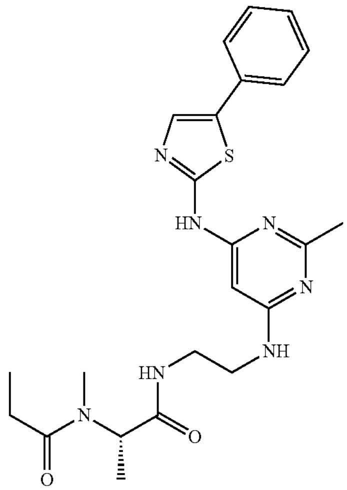
,
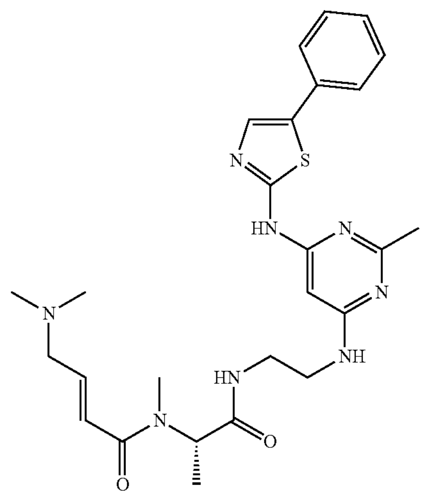
,
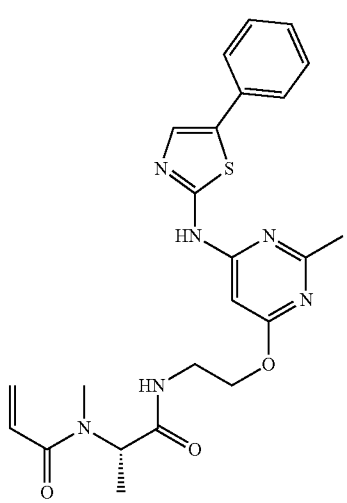
,
-continued
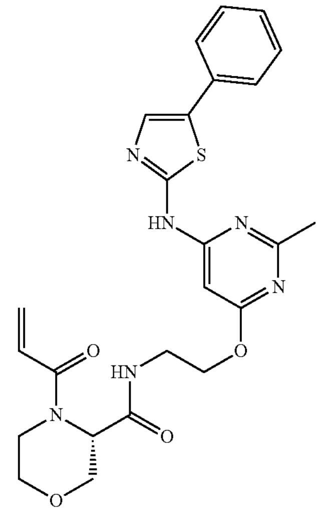
,
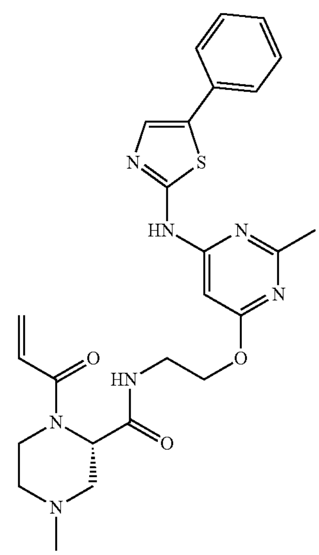
,
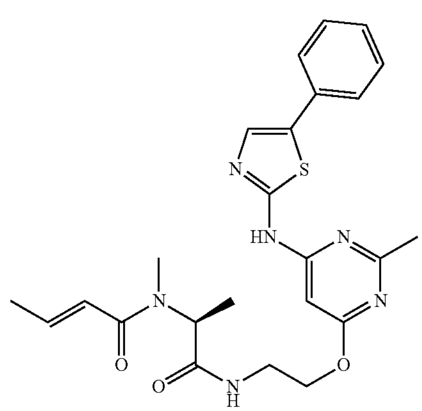
, -continued
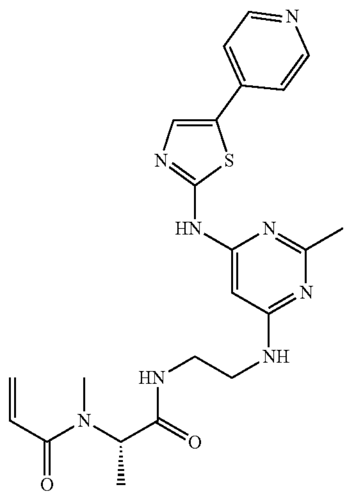
,
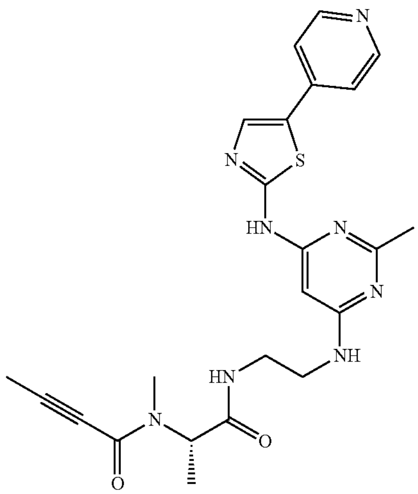
,
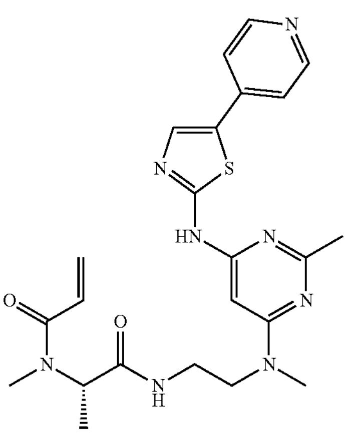
,
-continued
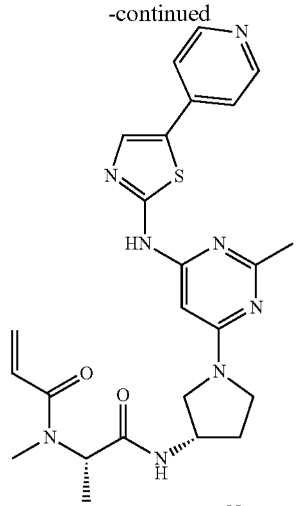
,
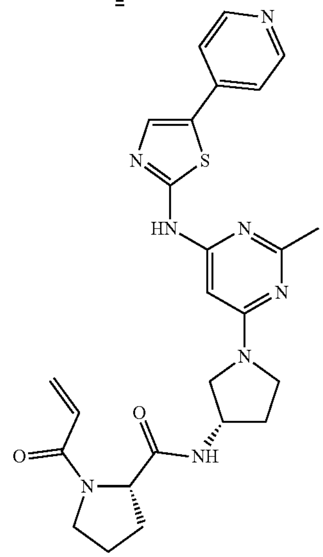
, and
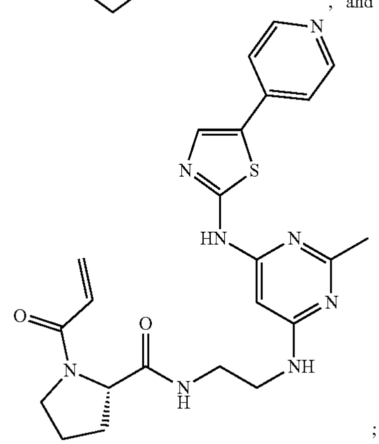
;
or an optically pure stereoisomer, pharmaceutically acceptable salt, or solvate thereof.
* * * * *